US010173981B2

United States Patent
Buchan et al.

(10) Patent No.: US 10,173,981 B2
(45) Date of Patent: *Jan. 8, 2019

(54) PICOLINAMIDES AS FUNGICIDES

(71) Applicant: DOW AGROSCIENCES LLC, Indianapolis, IN (US)

(72) Inventors: Zachary A. Buchan, Indianapolis, IN (US); Kyle A. DeKorver, Indianapolis, IN (US); David M. Jones, Indianapolis, IN (US); Jessica Herrick, Indianapolis, IN (US); Jeremy Wilmot, Indianapolis, IN (US); Jared W. Rigoli, Indianapolis, IN (US); Brian A. Loy, Indianapolis, IN (US); Yu Lu, Indianapolis, IN (US); Kevin G. Meyer, Indianapolis, IN (US); Chenglin Yao, Indianapolis, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/540,565

(22) PCT Filed: Dec. 21, 2015

(86) PCT No.: PCT/US2015/067206
§ 371 (c)(1),
(2) Date: Jun. 28, 2017

(87) PCT Pub. No.: WO2016/109304
PCT Pub. Date: Jul. 7, 2016

(65) Prior Publication Data
US 2018/0000080 A1    Jan. 4, 2018

Related U.S. Application Data

(60) Provisional application No. 62/098,089, filed on Dec. 30, 2014, provisional application No. 62/098,097, filed on Dec. 30, 2014, provisional application No. 62/255,163, filed on Nov. 13, 2015, provisional application No. 62/255,168, filed on Nov. 13, 2015.

(51) Int. Cl.
| | | |
|---|---|---|
| *C07D 213/81* | (2006.01) |
| *A01N 43/40* | (2006.01) |
| *A01N 47/12* | (2006.01) |
| *A01N 25/10* | (2006.01) |
| *C07D 401/12* | (2006.01) |
| *C07D 409/12* | (2006.01) |
| *C07D 417/12* | (2006.01) |
| *A01N 37/44* | (2006.01) |
| *A01N 43/78* | (2006.01) |

(52) U.S. Cl.
CPC .......... *C07D 213/81* (2013.01); *A01N 25/10* (2013.01); *A01N 37/44* (2013.01); *A01N 43/40* (2013.01); *A01N 43/78* (2013.01); *A01N 47/12* (2013.01); *C07D 401/12* (2013.01); *C07D 409/12* (2013.01); *C07D 417/12* (2013.01)

(58) Field of Classification Search
CPC ........ A01N 43/40; A01N 37/44; A01N 25/10; A01N 43/78; A01N 47/12; C07D 401/12; C07D 213/81; C07D 417/12; C07D 409/12
See application file for complete search history.

(56) References Cited

U.S. PATENT DOCUMENTS

| | | |
|---|---|---|
| 4,051,173 A | 9/1977 | Schact et al. |
| 4,588,735 A | 5/1986 | Spatz |
| 5,342,835 A | 8/1994 | Pepin et al. |
| 5,401,871 A | 3/1995 | Feldmann-Krane et al. |
| 5,475,132 A | 12/1995 | Pepin et al. |
| 5,563,165 A | 10/1996 | Talley |
| 5,760,068 A | 6/1998 | Talley |
| 5,852,042 A | 12/1998 | Jakobi et al. |
| 6,355,660 B1 | 3/2002 | Ricks et al. |
| 6,410,572 B1 | 6/2002 | Schelberger et al. |
| 6,436,421 B1 | 8/2002 | Schindler et al. |
| 6,521,622 B1 | 2/2003 | Ricks et al. |
| 6,706,740 B2 | 3/2004 | Ricks et al. |
| 6,861,390 B2 | 3/2005 | Meyer et al. |
| 6,903,219 B2 | 6/2005 | Niyaz et al. |
| 6,916,932 B2 | 7/2005 | Meyer et al. |

(Continued)

FOREIGN PATENT DOCUMENTS

| | | |
|---|---|---|
| CL | 2015001862 | 10/2015 |
| CN | 101530104 | 9/2009 |

(Continued)

OTHER PUBLICATIONS

Anonymous, Synergistic Fungicidal Composition of Heterocyclic Aromatic Amides and Triazoles, IP.com Journal, IP.com, Electronic Publication, West Henrietta, NY, US, Jul. 2004, 11 pages.
Backman, P., Fungicide Formulation: Relationship to Biological Activity, Ann. Rev. Phytopathol, 1978, 16, pp. 211-237.
BASF New Fungicide Xemium Got Full Approval in EU, Agronews, Jul. 18, 2012 [retrieved on Feb. 2, 2014]. Retrieved from the Internet: ,URL:http://news.agropages.com/News/NewsDetail---7386. htm, 1 page.
Bolton, M. et al., "Wheat leaf rust caused by Puccinia triticina," Molecular Plant Pathology, vol. 9, No. 5, 2008, pp. 563-575 [online] [retrieved on Feb. 3, 2016]. Retrieved from the Internet URL: https://www.researchgate.net/profile/Melvin_Bolton/publication/23483068_Wheat_leaf_rust_caused_by_Puccinia_triticina/links/0046352d94b8d5f2c9000000.pdf.

(Continued)

Primary Examiner — John M Mauro
(74) Attorney, Agent, or Firm — Faegre Baker Daniels LLP

(57) ABSTRACT

This disclosure relates to picolinamides of Formula I and their use as fungicides.

25 Claims, No Drawings

(56) References Cited

U.S. PATENT DOCUMENTS

| | | |
|---|---|---|
| 6,927,225 B2 | 8/2005 | Ricks et al. |
| 6,953,807 B2 | 10/2005 | Hutin |
| 7,034,035 B2 | 4/2006 | Ricks et al. |
| 7,183,278 B1 | 2/2007 | Imamura et al. |
| 7,241,804 B1 | 7/2007 | Hockenberry et al. |
| 7,250,389 B1 | 7/2007 | Sakanaka et al. |
| RE39,991 E | 1/2008 | Ricks et al. |
| 7,442,672 B2 | 12/2008 | Muller et al. |
| 7,459,581 B2 | 12/2008 | Derrer et al. |
| 7,560,565 B2 | 7/2009 | Bacque et al. |
| 7,927,617 B2 | 4/2011 | Koltzenburg |
| 8,008,231 B2 | 8/2011 | Leatherman |
| 8,153,819 B2 | 4/2012 | Dietz |
| 8,236,962 B2 | 8/2012 | Hoekstra et al. |
| 8,349,877 B2 | 1/2013 | Brix et al. |
| 8,415,274 B2 | 4/2013 | Wachendorff-Neumann et al. |
| 8,465,562 B2 | 6/2013 | Chen |
| 8,470,840 B2 | 6/2013 | Klittich et al. |
| 8,476,193 B2 | 7/2013 | Keeney et al. |
| 8,580,959 B2 | 11/2013 | Devasthale et al. |
| 8,586,550 B2 | 11/2013 | Lee et al. |
| 8,604,215 B2 | 12/2013 | Phiasivongsa et al. |
| 8,785,479 B2 | 7/2014 | Meyer et al. |
| 8,835,462 B2 | 9/2014 | Meyer et al. |
| 8,883,811 B2 | 11/2014 | Owen et al. |
| 8,916,579 B2 | 12/2014 | Boebel et al. |
| 9,006,259 B2 | 4/2015 | Boebel et al. |
| 9,084,418 B2 | 7/2015 | Ehr et al. |
| 9,131,690 B2 | 9/2015 | Meyer et al. |
| 9,144,239 B2 | 9/2015 | Meyer et al. |
| 9,155,305 B2 | 10/2015 | Gary |
| 9,156,816 B2 | 10/2015 | Ito et al. |
| 9,179,674 B2 | 11/2015 | Martin et al. |
| 9,185,911 B2 | 11/2015 | Inami et al. |
| 9,198,419 B2 | 12/2015 | Owen et al. |
| 9,247,741 B2 | 2/2016 | DeLorbe et al. |
| 9,265,253 B2 | 2/2016 | Li et al. |
| 9,265,255 B2 | 2/2016 | Funke |
| 9,271,496 B2 | 3/2016 | Kemmitt |
| 9,271,497 B2 | 3/2016 | Lorsbach |
| 9,414,596 B2 | 8/2016 | Hoekstra et al. |
| 9,439,422 B2 | 9/2016 | Martin et al. |
| 9,482,661 B2 | 11/2016 | Ross |
| 9,549,555 B2 | 1/2017 | DeLorbe et al. |
| 9,549,556 B2 | 1/2017 | DeKorver et al. |
| 9,629,365 B2 | 4/2017 | Li et al. |
| 9,681,664 B2 | 6/2017 | LaLonde et al. |
| 9,686,984 B2 | 6/2017 | DeKorver et al. |
| 9,700,047 B2 | 7/2017 | Lu |
| 9,750,248 B2 | 9/2017 | Ouimette et al. |
| 9,840,475 B2 | 12/2017 | Lorsbach |
| 9,936,697 B2 | 4/2018 | Hopkins |
| 9,955,690 B2 | 5/2018 | Owen |
| 9,955,691 B2 | 5/2018 | Boebel |
| 9,974,304 B2 | 5/2018 | DeKorver |
| 2002/0119979 A1 | 8/2002 | Degenhardt et al. |
| 2002/0177578 A1 | 11/2002 | Ricks et al. |
| 2003/0018052 A1 | 1/2003 | Ricks et al. |
| 2003/0022902 A1 | 1/2003 | Ricks et al. |
| 2003/0022903 A1 | 1/2003 | Ricks et al. |
| 2005/0239873 A1 | 10/2005 | Hockenbery et al. |
| 2006/0167281 A1 | 7/2006 | Meijer |
| 2007/0010401 A1 | 1/2007 | Noon |
| 2007/0066629 A1 | 3/2007 | Tormo i Blasco et al. |
| 2009/0203770 A1 | 8/2009 | Hockenberry et al. |
| 2009/0306142 A1 | 12/2009 | Carson et al. |
| 2010/0016163 A1 | 1/2010 | Keiper et al. |
| 2011/0070278 A1 | 3/2011 | Lopez |
| 2011/0082162 A1 | 4/2011 | Lorsbach et al. |
| 2012/0245031 A1 | 9/2012 | Gewehr et al. |
| 2013/0296372 A1 | 11/2013 | Owen et al. |
| 2014/0051678 A1 | 2/2014 | Clement-Schatlo et al. |
| 2014/0128411 A1 | 5/2014 | Ogawa et al. |
| 2014/0187587 A1 | 7/2014 | Ouimette et al. |
| 2014/0357713 A1 | 12/2014 | Damaj et al. |
| 2015/0018374 A1 | 1/2015 | Taggi et al. |
| 2015/0065529 A1 | 3/2015 | Owen et al. |
| 2015/0181868 A1 | 7/2015 | DeKorver et al. |
| 2015/0289508 A1 | 10/2015 | Meyer et al. |
| 2015/0322051 A1 | 11/2015 | Lu et al. |
| 2016/0007601 A1 | 1/2016 | Boebel et al. |
| 2016/0037774 A1 | 2/2016 | Schulz |
| 2016/0183526 A1 | 6/2016 | Hopkins et al. |
| 2016/0183527 A1 | 6/2016 | Hopkins et al. |
| 2016/0183528 A1 | 6/2016 | Hopkins et al. |
| 2017/0183324 A1 | 6/2017 | Li et al. |
| 2017/0360038 A1 | 6/2017 | Yao |
| 2017/0273303 A1 | 9/2017 | DeKorver et al. |
| 2017/0273306 A1 | 9/2017 | LaLonde et al. |
| 2017/0290333 A1 | 10/2017 | Bravo-Altamirano et al. |
| 2017/0295792 A1 | 10/2017 | Bravo-Altamirano et al. |
| 2017/0369421 A1 | 12/2017 | Yao |
| 2018/0000075 A1 | 1/2018 | Bravo-Altamirano et al. |
| 2018/0000084 A1 | 1/2018 | Yao |
| 2018/0000085 A1 | 1/2018 | Bravo-Altamirano et al. |
| 2018/0002288 A1 | 1/2018 | Buchan |
| 2018/0002319 A1 | 1/2018 | Wilmot |
| 2018/0002320 A1 | 1/2018 | Wilmot |
| 2018/0037541 A1 | 2/2018 | Yao |

FOREIGN PATENT DOCUMENTS

| | | |
|---|---|---|
| FR | 2649699 | 1/1991 |
| JP | 19940026884 | 9/1995 |
| JP | 1998053583 | 2/1998 |
| JP | H10-045747 | 2/1998 |
| WO | 1996010016 | 4/1996 |
| WO | 199637472 | 11/1996 |
| WO | 1997019908 | 6/1997 |
| WO | 199741103 | 11/1997 |
| WO | 1998018751 | 5/1998 |
| WO | 1999011127 | 11/1999 |
| WO | 2000076979 | 12/2000 |
| WO | 200114339 | 3/2001 |
| WO | 2005121069 | 12/2005 |
| WO | 2008079387 | 7/2008 |
| WO | 2012016989 | 2/2012 |
| WO | 2012020777 | 2/2012 |
| WO | 2014105844 | 7/2014 |
| WO | 2016007525 | 1/2016 |
| WO | 2016109288 | 7/2016 |
| WO | 2016109289 | 7/2016 |
| WO | 2016109290 | 7/2016 |
| WO | 2016109291 | 7/2016 |
| WO | 2016109300 | 7/2016 |
| WO | 2016109301 | 7/2016 |
| WO | 2016109302 | 7/2016 |
| WO | 2016109303 | 7/2016 |
| WO | 2016109305 | 7/2016 |
| WO | 2015005355 | 3/2017 |

OTHER PUBLICATIONS

Davari, M. et al. "Quantum Chemical Investigation of Intramolecular Thione-Thiol Tautomerism of 1, 2, 4-triazole-3-thione and its disubstituted derivatives," Journal of Molecular Modeling, Sep. 2009, 16(5), pp. 841-855.

FRAC Code List: Fungicides Sorted by Mode of Action (including FRAC Code numbering), Fungicide Resistance Action Committee, Dec. 2008, 10 pages.

Fungicidal Mixtures, IP.com Prior Art Database Technical Disclosure, (Jul. 5, 2005), XP055073888, DOI: http://ip.com/pdf/ipcompad/IPCOM000126160D.pdf, 12 pages.

Gisi, U., "Synergistic Interaction of Fungicides in Mixtures," The American Phytopathological Society, vol. 86, No. 11, 1996, pp. 1273-1279.

Hu, Z. et al., "Synthesis of Novel Analogues of Antimycin A3," Tetrahedron Letters 49 (2008), pp. 5192-5195.

Huang, C. et al., "Synergistic Interactions between Chitinase ChiCW and Fungicides Against Plant Fungal Pathogens," J. Microbiol. Biotechnol., 2008, 18(4), pp. 784-787.

(56) References Cited

OTHER PUBLICATIONS

Kissling, E., "Crop Protection Pipeline Value Jumps to Euro 2.4 Billion," BASF SE, Mar. 10, 2011 [retrieved on Feb. 4, 2014], Retrieved from the internet: ,URL:http://agro.basf.com/agri/AP-Internet/en/content/news_room/news/basf-crop-protection-pipeline-value, 4 pages.
Koyanagi, T. et al., "Bioisoterism in Agrochemicals," Synthesis and Chemistry of Agrochemicals IV; Baker, D. et al., ACS Symposium Series; American Chemical Society: Washington, D.C., 1995, pp. 15-24.
Latin, R., et al, "Re-Examining Fungicide Synergism for Dollar Spot Control;" GCM, Jul. 2008, pp. 84-87.
Ueki, M., et al., "UK-2A, B, C, and D, Novel Antifungal Antibiotics from Streptomyces sp. 517-02 I. Fermentation, Isolation, and Biological Properties," The Journal of Antibiotics, vol. 49, No. 7, Jul. 1996, pp. 639-643.
O'Sullivan, E., et al., "Fungicide Resistance—an Increasing Problem," Proceedings of National Tillage Conference 2007, Published by Crop Research Centre, Oak Park, Carlow, Jan. 31, 2007, pp. 43-56.
Parker, J.E., et al., "Mechanism of Binding of Prothioconazole to Mycosphaerella graminicola CYP51 Differs from That of Other Azole Antifungals," Applied and Environmental Microbiology, vol. 77, No. 4, Feb. 2011, pp. 1460-1465.
PubChem: Open Chemistry Database, Substance Record for SID 74383515. Deposit Date Jun. 11, 2009 [retrieved on May 25, 2016] Retrieved from internet. <URL:https://pubchem.ncbi.nlm.nih.gov/substance/74383515#section=Top>, 5 pages.
Science for a Better Life, Bayer CropScience "Positioned for Growth", Jun. 2008, 22 pages.
Calcium Dodecyl Benzene Sulfonate, CAS 26264-06-2, (http://www.hichem.com/product/showproduct.php?id=334639) Mar. 28, 2013, 4 pages.
Tani, K. et al., The Journal of Antibiotics, vol. 55, No. 3, Mar. 2002, pp. 315-321.
The Merck Index, Twelfth Edition, S. Budavari, Ed., Merck and Co., Inc., Whitehouse Station, NJ, 1996, pp. 2220, 3666, 7937 and 7946.
Usuki, Y., et al., "Semi-synthesis and biological evaluation of analogues of UK-2A, a novel antifungal antibiotic from Streptomyces sp. 517-02," Bioorganic & Medicinal Chemistry Letters, vol. 15, No. 8, 2005, pp. 2011-2014.
Usuki, Y. et al., Journal of Antibiotics, vol. 55, No. 6, Jun. 2002, pp. 607-610.
Webster's New World Dictionary, Second College Edition, Guralnik, D, Ed., The World Publishing Co., New York, p. 1127 (1972).
Wilson, C.L. et al. "Fruit Volatiles Inhibitory to Monilinia Fruiticola and Botrytis cinerea," 1987, Plant Disease, vol. 71, No. 4, pp. 316-319.
Written Opinion and Search Report for PCT Patent Application No. PCT/US2015/067206 dated Mar. 7, 2016, 8 pages.
Cantacuzene, D., "Optimization of the papain catalyzed esterification of amino acids by alcohols and diols," Tetrahedron, vol. 45, Issue 3 (1989), pp. 741-748.
Washburn, W.N., "Identification of a nonbasic melanin hormone receptor 1 antagonist as an antiobesity clinical candidate," Journal of Medicinal Chemistry, 57, 18 (Aug. 28, 2014), pp. 7509-7522.
Guseynov et al: "Study of the reaction of aminoacetic acid with dihydric alcohols and production of epoxy esters" Chemical Problems, 2009 (1), pp. 188-190. English Machine Translation attached.
Amiri et al. "Sensitivity of Botrytis cinerea field isolates to the novel succinate dehydrogenase inhibitors fluopyram, penthiopyrad, and fluxapuroxad". Annual Meeting of the American Phytopathological Society, Phytopathology, vol. 102 (2012).
Cooke et al. "The effect of fungicide programmes based on epoxiconazole on the control and DMI sensitivity of Rhynchosporium secalis in winter barley." Crop Protection, vol. 23, No. 5, pp. 393-406 (2004).
Fujita T, Ed. "Quantitative structure-activity analysis and database-aided bioisosteric structural transformation procedure as methodologies of agrochemical design"; Classical and Three Dimensional QSAR in Agrochemistry, American Chemical Society Symposium Series, Washington, D.C. vol. 606, pp. 13-34 (1995).
Goellner et al. "Phakopsora pachyrhizi, the causal agent of Asian soybean rust." Molecular Plant Pathology, vol. 11, No. 2, pp. 169-177 (2010).
Kendall, S. et al. "Changes in sensitivity to DMI fungicides in Rhynchosporium secalis". Crop Protection, vol. 12, No. 5, pp. 357-362 (1993).
Lippard, S. "The Art of Chemistry". Nature, vol. 416, p. 587 (2002).
Patani et al. "Biosterism: A rational approach in drug design". Chemical Reviews, vol. 96, No. 8, pp. 3147-3176 (1996).
Shimano et al. "Total synthesis of the antifungal dilactones UK-2A and UK-3A: The determination of their relative and absolute configurations, analog synthesis and antifungal activities". Tetrahedron, vol. 54, pp. 12745-12774 (1998).
Chitwood, D. "Nematicides". Encyclopedia of Agrochemicals (3), pp. 1104-1115, John Wiley & Sons, New York, NY, http://naldc.na.usda.gov/download/43874/PDF (2003).
Hanafi et al. "UK2A, B, C, and D, Novel Antifungal Antibiotics from Streptomyces sp. 517-02 II. Structural Elucidation." The Journal of Antibiotics, vol. 49, Issue 12, pp. 1226-1231 (1996).
Shibata et al. "UK1, A Novel Cytotoxic Metabolite from Streptomyces sp. 517-02 II. Structural Elucidation." The Journal of Antibiotics, vol. 46, Issue 7, pp. 1095-1100 (1993).
Shimano et al. "Enantioselective Total Synthesis of the Antifungal Dilactone, UK-2A: The Determination of the Relative and Absolute Configurations". Tetrahedron Letters, vol. 39, pp. 4363-4366 (1998).
Stephenson, G., et al. "Glossary of terms relating to pesticides". Pure and Applied Chemistry, vol. 78, No. 11, pp. 2075-2154, International Union of Pure and Applied Chemistry (2006).
Ueki, M., et al., "UK-1, A Novel Cytotoxic Metabolite from Streptomyces sp. 517-02 I. Taxonomy, Fermentation, Isolation, Physico-chemical and Biological Properties." The Journal of Antibiotics, vol. 46, No. 7, pp. 1089-1094 (1993).
Ueki et al. "UK-3A, A Novel Antifungal Antibiotic from Streptomyces sp. 517-02: Fermentation, Isolation, Structural Elucidation and Biological Properties". The Journal of Antibiotics, vol. 50, Issue 7, pp. 551-555 (1997).
Ueki et al. "The mode of action of UK-2A and UK-3A, Novel antifungal antibiotics from Streptomyces sp. 517-02". The Journal of Antibiotics, vol. 50, Issue 12, pp. 1052-1057 (1997).
International Searching Authority, International Search Report for PCT/US14/058070 dated Dec. 15, 2014, 4 pages.
International Searching Authority, Written Opinion for PCT/US14/058070, dated Dec. 15, 2014, 5 pages.
International Searching Authority, International Search Report and Written Opinion for PCT/US14/58061 dated Dec. 15, 2014, 9 pages.
International Searching Authority, International Search Report and Written Opinion for PCT/US1458065 dated Dec. 22, 2014, 9 pages.
International Searching Authority, International Search Report and Written Opinion for PCT/US1528407 dated Aug. 5, 2015, 8 pages.
International Searching Authority, International Search Report and Written Opinion for PCT/US1539407 dated Sep. 30, 2015, 9 pages.
International Searching Authority, International Search Report and Written Opinion for PCT/US1539409 dated Oct. 5, 2015, 10 pages.
International Searching Authority, International Search Report and Written Opinion for PCT/US1544383 dated Mar. 16, 2016, 11 pages.
International Searching Authority, International Search Report and Written Opinion for PCT/US1567111 dated Mar. 11, 2016, 11 pages.
International Searching Authority, International Search Report and Written Opinion for PCT/US1567113 dated Mar. 11, 2016, 10 pages.
International Searching Authority, International Search Report and Written Opinion for PCT/US1567116 dated Mar. 7, 2016, 8 pages.
International Searching Authority, International Search Report and Written Opinion for PCT/US1567199 dated Mar. 11, 2016, 9 pages.
International Searching Authority, International Search Report and Written Opinion for PCT/US1567200 dated Mar. 10, 2016, 10 pages.

(56) References Cited

OTHER PUBLICATIONS

International Searching Authority, International Search Report and Written Opinion for PCT/US1567201 dated Mar. 11, 2016, 8 pages.
International Searching Authority, International Search Report and Written Opinion for PCT/US1567204 dated Mar. 7, 2016, 10 pages.
International Searching Authority, International Search Report and Written Opinion for PCT/US1567207 dated Mar. 11, 2016, 12 pages.
International Searching Authority, International Search Report and Written Opinion for PCT/US2013039726 dated Sep. 17, 2013, 9 pages.
International Searching Authority, International Search Report and Written Opinion for PCT/US2013039735 dated Oct. 18, 2013, 8 pages.
International Searching Authority, International Search Report and Written Opinion for PCT/US2013077472 dated Apr. 16, 2014, 9 pages.
International Searching Authority, International Search Report and Written Opinion for PCT/US2013077537 dated Apr. 16, 2014, 11 pages.
International Searching Authority, International Search Report and Written Opinion for PCT/US2014071692 dated Apr. 20, 2015, 6 pages.
International Searching Authority, International Search Report and Written Opinion for PCT/US2014071695 dated Apr. 17, 2015, 6 pages.
International Searching Authority, International Search Report and Written Opinion for PCT/US2014071699 dated Apr. 20, 2015, 6 pages.
International Searching Authority, International Search Report and Written Opinion for PCT/US2014071700 dated Apr. 17, 2015, 9 pages.
International Searching Authority, International Search Report and Written Opinion for PCT/US2015066760 dated Apr. 14, 2016, 11 pages.
International Searching Authority, International Search Report and Written Opinion for PCT/US2015066764 dated Apr. 28, 2016, 11 pages.
International Searching Authority, International Search Report and Written Opinion for PCT/US20150051598 dated Dec. 6, 2010, 5 pages.
International Searching Authority, International Search Report for PCT/US14/058067, dated Dec. 22, 2014, 4 pages.
International Searching Authority, Written Opinion for PCT/US14/058067, dated Dec. 22, 2014, 5 pages.
International Searching Authority, International Search Report and Written Opinion for PCT/US2015/067115, dated Mar. 11, 2016, 6 pages.
International Searching Authority, International Search Report PCT/US2000/021523 dated Jul. 7, 2001, 7 pages.
Database Chemabs Online, Chemical Abstracts Service, Columbus Ohio, US: accession No. CA63:16300d XP002164206.

PICOLINAMIDES AS FUNGICIDES

CROSS REFERENCE TO RELATED APPLICATIONS

This application is a U.S. National Phase filing of International Application No. PCT/US2015/067206, filed Dec. 21, 2015, which claims the benefit of U.S. Provisional Patent Application Serial Nos. 62/098,089 filed Dec. 30, 2014, 62/098,097 filed Dec. 30, 2014, 62/255,163 filed Nov. 13, 2015 and 62/255,168 filed Nov. 13, 2015, the disclosures of which are hereby expressly incorporated by reference herein in their entirety.

BACKGROUND & SUMMARY

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to picolinamides and their use as fungicides. The compounds of the present disclosure may offer protection against ascomycetes, basidiomycetes, deuteromycetes and oomycetes.

One embodiment of the present disclosure may include compounds of Formula I:

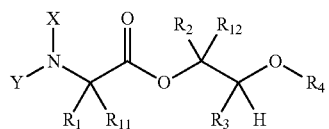

I

X is hydrogen or $C(O)R_5$;
Y is hydrogen, $C(O)R_5$, or Q;
Q is

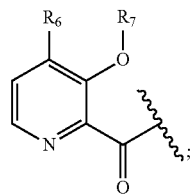

$R_1$ and $R_{11}$ are independently chosen from hydrogen or alkyl, optionally substituted with 0, 1 or multiple $R_8$; Alternatively, $R_1$ and $R_{11}$ may be taken together to form a 3-6 membered saturated or partially saturated carbocycle or heterocycle, optionally substituted with 0, 1 or multiple $R_8$;

$R_2$ and $R_{12}$ are independently chosen from hydrogen or methyl;

$R_3$ is chosen from aryl or heteroaryl, each optionally substituted with 0, 1 or multiple $R_8$;

$R_4$ is chosen from alkyl, aryl, or acyl, each optionally substituted with 0, 1 or multiple $R_8$;

$R_5$ is chosen from alkoxy or benzyloxy, each optionally substituted with 0, 1, or multiple $R_8$;

$R_6$ is chosen from hydrogen, alkoxy, or halo, each optionally substituted with 0, 1, or multiple $R_8$;

$R_7$ is chosen from hydrogen, $-C(O)R_9$, or $-CH_2OC(O)R_9$;

$R_8$ is chosen from hydrogen, alkyl, aryl, acyl, halo, alkenyl, alkoxy, or heterocyclyl, each optionally substituted with 0, 1, or multiple $R_{10}$;

$R_9$ is chosen from alkyl, alkoxy, or aryl, each optionally substituted with 0, 1, or multiple $R_8$;

$R_{10}$ is chosen from hydrogen, alkyl, aryl, acyl, halo, alkenyl, alkoxy, or heterocyclyl.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, and an area adjacent to the plant.

It will be understood by those skilled in the art that the following terms may include generic "R"-groups within their definitions, e.g., "the term alkoxy refers to an —OR substituent". It is also understood that within the definitions for the following terms, these "R" groups are included for illustration purposes and should not be construed as limiting or being limited by substitutions about Formula I.

The term "alkyl" refers to a branched, unbranched, or saturated cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl, and the like.

The term "alkenyl" refers to a branched, unbranched or cyclic carbon chain containing one or more double bonds including, but not limited to, ethenyl, propenyl, butenyl, isopropenyl, isobutenyl, cyclobutenyl, cyclopentenyl, cyclohexenyl, and the like.

The terms "aryl" and "Ar" refer to any aromatic ring, mono- or bi-cyclic, containing 0 heteroatoms.

The term "heterocyclyl" refers to any aromatic or non-aromatic ring, mono- or bi-cyclic, containing one or more heteroatoms The term "alkoxy" refers to an —OR substituent.
The term "hydroxyl" refers to a —OH substituent.
The term "amino" refers to an $-N(R)_2$ substituent.
The term "halogen" or "halo" refers to one or more halogen atoms, defined as F, Cl, Br, and I.
The term "nitro" refers to a $-NO_2$ substituent.
The term thioalkyl refers to a —SR substituent.

Throughout the disclosure, reference to the compounds of Formula I is read as also including all stereoisomers, for example diastereomers, enantiomers, and mixtures thereof. In another embodiment, Formula (I) is read as also including salts or hydrates thereof. Exemplary salts include, but are not limited to: hydrochloride, hydrobromide, hydroiodide, trifluoroacetate, and trifluoromethane sulfonate.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or roots.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DETAILED DESCRIPTION

The compounds of the present disclosure may be applied by any of a variety of known techniques, either as the compounds or as formulations comprising the compounds. For example, the compounds may be applied to the roots or foliage of plants for the control of various fungi, without damaging the commercial value of the plants. The materials may be applied in the form of any of the generally used formulation types, for example, as solutions, dusts, wettable powders, flowable concentrate, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and used as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil-soluble salts or sulfated polyglycol ethers and appropriate salts of phosphated polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting, and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzyl-cocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, *Bacillus subtilis* strain QST713, benalaxyl, benomyl, benthiavalicarb-isopropyl, benzovindiflupyr benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila*, *Fusarium oxysporum*, *Gliocladium* spp., *Phlebiopsis gigantea*, *Streptomyces griseoviridis*, *Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

Additionally, the compounds described herein may be combined with other pesticides, including insecticides, nematocides, miticides, arthropodicides, bactericides or combinations thereof that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, niflutidide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoximmethyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds described herein may be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, diallate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-P, glyphosate, halauxifen, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxsulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vernolate, and xylachlor.

Another embodiment of the present disclosure is a method for the control or prevention of fungal attack. This method comprises applying to the soil, plant, roots, foliage, or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those skilled in the art that the efficacy of the compound for the foregoing fungi establishes the general utility of the compounds as fungicides.

The compounds have broad ranges of activity against fungal pathogens. Exemplary pathogens may include, but are not limited to, causing agent of wheat leaf blotch (*Zymoseptoria tritici*), wheat brown rust (*Puccinia triticina*), wheat stripe rust (*Puccinia striiformis*), scab of apple (*Venturia inaequalis*), powdery mildew of grapevine (Uncinula necator), barley scald (*Rhynchosporium secalis*), blast of rice (*Pyricularia oryzae*), rust of soybean (*Phakopsora pachyrhizi*), glume blotch of wheat (*Leptosphaeria nodorum*), powdery mildew of wheat (*Blumeria graminis* f. sp. *tritici*), powdery mildew of barley (*Blumeria graminis* f. sp. *hordei*), powdery mildew of cucurbits (*Erysiphe cichoracearum*), anthracnose of cucurbits (*Colletotrichum lagenarium*), leaf spot of beet (*Cercospora beticola*), early blight of tomato (*Alternaria solani*), and spot blotch of barley (*Cochliobolus sativus*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, g/m$^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

General Schemes

The following schemes illustrate approaches to generating picolinamide compounds of Formula (I). The following descriptions and examples are provided for illustrative purposes and should not be construed as limiting in terms of substituents or substitution patterns.

Compounds of Formulae 1.1, 1.2, 1.3, and 1.4, wherein $R_3$ is as originally defined, can be prepared by the methods shown in Scheme 1, steps a-c. Compounds of Formula 1.0, wherein Z is ethoxy (—OCH$_2$CH$_3$, OEt) or pyrrolidine and P.G. is Bn or PMB, can be treated with a mixture of an organometallic nucleophile, such as phenylmagnesium bromide or phenyllithium, and a reducing agent, such as lithium borohydride (LiBH$_4$), in a polar, aprotic solvent such as tetrahydrofuran (THF) or diethyl ether (Et$_2$O) at a reduced temperature of about −78° C. to about 0° C. to afford compounds of Formula 1.1, wherein $R_3$ is as previously defined, as shown in step a. Alternatively, the compound of Formula 1.0, wherein Z is OEt and P.G. is Bn or PMB, can be converted to the aldehyde of Formula 1.2 by treating with a catalyst, such as chlorobis(cyclooctene)iridium(I) dimer (Ir$_2$(coe)$_4$Cl$_2$), and a reducing agent, such as diethylsilane (Et$_2$SiH$_2$), in a halogenated solvent such as dichloromethane (CH$_2$Cl$_2$), as described by Cheng, C.; Brookhart, M. *Angew. Chem. Int. Ed.* 2012, 51, 9422-9424 and shown in step b. Compounds of Formulas 1.3 and 1.4, wherein $R_3$ is as previously defined, can be obtained by treating the aldehyde of Formula 1.2 with a carbon nucleophile, such as phenyl magnesium bromide, in a polar aprotic solvent, such as THF, at a reduced temperature of about −78° C. to about 23° C., as depicted in step c.

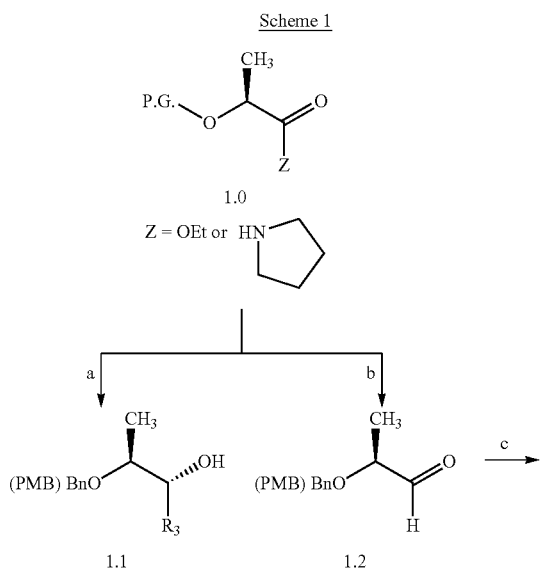

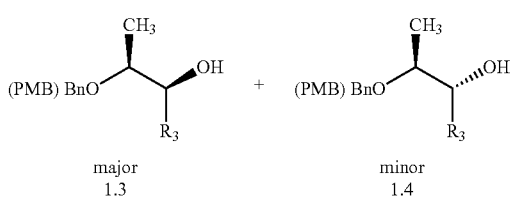

Compounds of Formulas 2.1, 2.2 and 2.3, wherein $R_3$ is as originally defined, can be obtained using the methods outlined in Scheme 2, steps a-d. Compounds of Formula 2.1, wherein $R_3$ is as previously defined and $R_4$ is aryl, can be prepared by treating solutions of compounds of Formula 2.0, wherein $R_3$ is as originally defined, in a solvent such as toluene, with an organometallic species, such as bis(acetato-O)triphenyl-bismuth(V) ($Ph_3Bi(OAc)_2$), in the presence of a catalyst, such as copper(II) acetate ($Cu(OAc)_2$), at an elevated temperature of about 50° C., as shown in step a. Alternatively, arylated products of Formula 2.1, wherein $R_3$ is as previously defined, can be prepared by treating compounds of Formula 2.0, wherein $R_3$ is as previously defined, with an aryl fluoride, such as 1,3-difluorobenzene, and an alkoxide base, such as potassium tert-butoxide (KOt-Bu) or sodium hydride (NaH), in a polar aprotic solvent, such as N,N-dimethyl formamide (DMF) or dimethyl sulfoxide (DMSO), at an elevated temperature of about 50° C. to about 70° C., as shown in step b. Compounds of Formula 2.2, wherein $R_3$ is as previously defined and $R_4$ is alkyl, can be prepared from compounds of Formula 2.0, wherein $R_3$ is as previously defined, by treating with a base, such as KOt-Bu or NaH, and an electrophile, such as an alkyl halide such as (bromomethyl)cyclopropane, in a polar aprotic solvent such as DMF, at an elevated temperature of about 50° C., as shown in step c. Compounds of Formula 2.3, wherein $R_3$ is as previously defined and $R_4$ is acyl, can be prepared from compounds of Formula 2.0, by treating with an acyl electrophile, such as an acyl chloride, in a pyridine solvent at ambient temperature as shown in step d.

Compounds of Formula 3.2, wherein $R_4$ and $R_8$ are as originally defined, can be prepared according to the methods outlined in Scheme 3, steps a-c. Compounds of Formula 3.0, wherein $R_4$ is as originally defined, can be subjected to a palladium catalyst, such as tetrakis(triphenylphosphine)palladium(0) ($Pd(PPh_3)_4$), and a secondary amine, such as morpholine, in a polar aprotic solvent, such as THF, at a temperature of about 23° C. to afford compounds of Formula 3.1, wherein $R_4$ is as originally defined, as shown in step a. Compounds of Formula 3.2, wherein $R_4$ is as originally defined and $R_8$ is alkyl, can be prepared from compounds of Formula 3.1, wherein $R_4$ is as originally defined, by treatment with a base, such as potassium carbonate ($K_2CO_3$), and an alkyl bromide, such as (bromomethyl)cyclohexane, in a polar aprotic solvent, such as acetone, at a temperature of about 25° C. to about 50° C., as shown in step b. Additionally, compounds of Formula 3.2, wherein $R_4$ is as originally defined and $R_8$ is aryl, can be prepared from alcohols of Formula 3.1, wherein $R_4$ is as previously defined, by treatment with a copper catalyst, such as $Cu(OAc)_2$, an aryl boronic acid, such as phenyl boronic acid, and a tertiary amine, such as triethylamine ($NEt_3$), in a halogenated solvent, such as $CH_2Cl_2$, in the presence of 4 Å molecular sieves at a temperature of approximately 23° C., as described by Nie, Z.; Perretta, C.; Lu, J.; Su, Y.; Margosiak, S.; Gajiwala, K. S.; Cortez, J.; Nikulin, V.; Yager, K. M.; Appelt, K.; Chu, S. *J. Med. Chem.*, 2005, 48 (5), pp 1596-1609, and shown in step c.

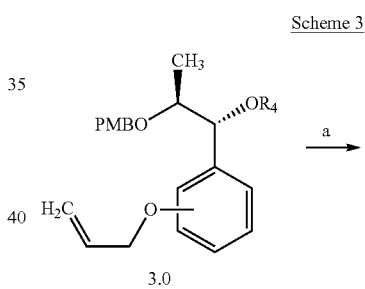

Scheme 3

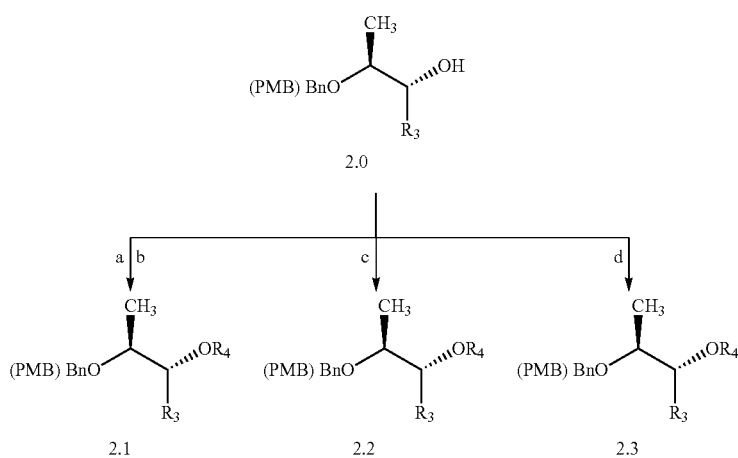

Scheme 2

-continued

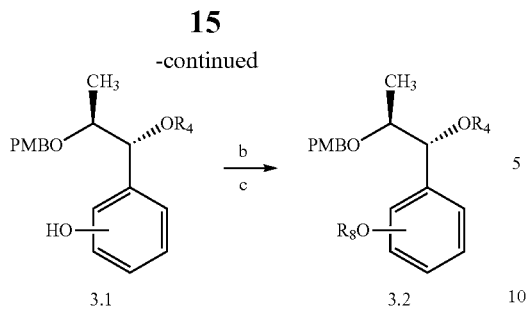

Compounds of Formula 4.2, wherein $R_3$ and $R_4$ are as originally defined, can be prepared according to the methods outlined in Scheme 4, steps a-c. Compounds of Formula 4.2, wherein $R_3$ and $R_4$ are as previously defined but not alkenyl, can be prepared by treating compounds of Formula 4.0, wherein $R_3$ and $R_4$ are originally defined, with a catalyst, such as palladium on carbon (Pd/C), in the presence of hydrogen gas ($H_2$) in a polar solvent, such as ethyl acetate (EtOAc) or MeOH, or with an alternate source of hydrogen, such as cyclohexene, in a polar solvent such as EtOH, as shown in step a. Additionally, compounds of Formula 4.0, wherein $R_3$ is as previously defined and $R_4$ is an aryl chloride, can be subjected to modified hydrogenolysis conditions, by exposing an EtOH solution of the aryl chloride to $H_2$ in the presence of Pd/C and $NEt_3$ to afford compounds of Formula 4.2, wherein $R_3$ and $R_4$ are as originally defined, but not alkenyl or chloro, as shown in step b. Compounds of Formula 4.2, wherein $R_3$ and $R_4$ are as originally defined, can be obtained by treating compounds of Formula 4.1, wherein $R_3$ and $R_4$ are as originally defined, with an oxidant, such as 2,3-dichloro-5,6-dicyano-1,4-benzoquinone (DDQ), in a solvent mixture, such as aqueous $CH_2Cl_2$, as indicated in step c.

Scheme 4

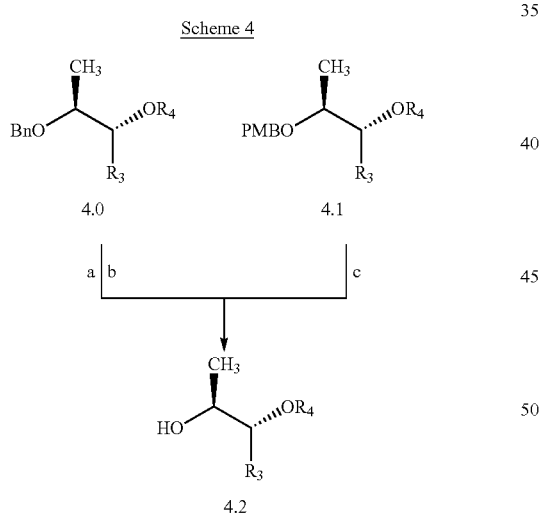

Compounds of Formula 5.2, wherein $R_1$, $R_2$, $R_3$, $R_4$, $R_{11}$, and $R_{12}$, are as originally defined, can be prepared according to the method outlined in Scheme 5, step a. Alcohols of Formula 5.0, wherein $R_2$, $R_3$, $R_4$, and $R_{12}$, are as originally defined, can be treated with compounds of Formula 5.1, wherein $R_1$ and $R_{11}$ are as originally defined, a coupling reagent, such as 3-(ethyliminomethyleneamino)-N,N-dimethylpropan-1-amine hydrochloride (EDC) or a polymer-supported carbodiimide (PS-CDT), and a catalyst, such as N,N-dimethylpyridin-4-amine (DMAP), in a halogenated solvent, such as $CH_2Cl_2$, to afford compounds of Formula 5.2, wherein $R_1$, $R_2$, $R_3$, $R_4$, $R_{11}$, and $R_{12}$ are as previously defined, as shown in step a.

Scheme 5

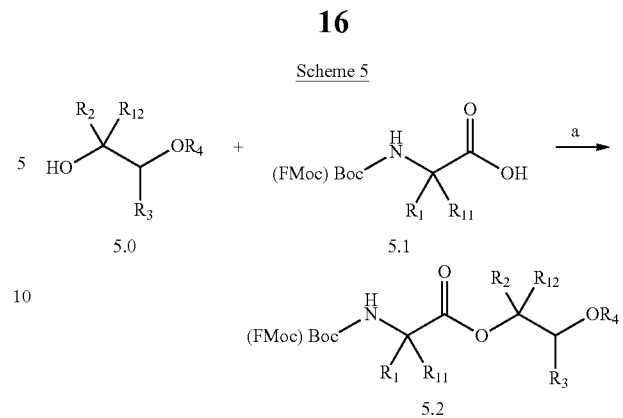

Compounds of Formula 6.4, wherein $R_1$, $R_2$, $R_3$, $R_4$, $R_6$, $R_{11}$, and $R_{12}$ are as originally defined, can be prepared according to the methods outlined in Scheme 6, steps a-d. Compounds of Formula 6.0, wherein $R_1$, $R_2$, $R_3$, $R_4$, $R_{11}$, and $R_{12}$ are as originally defined, but not alkenyl, can be treated with an acid, such as a 4 N solution of HCl in dioxane, in a halogenated solvent such as $CH_2Cl_2$ to afford compounds of Formula 6.1, wherein $R_1$, $R_2$, $R_3$, $R_4$, $R_{11}$, and $R_{12}$, are as originally defined, but not alkenyl, as shown in step a. Compounds of Formula 6.2, wherein $R_1$, $R_2$, $R_3$, $R_4$, $R_{11}$, and $R_{12}$ are as originally defined, can be prepared by treating compounds of Formula 6.0, wherein $R_1$, $R_2$, $R_3$, $R_4$, $R_{11}$, and $R_{12}$ are as originally defined, with an acid, such as 2,2,2-trifluoroacetic acid, in a halogenated solvent such as $CH_2Cl_2$, as shown in step b. Compounds of Formulas 6.1 and 6.2, wherein $R_1$, $R_2$, $R_3$, $R_4$, $R_{11}$, and $R_{12}$ are as originally defined, can be treated with compounds of Formula 6.3, wherein $R_6$ is as originally defined, in the presence of a base, such as diisopropylethylamine, and a peptide coupling reagent, such as benzotriazol-1-yl-oxytripyrrolidinophosphonium hexafluorophosphate (PyBOP) or O-(7-azabenzo-triazol-1-yl)-N,N,N',N'-tetramethyluronium hexafluorophosphate (HATU), in an halogenated solvent such as $CH_2Cl_2$, to afford compounds of Formula 6.4, wherein $R_1$, $R_2$, $R_3$, $R_4$, $R_6$, $R_{11}$, and $R_{12}$ are as previously defined, as shown in step c.

Scheme 6

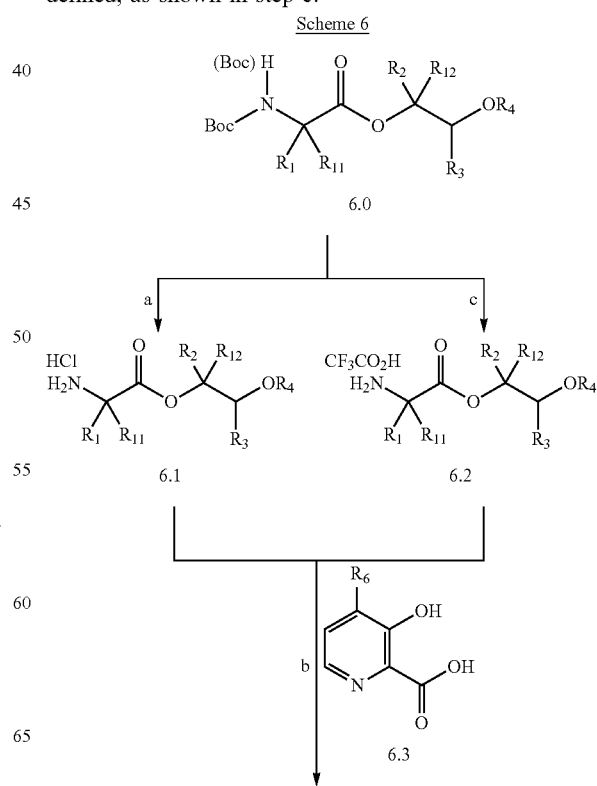

-continued

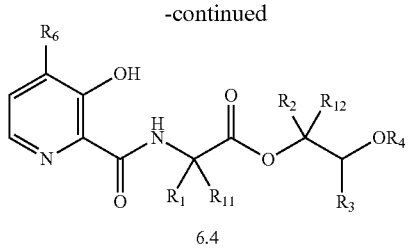

6.4

Compounds of Formula 7.1, wherein $R_1$, $R_2$, $R_3$, $R_6$, $R_{11}$, and $R_{12}$ are as originally defined, but not alkenyl, and $R_8$ is as originally defined, but not alkenyl or chloro, can be prepared according to the method outlined in Scheme 7, step a. Compounds of Formula 7.0, wherein $R_1$, $R_2$, $R_3$, $R_6$, $R_8$, $R_{11}$, and $R_{12}$ are as originally defined, can be subjected to the hydrogenation conditions described in Scheme 4, step b to afford compounds of Formula 7.1, wherein $R_1$, $R_2$, $R_3$, $R_6$, $R_8$, $R_{11}$, and $R_{12}$ are as previously defined, as depicted in step a.

Scheme 7

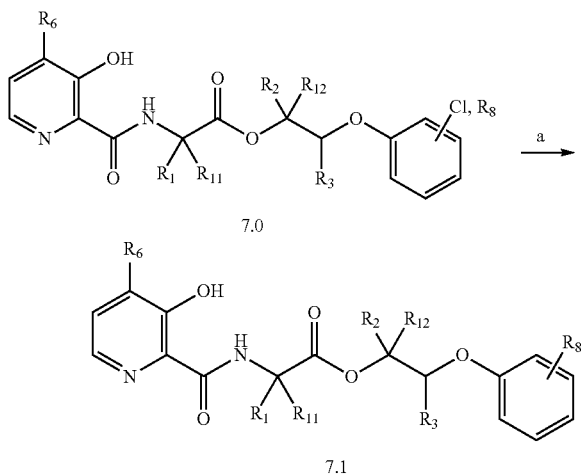

Compounds of Formula 8.1, wherein $R_1$, $R_2$, $R_3$, $R_4$, $R_6$, $R_7$, $R_{11}$, and $R_{12}$ are as originally defined, can be prepared according to the method outlined in Scheme 8, steps a or b. Compounds of Formula 8.0, wherein $R_1$, $R_2$, $R_3$, $R_4$, $R_6$, $R_{11}$, and $R_{12}$ are as previously defined, can be treated with an appropriate alkyl halide with or without a reagent such as sodium iodide (NaI) and an alkali carbonate base, such as $Na_2CO_3$ or potassium carbonate ($K_2CO_3$), in a solvent such as acetone, as shown in step a. Or, alternatively, by treatment with an acyl halide or anhydride in the presence of an amine base, such as pyridine, $NEt_3$, DMAP, or mixtures thereof, in an aprotic solvent, such as $CH_2Cl_2$, to afford compounds of Formula 8.1, wherein $R_1$, $R_2$, $R_3$, $R_4$, $R_6$, $R_7$, $R_{11}$, and $R_{12}$ are as previously defined, as shown in step b.

Scheme 8

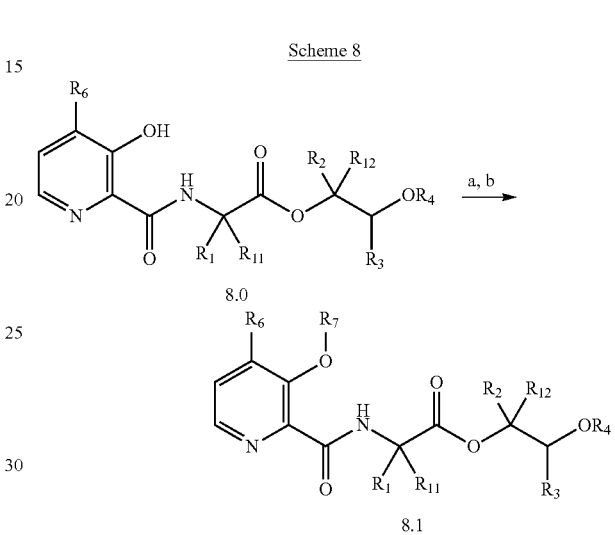

Compounds of Formula 9.1 and 9.2, wherein $R_1$, $R_2$, $R_4$, $R_6$, $R_{11}$, and $R_{12}$ are as originally defined, but not alkenyl, and $R_8$ is as originally defined, but not allyloxy or alkenyl, can be prepared according to the method outlined in Scheme 9, step a. Compounds of Formula 9.0, wherein $R_1$, $R_2$, $R_4$, $R_6$, $R_8$, $R_{11}$, and $R_{12}$ are as originally defined, can be treated with a ruthenium catalyst, such as ruthenium trichloride n-hydrate, and a hydride source, such as sodium borohydride ($NaBH_4$), in a polar aprotic solvent, such as THF, in the presence of water, at a temperature of about 0° C. to afford compounds of Formula 9.1 and 9.2, as described by Sharma, P. K.; Kumar, S.; Kumar, P.; Nielson, P. *Tet. Lett.* 2012, 48, 8704-8708 and shown in step a.

Scheme 9

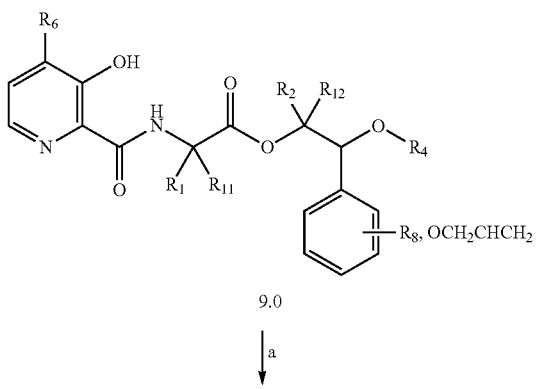

9.0

↓ a

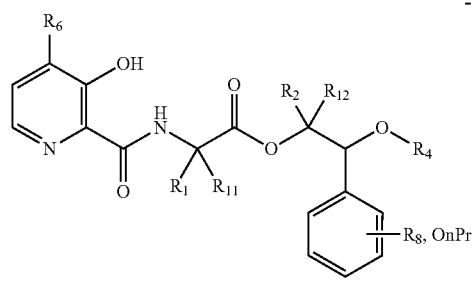

9.1

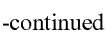

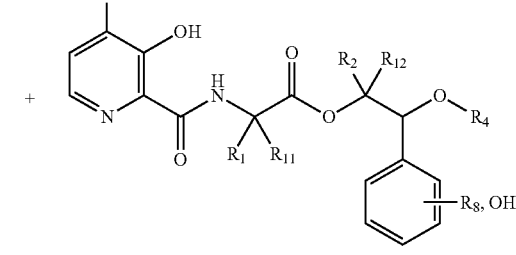

9.2

Compounds of Formula 10.3, wherein $R_2$, $R_3$, $R_4$ and $R_{12}$ are as originally defined, can be prepared according to the methods outlined in Scheme 10, steps a-c. Compounds of Formula 10.0, wherein $R_3$ is as originally defined, can be transformed into a Grignard reagent by being subjected to magnesium metal in the presence of a lithium salt, such as lithium chloride (LiCl) in a polar aprotic solvent, such as THF, at an elevated temperature of about 70° C. The subsequent Grignard reagent can then be subjected to an iron catalyst, such as tris(acetylacetonato) iron(III) (Fe(acac)$_3$), and an alkyl chloride, such as allyl chloride, in a polar aprotic solvent, such as THF, at an elevated temperature of about 70° C. to afford compounds of Formula 10.1, wherein $R_2$, $R_3$, $R_{12}$ are as originally defined, as described by Mayer, M.; Welther, A.; von Wangelin, A. J. *Chem Cat Chem*, 2011, 3, pp 1567-1571, and as shown in step a. Compounds of Formula 10.2, wherein $R_2$, $R_3$, and $R_{12}$ are as originally defined, can be prepared from compounds of Formula 10.1, wherein $R_2$, $R_3$, and $R_{12}$ are as originally defined, by treatment with an ammonium salt such as tetra n-butylammonium hydrogen sulfate, an epoxidation catalyst, such as 1,2:4,5-Bis-O-(isopropylidene)-β-L-erythro-2,3-hexodiulo-2,6-pyranose (Shi epoxidation catalyst enantiomer), a buffer solution, such as 0.05 M Na$_2$B$_4$O$_7$-10H$_2$O in 4×10$^{-4}$ M aqueous Na$_2$(EDTA), in a polar aprotic solvent, such as acetonitrile, at a temperature of about 0° C. Followed by slow addition of an oxidant such as Oxone in a solution of Na$_2$(EDTA) and simultaneous slow addition of a solution of a base such as K$_2$CO$_3$ in water as described by Wang, Z.-X.; Tu, Y.; Frohn, M.; Zhang, J.-R.; Shi, Y. *J. Am. Chem. Soc*, 1997, 119, pp 11224-11235, and as shown in step b. Additionally, compounds of Formula 10.3, wherein $R_2$, $R_3$, $R_4$ and $R_{12}$ are as originally defined, can be prepared from epoxides of Formula 10.2, wherein $R_2$, $R_3$, $R_{12}$ are as previously defined, by treatment with an acid, such as sulfuric acid (H$_2$SO$_4$) in a mixture of an alcohol substituted with $R_4$ wherein $R_4$ is as previously defined, such as cyclopropanol, at a reduced temperature of about 0° C., as described by Aggarwal, V. K; Bae, I; Lee, H.-Y. *Tetrahedron*, 2006, 60 (43), pp 9725-9733, and shown in step c.

Scheme 10

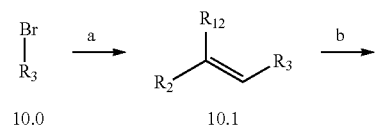

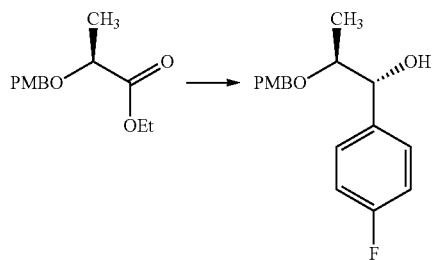

10.2    10.3

EXAMPLES

Example 1A: Preparation of (1R,2S)-1-(4-fluorophenyl)-2-((4-methoxybenzyl)oxy)propan-1-ol To a solution of (4-fluorophenyl)magnesium bromide (7.08 mL, 5.67 mmol) and lithium borohydride (LiBH$_4$) (2.83 mL, 5.67 mmol, 2.0 molar (M) in THF) in anhydrous Et$_2$O (11.45 mL) at −15° C. was added (S)-ethyl 2-((4-methoxybenzyl)oxy)propanoate (1.35 g, 5.67 mmol) as a 1M solution in anhydrous Et$_2$O (5.67 mL) via addition funnel over approximately a 40 minute (min) period at a rate that maintained an internal temperature between −7 and −15° C. The reaction vessel was allowed to slowly warm to room temperature (rt) overnight. The reaction mixture was cooled to 0° C. and quenched via slow addition of saturated aqueous ammonium chloride (NH$_4$Cl, 25 mL) followed by water (H$_2$O, 25 mL). The mixture was transferred to a separatory funnel, and the aqueous (aq.) phase was extracted with Et$_2$O (3×50 mL). The combined organic phases were dried over magnesium sulfate (MgSO$_4$), filtered, and concentrated. The resulting residue was purified by flash column chromatography (silica gel (SiO$_2$), 5→25% acetone in hexanes) to afford the title compound (214 mg, 13%) as a colorless oil: $^1$H NMR (400 MHz, CDCl$_3$) δ 7.33-7.27 (m, 2H), 7.25-7.21 (m, 2H), 7.05-6.98 (m, 2H), 6.91-6.86 (m, 2H), 4.85 (t, J=3.3 Hz, 1H), 4.57 (d, J=11.4 Hz, 1H), 4.46 (d, J=11.4 Hz, 1H), 3.81 (s, 3H), 3.69 (qd, J=6.3, 4.0 Hz, 1H), 2.53 (d, J=2.9 Hz, 1H), 1.02 (d, J=6.3 Hz, 3H); $^{19}$F NMR (376 MHz, CDCl$_3$) δ −115.49 (s); ESIMS m/z 603 ([2M+Na]$^+$).

Example 1B: Preparation of (S)-2-((4-methoxybenzyl)oxy)propanal

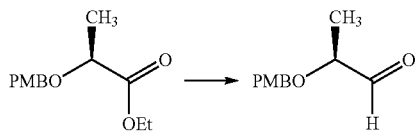

To a solution of (S)-ethyl 2-((4-methoxybenzyl)oxy)propanoate (5.00 g, 21.0 mmol) in CH$_2$Cl$_2$ (30 mL) at 0° C. was added chlorobis(cyclooctene)iridium(I) dimer (Ir$_2$Cl$_2$(coe)$_4$); 94.0 milligrams (mg), 0.105 mmol) followed by diethylsilane (Et$_2$SiH$_2$; 4.08 mL, 31.5 mmol) over 10 min. The mixture was stirred at 0° C. for 30 min, then was warmed to rt and stirred for 3 h. The reaction mixture was cooled to 0° C. and quenched by adding 1 normal (N) aq. hydrogen chloride (HCl; 12 mL). The resulting solution was warmed to rt and stirred for 15 min. The phases were separated, and the aq. phase was extracted with CH$_2$Cl$_2$ (3×30 mL). The combined organic phases were washed with brine, dried over sodium sulfate (Na$_2$SO$_4$), filtered, evaporated, and purified by flash column chromatography (SiO$_2$, 2→50% acetone in hexanes) to afford the title compound (4.27 g, 100%) as a yellow oil: IR (Thin Film) 2934, 2837, 2865, 1731, 1512 cm$^{-1}$; $^1$H NMR (300 MHz, CDCl$_3$) δ 9.64 (d, J=1.9 Hz, 1H), 7.35-7.21 (m, 2H), 6.95-6.79 (m, 2H), 4.63-4.40 (m, 2H), 3.94-3.76 (m, 1H), 3.81 (s, 3H), 1.31 (d, J=6.9 Hz, 3H); $^{13}$C NMR (101 MHz, CDCl$_3$) δ 203.58, 159.54, 129.65, 129.37, 113.98, 79.14, 71.75, 55.30, 15.34.

Example 1C: Preparation of (1S,2S)-2-((4-methoxybenzyl)oxy)-1-phenylpropan-1-ol

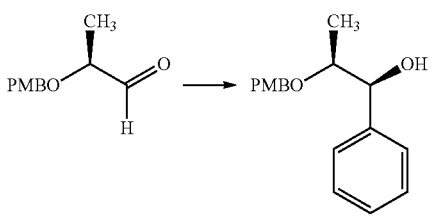

To a solution of (S)-2-((4-methoxybenzyl)oxy)propanal (3.38 g, 17.4 mmol) in Et$_2$O (58 mL) at −78° C. was added phenylmagnesium bromide (34.8 mL, 34.8 mmol, 1 M in THF) dropwise. The reaction mixture was stirred and allowed to warm to rt overnight. The reaction was quenched by addition of sat. aq. ammonium chloride (NH$_4$Cl). The mixture was partitioned between H$_2$O and EtOAc, the phases were separated, and the aqueous phase was extracted with EtOAc (2×). The combined organic phases were washed with brine, dried over Na$_2$SO$_4$, filtered and concentrated. Purification via flash column chromatography (SiO$_2$, 2→50% acetone in hexanes) afforded an inseparable mixture of diastereomers (d.r. 3:1 SS:RS) of the title compound (3.29 g, 66%) as a yellow oil: $^1$H NMR (400 MHz, CDCl$_3$; major) δ 7.37-7.25 (m, 7H), 6.89 (d, J=8.6 Hz, 2H), 4.62 (d, J=11.0 Hz, 1H), 4.44 (dd, J=7.8, 2.1 Hz, 1H), 4.41 (d, J=11.0 Hz, 1H), 3.82 (s, 3H), 3.60 (dq, J=7.8, 6.2 Hz, 1H), 3.21 (d, J=2.1 Hz, 1H), 1.05 (d, J=6.2 Hz, 3H); $^{13}$C NMR (101 MHz, CDCl$_3$) δ 159.34, 140.56, 130.21, 129.46, 128.31, 127.25, 126.31, 113.93, 79.66, 78.32, 70.92, 55.30, 15.56; ESIMS m/z 295 ([M+Na]$^+$).

Example 1D: Preparation of (1S,2S)-2-((4-methoxybenzyl)oxy)-1-(thiophen-2-yl)propan-1-ol and (1R,2S)-2-((4-methoxybenzyl)oxy)-1-(thiophen-2-yl)propan-1-ol

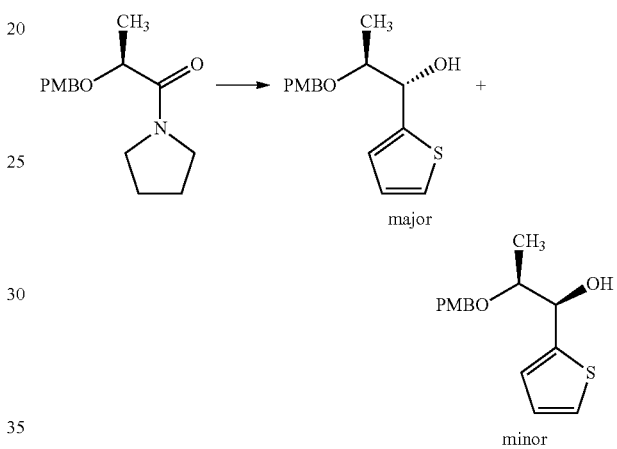

To a solution of thiophen-2-yllithium (4.00 mL, 4.00 mmol, 1 M in THF) and lithium borohydride (LiBH$_4$; 1.30 mL, 2.60 mmol, 2 M in THF) in THF (10 mL) at −10° C. was added neat (S)-2-((4-methoxybenzyl)oxy)-1-(pyrrolidin-1-yl)propan-1-one (0.527 g, 2.00 mmol) (for preparation see: Pellicena, M.; Solsona, J. G.; Romea, P.; Urpi, F. *Tetrahedron* 2012, 68, 10338.) dropwise via syringe pump addition over approximately a 1 h period, at a rate which maintained the internal temperature below −5° C. The reaction vessel was allowed to slowly warm to rt overnight. The reaction mixture was quenched by addition of sat. aq. NH$_4$Cl. The aqueous phase was extracted with Et$_2$O (3×). The combined organic phases were washed with brine, dried over Na$_2$SO$_4$, filtered, and concentrated. Purification via flash column chromatography (SiO$_2$, 2→10% acetone in hexanes) afforded the title compounds (0.231 g, 41% and 0.175 g, 31%, respectively) as colorless oils: major: $^1$H NMR (300 MHz, CDCl$_3$) δ 7.32-7.21 (m, 3H), 7.05-6.93 (m, 2H), 6.94-6.83 (m, 2H), 5.03 (t, J=4.2 Hz, 1H), 4.61 (d, J=11.4 Hz, 1H), 4.48 (d, J=11.3 Hz, 1H), 3.81 (s, 3H), 3.88-3.73 (m, 1H), 2.59 (d, J=4.4 Hz, 1H), 1.13 (d, J=6.3 Hz, 3H); ESIMS m/z 579 ([2M+Na]$^+$); minor: $^1$H NMR (300 MHz, CDCl$_3$) δ 7.34-7.22 (m, 3H), 7.06-6.92 (m, 2H), 6.95-6.84 (m, 2H), 4.73 (dd, J=7.3, 2.7 Hz, 1H), 4.63 (d, J=10.9 Hz, 1H), 4.44 (d, J=11.0 Hz, 1H), 3.82 (s, 3H), 3.67 (dq, J=7.3, 6.2 Hz, 1H), 3.29 (d, J=2.8 Hz, 1H), 1.14 (d, J=6.1 Hz, 3H); ESIMS m/z 579 ([2M+Na]$^+$).

Example 1E: Preparation of (1R,2S)-1-(4-fluoro-2-methoxyphenyl)-2-((4-methoxybenzyl)oxy)propan-1-ol

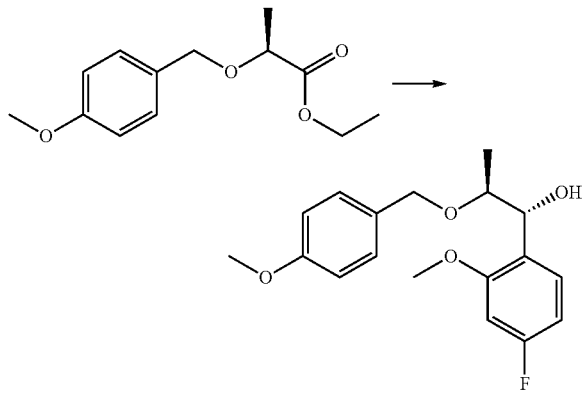

To a reaction flask was added 1-bromo-4-fluoro-2-methoxybenzene (0.4 g, 1.951 mmol) and dry diethyl ether (9.75 ml). The flask was sealed, evacuated and backfilled with nitrogen, and cooled to −78° C. Then, n-BuLi (2.5 M in hexanes, 0.780 ml, 1.951 mmol) was added to the reaction, and the reaction mixture was stirred at −78° C. for 1 h. LiBH$_4$ (2.0M in THF, 0.975 ml, 1.951 mmol) was added, followed by dropwise addition of (9-ethyl 2-((4-methoxybenzyl)oxy)propanoate (0.465 g, 1.951 mmol) as a 0.5 M solution in dry diethyl ether. The reaction was allowed to gradually warm to rt as the cooling bath expired overnight. The reaction was quenched by careful addition of 2 mL sat. aq. NH$_4$Cl (gas evolution noted), and allowed to stir for 30 min. At this point the mixture was transferred to a separatory funnel containing water and extracted 3× with diethyl ether. The combined organic layers were dried over MgSO$_4$, filtered and concentrated in vacuo. The resulting residue was purified via flash chromatography (SiO$_2$, 5→30% acetone in hexanes) to afford the title compound (290 mg, 46%) as a colorless oil. $^1$H NMR (300 MHz, CDCl$_3$) δ 7.42 (dd, J=8.1, 7.2 Hz, 1H), 7.27-7.21 (m, 2H), 6.91-6.85 (m, 2H), 6.66 (td, J=8.4, 2.4 Hz, 1H), 6.55 (dd, J=10.9, 2.4 Hz, 1H), 5.15 (t, J=3.5 Hz, 1H), 4.57 (d, J=11.6 Hz, 1H), 4.50 (d, J=11.6 Hz, 1H), 3.86-3.78 (m, 4H), 3.76 (s, 3H), 2.65 (dd, J=3.4, 2.0 Hz, 1H), 1.00 (d, J=6.4 Hz, 3H); $^{13}$C NMR (101 MHz, CDCl$_3$) δ 162.88 (d, J=244.4 Hz), 159.19, 157.03 (d, J=9.6 Hz), 130.66, 129.30, 128.47 (d, J=9.9 Hz), 124.48 (d, J=3.2 Hz), 113.76, 106.79 (d, J=20.9 Hz), 98.43 (d, J=25.9 Hz), 75.79 (d), 70.35, 69.97, 55.45, 55.30, 13.46; ESIMS m/z 663 ([2M+Na]$^+$).

Example 2A: Preparation of 1-methoxy-2-((1R,2S)-2-((4-methoxybenzyl)oxy)-1-phenoxypropyl)benzene

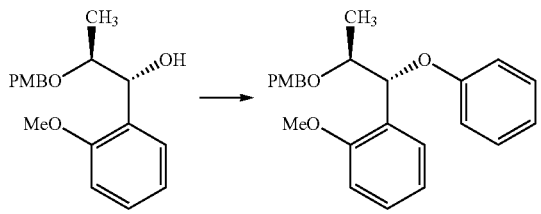

To a solution of (1R,2S)-2-((4-methoxybenzyl)oxy)-1-(2-methoxyphenyl)propan-1-ol (500 mg, 1.654 mmol), N-cyclohexyl-N-methylcyclohexanamine (531 µl, 2.480 mmol) and Cu(OAc)$_2$ (60.1 mg, 0.331 mmol) in toluene (8.267 mL) was added Ph$_3$Bi(OAc)$_2$ (1385 mg, 2.480 mmol). The resulting blue suspension was heated to and stirred at 50° C. for 16 h. The reaction was cooled to rt, filtered through a plug of Celite™, and concentrated. The resulting crude material was purified via flash column chromatography (SiO$_2$, 0→30% acetone in hexanes) to give the title compound (555 mg, 67%) as a yellow oil: $^1$H NMR (300 MHz, CDCl$_3$) δ 7.41-7.33 (m, 3H), 7.18 (q, J=8.2 Hz, 5H), 7.08 (d, J=8.0 Hz, 1H), 6.89-6.81 (m, 7H), 5.73 (d, J=3.5 Hz, 1H), 4.60-4.49 (m, 2H), 3.88-3.82 (m, 4H), 3.79 (s, 3H), 1.25 (d, J=6.4 Hz, 3H); $^{13}$C NMR (101 MHz, CDCl$_3$) δ 158.98, 158.27, 156.42, 129.42, 129.18, 128.47, 127.69, 125.82, 121.56, 120.76, 120.46, 115.71, 113.59, 110.12, 76.32, 75.29, 70.61, 55.38, 55.27, 14.75; ESIMS m/z 779 ([2M+Na]$^+$).

Example 2B: Preparation of 2-chloro-1-((1R,2S)-1-(4-fluoro-2-methoxyphenyl)-2-((4-methoxybenzyl)oxy)propoxy)-4-methylbenzene

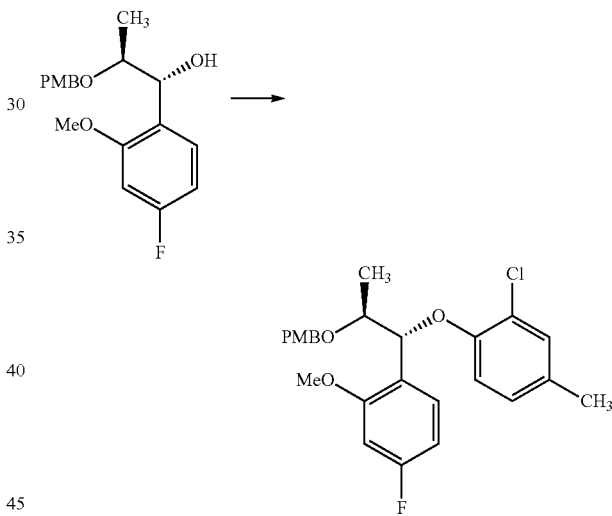

To a solution of (1R,2S)-1-(4-fluoro-2-methoxyphenyl)-2-((4-methoxybenzyl)oxy)propan-1-ol (190 mg, 0.593 mmol) in anhydrous DMSO (2.97 mL) was added NaH (29.7 mg, 0.741 mmol, 60 wt % in mineral oil). After stirring for 10 min, 2-chloro-1-fluoro-4-methylbenzene (686 mg, 4.74 mmol) was added, and the reaction mixture was heated to 60° C. for 15 h. The reaction was quenched by slow addition of H$_2$O. The mixture was extracted Et$_2$O (3×50 mL) and the combined organic layers were dried by passing through a phase separator. Volatiles were removed under a gentle stream of N$_2$ and the resulting residue was purified via flash column chromatography (SiO$_2$, 0→30% acetone in hexanes) to afford the title compound (217 mg, 82%) as a colorless oil: $^1$HNMR (400 MHz, CDCl$_3$) δ 7.34 (dd, J=9.2, 6.8 Hz, 1H), 7.19 (d, J=8.7 Hz, 2H), 7.14 (d, J=1.7 Hz, 1H), 6.85-6.77 (m, 3H), 6.62-6.55 (m, 3H), 5.63 (d, J=3.8 Hz, 1H), 4.63 (d, J=11.9 Hz, 1H), 4.57 (d, J=11.9 Hz, 1H), 3.89 (qd, J=6.4, 3.9 Hz, 1H), 3.83 (s, 3H), 3.79 (s, 3H), 2.19 (s, 3H), 1.25 (d, J=6.4 Hz, 3H); $^{19}$F NMR (376 MHz, CDCl$_3$) δ −112.06 (s); ESIMS m/z 467 ([M+Na]$^+$).

Example 2C: Preparation of 4-((1R,2S)-2-(benzyloxy)-1-(cyclopropylmethoxy)-propyl)-1,1'-biphenyl

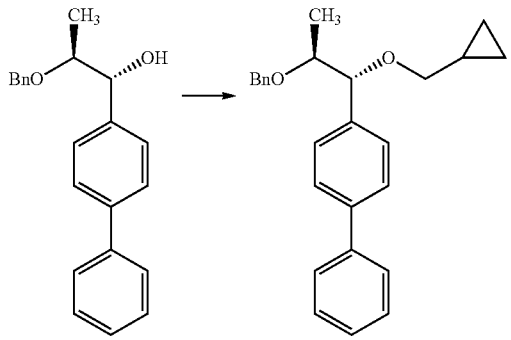 [SMILES: C[C@H](OCc1ccccc1)[C@H](O)c1ccc(-c2ccccc2)cc1 ; C[C@H](OCc1ccccc1)[C@H](OCC1CC1)c1ccc(-c2ccccc2)cc1]

To a solution of (1R,2S)-1-([1,1'-biphenyl]-4-yl)-2-(benzyloxy)propan-1-ol (272 mg, 0.854 mmol) in anhydrous DMF (2.8 mL) at 0° C. was added sodium hydride (NaH; 59.8 mg, 1.50 mmol, 60 wt % in mineral oil). The reaction mixture was stirred at 0° C. for 15 min. The mixture was removed from the ice bath, was stirred for 15 min, and then was recooled back to 0° C. The reaction was treated with (bromomethyl)cyclopropane (84 µL, 0.854 mmol) and was allowed to stir at 0° C. After 10 min, the reaction vessel was removed from the ice bath and the reaction mixture was allowed to stir and warm to rt overnight. The reaction mixture was carefully quenched by the addition of $H_2O$. The crude reaction mixture was stirred for 10 min, and the phases were separated. The aq. phase was extracted with $Et_2O$ (3×), and the combined organic phases were dried over $Na_2SO_4$, filtered, and concentrated. The resulting oil was purified by flash column chromatography ($SiO_2$, 0→10% acetone in hexanes) to afford the title compound (251 mg, 79%) as a colorless oil: $^1H$ NMR (400 MHz, $CDCl_3$) δ 7.64-7.60 (m, 2H), 7.57 (d, J=8.2 Hz, 2H), 7.48-7.32 (m, 5H), 7.24-7.19 (m, 3H), 7.10-7.06 (m, 2H), 4.46 (d, J=11.9 Hz, 1H), 4.30 (d, J=11.9 Hz, 1H), 4.27 (d, J=6.4 Hz, 1H), 3.64 (p, J=6.2 Hz, 1H), 3.28-3.20 (m, 2H), 1.32 (d, J=6.2 Hz, 3H), 1.12-1.01 (m, 1H), 0.56-0.45 (m, 2H), 0.22-0.10 (m, 2H); $^{13}C$ NMR (101 MHz, CDCl3) δ 141.03, 140.33, 139.54, 138.60, 128.75, 128.18, 128.14, 127.67, 127.30, 127.18, 127.06, 126.73, 84.36, 78.56, 73.75, 71.47, 16.71, 10.74, 3.18, 2.83; ESIMS m/z 395 ([M+Na]$^+$).

Example 2D: Preparation (1R,2S)-1-(4-fluoro-2-methoxyphenyl)-2-((4-methoxybenzyl)oxy)propyl pivalate

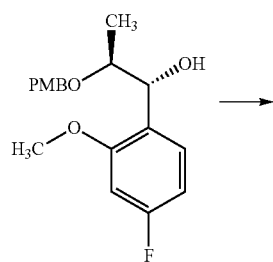

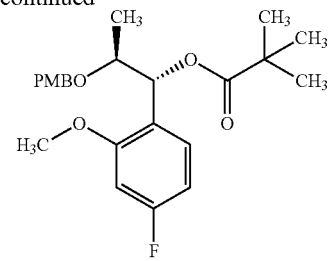

To a solution of (1R,2S)-1-(4-fluoro-2-methoxyphenyl)-2-((4-methoxybenzyl)oxy)propan-1-ol (85 mg, 0.265 mmol)) in anhydrous pyridine (0.858 mL) at 25° C. was added pivaloyl chloride (65.3 µL, 0.531 mmol). The reaction mixture was stirred at 25° C. for 16 h. The reaction was diluted with toluene and volatiles were removed by rotary evaporation. The resulting oil was purified by flash column chromatography ($SiO_2$, 5→30% acetone in hexanes) to afford the title compound (91 mg, 85%) as a colorless oil: $^1H$ NMR (300 MHz, $CDCl_3$) δ 7.22 (dt, J=5.8, 2.9 Hz, 3H), 6.88-6.82 (m, 2H), 6.67-6.54 (m, 2H), 6.39 (d, J=3.3 Hz, 1H), 4.60 (d, J=11.6 Hz, 1H), 4.49 (d, J=11.6 Hz, 1H), 3.83-3.74 (m, 7H), 1.26 (s, 9H), 1.10 (d, J=6.5 Hz, 3H); $^{19}F$ NMR (471 MHz, $CDCl_3$) δ −112.37−−112.55 (m); ESIMS m/z 427 ([M+Na]$^+$).

Example 3A: Preparation of 5-fluoro-2-((1R,2S)-2-((4-methoxybenzyl)oxy)-1-phenoxypropyl)phenol

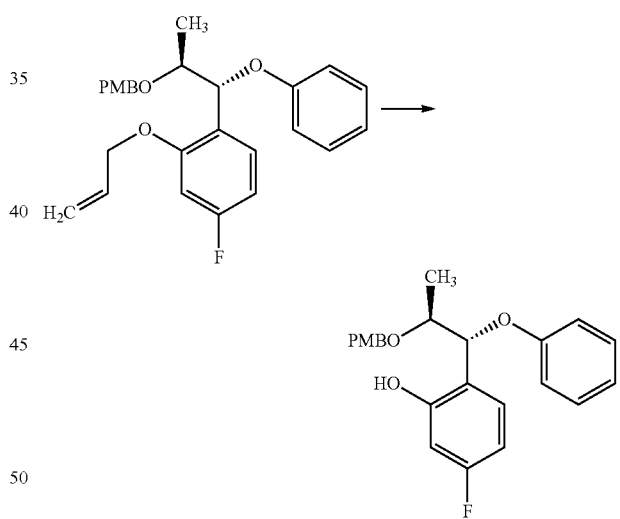

To solution of 2-(allyloxy)-4-fluoro-1-((1R,2S)-2-((4-methoxybenzyl)oxy)-1-phenoxypropyl)benzene (294 mg, 0.696 mmol) and morpholine (72.8 µL, 0.835 mmol) in anhydrous THF (3.48 mL) was added $Pd(PPh_3)_4$ (40.2 mg, 0.035 mmol). The mixture was stirred at 25° C. for 5 h, and then was quenched by the addition of water. The mixture was diluted with $Et_2O$, transferred to a separatory funnel and washed with 1N HCl (3×50 mL). The organic layer was dried by passing through a phase separator, and the volatiles were removed in vacuo. The resulting residue was purified by flash column chromatography ($SiO_2$, 5→15% acetone in hexanes) to afford the title compound (228 mg, 86%) as a viscous oil: $^1H$ NMR (400 MHz, $CDCl_3$) δ 8.01 (s, 1H), 7.18 (ddt, J=9.8, 4.7, 2.4 Hz, 4H), 7.07 (dd, J=8.5, 6.6 Hz, 1H), 6.91 (t, J=7.4 Hz, 1H), 6.86-6.79 (m, 4H), 6.61 (dd, J=10.3, 2.5 Hz, 1H), 6.54 (td, J=8.3, 2.6 Hz, 1H), 5.01 (d, J=6.3 Hz, 1H), 4.60 (d, J=11.2 Hz, 1H), 4.43 (d, J=11.2 Hz, 1H), 4.03 (p, J=6.2 Hz, 1H), 3.80 (s, 3H), 1.30 (d, J=6.2 Hz, 3H); $^{19}$F NMR (376 MHz, CDCl$_3$) δ -112.86 (s); ESIMS m/z 381 ([M–H]$^-$).

Example 3B: Preparation of 2-(cyclopropylmethoxy)-4-fluoro-1-((1R,2S)-2-((4-methoxybenzyl)oxy)-1-phenoxypropyl)benzene

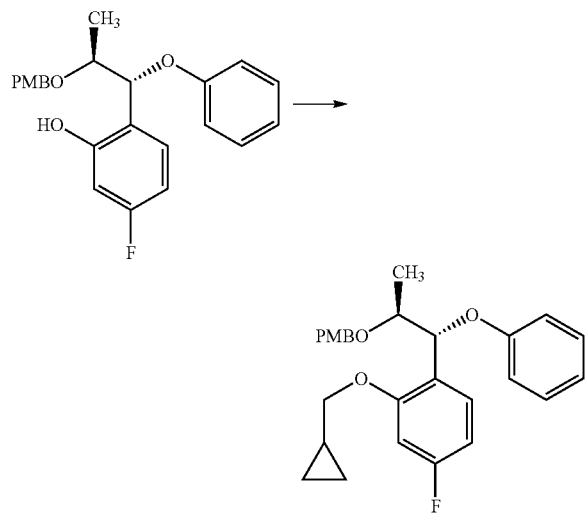

To a mixture of 5-fluoro-2-((1R,2S)-2-((4-methoxybenzyl)oxy)-1-phenoxypropyl)phenol (114 mg, 0.298 mmol), and K$_2$CO$_3$ (82 mg, 0.596 mmol) in acetone (1.49 mL) was added (bromomethyl)cyclopropane (43.4 µL, 0.447 mmol). The reaction mixture was stirred at 25° C. for 24 h. Potassium carbonate (82 mg, 0.596 mmol) and (bromomethyl)cyclopropane (43.4 µL, 0.447 mmol), and DMSO (1.49 mL) were then added to the reaction mixture. The reaction was stirred at 50° C. for 24 h at which point the volatiles were removed under a stream of nitrogen. The resulting residue was purified by flash column chromatography (SiO$_2$, 0→30% acetone in hexanes) to afford the title compound (104 mg, 80%) as a colorless oil: $^1$H NMR (400 MHz, CDCl$_3$) δ 7.34-7.28 (m, 1H), 7.22-7.14 (m, 4H), 6.84 (dt, J=11.4, 8.1 Hz, 5H), 6.57 (dd, J=12.5, 6.0 Hz, 2H), 5.73 (d, J=3.3 Hz, 1H), 4.60 (s, 2H), 3.94-3.78 (m, 3H), 3.78 (s, 3H), 1.34-1.23 (m, 4H), 0.68-0.62 (m, 2H), 0.38 (q, J=4.8 Hz, 2H); $^{19}$F NMR (376 MHz, CDCl$_3$) δ -112.62 (s); ESIMS m/z 459 ([M+Na]$^+$).

Example 3C: Preparation of 1-((1R,2S)-1-(2-chlorophenoxy)-2-((4-methoxybenzyl)oxy)propyl)-4-fluoro-2-phenoxybenzene

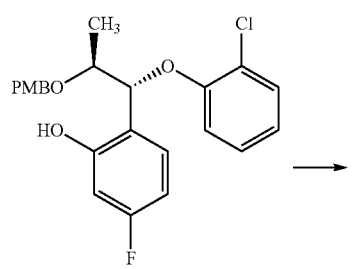

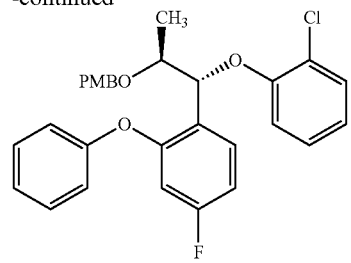

To a solution of 2-((1R,2S)-1-(2-chlorophenoxy)-2-((4-methoxybenzyl)oxy)propyl)-5-fluorophenol (197 mg, 0.473 mmol), and phenylboronic acid (144 mg, 1.181 mmol) in anhydrous CH$_2$Cl$_2$ (2.36 mL) was added NEt$_3$ (329 µL, 2.363 mmol), Cu(OAc)$_2$ (94 mg, 0.520 mmol) and 4 Å molecular sieves. The reaction mixture was stirred at 23° C. for 3 days (d), and then was filtered through Celite™ and concentrated. The resulting residue was purified by flash column chromatography (SiO$_2$, 0→30% acetone in hexanes) to afford the title compound (102 mg, 44%) as a colorless oil: $^1$HNMR (400 MHz, CDCl$_3$) δ 7.50 (dd, J=8.6, 6.7 Hz, 1H), 7.35 (ddd, J=10.0, 7.8, 1.8 Hz, 3H), 7.18 (dd, J=17.1, 8.0 Hz, 3H), 7.07-7.01 (m, 1H), 7.01-6.97 (m, 2H), 6.84-6.70 (m, 5H), 6.46 (dd, J=10.1, 2.4 Hz, 1H), 5.77 (d, J=3.9 Hz, 1H), 4.64 (d, J=11.8 Hz, 1H), 4.58 (d, J=11.8 Hz, 1H), 4.05-3.97 (m, 1H), 3.77 (s, 3H), 1.33 (d, J=6.4 Hz, 3H); $^{19}$F NMR (376 MHz, CDCl$_3$) δ -111.43 (d, J=2.1 Hz); ESIMS m/z 515 ([M+H]$^+$).

Example 4A: Preparation of (1R,2S)-1-([1,1'-biphenyl]-4-yl)-1-phenoxypropan-2-ol

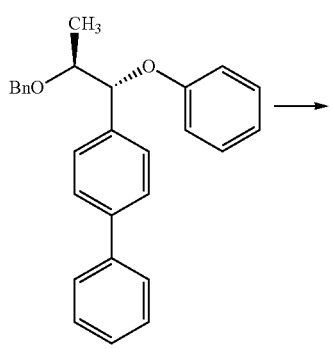

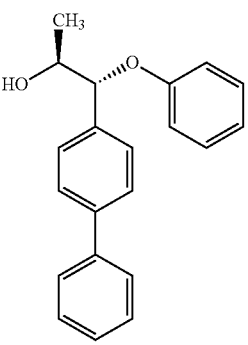

To a magnetically stirred mixture of 4-((1R,2S)-2-(benzyloxy)-1-phenoxypropyl)-1,1'-biphenyl (72 mg, 0.183 mmol) in ethanol (1.22 mL) and cyclohexene (608 µL) was added Pd/C (78 mg, 0.018 mmol, 2.5 wt %). The reaction mixture was stirred at 70° C. for 2 h. The reaction mixture was cooled to rt, filtered through Celite™, and concentrated. The resulting residue was purified via flash column chromatography (SiO$_2$, 5→30% acetone in hexanes) to afford the title compound (43 mg, 77%) as a white solid. ¹H NMR (400 MHz, CDCl₃) δ 7.59-7.54 (m, 4H), 7.43 (dd, J=12.1, 5.0 Hz, 4H), 7.33 (t, J 7.3 Hz, 1H), 7.20 (t, J 8.0 Hz, 2H), 6.90 (t, J 8.1 Hz, 3H), 5.10 (d, J 4.7 Hz, 1H), 4.20-4.12 (m, 1H), 2.00 (s, 1H), 1.29 (d, J=6.4 Hz, 3H); ¹³C NMR (101 MHz, CDCl₃) δ 157.83, 140.92, 140.61, 136.78, 129.42, 128.78, 127.45, 127.39, 127.31, 127.05, 121.12, 115.90, 83.43, 71.14, 18.11; ESIMS m/z 631 ([2M+Na]⁺).

Example 4B: Preparation of (1S,2S)-1-phenoxy-1-(thiophen-2-yl)propan-2-ol

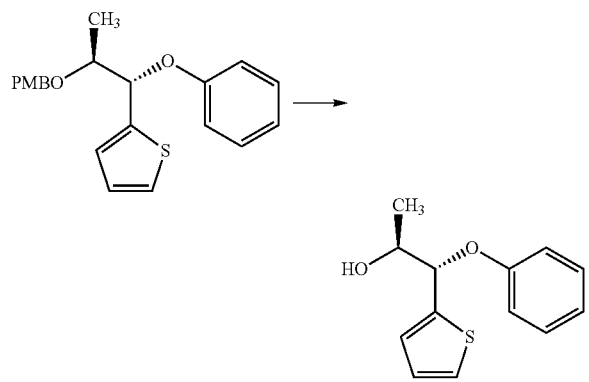

To a solution of 2-((1S,2S)-2-((4-methoxybenzyl)oxy)-1-phenoxypropyl)thiophene (0.223 g, 0.630 mmol) in a mixture of CH₂Cl₂ (3 mL) and H₂O (0.3 mL) at 0° C. was added 4,5-dichloro-3,6-dioxocyclohexa-1,4-diene-1,2-dicarbonitrile (0.150 g, 0.661 mmol). The reaction mixture was stirred for 30 min. The reaction was quenched by addition of aq. 1 N NaOH (0.66 mL) and was diluted with CH₂Cl₂ (10 mL). The phases were separated, and the aq. phase was extracted with CH₂Cl₂ (2×10 mL). The combined organic phases were dried over Na₂SO₄, filtered, and concentrated. Purification via flash column chromatography (SiO₂, 2→20% acetone in hexanes) afforded the title compound (116 mg, 75%) as a colorless oil: IR (Thin Film) 3390, 2923, 2851, 2865, 1597 cm⁻¹; ¹HNMR (300 MHz, CDCl₃) δ 7.33-7.16 (m, 3H), 7.07 (ddd, J=3.5, 1.2, 0.7 Hz, 1H), 7.03-6.88 (m, 4H), 5.26 (d, J=4.9 Hz, 1H), 4.28-4.09 (m, 1H), 2.08 (d, J=4.9 Hz, 1H), 1.29 (d, J=6.3 Hz, 3H); ¹³C NMR (101 MHz, CDCl₃) δ 157.60, 140.58, 129.43, 126.59, 126.50, 125.94, 121.60, 116.21, 80.60, 70.73, 18.33.

Example 5: Preparation of (S)-(1R,2S)-1-phenoxy-1-(p-tolyl)propan-2-yl 2-((tert-butoxycarbonyl)amino)propanoate

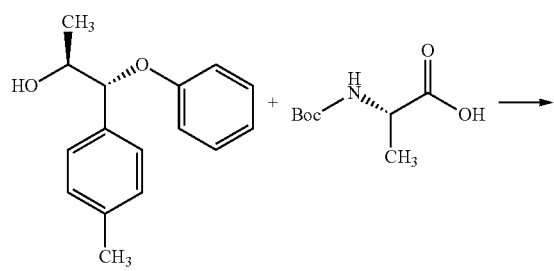

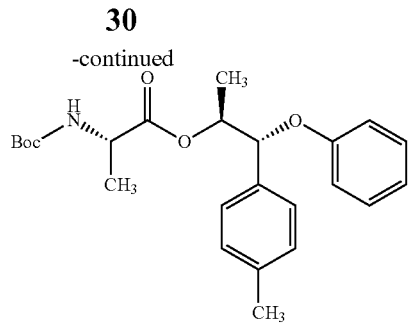

To a solution of (1R,2S)-1-phenoxy-1-(p-tolyl)propan-2-ol (99 mg, 0.409 mmol) and (1R,2S)-1-phenoxy-1-(p-tolyl)propan-2-ol (99 mg, 0.409 mmol) in CH₂Cl₂ (2.04 mL) at 0° C. was added (S)-2-((tert-butoxycarbonyl)amino)propanoic acid (Boc-Ala-OH; 85 mg, 0.449 mmol), DMAP (4.99 mg, 0.041 mmol), and N¹-((ethylimino)methylene)-N³,N³-dimethylpropane-1,3-diamine hydrochloride (EDC; 157 mg, 0.817 mmol). The reaction mixture was stirred at rt overnight. The reaction mixture was concentrated. Purification via flash column chromatography (SiO₂, 5→30% acetone in hexanes) afforded the title compound (164 mg, 97%) as a colorless oil: ¹HNMR (400 MHz, CDCl₃) δ 7.27 (d, J=6.8 Hz, 3H), 7.19-7.11 (m, 4H), 6.87 (t, J=7.4 Hz, 1H), 6.82 (d, J=7.8 Hz, 2H), 5.28-5.21 (m, 1H), 5.15 (d, J=4.8 Hz, 1H), 4.96 (d, J=7.2 Hz, 1H), 4.29-4.19 (m, 1H), 2.31 (s, 3H), 1.42 (s, 9H), 1.35 (d, J=6.4 Hz, 3H), 1.14 (d, J=7.2 Hz, 3H); ¹³C NMR (100 MHz, CDCl₃) δ 172.73, 157.95, 137.83, 134.48, 129.33, 129.19, 126.87, 121.09, 115.96, 81.07, 74.22, 28.31, 21.15, 18.51, 14.93; ESIMS m/z 414 ([M+H]⁺).

Example 6A: Preparation of (S)-(1R,2S)-1-(4-fluorophenyl)-1-phenoxypropan-2-yl 2-aminopropanoate hydrochloride

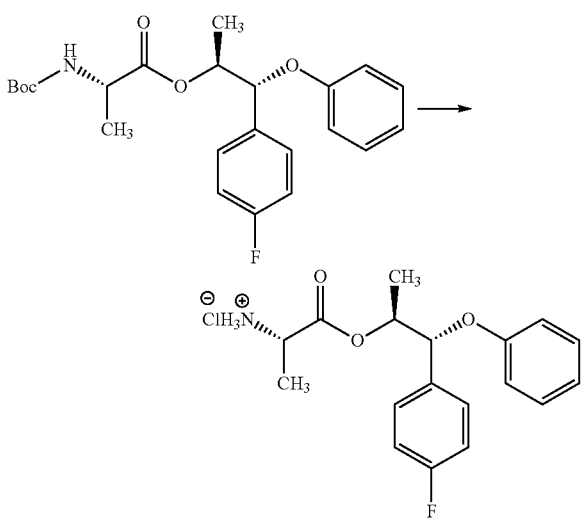

To a solution of ((S)-(1R,2S)-1-(4-fluorophenyl)-1-phenoxypropan-2-yl 2-((tert-butoxycarbonyl)amino)propanoate (220 mg, 0.527 mmol) was added a 4 N solution of HCl in dioxane (1.98 mL, 7.9 mmol). The mixture was stirred for 1 h at rt. The solvent was evaporated under a stream of N₂ to provide the title compound as a colorless, viscous oil, which was used in the next step without further purification: ESIMS m/z 318 ([M+H]⁺).

Example 6B: Preparation of (S)-(1R,2S)-1-(4-fluorophenyl)-1-phenoxypropan-2-yl 2-(3-hydroxy-4-methoxypicolinamido)propanoate

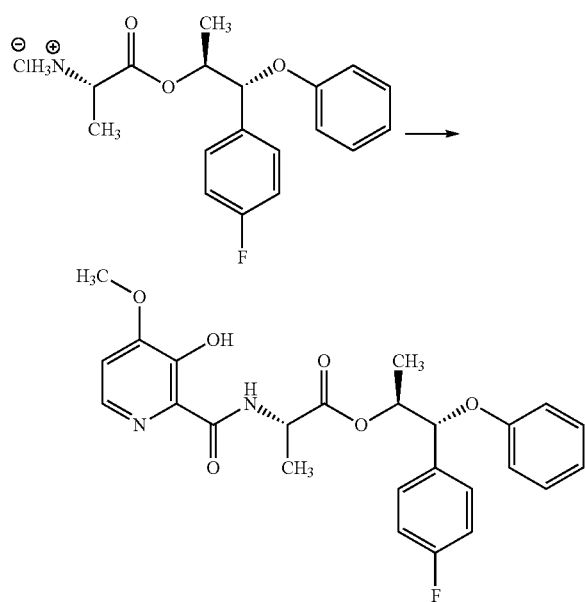

To a solution of (S)-(1R,2S)-1-(4-fluorophenyl)-1-phenoxypropan-2-yl 2-aminopropanoate hydrochloride (186 mg, 0.526 mmol), 3-hydroxy-4-methoxypicolinic acid (98 mg, 0.578 mmol), and PyBOP (301 mg, 0.578 mmol) in CH$_2$Cl$_2$ (2.63 mL) was added N,N-diisopropylethylamine (DIEA) (303 µL, 1.74 mmol). The reaction mixture was stirred overnight at room temperature. The solvent was evaporated, and the crude oil was purified by flash column chromatography (SiO$_2$, 5→30% acetone in hexanes) to afford the title compound (215 mg, 80%) as a colorless oil: $^1$H NMR (400 MHz, CDCl$_3$) δ 12.06 (s, 1H), 8.39 (d, J=7.7 Hz, 1H), 7.97 (d, J=5.2 Hz, 1H), 7.40-7.34 (m, 2H), 7.20-7.13 (m, 2H), 7.03-6.96 (m, 2H), 6.88 (dd, J=15.2, 6.3 Hz, 2H), 6.82-6.78 (m, 2H), 5.31-5.24 (m, 1H), 5.18 (d, J=5.2 Hz, 1H), 4.64 (p, J=7.2 Hz, 1H), 3.93 (s, 3H), 1.39 (d, J=6.4 Hz, 3H), 1.33 (d, J=7.2 Hz, 3H); $^{13}$C NMR (101 MHz, CDCl$_3$) δ 171.49, 168.69, 163.72, 161.27, 157.58, 155.39, 148.76, 140.48, 133.27, 133.24, 130.37, 129.41, 128.75, 128.67, 121.41, 115.95, 115.64, 115.43, 109.49, 80.61, 74.32, 56.07, 47.95, 18.01, 15.20; $^{19}$F NMR (376 MHz, CDCl$_3$) δ −113.62 (s); HRMS-ESI (m/z)([M+H]$^+$) calcd for C$_{25}$H$_{26}$FN$_2$O$_6$, 469.1769; found, 469.1777.

Example 7: Preparation of (S)-(1R,2S)-1-(4-fluoro-2-methoxyphenyl)-1-(p-tolyloxy)propan-2-yl 2-(3-hydroxy-4-methoxypicolinamido)propanoate

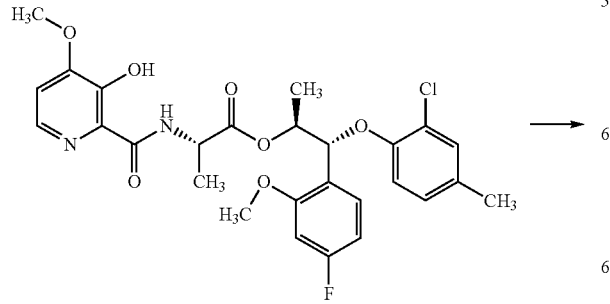

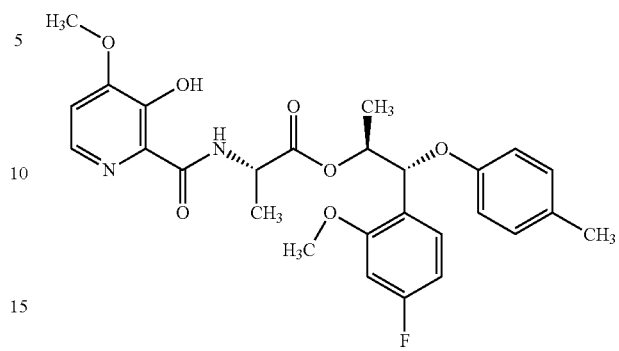

To a reaction vial was added (S)-(1R,2S)-1-(2-chloro-4-methylphenyl)-1-(4-fluoro-2-methoxyphenyl)propan-2-yl 2-(3-hydroxy-4-methoxypicolinamido)propanoate (79 mg, 0.144 mmol), NEt$_3$ (60.4 µL, 0.433 mmol)), and 5% Pd/C (61.5 mg, 0.014 mmol). EtOAc (1.44 mL) was added, and the vial was sealed and stirred under approximately 1 atm (balloon) of H$_2$ at rt for 6.5 h. The reaction mixture was filtered through a pad of Celite™ and the filtrate was concentrated to give an oil, which was purified by flash column chromatography (SiO$_2$, 5→30% acetone in hexanes) to afford the title compound (66 mg, 85%) as a white foam: $^1$H NMR (400 MHz, CDCl$_3$) δ 12.11 (s, 1H), 8.44 (d, J=7.8 Hz, 1H), 7.95 (d, J=5.2 Hz, 1H), 7.33 (dd, J=8.2, 6.8 Hz, 1H), 6.95 (d, J 8.3 Hz, 2H), 6.85 (d, J=5.2 Hz, 1H), 6.69 (t, J=5.7 Hz, 2H), 6.63-6.55 (m, 2H), 5.57 (d, J=4.6 Hz, 1H), 5.40-5.33 (m, 1H), 4.66 (p, J=7.2 Hz, 1H), 3.93 (s, 3H), 3.88 (s, 3H), 2.21 (s, 3H), 1.37 (d, J=7.2 Hz, 3H), 1.33 (d, J=6.5 Hz, 3H); $^{13}$C NMR (101 MHz, CDCl$_3$) δ 171.43, 168.68, 163.36 (d, J=246.2 Hz), 157.81 (d, J=9.8 Hz), 155.53, 155.36, 148.76, 140.41, 130.49, 130.27, 129.77, 129.04 (d, J=10.1 Hz), 121.33 (d, J=3.2 Hz), 115.43, 109.42, 107.35 (d, J=21.3 Hz), 98.66 (d, J=25.9 Hz), 74.65, 73.23, 56.04, 55.77, 48.01, 20.42, 18.09, 15.00; $^{19}$F NMR (376 MHz, CDCl$_3$) δ −111.31 (s); HRMS-ESI (m/z)([M+H]$^+$) calcd for C$_2$H$_{30}$FN$_2$O$_7$, 513.2032; found, 513.2027.

Example 8A: Preparation of (S)-(1R,2S)-1-phenoxy-1-(p-tolyl)propan-2-yl 2-(3-(acetoxymethoxy)-4-methoxypicolinamido)propanoate

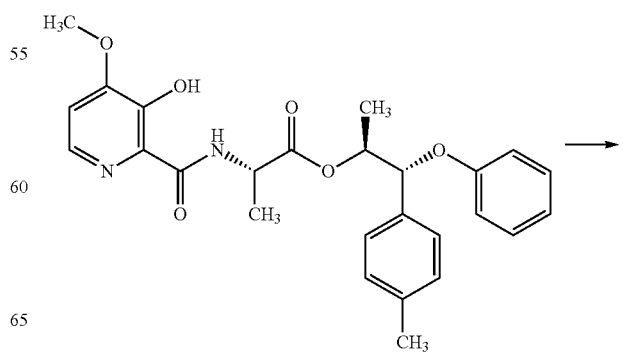

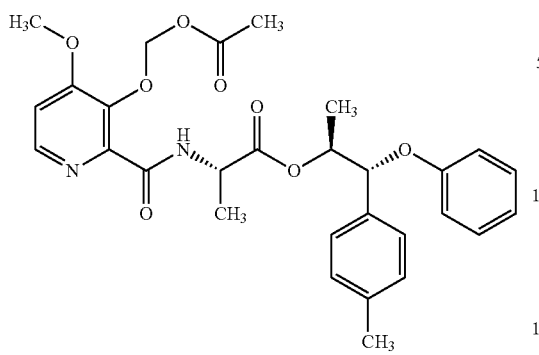

To a suspension of (S)-(1R,2S)-1-phenoxy-1-(p-tolyl)propan-2-yl 2-(3-hydroxy-4-methoxypicolinamido)propanoate (110 mg, 0.237 mmol), and K$_2$CO$_3$ (65.5 mg, 0.474 mmol) in acetone (2.37 mL) was added bromomethyl acetate (30.2 µL, 0.308 mmol) at rt. The reaction mixture was heated to 40° C. and stirred overnight. The solvent was evaporated, and the resulting crude material was purified by flash column chromatography (SiO$_2$, 5→30% acetone in hexanes) to afford the title compound (94 mg, 74%) as a colorless oil: $^1$H NMR (400 MHz, CDCl$_3$) δ 8.28 (d, J=7.8 Hz, 1H), 8.24 (d, J=5.4 Hz, 1H), 7.28 (d, J=8.0 Hz, 2H), 7.19-7.10 (m, 4H), 6.93 (d, J=5.4 Hz, 1H), 6.87 (t, J=7.4 Hz, 1H), 6.84-6.80 (m, 2H), 5.75-5.70 (m, 2H), 5.26 (dt, J=11.4, 5.7 Hz, 1H), 5.18 (d, J=5.0 Hz, 1H), 4.67 (p, J=7.2 Hz, 1H), 3.90 (s, 3H), 2.31 (s, 3H), 2.06 (s, 3H), 1.38 (d, J=6.4 Hz, 3H), 1.28 (d, J=7.2 Hz, 3H); $^{13}$C NMR (101 MHz, CDCl$_3$) δ 172.25, 170.27, 162.95, 160.27, 157.96, 145.68, 144.01, 142.49, 137.82, 134.51, 129.31, 129.19, 126.89, 121.06, 115.98, 109.53, 89.58, 81.10, 74.38, 56.17, 48.16, 21.14, 20.87, 18.23, 15.00; HRMS-ESI (m/z)([M+H]$^+$) calcd for C$_{29}$H$_{33}$N$_2$O$_8$, 537.2231; found, 537.2235.

Example 8B: Preparation of (S)-(1R,2S)-1-(2-chloro-4-methylphenoxy)-1-(4-fluoro-2-methoxyphenyl)propan-2-yl 2-(3-acetoxy-4-methoxypicolinamido)propanoate

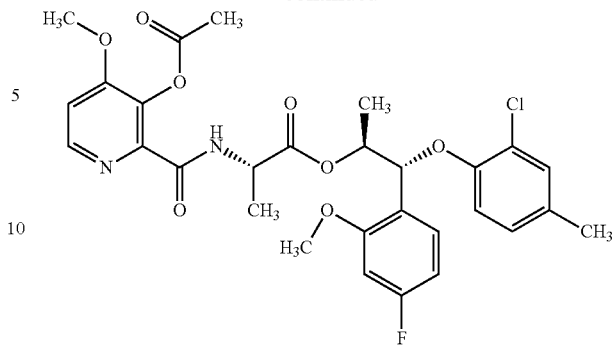

To a solution of (S)-(1R,2S)-1-(2-chloro-4-methylphenoxy)-1-(4-fluoro-2-methoxyphenyl)propan-2-yl 2-(3-hydroxy-4-methoxypicolinamido)propanoate (59 mg, 0.108 mmol) in pyridine (539 µL, 6.58 mmol) was added acetic anhydride (539 µL, 5.61 mmol). The reaction was stirred for 1 h and then the volatiles were removed in vacuo. The resulting residue was dissolved in toluene, and the volatiles were again removed in vacuo. The resulting residue was purified via flash column chromatography (SiO$_2$, 5→30% acetone in hexanes) to afford the title compound (62 mg, 98%) as a white foam: $^1$H NMR (400 MHz, CDCl$_3$) δ 8.50 (d, J=6.6 Hz, 1H), 8.28 (d, J=5.4 Hz, 1H), 7.38 (dd, J=9.2, 6.7 Hz, 1H), 7.12 (d, J=1.7 Hz, 1H), 6.98 (d, J=5.5 Hz, 1H), 6.81-6.76 (m, 1H), 6.61 (ddd, J=10.8, 5.5, 2.3 Hz, 2H), 6.55 (d, J=8.4 Hz, 1H), 5.63 (d, J=4.4 Hz, 1H), 5.42-5.35 (m, 1H), 4.72-4.64 (m, 1H), 3.90 (s, 3H), 3.88 (s, 3H), 2.39 (s, 3H), 2.19 (s, 3H), 1.35 (d, J=6.5 Hz, 3H), 1.33 (d, J=7.2 Hz, 3H); $^{13}$C NMR (101 MHz, CDCl$_3$) δ 171.95, 168.85, 163.47 (d, J=246.5 Hz), 159.42, 162.34, 157.82 (d, J=9.7 Hz), 150.89, 146.60, 141.58, 137.48, 131.22, 130.67, 129.17 (d, J=10.1 Hz), 127.84, 122.93, 120.74 (d, J=3.4 Hz), 114.38, 109.67, 107.46 (d, J=21.3 Hz), 98.64 (d, J=25.9 Hz), 75.32, 73.02, 56.25, 55.78, 47.97, 20.71, 20.20, 18.44, 14.99; $^{19}$F NMR (376 MHz, CDCl$_3$) δ −110.97 (d, J=2.0 Hz); HRMS-ESI (m/z) ([M+H]$^+$) calcd for C$_{29}$H$_{31}$ClFN$_2$O$_8$, 589.1747; found, 589.1749.

Example 9: Preparation of (S)-(1R,2S)-1-(4-fluoro-2-propoxyphenyl)-1-phenoxypropan-2-yl 2-(3-hydroxy-4-methoxypicolinamido)propanoate and (S)-(1R,2S)-1-(4-fluoro-2-hydroxyphenyl)-1-phenoxypropan-2-yl 2-(3-hydroxy-4-methoxypicolinamido)propanoate

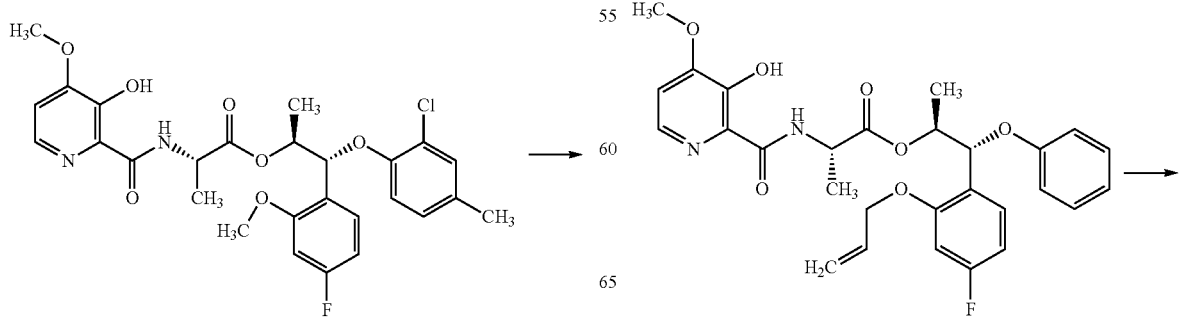

-continued

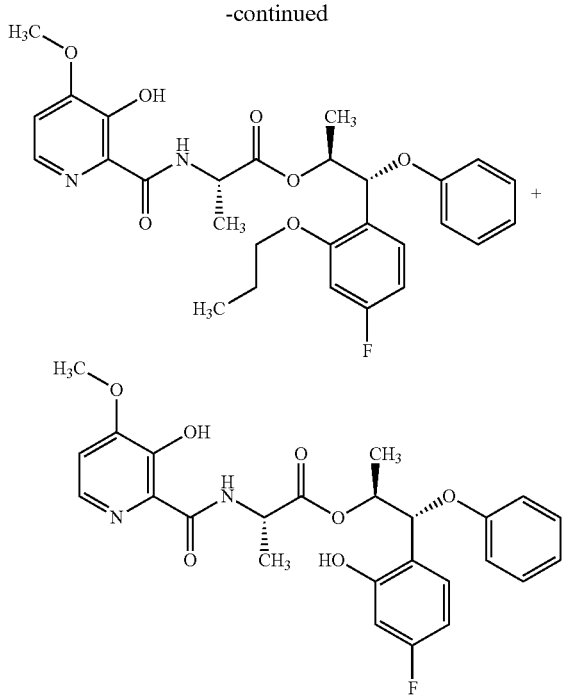

To a magnetically stirred mixture of (S)-(1R,2S)-1-(2-(allyloxy)-4-fluorophenyl)-1-phenoxypropan-2-yl 2-(3-hydroxy-4-methoxypicolinamido)propanoate (91 mg, 0.173 mmol), and ruthenium chloride n-hydrate (3.91 mg, 0.017 mmol) in THF (651 µL) and water (217 µL) was added NaBH$_4$ (13.13 mg, 0.347 mmol) (Note—rigorous gas evolution) under a N$_2$ atmosphere according to the procedure of Sharma, P. K.; Kumar, S.; Kumar, P.; Nielsen, P. *Tet. Lett.* 2012, 48, 8704-8708. The reaction mixture was stirred at 0° C. for 1 h, at which point the reaction was carefully quenched by the addition of water and was extracted 3× with CH$_2$Cl$_2$. The combined organic extracts were dried by passing through a phase separator and volatiles were removed under a gentle stream of N$_2$. The resulting residue was purified via flash chromatography (SiO$_2$, 5→30% acetone in hexanes) to afford the title compounds (29 mg, 32%) as a colorless oil: $^1$H NMR (400 MHz, CDCl$_3$) δ 12.12 (s, 1H), 8.43 (d, J=7.8 Hz, 1H), 7.96 (d, J=5.2 Hz, 1H), 7.32 (dd, J=8.3, 6.8 Hz, 1H), 7.20-7.13 (m, 2H), 6.86 (dd, J=10.0, 6.2 Hz, 2H), 6.82-6.77 (m, 2H), 6.61-6.53 (m, 2H), 5.62 (d, J=4.5 Hz, 1H), 5.43-5.36 (m, 1H), 4.66 (p, J=7.2 Hz, 1H), 3.98 (t, J=6.4 Hz, 2H), 3.94 (s, 3H), 1.96-1.86 (m, 2H), 1.37 (d, J=7.2 Hz, 3H), 1.34 (d, J=6.5 Hz, 3H), 1.11 (t, J=7.4 Hz, 3H). $^{19}$F NMR (376 MHz, CDCl$_3$) δ −111.41 (s, 1F). $^{13}$C NMR (101 MHz, CDCl$_3$) δ 171.38, 168.68, 163.33 (d, J=246.1 Hz), 157.68, 157.21 (d, J=10.0 Hz), 155.36, 148.76, 140.40, 130.49, 129.30, 128.95 (d, J=10.2 Hz), 121.10 (d, J=3.2 Hz), 120.99, 115.53, 109.42, 107.16 (d, J=21.5 Hz), 99.24 (d, J=25.9 Hz), 74.64, 73.25, 70.01, 56.04, 48.01, 22.49, 18.13, 15.03, 10.67. HRMS-ESI (m/z) ([M+H]$^+$) calcd for C$_{28}$H$_{32}$FN$_2$O$_7$, 527.2188; found, 527.2188, and (33 mg, 39%) as an oily white solid: $^1$H NMR (400 MHz, CDCl$_3$) δ 12.44 (s, 1H), 9.00 (s, 1H), 8.35 (d, J=7.6 Hz, 1H), 8.09 (d, J=5.3 Hz, 1H), 7.22 (ddd, J=8.4, 7.0, 3.6 Hz, 3H), 6.97 (d, J=5.3 Hz, 1H), 6.94 (t, J=7.3 Hz, 1H), 6.88 (d, J=7.8 Hz, 2H), 6.54 (td, J=8.4, 2.5 Hz, 1H), 6.32 (dd, J=10.0, 2.2 Hz, 1H), 5.50 (d, J=6.9 Hz, 1H), 5.20 (p, J=6.1 Hz, 1H), 4.65 (p, J=7.1 Hz, 1H), 3.99 (s, 3H), 1.51 (d, J=6.3 Hz, 3H), 1.45 (d, J=7.1 Hz, 3H). $^{19}$F NMR (376 MHz, CDCl$_3$) δ −112.15 (s, 1F). $^{13}$C NMR (101 MHz, CDCl$_3$) δ 170.47, 168.33, 163.09 (d, J=246.5 Hz), 157.25, 156.26, 155.47 (d, J=11.1 Hz), 149.58, 140.15, 130.12, 129.54, 128.71 (d, J=10.3 Hz), 121.77, 119.93 (d, J=3.4 Hz), 115.76, 109.65, 107.75 (d, J=21.7 Hz), 103.82 (d, J=24.0 Hz), 74.78, 56.25, 48.98, 29.26, 18.55, 16.20. HRMS-ESI (m/z) ([M+H]$^+$) calcd for C$_{25}$H$_{26}$FN$_2$O$_7$, 485.1719; found, 485.1717, respectively.

Example 10A: (E)-4-fluoro-2-methoxy-1-(prop-1-en-1-yl)benzene

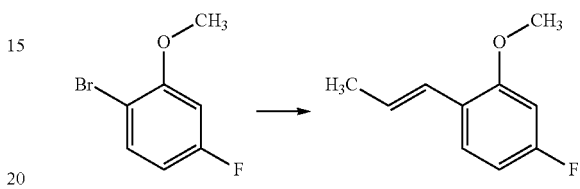

To a suspension of magnesium metal (486 mg, 20.0 mmol) and lithium chloride (933 mg, 22.0 mmol) in THF (20.0 mL) was added 1-bromo-4-fluoro-2-methoxybenzene (1.93 mL, 15.00 mmol) and the mixture was heated to 70° C. for 1 h at which point the reaction was cooled to 0° C. and Fe(acac)$_3$ (0.5 M in THF, 2.00 mL, 1.00 mmol) was added. After 1 min allyl chloride (0.814 mL, 10.0 mmol) was added and the reaction was stirred at 0° C. for 30 min, then at rt for 1 h. The reaction was then heated to 70° C. overnight. The reaction was quenched by addition of sat. NaHCO$_3$(aq) and diluted with petroleum ether and filtered through a pad of Celite™. The biphasic solution was extracted with petroleum ether and the combined organic phases were dried over Na$_2$SO$_4$, carefully concentrated in vacua (25° C., 250 mbar) and purified via flash column chromatography (SiO$_2$, 100% petroleum ether) to afford the title compound (1.07 g, 52%, 15:1 E:Z) as a colorless oil: $^1$H NMR (400 MHz, CDCl$_3$) δ 7.31 (dd, J=8.4, 6.8 Hz, 1H), 6.66-6.51 (m, 3H), 6.14 (dq, J=15.9, 6.6 Hz, 1H), 3.82 (s, 3H), 1.88 (dd, J=6.6, 1.7 Hz, 3H); $^{19}$F NMR (376 MHz, CDCl$_3$) δ −113.30 (s).

Example 10B: (2S,3S)-2-(4-fluoro-2-methoxyphenyl)-3-methyloxirane

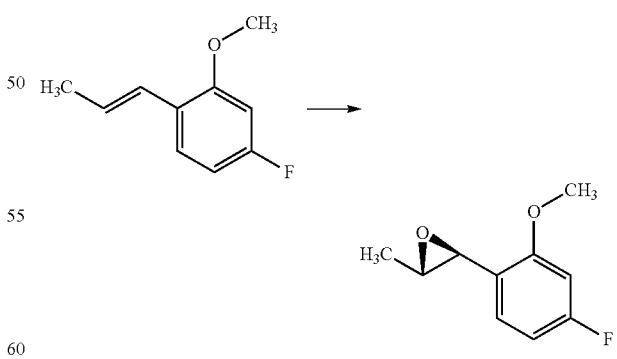

To a round-bottom flask was added buffer (0.05M Na$_2$B$_4$O$_7$. 10 H$_2$O in 4×10$^{-4}$ M aqueous Na$_2$(EDTA), 26.5 mL), acetonitrile (40.1 mL), (E)-4-fluoro-2-methoxy-1-(prop-1-1 en-1-yo)benzene (0.55 g, 2.65 mmol), tetrabutylammonium hydrogen sulfate (0.036 g, 0.106 mmol) and 1,2,4,5-Bis-O-(isopropylidene)-β-L-erythro-2,3-hexodiulo- 2,6-pyranose (Shi epoxidation catalyst enantiomer, 0.205 g, 0.794 mmol) and the reaction mixture was cooled to 0° C. A solution of Oxone (2.246 g, 3.65 mmol) in aqeuous Na$_2$(EDTA) (4×10$^{-4}$ M, 15 mL) and a solution of potassium carbonate (2.122 g, 15.36 mmol) in water 15 mL were simultaneously added dropwise through two syringe pumps over 1.5 h. Upon completion of the syring pump additions, the reaction was immediately quenched with petroluem ether and water. The mixture was extracted 3× with petroleum ether, washed with brine, dried over Na$_2$SO$_4$, filtered and concentrated in vacuo. The resulting residue was purified via flash column chromatography (SiO$_2$, 0→10% acetone in hexanes) to afford the title compound (455 mg, 85%, 15:1 dr) as a colorless oil: $^1$H NMR (400 MHz, CDCl$_3$) δ 7.06 (dd, J=8.3, 6.7 Hz, 1H), 6.67-6.52 (m, 2H), 3.89-3.80 (m, 1H), 3.84 (s, 3H), 2.91 (qd, J=5.1, 2.1 Hz, 1H), 1.45 (d, J=5.2 Hz, 3H); $^{19}$F NMR (376 MHz, CDCl$_3$) δ -112.15.

Example 10C: (1S,2S)-1-cyclopropoxy-1-(4-fluoro-2-methoxyphenyl)propan-2-ol and (1R,2S)-1-cyclopropoxy-1-(4-fluoro-2-methoxyphenyl)propan-2-ol

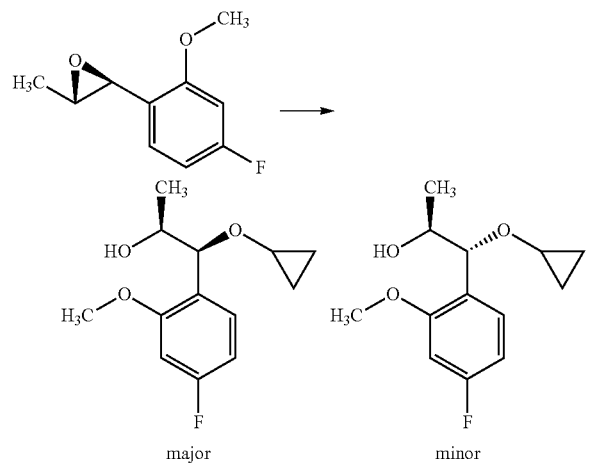

major  minor

To a solution of (2S,3S)-2-(4-fluoro-2-methoxyphenyl)-3-methyloxirane (50 mg, 0.274 mmol), in cyclopropanol (1.37 mL) was added sulfuric (1 drop). The reaction mixture was stirred at 0° C. for 10 min then quenched by addition of solid K$_2$CO$_3$. Volatiles were removed under a gentle stream of N$_2$ and the resulting residue was purified via flash chromatography (SiO2, 5→30% acetone in hexanes) to yield the title compounds as two diastereomers: Major (1S,2S) (32 mg, 49%): $^1$H NMR (400 MHz, CDCl$_3$) δ 7.31 (dd, J=8.4, 6.9 Hz, 1H), 6.69 (td, J=8.3, 2.4 Hz, 1H), 6.62 (dd, J=10.9, 2.4 Hz, 1H), 4.62 (d, J=7.5 Hz, 1H), 3.82 (s, 3H), 3.78 (dt, J=13.2, 4.6 Hz, 1H), 3.16 (dq, J=9.1, 3.0 Hz, 1H), 2.62 (s, 1H), 0.99 (d, J=6.4 Hz, 3H), 0.66-0.50 (m, 2H), 0.40 (dddd, J=16.3, 14.5, 10.4, 6.2 Hz, 2H); $^{19}$F NMR (376 MHz, CDCl$_3$) δ -112.05 (s); ESIMS m/z 263 ([M+Na]$^+$). Minor (1R,2S) (18 mg, 27%): $^1$H NMR (400 MHz, CDCl$_3$) δ 7.38 (dd, J=8.4, 7.0 Hz, 1H), 6.70 (td, J=8.4, 2.4 Hz, 1H), 6.61 (dd, J=10.9, 2.4 Hz, 1H), 4.83 (d, J=4.2 Hz, 1H), 4.00-3.91 (m, 1H), 3.82 (s, 3H), 3.24 (dq, J=9.2, 3.0 Hz, 1H), 1.94 (d, J=6.2 Hz, 1H), 1.00 (d, J=6.5 Hz, 3H), 0.70-0.63 (m, 1H), 0.59-0.52 (m, 1H), 0.51-0.43 (m, 1H), 0.42-0.35 (m, 1H); $^{19}$F NMR (376 MHz, CDCl$_3$) δ -112.65 (s); ESIMS m/z 263 ([M+Na]$^+$).

Example A: Evaluation of Fungicidal Activity: Leaf Blotch of Wheat (*Zymoseptoria tritici*; Bayer Code SEPTTR)

Technical grades of materials were dissolved in acetone, which were then mixed with nine volumes of water containing 110 ppm Triton X-100. The fungicide solutions were applied onto wheat seedlings using an automated booth sprayer to run-off. All sprayed plants were allowed to air dry prior to further handling. All fungicides were evaluated using the aforementioned method for their activity vs. all target diseases, unless stated otherwise. Wheat leaf blotch and brown rust activity were also evaluated using track spray applications, in which case the fungicides were formulated as EC formulations, containing 0.1% Trycol 5941 in the spray solutions.

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Zymoseptoria tritici* either prior to or after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a greenhouse set at 20° C. for disease to develop. When disease symptoms were fully expressed on the 1$^{st}$ leaves of untreated plants, infection levels were assessed on a scale of 0 to 100 percent disease severity. Percent disease control was calculated using the ratio of disease severity on treated plants relative to untreated plants.

Example B: Evaluation of Fungicidal Activity: Wheat Brown Rust (*Puccinia triticina*; Synonym: *Puccinia recondita* f. sp. *tritici*; Bayer code PUCCRT)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Puccinia* triticina either prior to or after fungicide treatments. After inoculation the plants were kept in a dark dew room at 22° C. with 100% relative humidity overnight to permit spores to germinate and infect the leaf. The plants were then transferred to a greenhouse set at 24° C. for disease to develop. Fungicide formulation, application and disease assessment followed the procedures as described in the Example A.

Example C: Evaluation of Fungicidal Activity: Wheat Glume Blotch (*Leptosphaeria nodorum*; Bayer Code LEPTNO)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Leptosphaeria nodorum* 24 hr after fungicide treatments. After inoculation the plants were kept in 100% relative humidity (one day in a dark dew chamber followed by two days in a lighted dew chamber at 20° C.) to permit spores to germinate and infect the leaf. The plants were then transferred to a greenhouse set at 20° C. for disease to develop. Fungicide formulation, application and disease assessment followed the procedures as described in the Example A.

Example D: Evaluation of Fungicidal Activity: Apple Scab (*Venturia inaequalis*; Bayer code VENTIN)

Apple seedlings (variety McIntosh) were grown in soil-less Metro mix, with one plant per pot. Seedlings with two expanding young leaves at the top (older leaves at bottom of the plants were trimmed) were used in the test. Plants were inoculated with a spore suspension of *Venturia inaequalis* 24 hr after fungicide treatment and kept in a 22° C. dew chamber with 100% relative humidity for 48 hr, and then moved to a greenhouse set at 20° C. for disease to develop. Fungicide formulation, application and disease assessment on the sprayed leaves followed the procedures as described in the Example A.

Example E: Evaluation of Fungicidal Activity: Leaf Spot of Sugar Beets (*Cercospora beticola*; Bayer Code CERCBE)

Sugar beet plants (variety HH88) were grown in soil-less Metro mix and trimmed regularly to maintain a uniform plant size prior to test. Plants were inoculated with a spore suspension 24 hr after fungicide treatments. Inoculated plants were kept in a dew chamber at 22° C. for 48 hr then incubated in a greenhouse set at 24° C. under a clear plastic hood with bottom ventilation until disease symptoms were fully expressed. Fungicide formulation, application and disease assessment on the sprayed leaves followed the procedures as described in the Example A.

Example F: Evaluation of Fungicidal Activity: Asian Soybean Rust (*Phakopsora pachyrhizi*; Bayer Code PHAKPA)

Technical grades of materials were dissolved in acetone, which were then mixed with nine volumes of water containing 0.011% Tween 20. The fungicide solutions were applied onto soybean seedlings using an automated booth sprayer to run-off. All sprayed plants were allowed to air dry prior to further handling.

Soybean plants (variety Williams 82) were grown in soil-less Metro mix, with one plant per pot. Two weeks old seedlings were used for testing. Plants were inoculated either 3 days prior to or 1 day after fungicide treatments. Plants were incubated for 24 h in a dark dew room at 22° C. and 100% relative humidity then transferred to a growth room at 23° C. for disease to develop. Disease severity was assessed on the sprayed leaves.

Example G: Evaluation of Fungicidal Activity: Barley Scald (*Rhyncosporium secalis*; Bayer code RHYNSE)

Barley seedlings (variety Harrington) were propagated in soil-less Metro mix, with each pot having 8 to 12 plants, and used in the test when first leaf was fully emerged. Test plants were inoculated by an aqueous spore suspension of *Rhyncosporium secalis* 24 hr after fungicide treatments. After inoculation the plants were kept in a dew room at 22° C. with 100% relative humidity for 48 hr. The plants were then transferred to a greenhouse set at 20° C. for disease to develop. Fungicide formulation, application and disease assessment on the sprayed leaves followed the procedures as described in the Example A.

Example H: Evaluation of Fungicidal Activity: Rice Blast (*Pyricularia oryzae*; Bayer Code PYRIOR)

Rice seedlings (variety *Japonica*) were propagated in soil-less Metro mix, with each pot having 8 to 14 plants, and used in the test when 12 to 14 days old. Test plants were inoculated with an aqueous spore suspension of *Pyricularia oryzae* 24 hr after fungicide treatments. After inoculation the plants were kept in a dew room at 22° C. with 100% relative humidity for 48 hr to permit spores to germinate and infect the leaf. The plants were then transferred to a greenhouse set at 24° C. for disease to develop. Fungicide formulation, application and disease assessment on the sprayed leaves followed the procedures as described in the Example A.

Example I: Evaluation of Fungicidal Activity: Tomato Early Blight (*Alternaria solani*; Bayer code ALTESO)

Tomato plants (variety Outdoor Girl) were propagated in soil-less Metro mix, with each pot having one plant, and used when 12 to 14 days old. Test plants were inoculated with an aqueous spore suspension of *Alternaria solani* 24 hr after fungicide treatments. After inoculation the plants were kept in a dew room at 22° C. with 100% relative humidity for 48 hr to permit spores to germinate and infect the leaf. The plants were then transferred to a growth room at 22° C. for disease to develop. Fungicide formulation, application and disease assessment on the sprayed leaves followed the procedures as described in the Example A.

Example J: Evaluation of Fungicidal Activity: Cucumber Anthracnose (*Colletotrichum Lagenarium*; Bayer Code COLLLA)

Cucumber seedlings (variety Bush Pickle) were propagated in soil-less Metro mix, with each pot having one plant, and used in the test when 12 to 14 days old. Test plants were inoculated with an aqueous spore suspension of *Colletotrichum* lagenarium 24 hr after fungicide treatments. After inoculation the plants were kept in a dew room at 22° C. with 100% relative humidity for 48 hr to permit spores to germinate and infect the leaf. The plants were then transferred to a growth room set at 22° C. for disease to develop. Fungicide formulation, application and disease assessment on the sprayed leaves followed the procedures as described in the Example A.

TABLE 1

Compound Structure, Appearance, and Preparation Method

| *Cmpd. No. | Structure | Prepared According to Example | Colorless Semi-Solid |
|---|---|---|---|
| 1 | 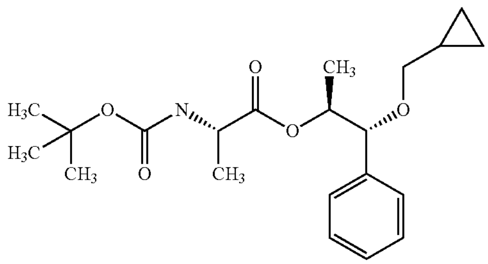 [SMILES: C[C@H](NC(=O)OC(C)(C)C)C(=O)O[C@@H](C)[C@H](OCC1CC1)c1ccccc1] | Example 1A; Example 2C; Example 4A; Example 5 | Colorless Semi-Solid |
| 2 | 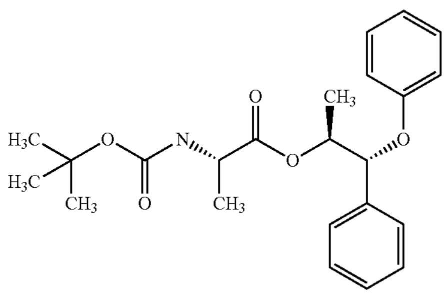 [SMILES: C[C@H](NC(=O)OC(C)(C)C)C(=O)O[C@@H](C)[C@H](Oc1ccccc1)c1ccccc1] | Example 1A; Example 2A; Example 4B; Example 5 | White Solid |
| 3 | 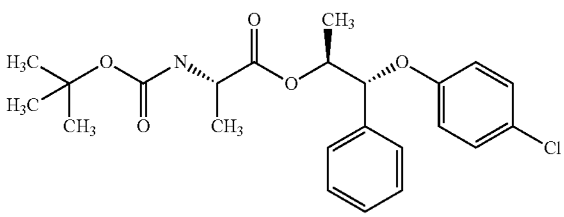 [SMILES: C[C@H](NC(=O)OC(C)(C)C)C(=O)O[C@@H](C)[C@H](Oc1ccc(Cl)cc1)c1ccccc1] | Example 1A; Example 2A; Example 4B; Example 5 | Sticky Oil |
| 4 | 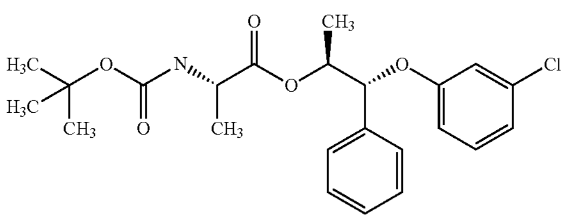 [SMILES: C[C@H](NC(=O)OC(C)(C)C)C(=O)O[C@@H](C)[C@H](Oc1cccc(Cl)c1)c1ccccc1] | Example 1A; Example 2B; Example 4A; Example 5 | Sticky Oil |
| 5 | 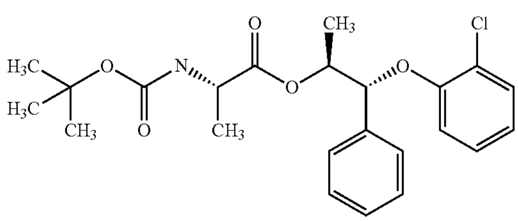 [SMILES: C[C@H](NC(=O)OC(C)(C)C)C(=O)O[C@@H](C)[C@H](Oc1ccccc1Cl)c1ccccc1] | Example 1A; Example 2B; Example 4A; Example 5 | Sticky Oil |
| 6 | 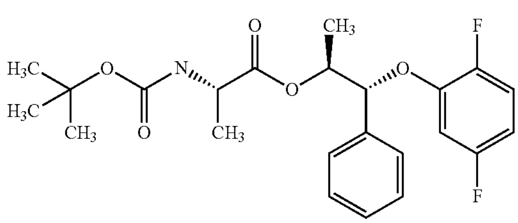 [SMILES: C[C@H](NC(=O)OC(C)(C)C)C(=O)O[C@@H](C)[C@H](Oc1cc(F)ccc1F)c1ccccc1] | Example 1A; Example 2B; Example 4A; Example 5 | Sticky Oil |

TABLE 1-continued

Compound Structure, Appearance, and Preparation Method

| *Cmpd. No. | Structure | Prepared According to Example | Colorless Semi-Solid |
|---|---|---|---|
| 7 | 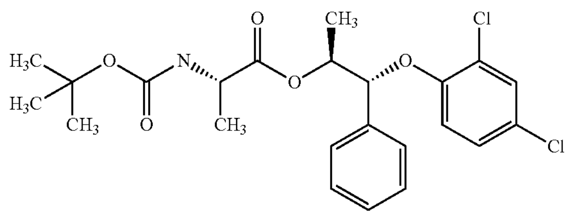 [SMILES: C[C@H](NC(=O)OC(C)(C)C)C(=O)O[C@@H](C)[C@H](Oc1ccc(Cl)cc1Cl)c1ccccc1] | Example 1A; Example 2B; Example 4A; Example 5 | Sticky Oil |
| 8 | 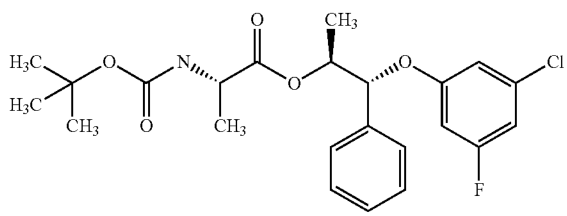 [SMILES: C[C@H](NC(=O)OC(C)(C)C)C(=O)O[C@@H](C)[C@H](Oc1cc(F)cc(Cl)c1)c1ccccc1] | Example 1A; Example 2B; Example 4A; Example 5 | Sticky Oil |
| 9 | 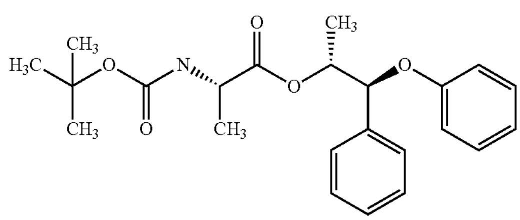 [SMILES: C[C@H](NC(=O)OC(C)(C)C)C(=O)O[C@H](C)[C@@H](Oc1ccccc1)c1ccccc1] | Example 1A; Example 2A; Example 4A; Example 5 | Sticky Wax |
| 10 | 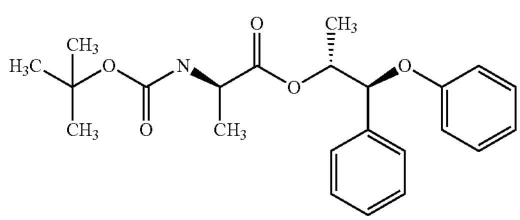 [SMILES: C[C@@H](NC(=O)OC(C)(C)C)C(=O)O[C@H](C)[C@@H](Oc1ccccc1)c1ccccc1] | Example 1A; Example 2A; Example 4A; Example 5 | Sticky Wax |
| 11 | 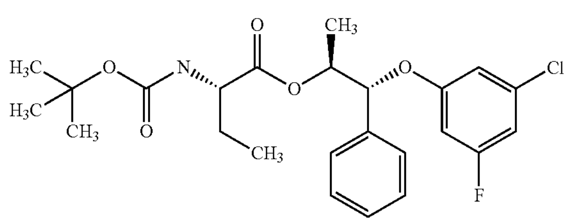 [SMILES: CC[C@H](NC(=O)OC(C)(C)C)C(=O)O[C@@H](C)[C@H](Oc1cc(F)cc(Cl)c1)c1ccccc1] | Example 1A; Example 2B; Example 4A; Example 5 | Sticky Oil |
| 12 | 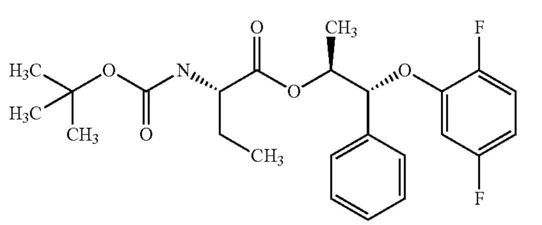 [SMILES: CC[C@H](NC(=O)OC(C)(C)C)C(=O)O[C@@H](C)[C@H](Oc1cc(F)ccc1F)c1ccccc1] | Example 1A; Example 2B; Example 4A; Example 5 | White Solid |

TABLE 1-continued

Compound Structure, Appearance, and Preparation Method

| *Cmpd. No. | Structure | Prepared According to Example | Colorless Semi-Solid |
|---|---|---|---|
| 13 | 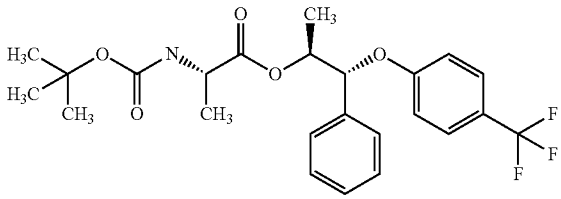 [SMILES: C[C@H](NC(=O)OC(C)(C)C)C(=O)O[C@@H](C)[C@H](Oc1ccc(C(F)(F)F)cc1)c1ccccc1] | Example 1A; Example 2B; Example 4A; Example 5 | Sticky Glass |
| 14 | 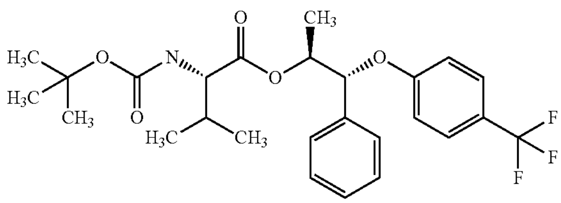 [SMILES: CC(C)[C@H](NC(=O)OC(C)(C)C)C(=O)O[C@@H](C)[C@H](Oc1ccc(C(F)(F)F)cc1)c1ccccc1] | Example 1A; Example 2B; Example 4A; Example 5 | Sticky Glass |
| 15 | 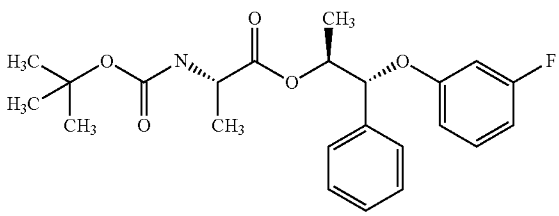 [SMILES: C[C@H](NC(=O)OC(C)(C)C)C(=O)O[C@@H](C)[C@H](Oc1cccc(F)c1)c1ccccc1] | Example 1A; Example 2B; Example 4A; Example 5 | Sticky Oil |
| 16 | 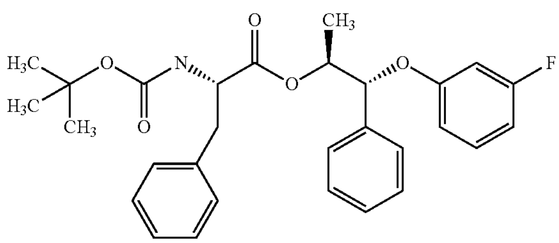 [SMILES: C[C@H](OC(=O)[C@H](Cc1ccccc1)NC(=O)OC(C)(C)C)[C@H](Oc1cccc(F)c1)c1ccccc1] | Example 1A; Example 2B; Example 4A; Example 5 | Semi-Solid |
| 17 | 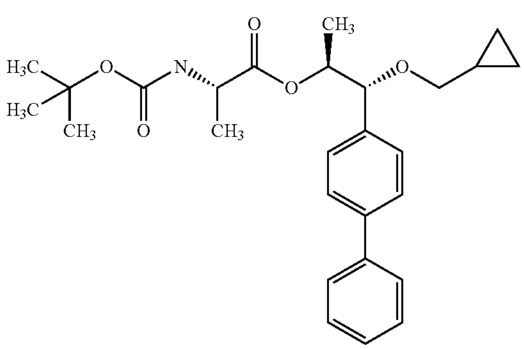 [SMILES: C[C@H](NC(=O)OC(C)(C)C)C(=O)O[C@@H](C)[C@H](OCC1CC1)c1ccc(-c2ccccc2)cc1] | Example 1A; Example 2C; Example 4A; Example 5 | Colorless Oil |
| 18 | 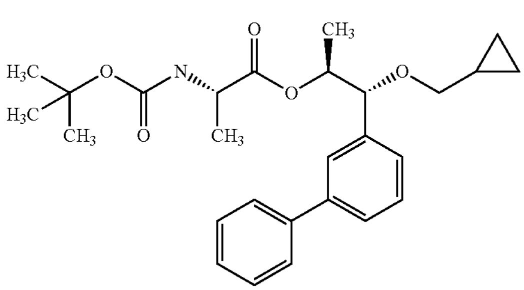 [SMILES: C[C@H](NC(=O)OC(C)(C)C)C(=O)O[C@@H](C)[C@H](OCC1CC1)c1cccc(-c2ccccc2)c1] | Example 1A; Example 2C; Example 4A; Example 5 | Colorless Oil |

TABLE 1-continued

Compound Structure, Appearance, and Preparation Method

| *Cmpd. No. | Structure | Prepared According to Example | Colorless Semi-Solid |
|---|---|---|---|
| 19 | 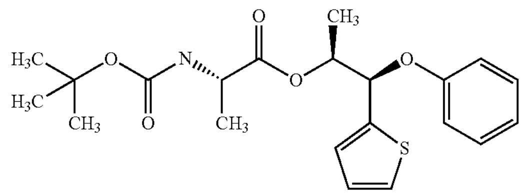 [SMILES: C[C@H](NC(=O)OC(C)(C)C)C(=O)O[C@@H](C)[C@@H](Oc1ccccc1)c1cccs1] | Example 1D; Example 2A; Example 4B; Example 5 | Colorless Oil |
| 20 | 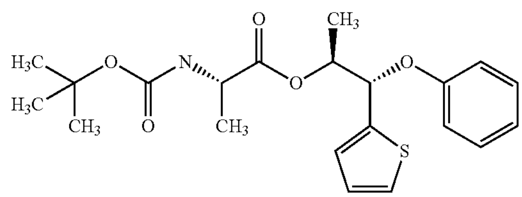 [SMILES: C[C@H](NC(=O)OC(C)(C)C)C(=O)O[C@@H](C)[C@H](Oc1ccccc1)c1cccs1] | Example 1D; Example 2A; Example 4B; Example 5 | Colorless Oil |
| 21 | 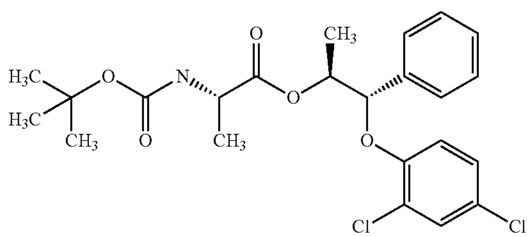 [SMILES: C[C@H](NC(=O)OC(C)(C)C)C(=O)O[C@@H](C)[C@@H](Oc1ccc(Cl)cc1Cl)c1ccccc1] | Example 1B; Example 1C; Example 2B; Example 4A; Example 5 | Colorless Oil |
| 22 | 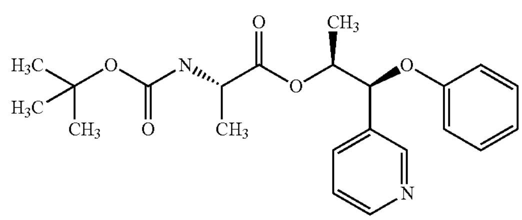 [SMILES: C[C@H](NC(=O)OC(C)(C)C)C(=O)O[C@@H](C)[C@@H](Oc1ccccc1)c1cccnc1] | Example 1D; Example 2A; Example 4B; Example 5 | Colorless Oil |
| 23 | 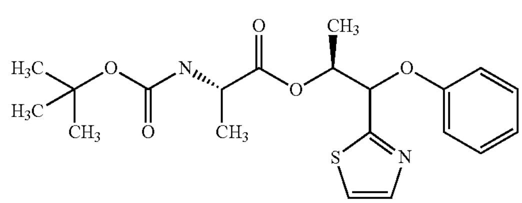 [SMILES: C[C@H](NC(=O)OC(C)(C)C)C(=O)O[C@@H](C)C(Oc1ccccc1)c1nccs1] | Example 1D; Example 2A; Example 4B; Example 5 | Colorless Oil |
| 24 | 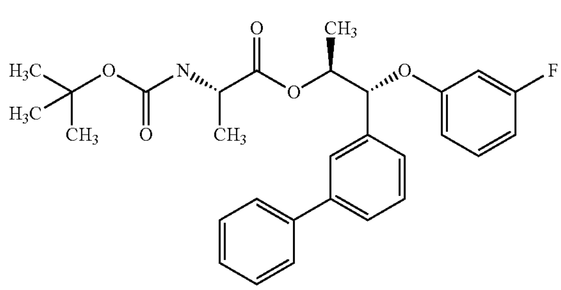 [SMILES: C[C@H](NC(=O)OC(C)(C)C)C(=O)O[C@@H](C)[C@H](Oc1cccc(F)c1)c1cccc(-c2ccccc2)c1] | Example 1B; Example 1C; Example 2C; Example 4A; Example 5 | Colorless Oil |

TABLE 1-continued

Compound Structure, Appearance, and Preparation Method

| *Cmpd. No. | Structure | Prepared According to Example | Colorless Semi-Solid |
|---|---|---|---|
| 25 | 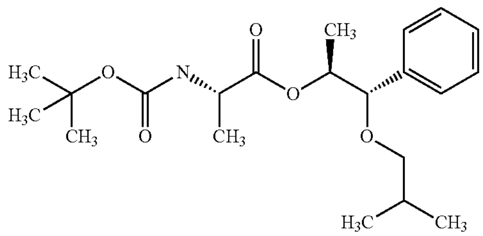 [SMILES: CC(C)CO[C@@H](c1ccccc1)[C@H](C)OC(=O)[C@H](C)NC(=O)OC(C)(C)C] | Example 1B; Example 1C; Example 2C; Example 4A; Example 5 | Colorless Oil |
| 26 | 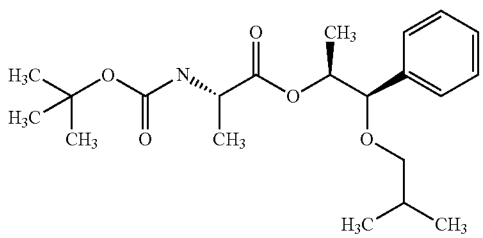 [SMILES: CC(C)CO[C@H](c1ccccc1)[C@H](C)OC(=O)[C@H](C)NC(=O)OC(C)(C)C] | Example 1B; Example 1C; Example 2C; Example 4A; Example 5 | Colorless Oil |
| 27 | 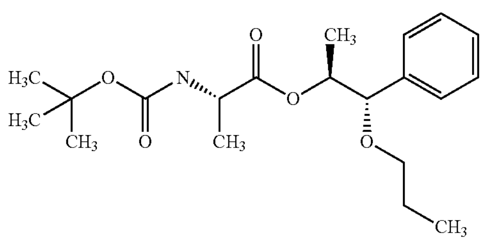 [SMILES: CCCO[C@@H](c1ccccc1)[C@H](C)OC(=O)[C@H](C)NC(=O)OC(C)(C)C] | Example 1B; Example 1C; Example 2C; Example 4A; Example 5 | Colorless Oil |
| 28 | 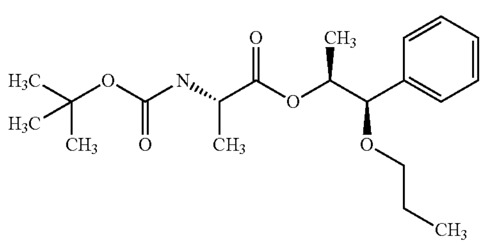 [SMILES: CCCO[C@H](c1ccccc1)[C@H](C)OC(=O)[C@H](C)NC(=O)OC(C)(C)C] | Example 1B; Example 1C; Example 2C; Example 4A; Example 5 | Colorless Oil |
| 29 | 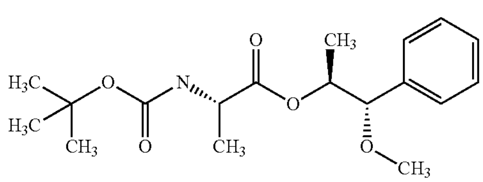 [SMILES: CO[C@@H](c1ccccc1)[C@H](C)OC(=O)[C@H](C)NC(=O)OC(C)(C)C] | Example 1B; Example 1C; Example 2C; Example 4A; Example 5 | Colorless Oil |
| 30 | 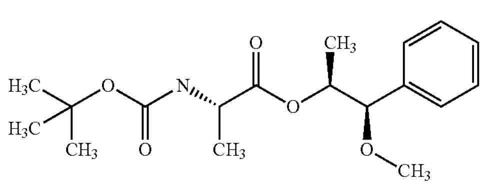 [SMILES: CO[C@H](c1ccccc1)[C@H](C)OC(=O)[C@H](C)NC(=O)OC(C)(C)C] | Example 1B; Example 1C; Example 2C; Example 4A; Example 5 | Colorless Oil |

TABLE 1-continued

Compound Structure, Appearance, and Preparation Method

| *Cmpd. No. | Structure | Prepared According to Example | Colorless Semi-Solid |
|---|---|---|---|
| 31 | 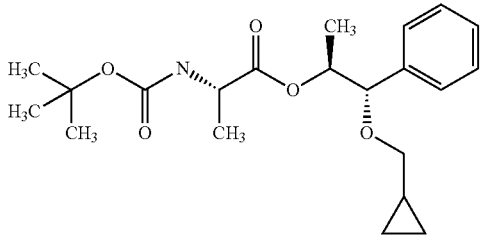 [SMILES: C[C@H](NC(=O)OC(C)(C)C)C(=O)O[C@@H](C)[C@@H](OCC1CC1)c1ccccc1] | Example 1B; Example 1C; Example 2C; Example 4A; Example 5 | Colorless Oil |
| 32 | 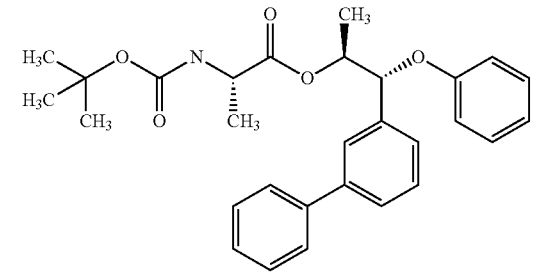 [SMILES: C[C@H](NC(=O)OC(C)(C)C)C(=O)O[C@@H](C)[C@H](Oc1ccccc1)c1cccc(-c2ccccc2)c1] | Example 1A; Example 2A; Example 4A; Example 5 | Colorless Oil |
| 33 | 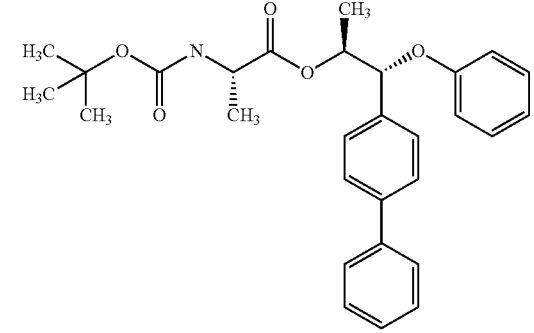 [SMILES: C[C@H](NC(=O)OC(C)(C)C)C(=O)O[C@@H](C)[C@H](Oc1ccccc1)c1ccc(-c2ccccc2)cc1] | Example 1A; Example 2A; Example 4A; Example 5 | Colorless Oil |
| 34 | 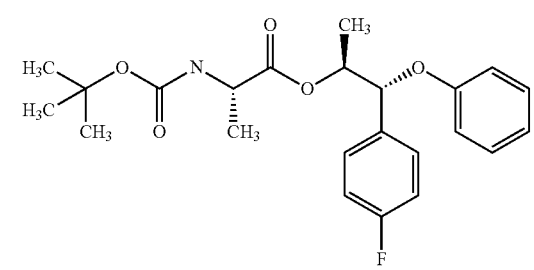 [SMILES: C[C@H](NC(=O)OC(C)(C)C)C(=O)O[C@@H](C)[C@H](Oc1ccccc1)c1ccc(F)cc1] | Example 1A; Example 2A; Example 4B; Example 5 | Colorless Oil |
| 35 | 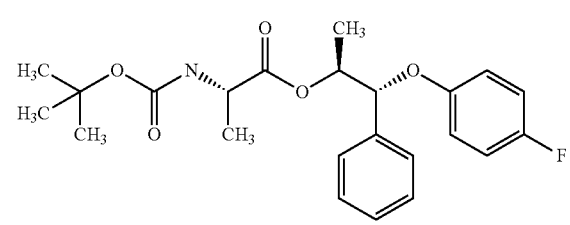 [SMILES: C[C@H](NC(=O)OC(C)(C)C)C(=O)O[C@@H](C)[C@H](Oc1ccc(F)cc1)c1ccccc1] | Example 1A; Example 2A; Example 4A; Example 5 | Colorless Oil |

TABLE 1-continued

Compound Structure, Appearance, and Preparation Method

| *Cmpd. No. | Structure | Prepared According to Example | Colorless Semi-Solid |
|---|---|---|---|
| 36 | 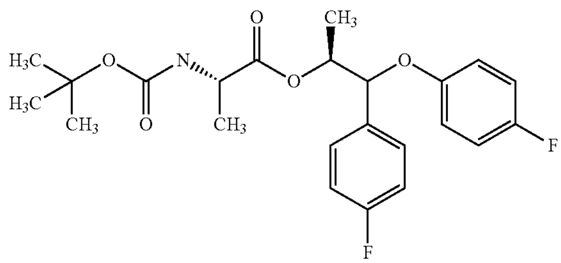 [SMILES: C[C@H](NC(=O)OC(C)(C)C)C(=O)O[C@@H](C)C(Oc1ccc(F)cc1)c1ccc(F)cc1] | Example 1A; Example 2A; Example 4A; Example 5 | Colorless Oil |
| 37 | 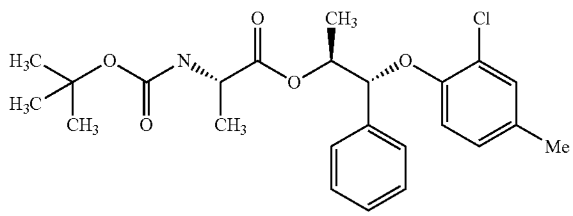 [SMILES: Cc1ccc(O[C@H](c2ccccc2)[C@H](C)OC(=O)[C@H](C)NC(=O)OC(C)(C)C)c(Cl)c1] | Example 1A; Example 2B; Example 4A; Example 5 | Colorless Oil |
| 38 | 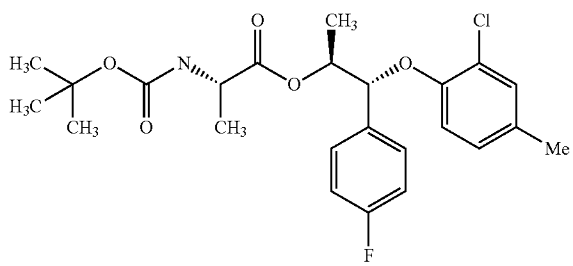 [SMILES: Cc1ccc(O[C@H](c2ccc(F)cc2)[C@H](C)OC(=O)[C@H](C)NC(=O)OC(C)(C)C)c(Cl)c1] | Example 1A; Example 2B; Example 4A; Example 5 | Colorless Oil |
| 39 | 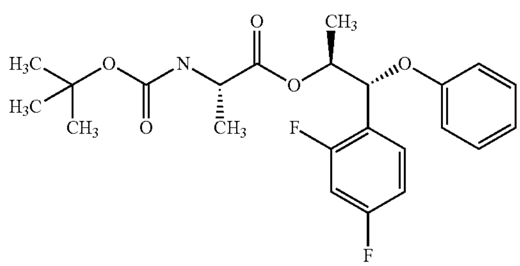 [SMILES: C[C@H](NC(=O)OC(C)(C)C)C(=O)O[C@@H](C)[C@H](Oc1ccccc1)c1ccc(F)cc1F] | Example 1A; Example 2A; Example 4A; Example 5 | Colorless Oil |
| 40 | 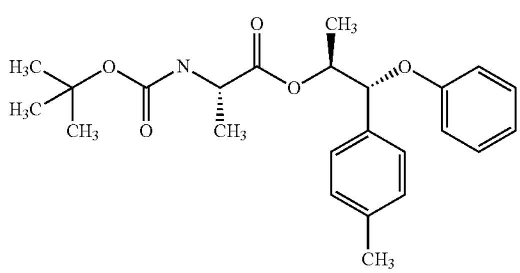 [SMILES: Cc1ccc([C@@H](Oc2ccccc2)[C@H](C)OC(=O)[C@H](C)NC(=O)OC(C)(C)C)cc1] | Example 1A; Example 2A; Example 4B; Example 5 | Colorless Oil |
| 41 | 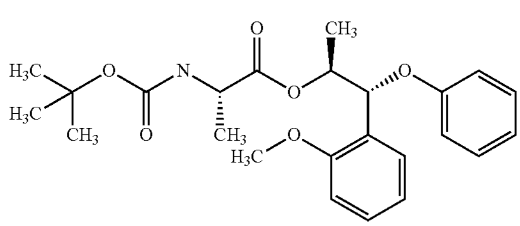 [SMILES: COc1ccccc1[C@@H](Oc1ccccc1)[C@H](C)OC(=O)[C@H](C)NC(=O)OC(C)(C)C] | Example 1A; Example 2A; Example 4B; Example 5 | Colorless Oil |

TABLE 1-continued

Compound Structure, Appearance, and Preparation Method

| *Cmpd. No. | Structure | Prepared According to Example | Colorless Semi-Solid |
|---|---|---|---|
| 42 | 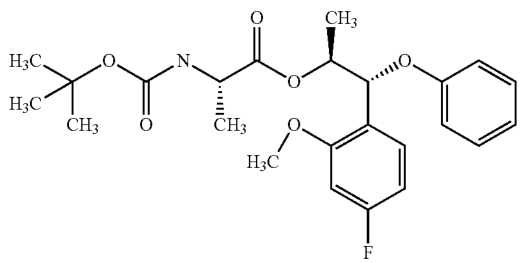 [SMILES: COc1cc(F)ccc1[C@@H](Oc1ccccc1)[C@H](C)OC(=O)[C@H](C)NC(=O)OC(C)(C)C] | Example 1A; Example 2A; Example 4B; Example 5 | Colorless Oil |
| 43 | 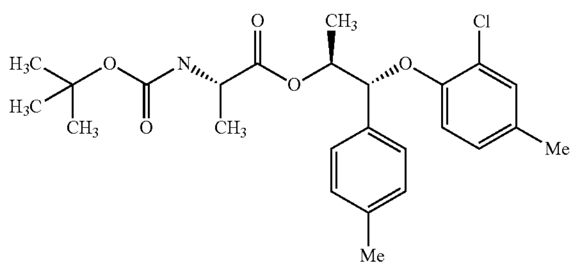 [SMILES: Cc1ccc([C@@H](Oc2ccc(C)cc2Cl)[C@H](C)OC(=O)[C@H](C)NC(=O)OC(C)(C)C)cc1] | Example 1A; Example 2B; Example 4B; Example 5 | Colorless Oil |
| 44 | 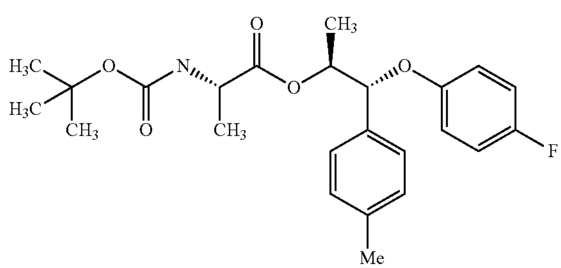 [SMILES: Cc1ccc([C@@H](Oc2ccc(F)cc2)[C@H](C)OC(=O)[C@H](C)NC(=O)OC(C)(C)C)cc1] | Example 1A; Example 2A; Example 4A; Example 5 | Colorless Oil |
| 45 | 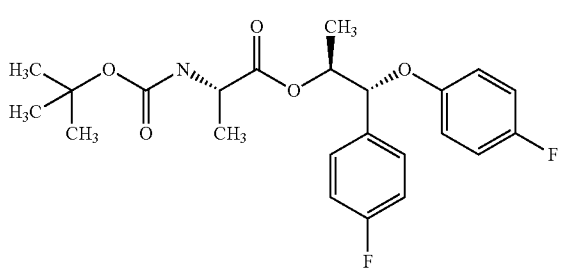 [SMILES: C[C@H](NC(=O)OC(C)(C)C)C(=O)O[C@@H](C)[C@H](Oc1ccc(F)cc1)c1ccc(F)cc1] | Example 1A; Example 2A; Example 4A; Example 5 | Colorless Oil |
| 46 | 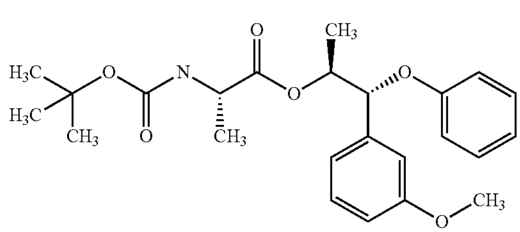 [SMILES: COc1cccc([C@@H](Oc2ccccc2)[C@H](C)OC(=O)[C@H](C)NC(=O)OC(C)(C)C)c1] | Example 1A; Example 2A; Example 4B; Example 5 | Colorless Oil |

TABLE 1-continued

Compound Structure, Appearance, and Preparation Method

| *Cmpd. No. | Structure | Prepared According to Example | Colorless Semi-Solid |
|---|---|---|---|
| 47 | 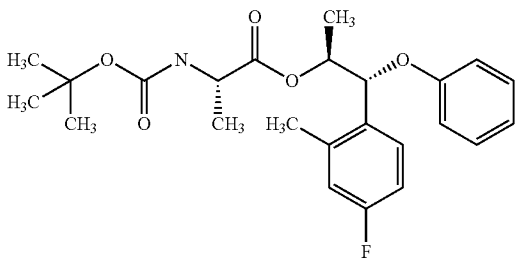 [SMILES: Cc1cc(F)ccc1[C@@H](Oc1ccccc1)[C@H](C)OC(=O)[C@H](C)NC(=O)OC(C)(C)C] | Example 1A; Example 2A; Example 4B; Example 5 | White Waxy Solid |
| 48 | 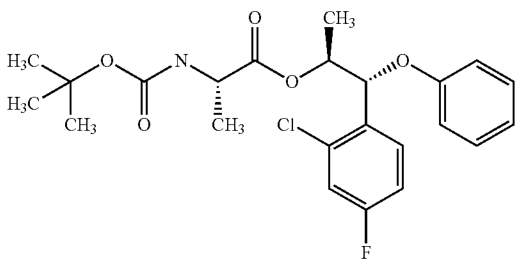 [SMILES: C[C@H](NC(=O)OC(C)(C)C)C(=O)O[C@@H](C)[C@H](Oc1ccccc1)c1ccc(F)cc1Cl] | Example 1A; Example 2A; Example 4B; Example 5 | Colorless Oil |
| 49 | 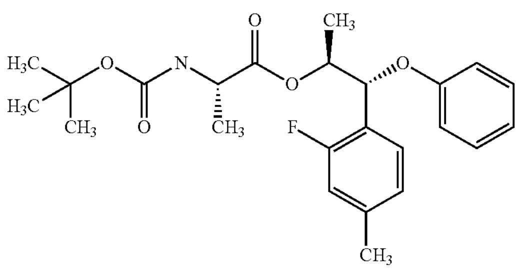 [SMILES: Cc1ccc([C@@H](Oc2ccccc2)[C@H](C)OC(=O)[C@H](C)NC(=O)OC(C)(C)C)c(F)c1] | Example 1E; Example 2A; Example 4B; Example 5 | Colorless Oil |
| 50 | 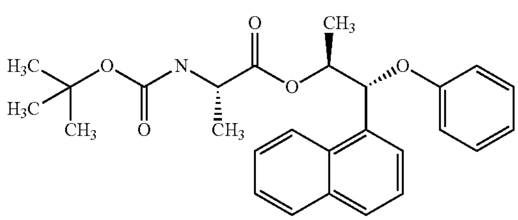 [SMILES: C[C@H](NC(=O)OC(C)(C)C)C(=O)O[C@@H](C)[C@H](Oc1ccccc1)c1cccc2ccccc12] | Example 1A; Example 2A; Example 4B; Example 5 | Colorless Oil |
| 51 | 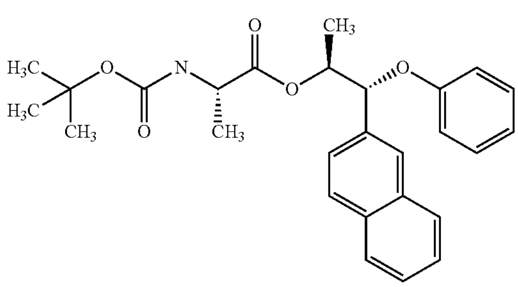 [SMILES: C[C@H](NC(=O)OC(C)(C)C)C(=O)O[C@@H](C)[C@H](Oc1ccccc1)c1ccc2ccccc2c1] | Example 1A; Example 2A; Example 4B; Example 5 | White Foam |

TABLE 1-continued

Compound Structure, Appearance, and Preparation Method

| *Cmpd. No. | Structure | Prepared According to Example | Colorless Semi-Solid |
|---|---|---|---|
| 52 | 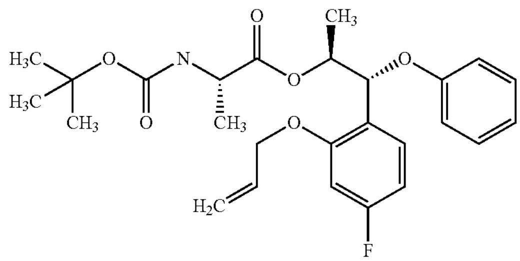 [SMILES: C=CCOc1cc(F)ccc1[C@@H](Oc1ccccc1)[C@H](C)OC(=O)[C@H](C)NC(=O)OC(C)(C)C] | Example 1E; Example 2A; Example 4B; Example 5 | Foamy Solid |
| 53 | 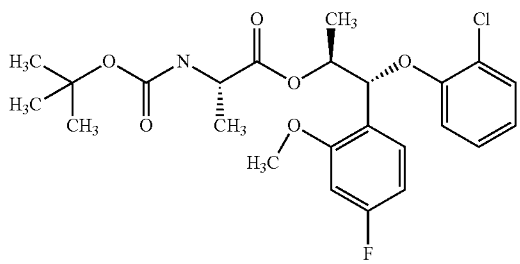 [SMILES: COc1cc(F)ccc1[C@@H](Oc1ccccc1Cl)[C@H](C)OC(=O)[C@H](C)NC(=O)OC(C)(C)C] | Example 1E; Example 2B; Example 4B; Example 5 | Colorless Oil |
| 54 | 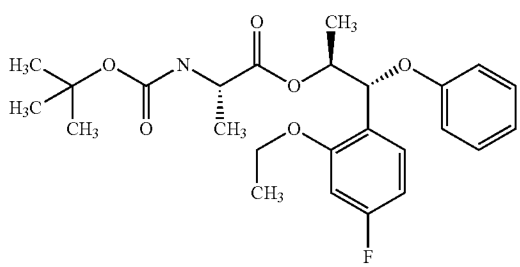 [SMILES: CCOc1cc(F)ccc1[C@@H](Oc1ccccc1)[C@H](C)OC(=O)[C@H](C)NC(=O)OC(C)(C)C] | Example 1E; Example 2A; Example 4B; Example 5 | Colorless Oil |
| 56 | 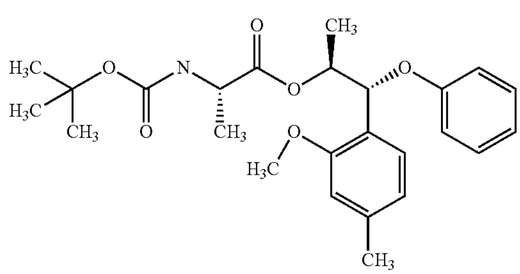 [SMILES: COc1cc(C)ccc1[C@@H](Oc1ccccc1)[C@H](C)OC(=O)[C@H](C)NC(=O)OC(C)(C)C] | Example 1E; Example 2A; Example 4B; Example 5 | White Foam |
| 57 | 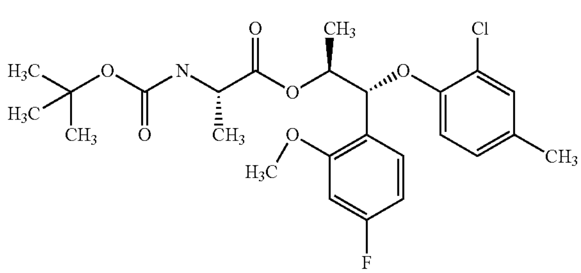 [SMILES: COc1cc(F)ccc1[C@@H](Oc1ccc(C)cc1Cl)[C@H](C)OC(=O)[C@H](C)NC(=O)OC(C)(C)C] | Example 1E; Example 2B; Example 4B; Example 5 | White Foam |

| *Cmpd. No. | Structure | Prepared According to Example | Colorless Semi-Solid |
|---|---|---|---|
| 58 | 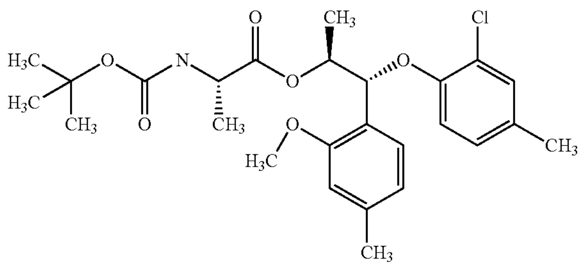 [SMILES: COc1cc(C)ccc1[C@@H](Oc1ccc(C)cc1Cl)[C@H](C)OC(=O)[C@H](C)NC(=O)OC(C)(C)C] | Example 1E; Example 2B; Example 4B; Example 5 | Colorless Oil |
| 59 | 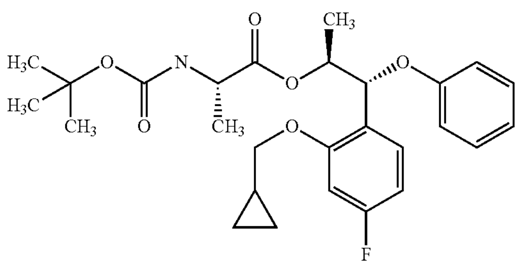 [SMILES: C[C@H](NC(=O)OC(C)(C)C)C(=O)O[C@@H](C)[C@H](Oc1ccccc1)c1ccc(F)cc1OCC1CC1] | Example 1E; Example 2A; Examples 3A,B; Example 4B; Example 5 | White Solid |
| 60 | 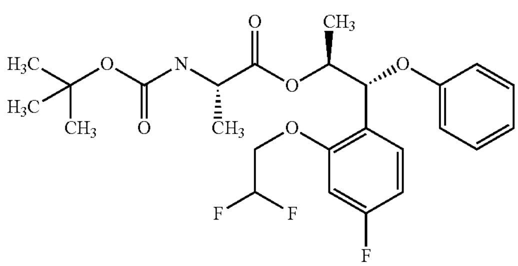 [SMILES: C[C@H](NC(=O)OC(C)(C)C)C(=O)O[C@@H](C)[C@H](Oc1ccccc1)c1ccc(F)cc1OCC(F)F] | Example 1E; Example 2A; Examples 3A,B; Example 4B; Example 5 | Colorless Oil |
| 61 | 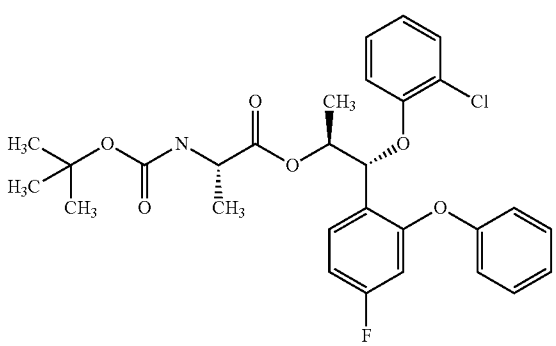 [SMILES: C[C@H](NC(=O)OC(C)(C)C)C(=O)O[C@@H](C)[C@H](Oc1ccccc1Cl)c1ccc(F)cc1Oc1ccccc1] | Example 1E; Example 2B; Examples 3A,C; Example 4B; Example 5 | Colorless Oil |
| 62 | 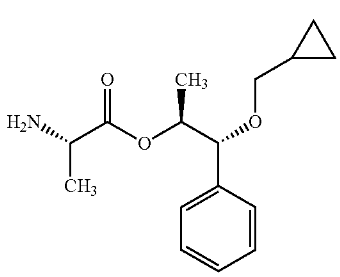 [SMILES: C[C@H](N)C(=O)O[C@@H](C)[C@H](OCC1CC1)c1ccccc1] | Example 6, Step 1 | White Solid |

TABLE 1-continued

Compound Structure, Appearance, and Preparation Method

| *Cmpd. No. | Structure | Prepared According to Example | Colorless Semi-Solid |
|---|---|---|---|
| 63 | (structure: H2N-alanine ester of 1-methyl-2-phenoxy-2-phenylethanol) | Example 6, Step 1 | White Solid |
| 64 | (structure: H2N-alanine ester of 1-methyl-2-phenoxy-2-phenylethanol, different stereochemistry) | Example 6, Step 1 | Clear Glass |
| 65 | (structure: H2N-alanine ester of 1-methyl-2-phenoxy-2-phenylethanol, different stereochemistry) | Example 6, Step 1 | Clear Glass |
| 66 | (structure: H2N-alanine ester with 2-chlorophenoxy group) | Example 6, step 1 | White Powder |
| 67 | (structure: H2N-alanine ester with 3-chlorophenoxy group) | Example 6, step 1 | White Powder |
| 68 | (structure: H2N-alanine ester with 4-chlorophenoxy group) | Example 6, step 1 | White Powder |

TABLE 1-continued

Compound Structure, Appearance, and Preparation Method

| *Cmpd. No. | Structure | Prepared According to Example | Colorless Semi-Solid |
|---|---|---|---|
| 69 | 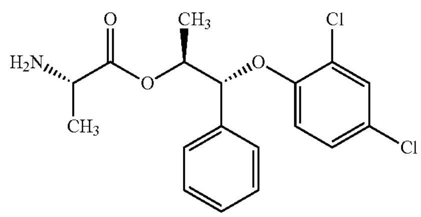 [SMILES: C[C@H](N)C(=O)O[C@@H](C)[C@H](Oc1ccc(Cl)cc1Cl)c1ccccc1] | Example 6, step 1 | White Powder |
| 70 | 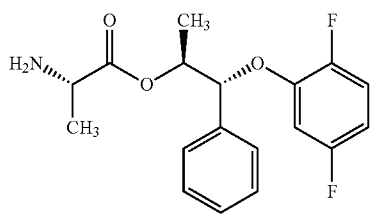 [SMILES: C[C@H](N)C(=O)O[C@@H](C)[C@H](Oc1cc(F)ccc1F)c1ccccc1] | Example 6, step 1 | White Powder |
| 71 | 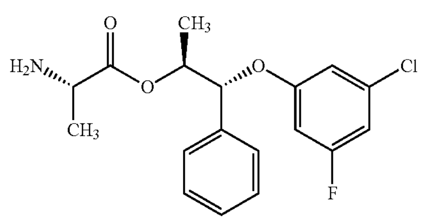 [SMILES: C[C@H](N)C(=O)O[C@@H](C)[C@H](Oc1cc(F)cc(Cl)c1)c1ccccc1] | Example 6, step 1 | White Powder |
| 72 | 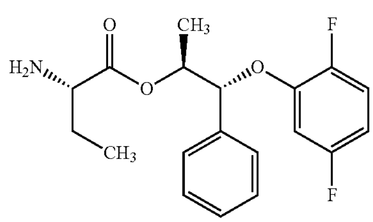 [SMILES: CC[C@H](N)C(=O)O[C@@H](C)[C@H](Oc1cc(F)ccc1F)c1ccccc1] | Example 6, step 1 | White Powder |
| 73 | 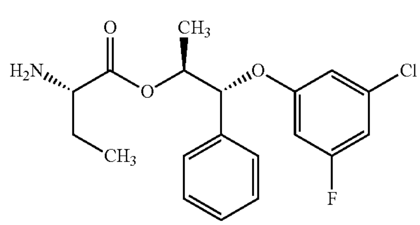 [SMILES: CC[C@H](N)C(=O)O[C@@H](C)[C@H](Oc1cc(F)cc(Cl)c1)c1ccccc1] | Example 6, step 1 | White Powder |
| 74 | 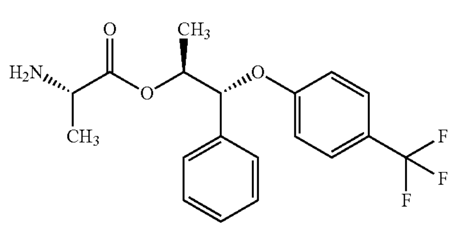 [SMILES: C[C@H](N)C(=O)O[C@@H](C)[C@H](Oc1ccc(C(F)(F)F)cc1)c1ccccc1] | Example 6, step 1 | White Powder |

TABLE 1-continued

Compound Structure, Appearance, and Preparation Method

| *Cmpd. No. | Structure | Prepared According to Example | Colorless Semi-Solid |
|---|---|---|---|
| 75 | 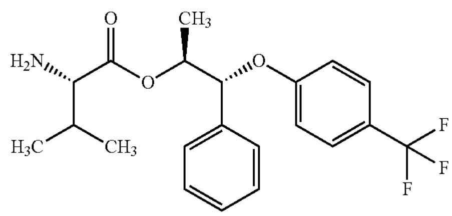 [SMILES: CC(C)[C@H](N)C(=O)O[C@@H](C)[C@H](Oc1ccc(C(F)(F)F)cc1)c1ccccc1] | Example 6, step 1 | White Powder |
| 76 | 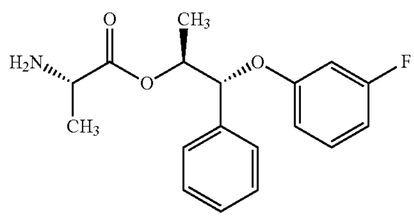 [SMILES: C[C@H](N)C(=O)O[C@@H](C)[C@H](Oc1cccc(F)c1)c1ccccc1] | Example 6, step 1 | White Powder |
| 77 | 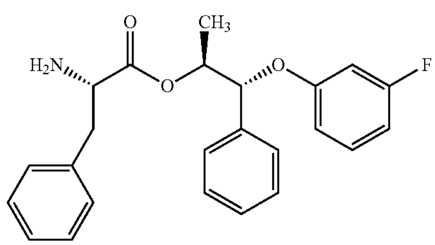 [SMILES: C[C@H](OC(=O)[C@@H](N)Cc1ccccc1)[C@H](Oc1cccc(F)c1)c1ccccc1] | Example 6, step 1 | White Powder |
| 78 | 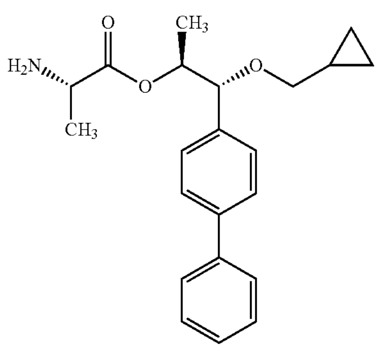 [SMILES: C[C@H](N)C(=O)O[C@@H](C)[C@H](OCC1CC1)c1ccc(-c2ccccc2)cc1] | Example 6, step 1 | Colorless Oil |
| 79 | 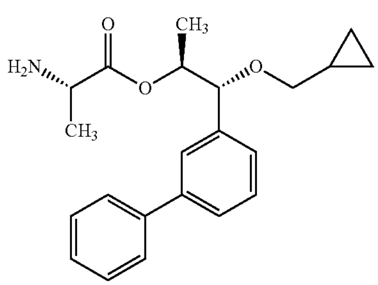 [SMILES: C[C@H](N)C(=O)O[C@@H](C)[C@H](OCC1CC1)c1cccc(-c2ccccc2)c1] | Example 6, step 1 | Colorless Oil |

TABLE 1-continued

Compound Structure, Appearance, and Preparation Method

| *Cmpd. No. | Structure | Prepared According to Example | Colorless Semi-Solid |
|---|---|---|---|
| 80 | 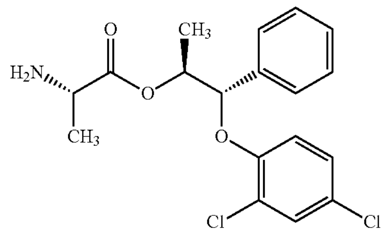 [SMILES: C[C@H](N)C(=O)O[C@@H](C)[C@@H](Oc1ccc(Cl)cc1Cl)c1ccccc1] | Example 6, Step 1 | Colorless Oil |
| 81 | 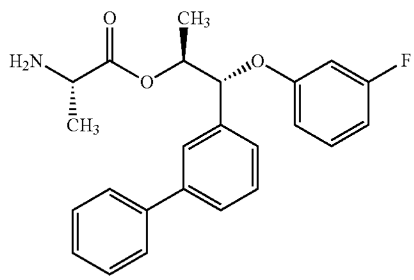 [SMILES: C[C@H](N)C(=O)O[C@@H](C)[C@H](Oc1cccc(F)c1)c1cccc(-c2ccccc2)c1] | Example 6, step 1 | Colorless Oil |
| 82 | 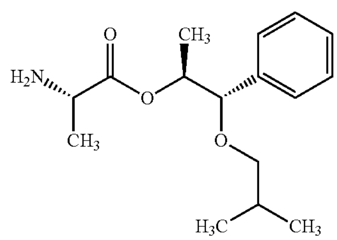 [SMILES: CC(C)CO[C@@H](c1ccccc1)[C@H](C)OC(=O)[C@H](C)N] | Example 6, Step 1 | Colorless Oil |
| 83 | 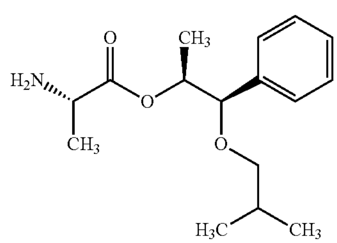 [SMILES: CC(C)CO[C@H](c1ccccc1)[C@H](C)OC(=O)[C@H](C)N] | Example 6, Step 1 | Colorless Oil |
| 84 | 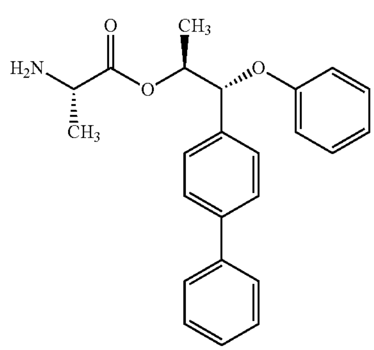 [SMILES: C[C@H](N)C(=O)O[C@@H](C)[C@H](Oc1ccccc1)c1ccc(-c2ccccc2)cc1] | Example 6, step 1 | Beige Solid |

TABLE 1-continued

Compound Structure, Appearance, and Preparation Method

| *Cmpd. No. | Structure | Prepared According to Example | Colorless Semi-Solid |
|---|---|---|---|
| 85 | 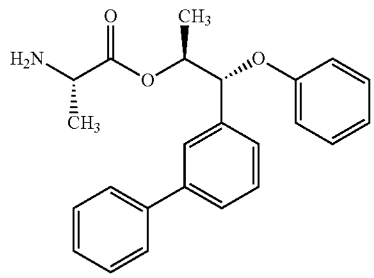 [SMILES: C[C@H](N)C(=O)O[C@@H](C)[C@H](Oc1ccccc1)c1cccc(-c2ccccc2)c1] | Example 6, step 1 | Colorless Oil |
| 86 | 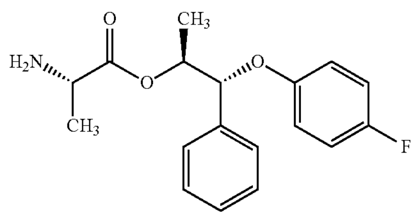 [SMILES: C[C@H](N)C(=O)O[C@@H](C)[C@H](Oc1ccc(F)cc1)c1ccccc1] | Example 6, Step 1 | Colorless Oil |
| 87 | 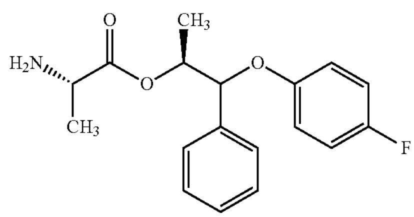 [SMILES: C[C@H](N)C(=O)O[C@@H](C)C(Oc1ccc(F)cc1)c1ccccc1] | Example 6, Step 1 | Colorless Oil |
| 88 | 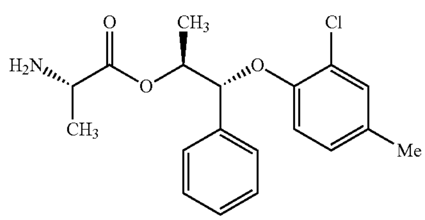 [SMILES: Cc1ccc(O[C@H](c2ccccc2)[C@H](C)OC(=O)[C@H](C)N)c(Cl)c1] | Example 6, Step 1 | Colorless Oil |
| 89 | 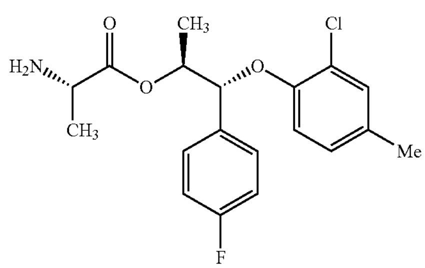 [SMILES: Cc1ccc(O[C@H](c2ccc(F)cc2)[C@H](C)OC(=O)[C@H](C)N)c(Cl)c1] | Example 6, Step 1 | Colorless Oil |
| 90 | 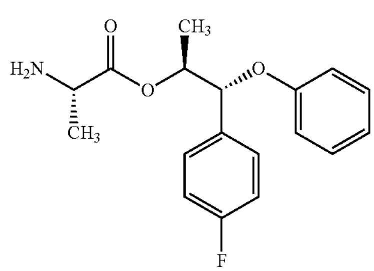 [SMILES: C[C@H](N)C(=O)O[C@@H](C)[C@H](Oc1ccccc1)c1ccc(F)cc1] | Example 6, step 1 | Colorless Viscous Oil |

TABLE 1-continued

Compound Structure, Appearance, and Preparation Method

| *Cmpd. No. | Structure | Prepared According to Example | Colorless Semi-Solid |
|---|---|---|---|
| 91 | 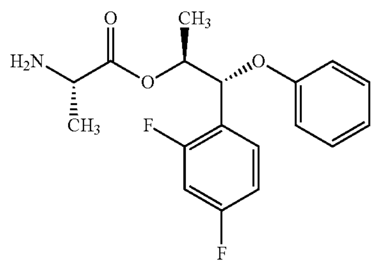 [SMILES: C[C@H](N)C(=O)O[C@@H](C)[C@H](Oc1ccccc1)c1ccc(F)cc1F] | Example 6, step 1 | Colorless Oil |
| 92 | 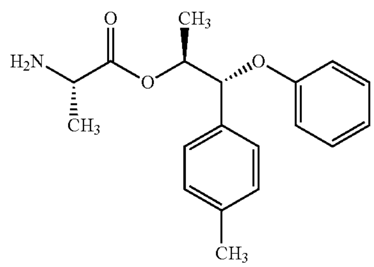 [SMILES: Cc1ccc([C@@H](Oc2ccccc2)[C@H](C)OC(=O)[C@H](C)N)cc1] | Example 6, step 1 | Oily White Solid |
| 93 | 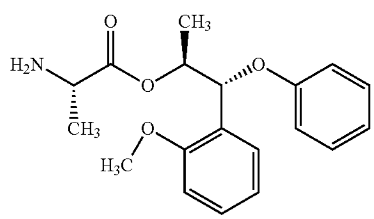 [SMILES: COc1ccccc1[C@@H](Oc1ccccc1)[C@H](C)OC(=O)[C@H](C)N] | Example 6, step 1 | Colorless Oil |
| 94 | 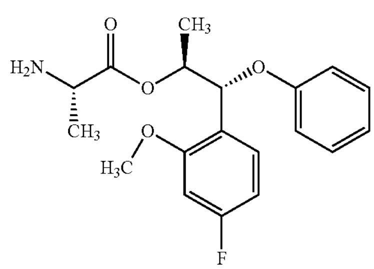 [SMILES: COc1cc(F)ccc1[C@@H](Oc1ccccc1)[C@H](C)OC(=O)[C@H](C)N] | Example 6, step 1 | Colorless Oil |
| 95 | 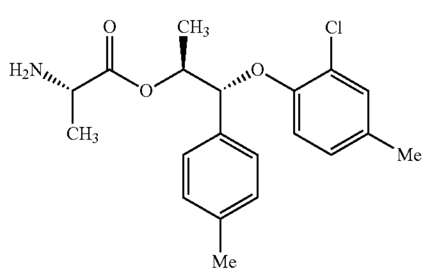 [SMILES: Cc1ccc([C@@H](Oc2ccc(C)cc2Cl)[C@H](C)OC(=O)[C@H](C)N)cc1] | Example 6, Step 1 | Colorless Oil |

TABLE 1-continued

Compound Structure, Appearance, and Preparation Method

| *Cmpd. No. | Structure | Prepared According to Example | Colorless Semi-Solid |
|---|---|---|---|
| 96 | 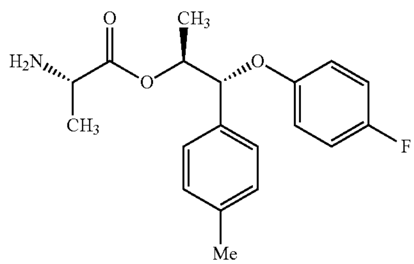 [SMILES: Cc1ccc([C@@H](Oc2ccc(F)cc2)[C@H](C)OC(=O)[C@H](C)N)cc1] | Example 6, Step 1 | Colorless Oil |
| 97 | 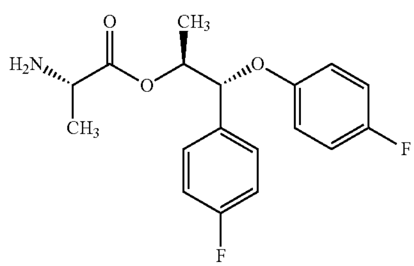 [SMILES: C[C@H](N)C(=O)O[C@@H](C)[C@H](Oc1ccc(F)cc1)c1ccc(F)cc1] | Example 6, Step 1 | Colorless Oil |
| 98 | 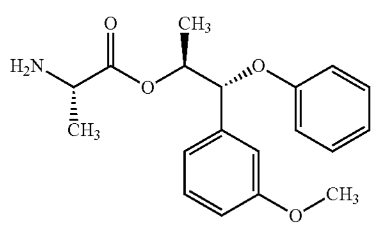 [SMILES: COc1cccc([C@@H](Oc2ccccc2)[C@H](C)OC(=O)[C@H](C)N)c1] | Example 6, step 1 | Colorless Oil |
| 99 | 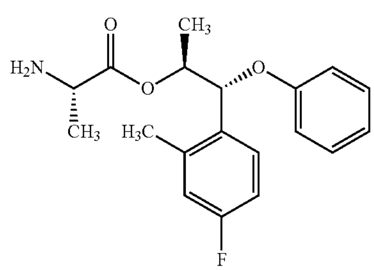 [SMILES: Cc1cc(F)ccc1[C@@H](Oc1ccccc1)[C@H](C)OC(=O)[C@H](C)N] | Example 6, step 1 | Clear Viscous Oil |
| 100 | 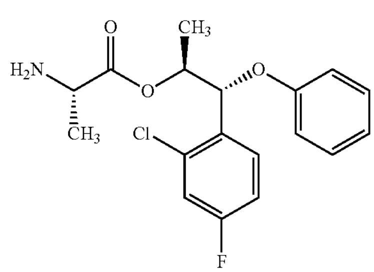 [SMILES: C[C@H](N)C(=O)O[C@@H](C)[C@H](Oc1ccccc1)c1ccc(F)cc1Cl] | Example 6, step 1 | Colorless Viscous Oil |

TABLE 1-continued

Compound Structure, Appearance, and Preparation Method

| *Cmpd. No. | Structure | Prepared According to Example | Colorless Semi-Solid |
|---|---|---|---|
| 101 | 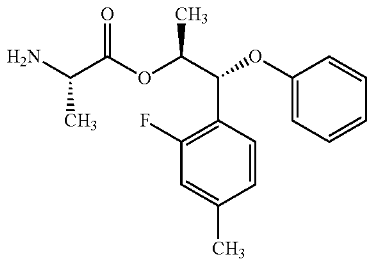 [SMILES: Cc1ccc([C@@H](Oc2ccccc2)[C@H](C)OC(=O)[C@H](C)N)c(F)c1] | Example 6, step 1 | Colorless Oil |
| 102 | 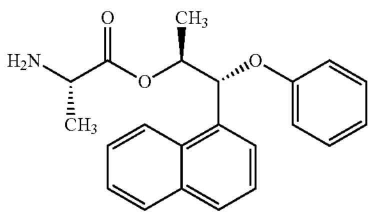 [SMILES: C[C@H](N)C(=O)O[C@@H](C)[C@H](Oc1ccccc1)c1cccc2ccccc12] | Example 6, step 1 | Colorless Oil |
| 103 | 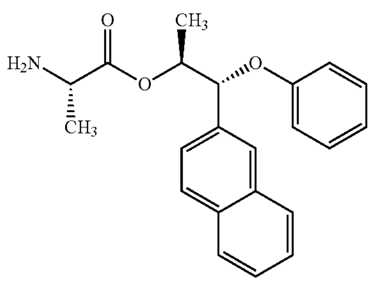 [SMILES: C[C@H](N)C(=O)O[C@@H](C)[C@H](Oc1ccccc1)c1ccc2ccccc2c1] | Example 6, step 1 | Colorless Oil |
| 104 | 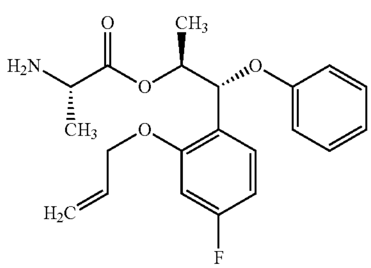 [SMILES: C=CCOc1cc(F)ccc1[C@@H](Oc1ccccc1)[C@H](C)OC(=O)[C@H](C)N] | Example 6, step 1 | Colorless Oil |
| 105 | 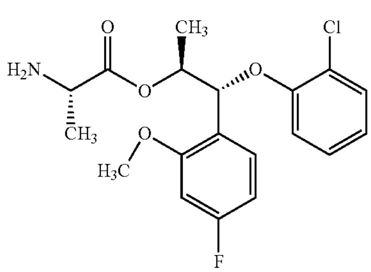 [SMILES: COc1cc(F)ccc1[C@@H](Oc1ccccc1Cl)[C@H](C)OC(=O)[C@H](C)N] | Example 6, step 1 | Oily White Solid |

TABLE 1-continued

Compound Structure, Appearance, and Preparation Method

| *Cmpd. No. | Structure | Prepared According to Example | Appearance |
|---|---|---|---|
| 106 | 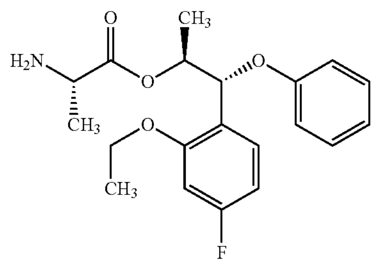 [SMILES: CCOc1cc(F)ccc1[C@@H](Oc1ccccc1)[C@H](C)OC(=O)[C@H](C)N] | Example 6, step 1 | Colorless Oil |
| 107 | 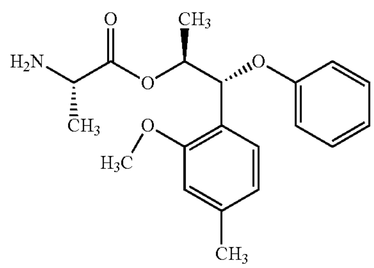 [SMILES: COc1cc(C)ccc1[C@@H](Oc1ccccc1)[C@H](C)OC(=O)[C@H](C)N] | Example 6, step 1 | Colorless Oil |
| 108 | 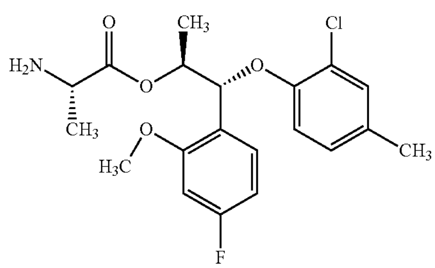 [SMILES: COc1cc(F)ccc1[C@@H](Oc1ccc(C)cc1Cl)[C@H](C)OC(=O)[C@H](C)N] | Example 6, step 1 | Oily White Solid |
| 109 | 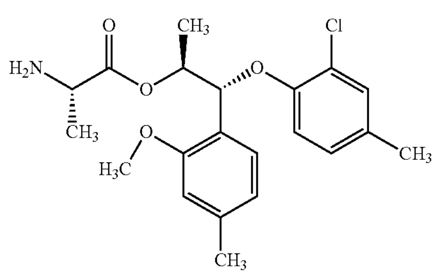 [SMILES: COc1cc(C)ccc1[C@@H](Oc1ccc(C)cc1Cl)[C@H](C)OC(=O)[C@H](C)N] | Example 6, step 1 | White Solid |
| 110 | 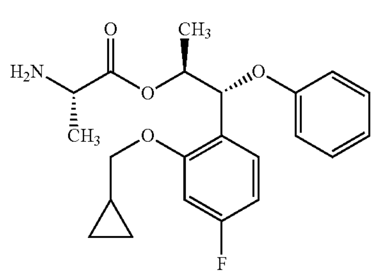 [SMILES: C[C@H](N)C(=O)O[C@@H](C)[C@H](Oc1ccccc1)c1ccc(F)cc1OCC1CC1] | Example 6, step 1 | Colorless Oil |

TABLE 1-continued

Compound Structure, Appearance, and Preparation Method

| *Cmpd. No. | Structure | Prepared According to Example | Colorless Semi-Solid |
|---|---|---|---|
| 111 | 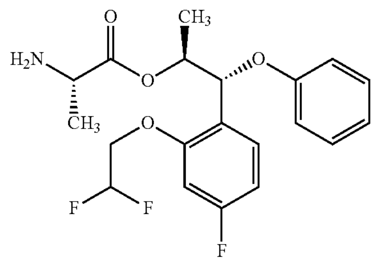 [SMILES: C[C@H](N)C(=O)O[C@@H](C)[C@H](Oc1ccccc1)c1ccc(F)cc1OCC(F)F] | Example 6, step 1 | Colorless Oil |
| 112 | 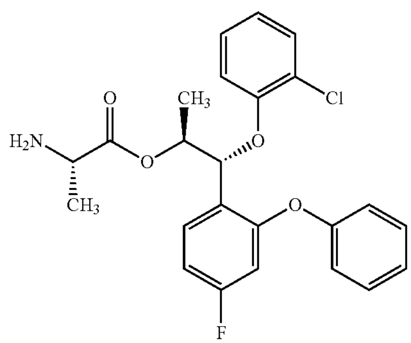 [SMILES: C[C@H](N)C(=O)O[C@@H](C)[C@H](Oc1ccccc1Cl)c1ccc(F)cc1Oc1ccccc1] | Example 6, step 1 | Colorless Oil |
| 113 | 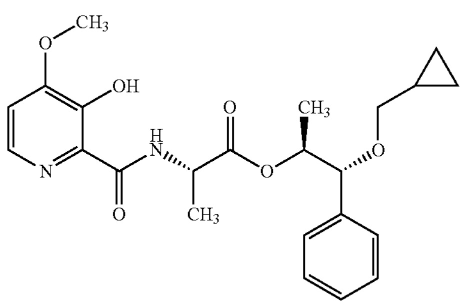 [SMILES: COc1ccnc(C(=O)N[C@@H](C)C(=O)O[C@@H](C)[C@H](OCC2CC2)c2ccccc2)c1O] | Example 6, Steps 1, 2 | Colorless Semi-Solid |
| 114 | 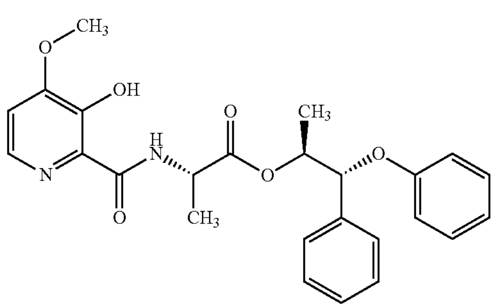 [SMILES: COc1ccnc(C(=O)N[C@@H](C)C(=O)O[C@@H](C)[C@H](Oc2ccccc2)c2ccccc2)c1O] | Example 6, Step 2 | White Solid |
| 115 | 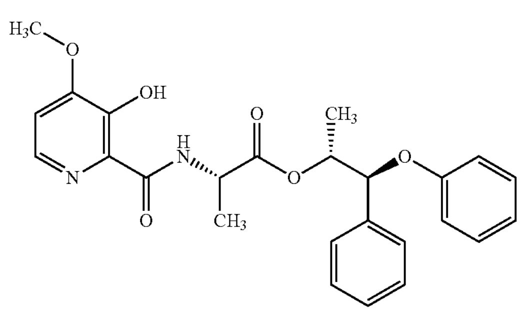 [SMILES: COc1ccnc(C(=O)N[C@@H](C)C(=O)O[C@H](C)[C@@H](Oc2ccccc2)c2ccccc2)c1O] | Example 6, Step 2 | White Foam |

TABLE 1-continued
Compound Structure, Appearance, and Preparation Method
| *Cmpd. No. | Structure | Prepared According to Example | Colorless Semi-Solid |
|---|---|---|---|
| 116 | 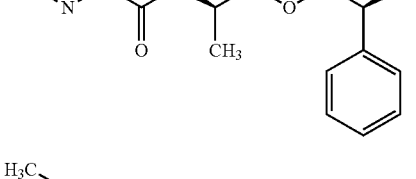 | Example 6, Step 2 | Whiote Foam |
| 117 | 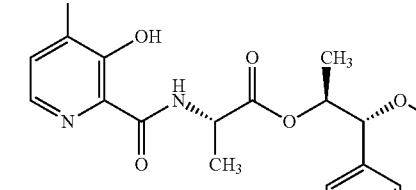 | Example 6, Step 2 | White Powder |
| 118 | 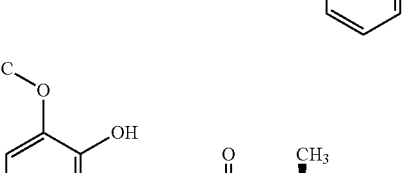 | Example 6, Step 2 | White Powder |
| 119 | 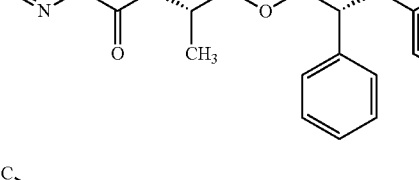 | Example 6, Step 2 | White Powder |
| 120 | 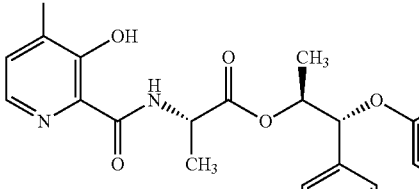 | Example 6, Step 2 | White Powder |

TABLE 1-continued

Compound Structure, Appearance, and Preparation Method

| *Cmpd. No. | Structure | Prepared According to Example | Colorless Semi-Solid |
|---|---|---|---|
| 121 | 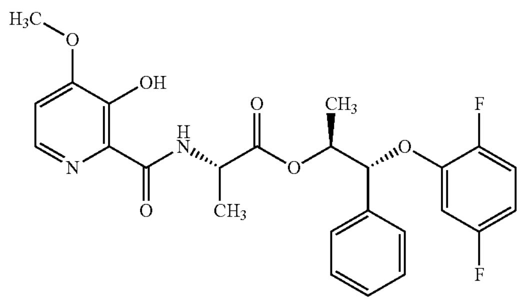 [SMILES: COc1ccnc(C(=O)N[C@@H](C)C(=O)O[C@@H](C)[C@H](Oc2cc(F)ccc2F)c2ccccc2)c1O] | Example 6, Step 2 | Hygroscopic White Powder |
| 122 | 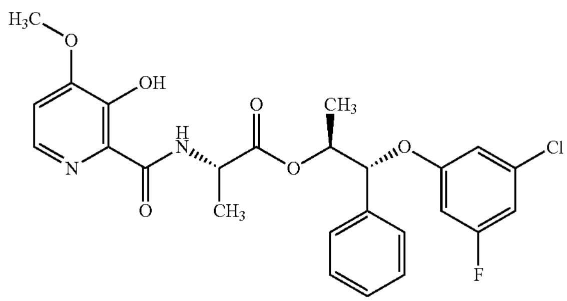 [SMILES: COc1ccnc(C(=O)N[C@@H](C)C(=O)O[C@@H](C)[C@H](Oc2cc(F)cc(Cl)c2)c2ccccc2)c1O] | Example 6, Step 2 | Hygroscopic White Powder |
| 123 | 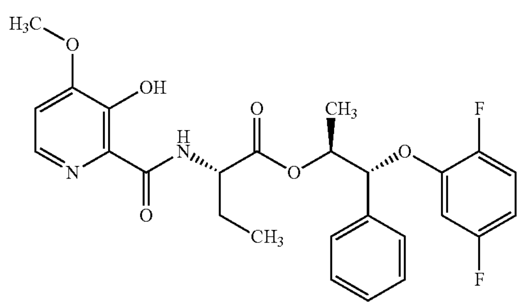 [SMILES: CC[C@H](NC(=O)c1nccc(OC)c1O)C(=O)O[C@@H](C)[C@H](Oc1cc(F)ccc1F)c1ccccc1] | Example 6, Step 2 | Hygroscopic White Powder |
| 124 | 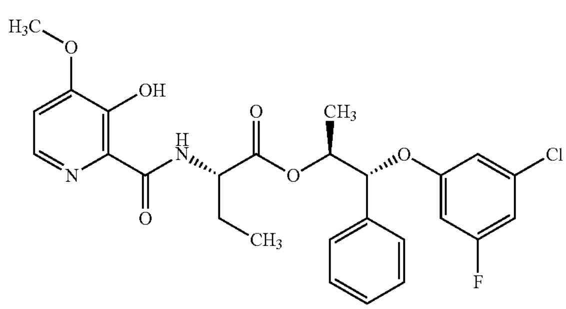 [SMILES: CC[C@H](NC(=O)c1nccc(OC)c1O)C(=O)O[C@@H](C)[C@H](Oc1cc(F)cc(Cl)c1)c1ccccc1] | Example 6, Step 2 | Hygroscopic White Powder |
| 125 | 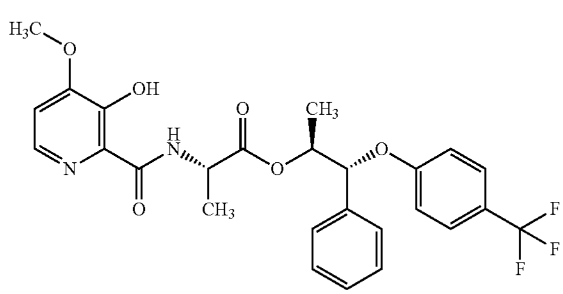 [SMILES: COc1ccnc(C(=O)N[C@@H](C)C(=O)O[C@@H](C)[C@H](Oc2ccc(C(F)(F)F)cc2)c2ccccc2)c1O] | Example 6, Step 2 | White Powder |

TABLE 1-continued

Compound Structure, Appearance, and Preparation Method

| *Cmpd. No. | Structure | Prepared According to Example | Colorless Semi-Solid |
|---|---|---|---|
| 126 | 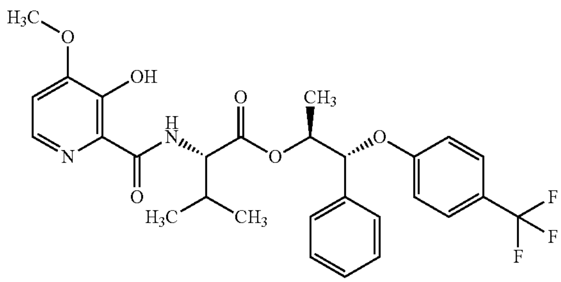 [SMILES: COc1ccnc(C(=O)N[C@H](C(=O)O[C@@H](C)[C@H](Oc2ccc(C(F)(F)F)cc2)c2ccccc2)C(C)C)c1O] | Example 6, Step 2 | White Powder |
| 127 | 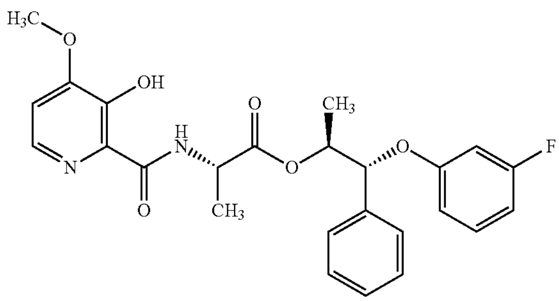 [SMILES: COc1ccnc(C(=O)N[C@@H](C)C(=O)O[C@@H](C)[C@H](Oc2cccc(F)c2)c2ccccc2)c1O] | Example 6, Step 2 | Hygroscopic White Powder |
| 128 | 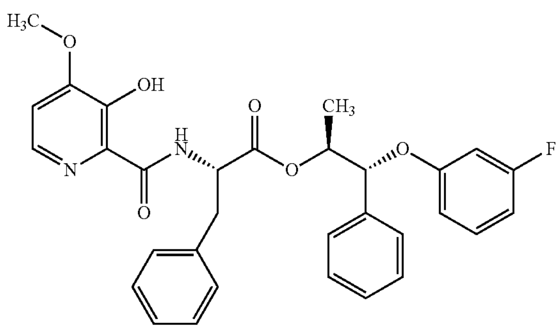 [SMILES: COc1ccnc(C(=O)N[C@@H](Cc2ccccc2)C(=O)O[C@@H](C)[C@H](Oc2cccc(F)c2)c2ccccc2)c1O] | Example 6, Step 2 | White Powder |
| 129 | 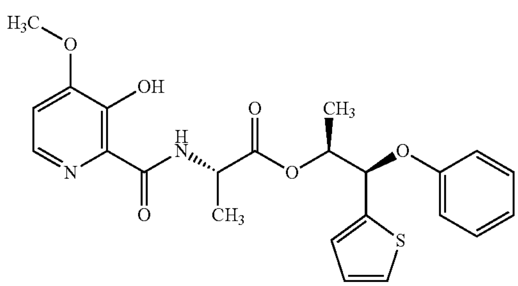 [SMILES: COc1ccnc(C(=O)N[C@@H](C)C(=O)O[C@@H](C)[C@@H](Oc2ccccc2)c2cccs2)c1O] | Example 6, Steps 1, 2 | Colorless Oil |
| 130 | 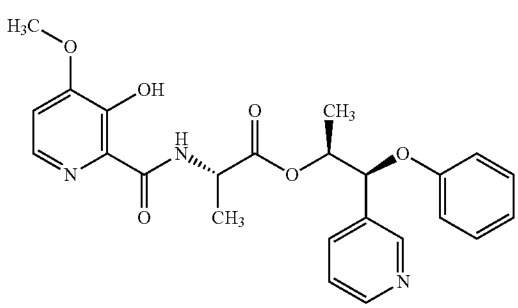 [SMILES: COc1ccnc(C(=O)N[C@@H](C)C(=O)O[C@@H](C)[C@@H](Oc2ccccc2)c2cccnc2)c1O] | Example 6, Steps 1, 2 | Colorless Oil |

TABLE 1-continued

Compound Structure, Appearance, and Preparation Method

| *Cmpd. No. | Structure | Prepared According to Example | Colorless Semi-Solid |
|---|---|---|---|
| 131 | 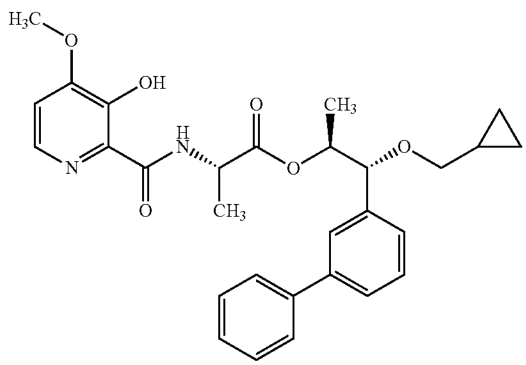 [SMILES: COc1ccnc(C(=O)N[C@@H](C)C(=O)O[C@@H](C)[C@H](OCC2CC2)c2cccc(-c3ccccc3)c2)c1O] | Example 6, Step 2 | Colorless Oil |
| 132 | 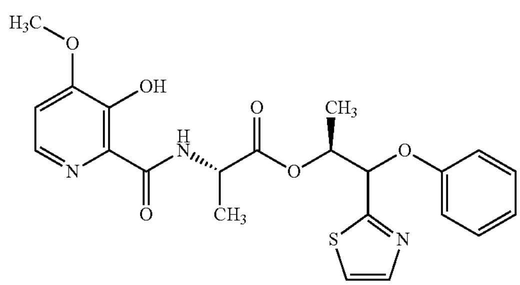 [SMILES: COc1ccnc(C(=O)N[C@@H](C)C(=O)O[C@@H](C)C(Oc2ccccc2)c2nccs2)c1O] | Example 6, Steps 1, 2 | Colorless Foam/Oil |
| 133 | 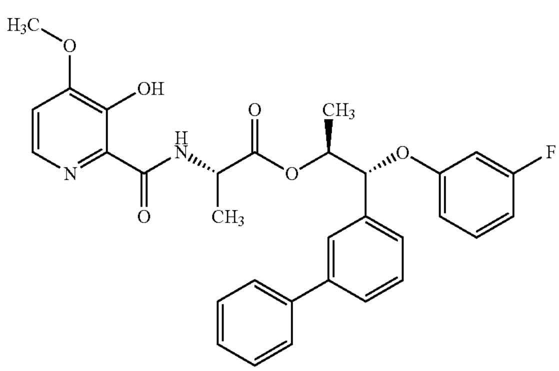 [SMILES: COc1ccnc(C(=O)N[C@@H](C)C(=O)O[C@@H](C)[C@H](Oc2cccc(F)c2)c2cccc(-c3ccccc3)c2)c1O] | Example 6, Step 2 | Foamy White Solid |
| 134 | 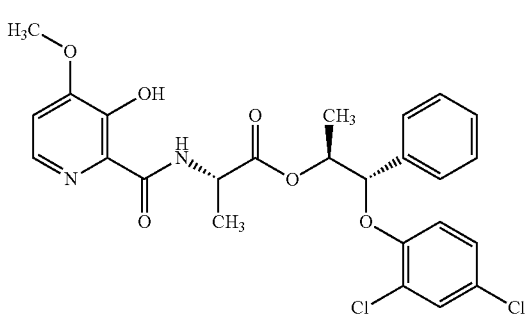 [SMILES: COc1ccnc(C(=O)N[C@@H](C)C(=O)O[C@@H](C)[C@@H](Oc2ccc(Cl)cc2Cl)c2ccccc2)c1O] | Example 6, Step 2 | White Foam |

TABLE 1-continued

Compound Structure, Appearance, and Preparation Method

| *Cmpd. No. | Structure | Prepared According to Example | Colorless Semi-Solid |
|---|---|---|---|
| 135 | 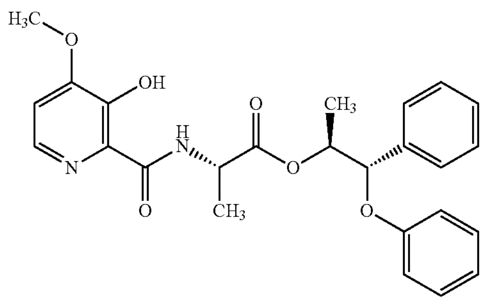 [SMILES: COc1ccnc(C(=O)N[C@@H](C)C(=O)O[C@@H](C)[C@@H](Oc2ccccc2)c2ccccc2)c1O] | Example 7A | Colorless Oil |
| 136 | 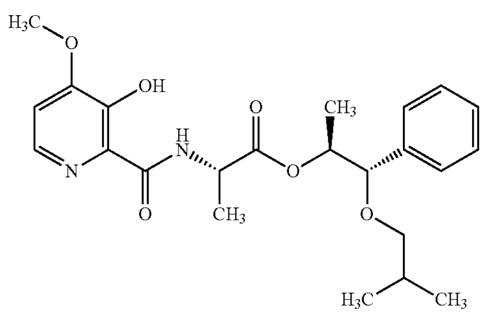 [SMILES: COc1ccnc(C(=O)N[C@@H](C)C(=O)O[C@@H](C)[C@@H](OCC(C)C)c2ccccc2)c1O] | Example 6, Step 2 | Colorless Oil |
| 137 | 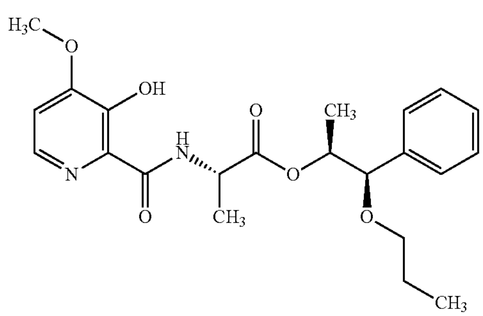 [SMILES: CCCO[C@H](c1ccccc1)[C@H](C)OC(=O)[C@H](C)NC(=O)c1nccc(OC)c1O] | Example 6, Step 2 | Colorless Oil |
| 138 | 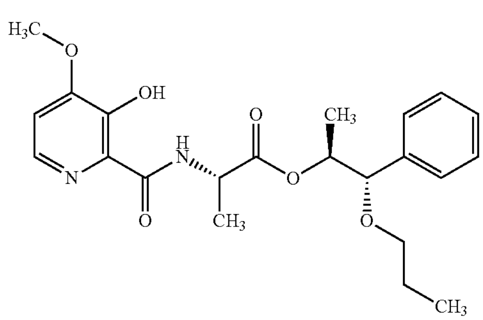 [SMILES: CCCO[C@@H](c1ccccc1)[C@H](C)OC(=O)[C@H](C)NC(=O)c1nccc(OC)c1O] | Example 6, Steps 1, 2 | Colorless Oil |

TABLE 1-continued
Compound Structure, Appearance, and Preparation Method
| *Cmpd. No. | Structure | Prepared According to Example | Colorless Semi-Solid |
|---|---|---|---|
| 139 | 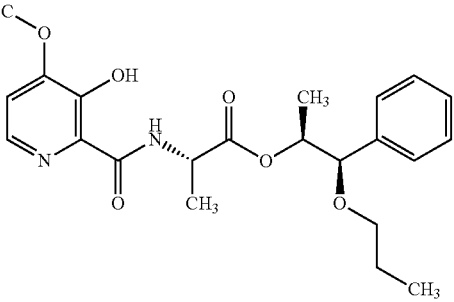 | Example 6, Steps 1, 2 | Colorless Oil |
| 140 | 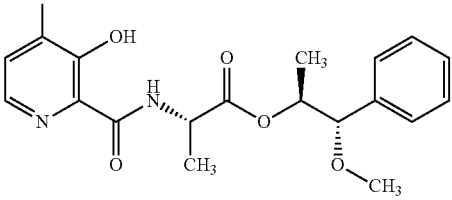 | Example 6, Steps 1, 2 | Colorless Oil |
| 141 | 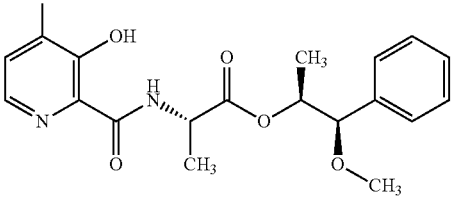 | Example 6, Steps 1, 2 | Colorless Oil |
| 142 | 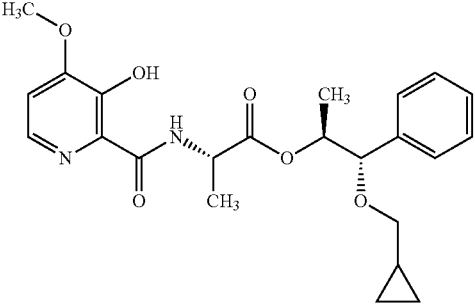 [SMILES: COc1ccnc(C(=O)N[C@@H](C)C(=O)O[C@@H](C)[C@@H](OCC2CC2)c2ccccc2)c1O] | Example 6, Steps 1, 2 | Colorless Oil |

TABLE 1-continued
Compound Structure, Appearance, and Preparation Method
| *Cmpd. No. | Structure | Prepared According to Example | Colorless Semi-Solid |
|---|---|---|---|
| 143 | 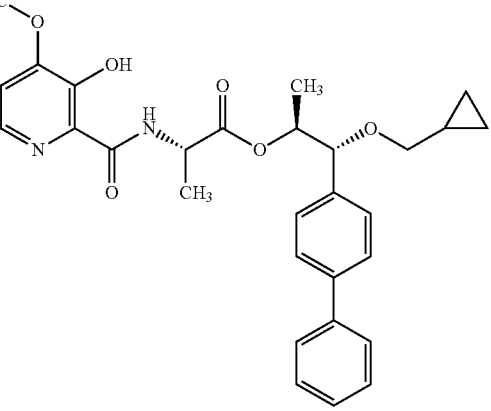 | Example 6, Step 2 | Beige Solid |
| 144 | 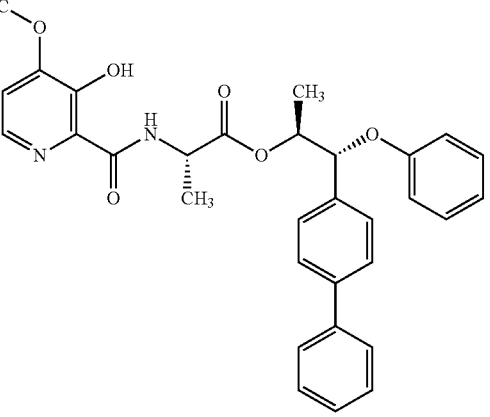 | Example 6, Step 2 | Colorless Oil |
| 145 | 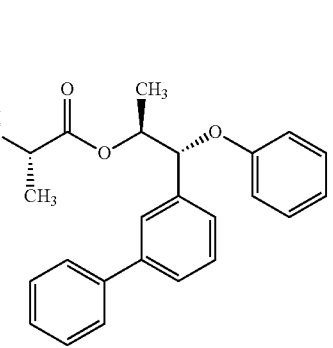 | Example 6, Step 2 | Colorless Oil |
| 146 | 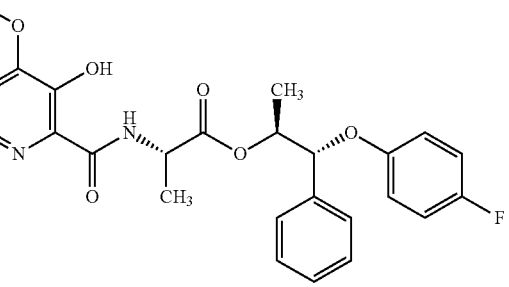 | Example 6, Step 2 | Colorless Oil |

TABLE 1-continued

Compound Structure, Appearance, and Preparation Method

| *Cmpd. No. | Structure | Prepared According to Example | Colorless Semi-Solid |
|---|---|---|---|
| 147 | 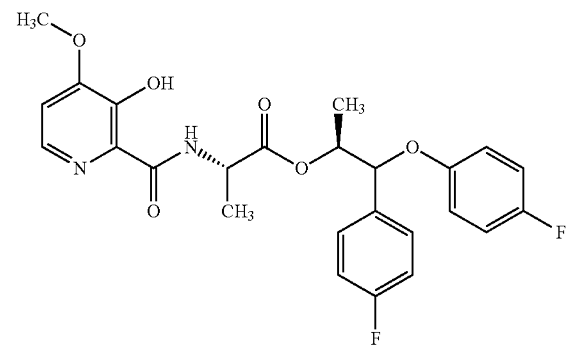 [SMILES: COc1ccnc(C(=O)N[C@@H](C)C(=O)O[C@@H](C)C(Oc2ccc(F)cc2)c2ccc(F)cc2)c1O] | Example 6, Step 2 | Colorless Oil |
| 148 | 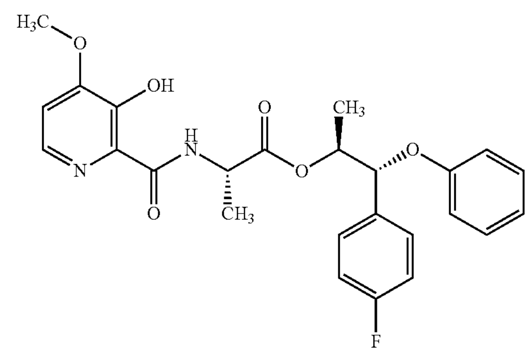 [SMILES: COc1ccnc(C(=O)N[C@@H](C)C(=O)O[C@@H](C)[C@H](Oc2ccccc2)c2ccc(F)cc2)c1O] | Example 6, Step 2 | Colorless Oil |
| 149 | 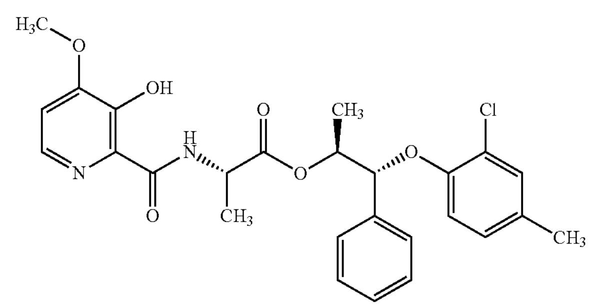 [SMILES: COc1ccnc(C(=O)N[C@@H](C)C(=O)O[C@@H](C)[C@H](Oc2ccc(C)cc2Cl)c2ccccc2)c1O] | Example 6, Step 2 | Colorless Oil |
| 150 | 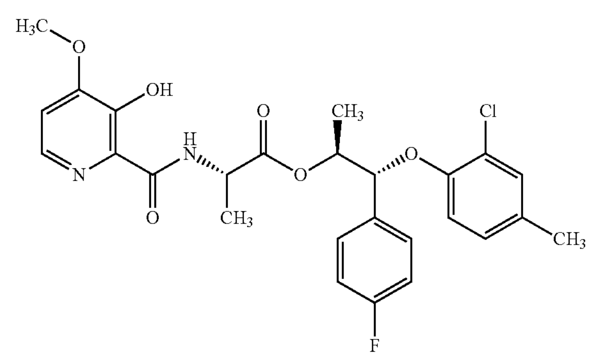 [SMILES: COc1ccnc(C(=O)N[C@@H](C)C(=O)O[C@@H](C)[C@H](Oc2ccc(C)cc2Cl)c2ccc(F)cc2)c1O] | Example 6, Step 2 | Colorless Oil |

TABLE 1-continued

Compound Structure, Appearance, and Preparation Method

| *Cmpd. No. | Structure | Prepared According to Example | Colorless Semi-Solid |
|---|---|---|---|
| 151 | 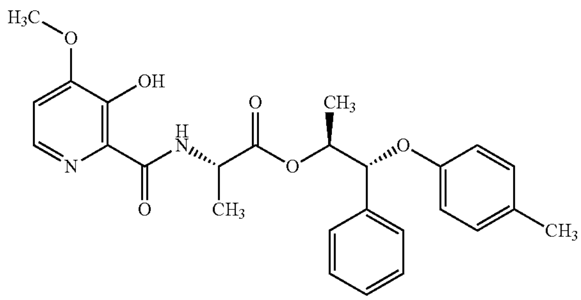 [SMILES: COc1ccnc(C(=O)N[C@@H](C)C(=O)O[C@@H](C)[C@H](Oc2ccc(C)cc2)c2ccccc2)c1O] | Example 7A | Colorless Oil |
| 152 | 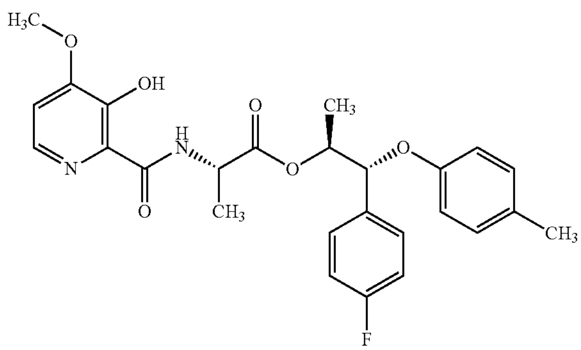 [SMILES: COc1ccnc(C(=O)N[C@@H](C)C(=O)O[C@@H](C)[C@H](Oc2ccc(C)cc2)c2ccc(F)cc2)c1O] | Example 7A | Colorless Oil |
| 153 | 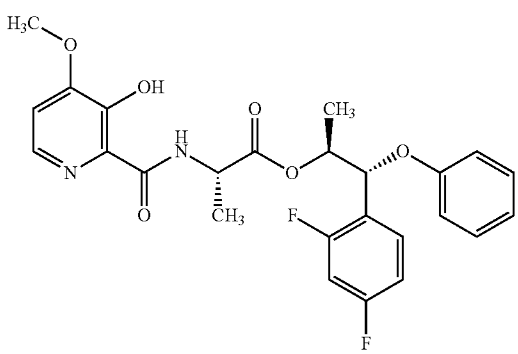 [SMILES: COc1ccnc(C(=O)N[C@@H](C)C(=O)O[C@@H](C)[C@H](Oc2ccccc2)c2ccc(F)cc2F)c1O] | Example 6, Step 2 | Colorless Oil |
| 154 | 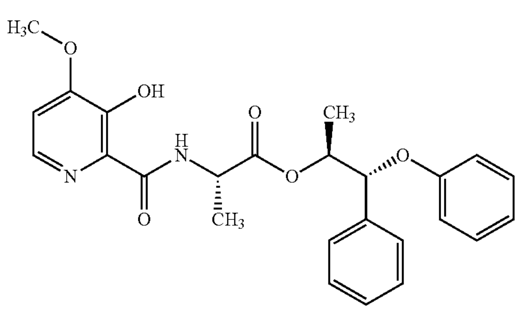 [SMILES: COc1ccnc(C(=O)N[C@@H](C)C(=O)O[C@@H](C)[C@H](Oc2ccccc2)c2ccccc2)c1O] | Example 6, Step 2 | Viscous Foam |

TABLE 1-continued

Compound Structure, Appearance, and Preparation Method

| *Cmpd. No. | Structure | Prepared According to Example | Colorless Semi-Solid |
|---|---|---|---|
| 155 | 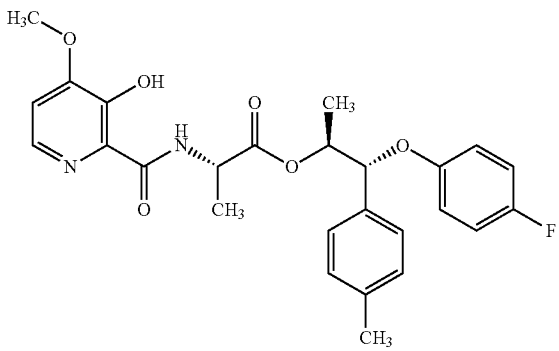 [SMILES: COc1ccnc(C(=O)N[C@@H](C)C(=O)O[C@@H](C)[C@H](Oc2ccc(F)cc2)c2ccc(C)cc2)c1O] | Example 6, Step 2 | Colorless Oil |
| 156 | 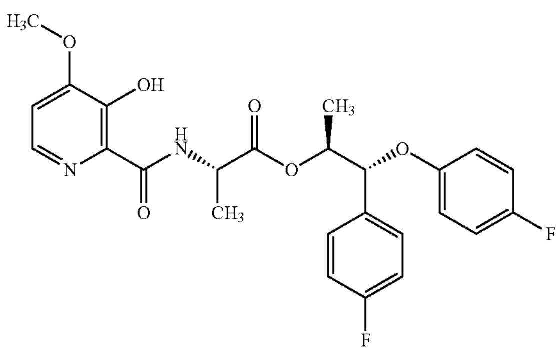 [SMILES: COc1ccnc(C(=O)N[C@@H](C)C(=O)O[C@@H](C)[C@H](Oc2ccc(F)cc2)c2ccc(F)cc2)c1O] | Example 6, Step 2 | Colorless Oil |
| 157 | 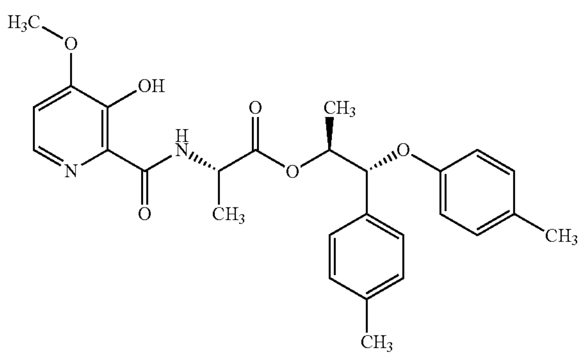 [SMILES: COc1ccnc(C(=O)N[C@@H](C)C(=O)O[C@@H](C)[C@H](Oc2ccc(C)cc2)c2ccc(C)cc2)c1O] | Example 7A | Colorless Oil |
| 158 | 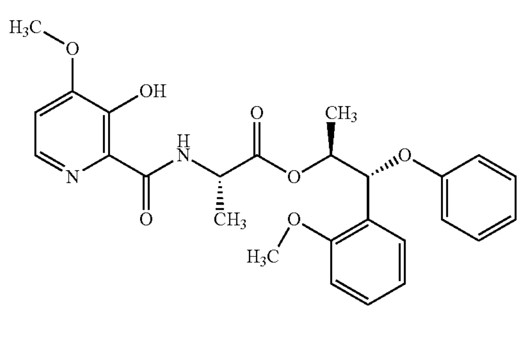 [SMILES: COc1ccccc1[C@@H](Oc1ccccc1)[C@H](C)OC(=O)[C@H](C)NC(=O)c1nccc(OC)c1O] | Example 6, Step 2 | Colorless Foam |

TABLE 1-continued

Compound Structure, Appearance, and Preparation Method

| *Cmpd. No. | Structure | Prepared According to Example | Colorless Semi-Solid |
|---|---|---|---|
| 159 | 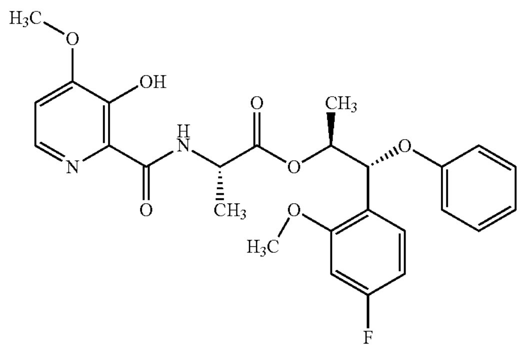 [SMILES: COc1cc(F)ccc1[C@@H](Oc1ccccc1)[C@H](C)OC(=O)[C@H](C)NC(=O)c1nccc(OC)c1O] | Example 6, Step 2 | Colorless Foam |
| 160 | 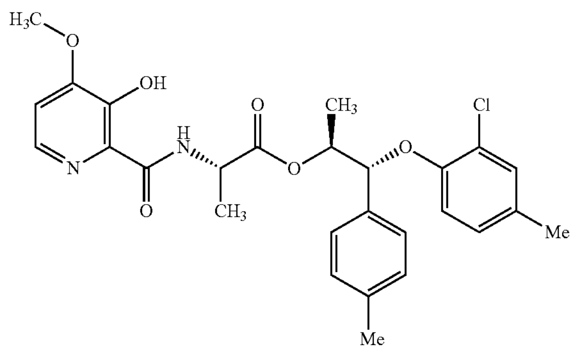 [SMILES: COc1ccnc(C(=O)N[C@@H](C)C(=O)O[C@@H](C)[C@H](Oc2ccc(C)cc2Cl)c2ccc(C)cc2)c1O] | Example 6, Step 2 | Colorless Oil |
| 161 | 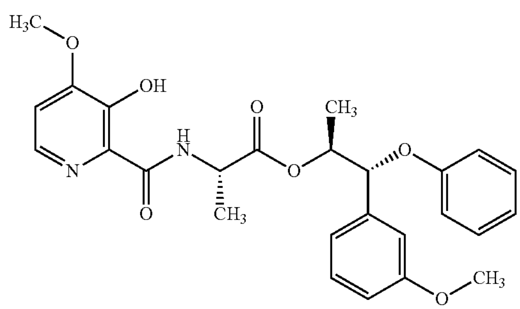 [SMILES: COc1cccc([C@@H](Oc2ccccc2)[C@H](C)OC(=O)[C@H](C)NC(=O)c2nccc(OC)c2O)c1] | Example 6, Step 2 | Colorless Oil |
| 162 | 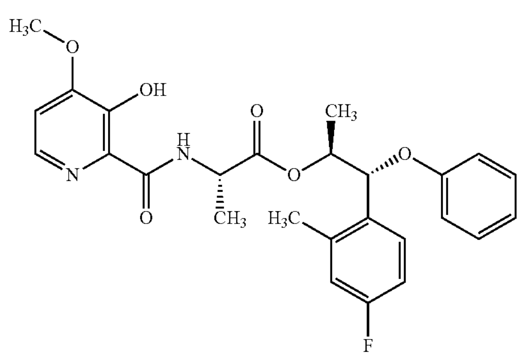 [SMILES: COc1ccnc(C(=O)N[C@@H](C)C(=O)O[C@@H](C)[C@H](Oc2ccccc2)c2ccc(F)cc2C)c1O] | Example 6, Step 2 | Colorless Oil |

TABLE 1-continued
Compound Structure, Appearance, and Preparation Method
| *Cmpd. No. | Structure | Prepared According to Example | Colorless Semi-Solid |
|---|---|---|---|
| 163 | 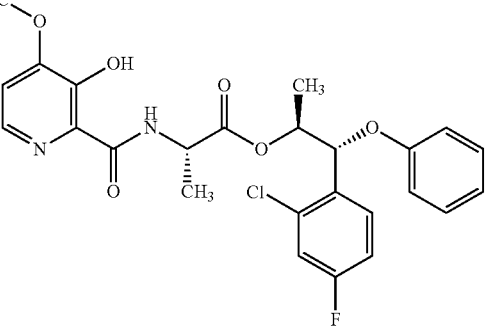 | Example 6, Step 2 | Colorless Foamy Oil |
| 164 | 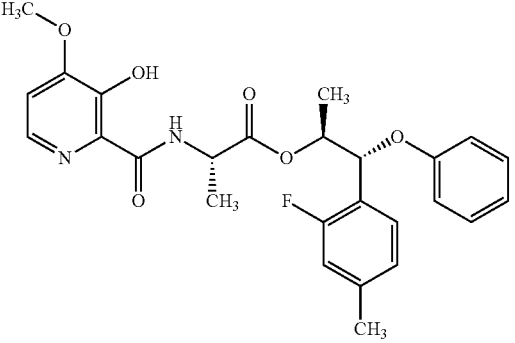 [SMILES: COc1ccnc(C(=O)N[C@@H](C)C(=O)O[C@@H](C)[C@H](Oc2ccccc2)c2ccc(C)cc2F)c1O] | Example 6, Step 2 | Colorless Oil |
| 165 | 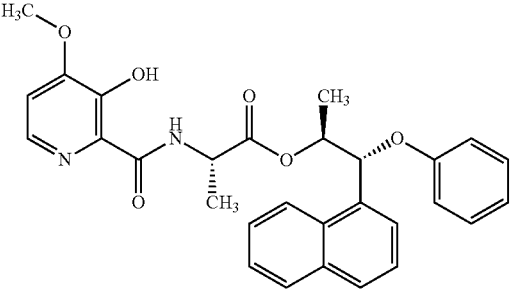 [SMILES: COc1ccnc(C(=O)N[C@@H](C)C(=O)O[C@@H](C)[C@H](Oc2ccccc2)c2cccc3ccccc23)c1O] | Example 6, Step 2 | White Foam |
| 166 | 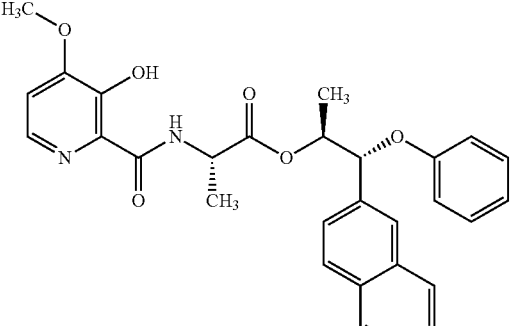 | Example 6, Step 2 | White Foam |

TABLE 1-continued

Compound Structure, Appearance, and Preparation Method

| *Cmpd. No. | Structure | Prepared According to Example | Colorless Semi-Solid |
|---|---|---|---|
| 167 | 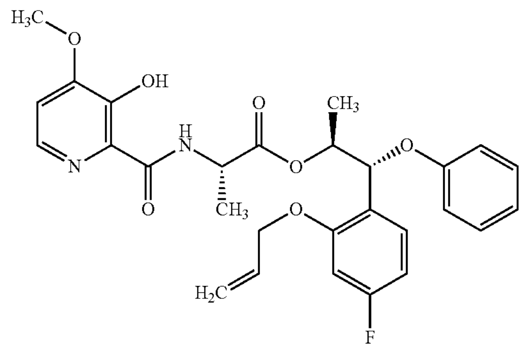 [SMILES: C=CCOc1cc(F)ccc1[C@@H](Oc1ccccc1)[C@H](C)OC(=O)[C@H](C)NC(=O)c1nccc(OC)c1O] | Example 6, Step 2 | Foamy White Solid |
| 168 | 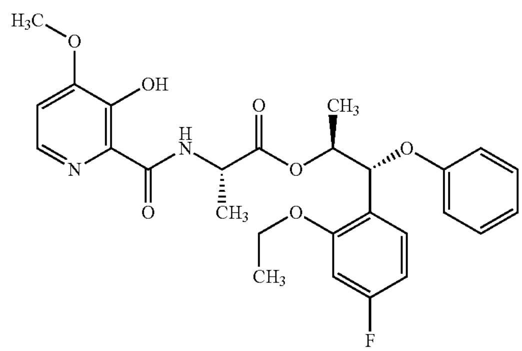 [SMILES: CCOc1cc(F)ccc1[C@@H](Oc1ccccc1)[C@H](C)OC(=O)[C@H](C)NC(=O)c1nccc(OC)c1O] | Example 6, Step 2 | White Foam |
| 169 | 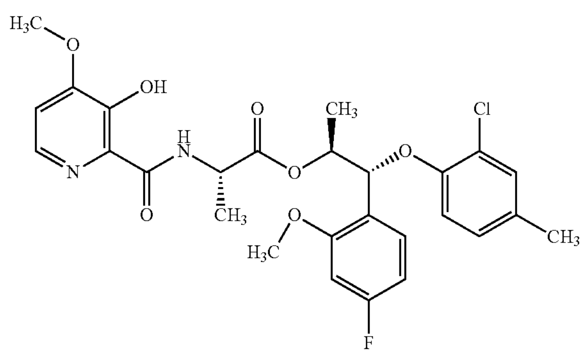 [SMILES: COc1cc(F)ccc1[C@@H](Oc1ccc(C)cc1Cl)[C@H](C)OC(=O)[C@H](C)NC(=O)c1nccc(OC)c1O] | Example 6, Step 2 | White Foam |
| 170 | 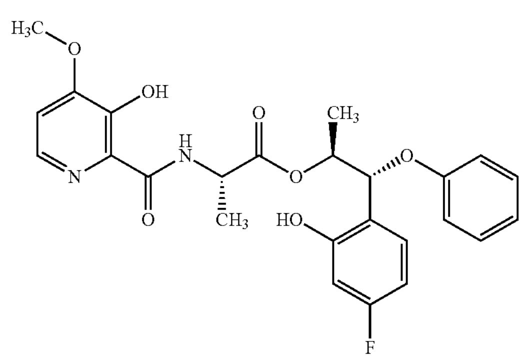 [SMILES: COc1ccnc(C(=O)N[C@@H](C)C(=O)O[C@@H](C)[C@H](Oc2ccccc2)c2ccc(F)cc2O)c1O] | Example 6, Step 2; Example 7B | Oily White Solid |

TABLE 1-continued

| *Cmpd. No. | Structure | Prepared According to Example | Colorless Semi-Solid |
|---|---|---|---|
| 171 | 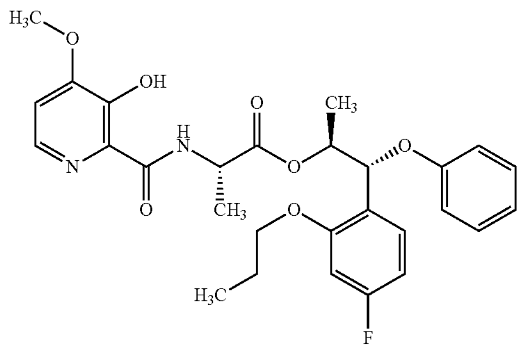 [SMILES: CCCOc1cc(F)ccc1[C@@H](Oc1ccccc1)[C@H](C)OC(=O)[C@H](C)NC(=O)c1nccc(OC)c1O] | Example 6, Step 2; Example 7B | Colorless Oil |
| 172 | 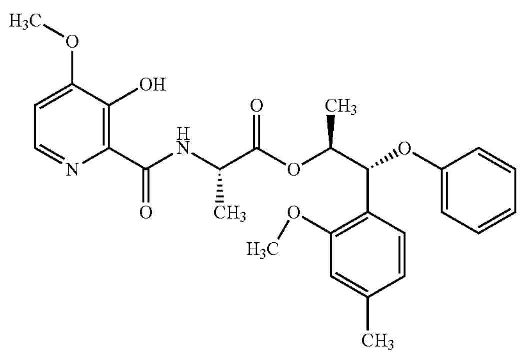 [SMILES: COc1cc(C)ccc1[C@@H](Oc1ccccc1)[C@H](C)OC(=O)[C@H](C)NC(=O)c1nccc(OC)c1O] | Example 6, Step 2 | White Foam |
| 173 | 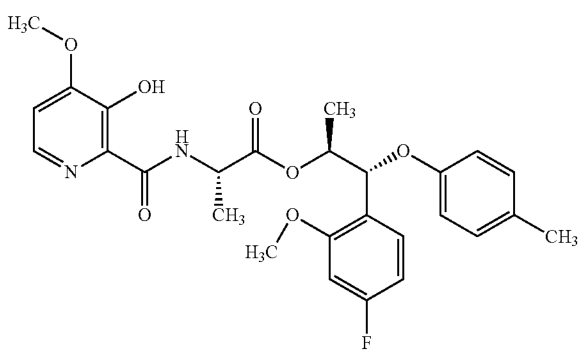 [SMILES: COc1cc(F)ccc1[C@@H](Oc1ccc(C)cc1)[C@H](C)OC(=O)[C@H](C)NC(=O)c1nccc(OC)c1O] | Example 6, Step 2; Example 7A | White Foam |
| 174 | 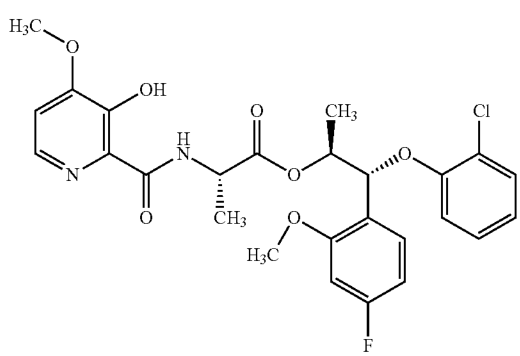 [SMILES: COc1cc(F)ccc1[C@@H](Oc1ccccc1Cl)[C@H](C)OC(=O)[C@H](C)NC(=O)c1nccc(OC)c1O] | Example 6, Step 2 | White Foamy Solid |

TABLE 1-continued
Compound Structure, Appearance, and Preparation Method
| *Cmpd. No. | Structure | Prepared According to Example | Colorless Semi-Solid |
|---|---|---|---|
| 175 | 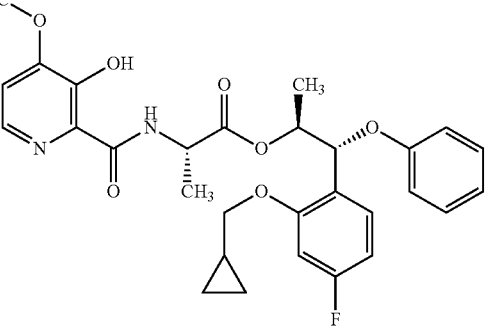 | Example 6, Step 2 | Colorless Oil |
| 176 | 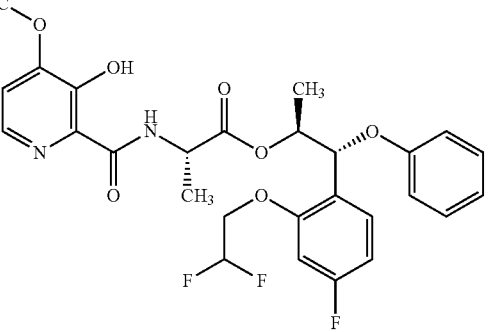 | Example 6, Step 2 | Colorless Oil |
| 177 | 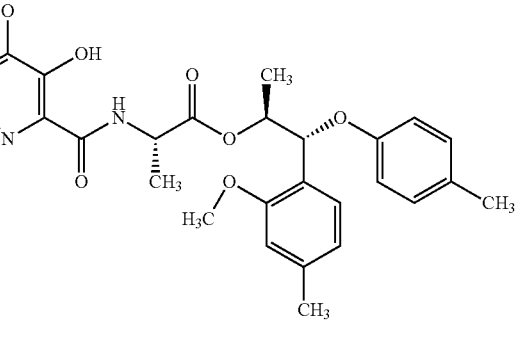 | Example 6, Step 2; Example 7A | Colorless Oil |
| 178 | 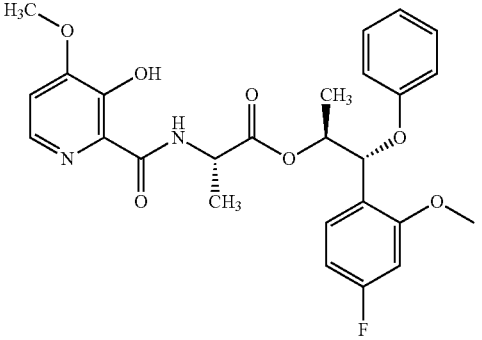 [SMILES: COc1cc(F)ccc1[C@@H](Oc1ccccc1)[C@H](C)OC(=O)[C@H](C)NC(=O)c1nccc(OC)c1O] | Example 6, Step 2; Example 7A | White Foam |

TABLE 1-continued

Compound Structure, Appearance, and Preparation Method

| *Cmpd. No. | Structure | Prepared According to Example | |
|---|---|---|---|
| 179 | 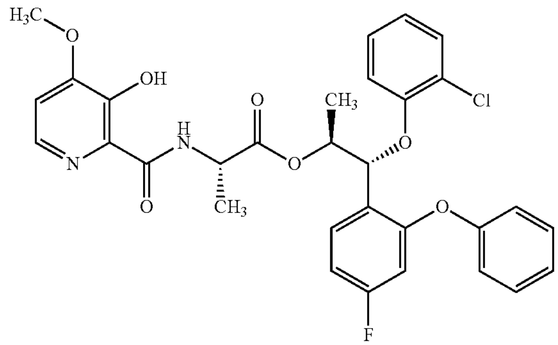 [SMILES: COc1ccnc(C(=O)N[C@@H](C)C(=O)O[C@@H](C)[C@H](Oc2ccccc2Cl)c2ccc(F)cc2Oc2ccccc2)c1O] | Example 6, Step 2 | White Foam |
| 180 | 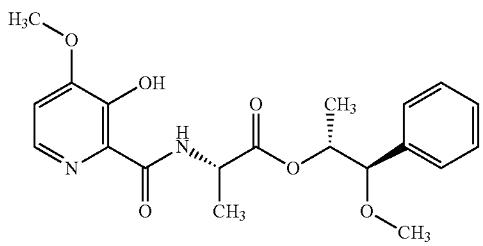 [SMILES: COc1ccnc(C(=O)N[C@@H](C)C(=O)O[C@H](C)[C@H](OC)c2ccccc2)c1O] | Example 6, Step 2 | Colorless Oil |
| 181 | 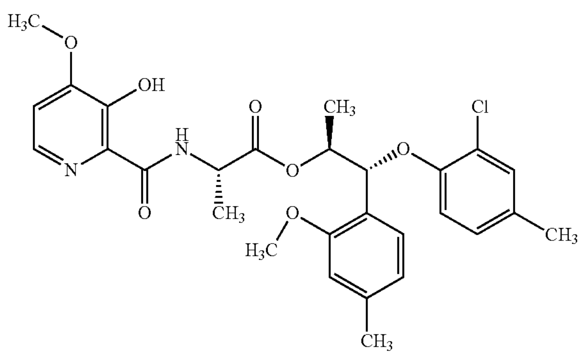 [SMILES: COc1cc(C)ccc1[C@@H](Oc1ccc(C)cc1Cl)[C@H](C)OC(=O)[C@H](C)NC(=O)c1nccc(OC)c1O] | Example 6, Step 2 | Colorless Oil |
| 182 | 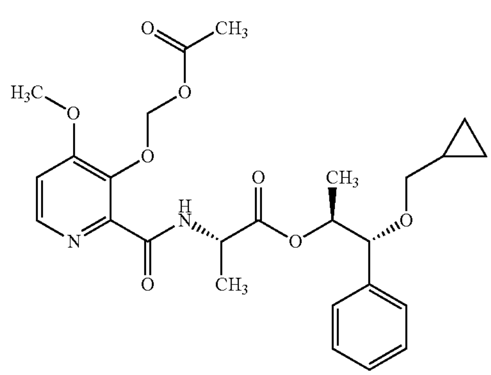 [SMILES: COc1ccnc(C(=O)N[C@@H](C)C(=O)O[C@@H](C)[C@H](OCC2CC2)c2ccccc2)c1OCOC(C)=O] | Example 8A | Light Yellow Semi-Solid |

TABLE 1-continued

Compound Structure, Appearance, and Preparation Method

| *Cmpd. No. | Structure | Prepared According to Example | Colorless Semi-Solid |
|---|---|---|---|
| 183 | 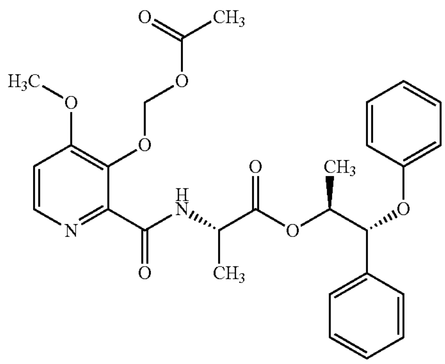 [SMILES: COc1ccnc(C(=O)N[C@@H](C)C(=O)O[C@@H](C)[C@H](Oc2ccccc2)c2ccccc2)c1OCOC(C)=O] | Example 8A | Yellow Solid |
| 184 | 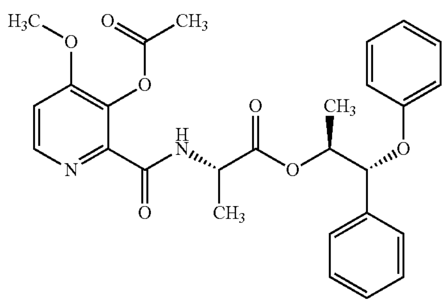 [SMILES: COc1ccnc(C(=O)N[C@@H](C)C(=O)O[C@@H](C)[C@H](Oc2ccccc2)c2ccccc2)c1OC(C)=O] | Example 8B | White Solid |
| 185 | 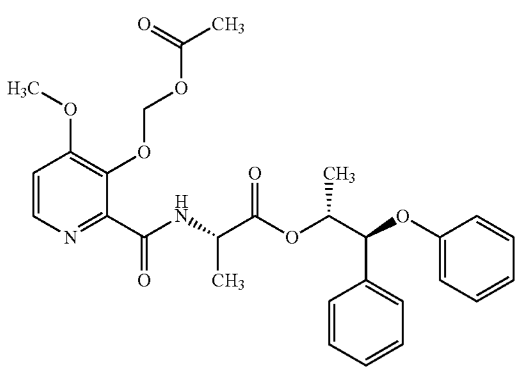 [SMILES: COc1ccnc(C(=O)N[C@@H](C)C(=O)O[C@H](C)[C@@H](Oc2ccccc2)c2ccccc2)c1OCOC(C)=O] | Example 8A | White Foam |
| 186 | 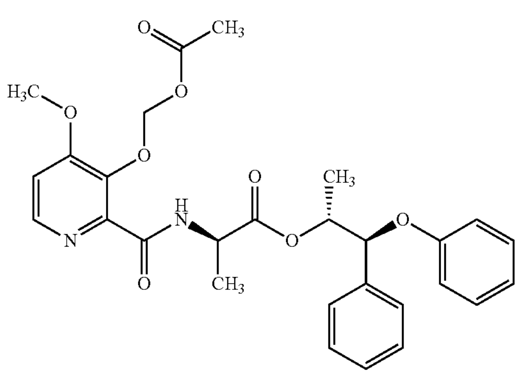 [SMILES: COc1ccnc(C(=O)N[C@H](C)C(=O)O[C@H](C)[C@@H](Oc2ccccc2)c2ccccc2)c1OCOC(C)=O] | Example 8A | White Foam |

TABLE 1-continued

Compound Structure, Appearance, and Preparation Method

| *Cmpd. No. | Structure | Prepared According to Example | Colorless Semi-Solid |
|---|---|---|---|
| 187 | 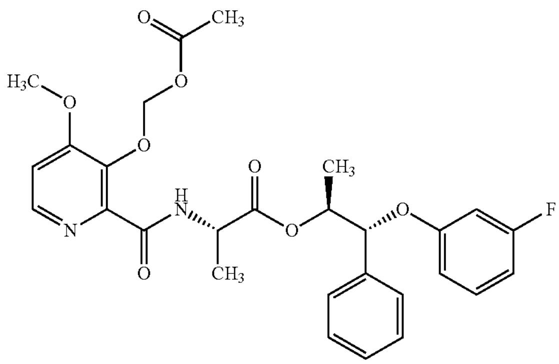 [SMILES: COc1ccnc(C(=O)N[C@@H](C)C(=O)O[C@@H](C)[C@H](Oc2cccc(F)c2)c2ccccc2)c1OCOC(C)=O] | Example 8A | White Powder |
| 188 | 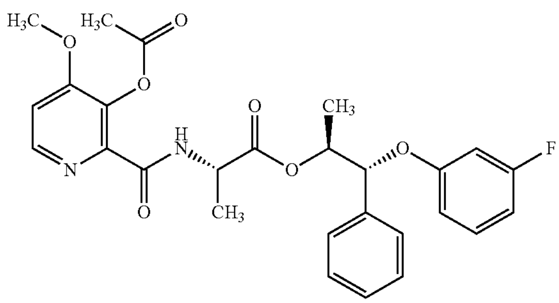 [SMILES: COc1ccnc(C(=O)N[C@@H](C)C(=O)O[C@@H](C)[C@H](Oc2cccc(F)c2)c2ccccc2)c1OC(C)=O] | Example 8B | White Powder |
| 189 | 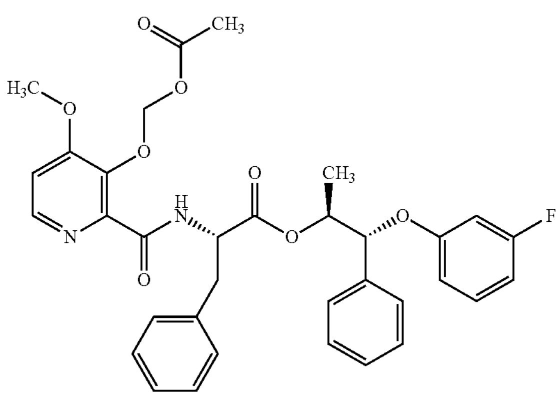 [SMILES: COc1ccnc(C(=O)N[C@@H](Cc2ccccc2)C(=O)O[C@@H](C)[C@H](Oc2cccc(F)c2)c2ccccc2)c1OCOC(C)=O] | Example 8A | White Powder |
| 190 | 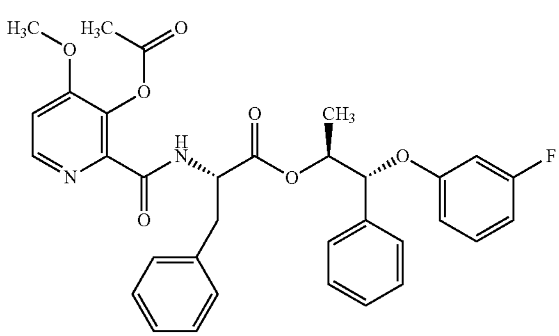 [SMILES: COc1ccnc(C(=O)N[C@@H](Cc2ccccc2)C(=O)O[C@@H](C)[C@H](Oc2cccc(F)c2)c2ccccc2)c1OC(C)=O] | Example 8B | White Powder |

TABLE 1-continued

Compound Structure, Appearance, and Preparation Method

| *Cmpd. No. | Structure | Prepared According to Example | Colorless Semi-Solid |
|---|---|---|---|
| 191 | 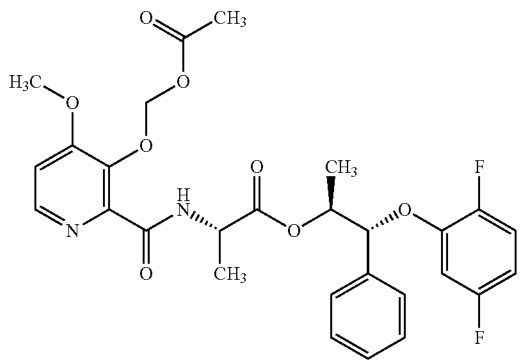 [SMILES: COc1ccnc(C(=O)N[C@@H](C)C(=O)O[C@@H](C)[C@H](Oc2cc(F)ccc2F)c2ccccc2)c1OCOC(C)=O] | Example 8A | White Powder |
| 192 | 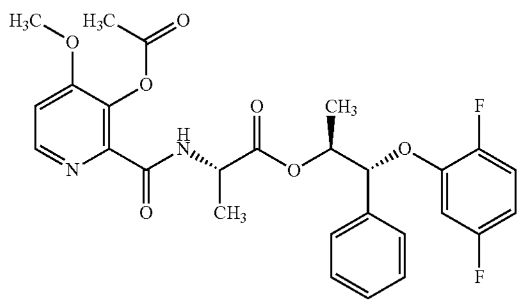 [SMILES: COc1ccnc(C(=O)N[C@@H](C)C(=O)O[C@@H](C)[C@H](Oc2cc(F)ccc2F)c2ccccc2)c1OC(C)=O] | Example 8B | White Powder |
| 193 | 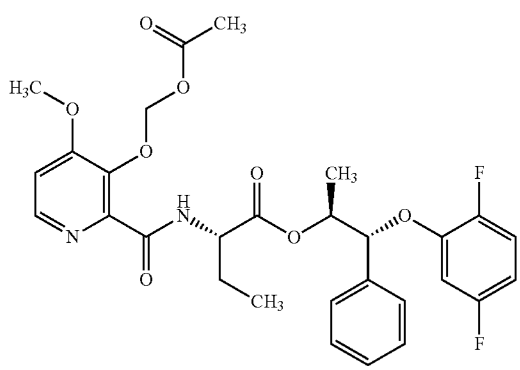 [SMILES: CC[C@H](NC(=O)c1nccc(OC)c1OCOC(C)=O)C(=O)O[C@@H](C)[C@H](Oc1cc(F)ccc1F)c1ccccc1] | Example 8A | Hygroscopic Solid |
| 194 | 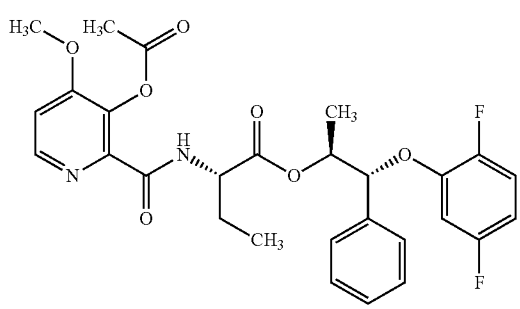 [SMILES: CC[C@H](NC(=O)c1nccc(OC)c1OC(C)=O)C(=O)O[C@@H](C)[C@H](Oc1cc(F)ccc1F)c1ccccc1] | Example 8B | White Powder |

TABLE 1-continued

Compound Structure, Appearance, and Preparation Method

| *Cmpd. No. | Structure | Prepared According to Example | Colorless Semi-Solid |
|---|---|---|---|
| 195 | 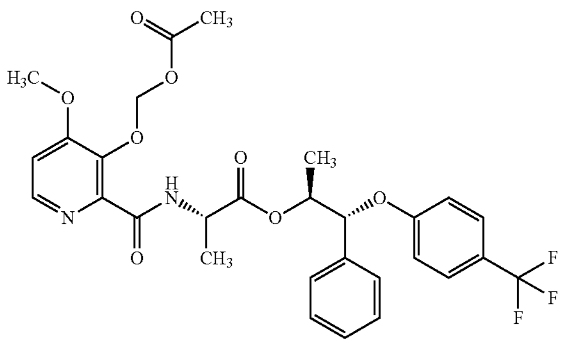 [SMILES: COc1ccnc(C(=O)N[C@@H](C)C(=O)O[C@@H](C)[C@H](Oc2ccc(C(F)(F)F)cc2)c2ccccc2)c1OCOC(C)=O] | Example 8A | White Powder |
| 196 | 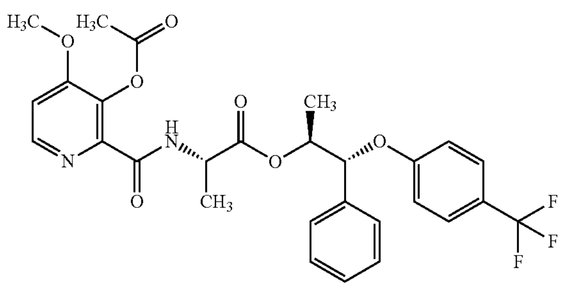 [SMILES: COc1ccnc(C(=O)N[C@@H](C)C(=O)O[C@@H](C)[C@H](Oc2ccc(C(F)(F)F)cc2)c2ccccc2)c1OC(C)=O] | Example 8B | White Powder |
| 197 | 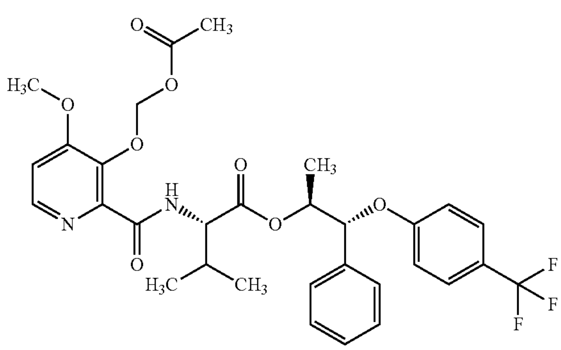 [SMILES: COc1ccnc(C(=O)N[C@H](C(=O)O[C@@H](C)[C@H](Oc2ccc(C(F)(F)F)cc2)c2ccccc2)C(C)C)c1OCOC(C)=O] | Example 8A | Hygroscopic Powder |
| 198 | 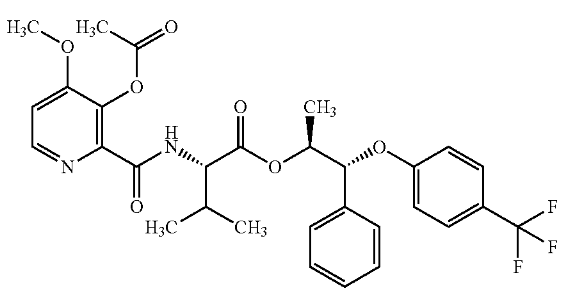 [SMILES: COc1ccnc(C(=O)N[C@H](C(=O)O[C@@H](C)[C@H](Oc2ccc(C(F)(F)F)cc2)c2ccccc2)C(C)C)c1OC(C)=O] | Example 8B | White Powder |

TABLE 1-continued

Compound Structure, Appearance, and Preparation Method

| *Cmpd. No. | Structure | Prepared According to Example | Colorless Semi-Solid |
|---|---|---|---|
| 199 | 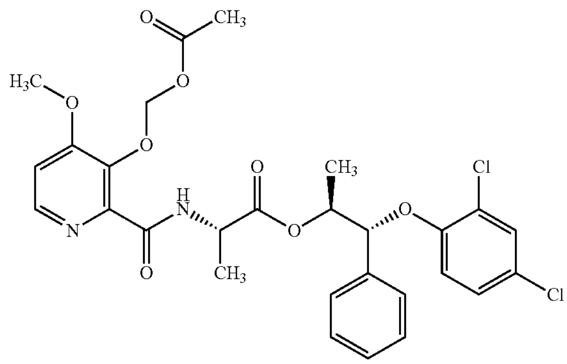 [SMILES: COc1ccnc(C(=O)N[C@@H](C)C(=O)O[C@@H](C)[C@H](Oc2ccc(Cl)cc2Cl)c2ccccc2)c1OCOC(C)=O] | Example 8A | White Powder |
| 200 | 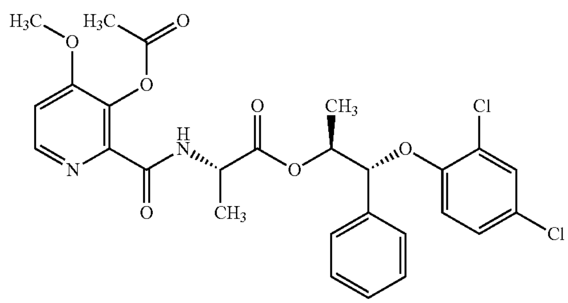 [SMILES: COc1ccnc(C(=O)N[C@@H](C)C(=O)O[C@@H](C)[C@H](Oc2ccc(Cl)cc2Cl)c2ccccc2)c1OC(C)=O] | Example 8B | White Powder |
| 201 | 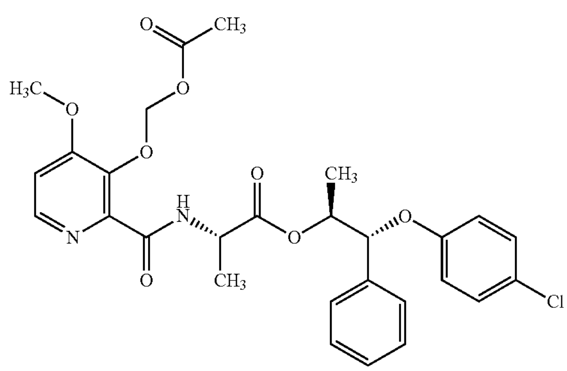 [SMILES: COc1ccnc(C(=O)N[C@@H](C)C(=O)O[C@@H](C)[C@H](Oc2ccc(Cl)cc2)c2ccccc2)c1OCOC(C)=O] | Example 8A | White Powder |
| 202 | 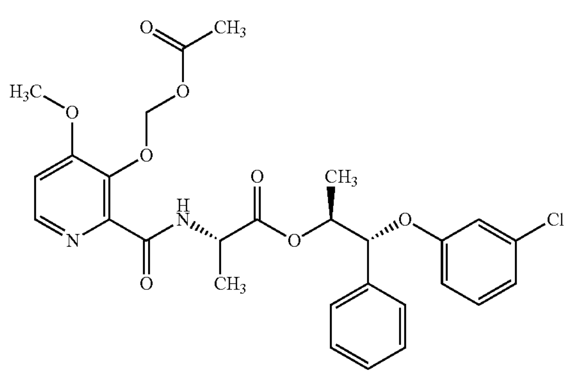 [SMILES: COc1ccnc(C(=O)N[C@@H](C)C(=O)O[C@@H](C)[C@H](Oc2cccc(Cl)c2)c2ccccc2)c1OCOC(C)=O] | Example 8A | Sticky Oil |

TABLE 1-continued

Compound Structure, Appearance, and Preparation Method

| *Cmpd. No. | Structure | Prepared According to Example | Colorless Semi-Solid |
|---|---|---|---|
| 203 | 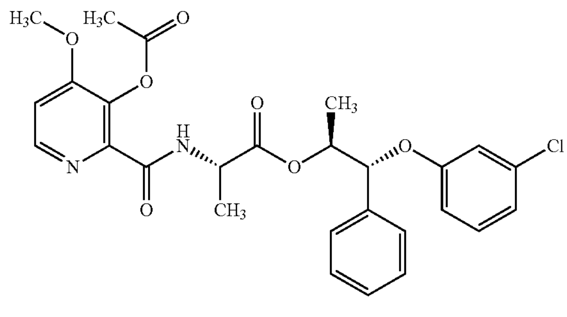 [SMILES: COc1ccnc(C(=O)N[C@@H](C)C(=O)O[C@@H](C)[C@H](Oc2cccc(Cl)c2)c2ccccc2)c1OC(C)=O] | Example 8B | White Powder |
| 204 | 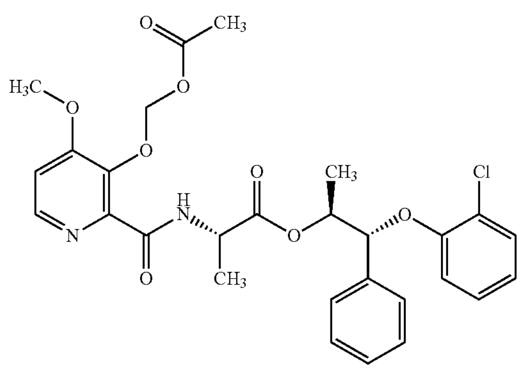 [SMILES: COc1ccnc(C(=O)N[C@@H](C)C(=O)O[C@@H](C)[C@H](Oc2ccccc2Cl)c2ccccc2)c1OCOC(C)=O] | Example 8A | White Powder |
| 205 | 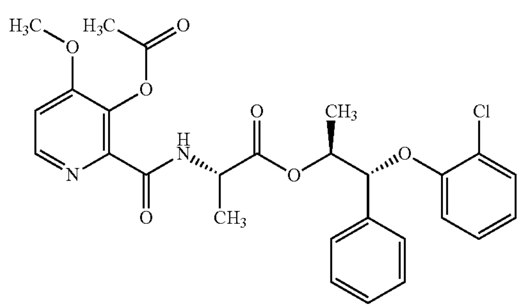 [SMILES: COc1ccnc(C(=O)N[C@@H](C)C(=O)O[C@@H](C)[C@H](Oc2ccccc2Cl)c2ccccc2)c1OC(C)=O] | Example 8B | White Powder |
| 206 | 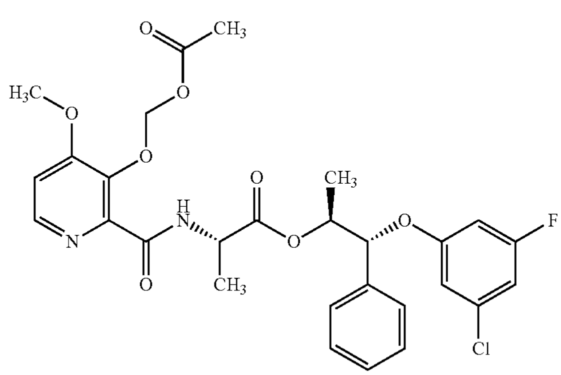 [SMILES: COc1ccnc(C(=O)N[C@@H](C)C(=O)O[C@@H](C)[C@H](Oc2cc(F)cc(Cl)c2)c2ccccc2)c1OCOC(C)=O] | Example 8A | Semi-Solid |

TABLE 1-continued

Compound Structure, Appearance, and Preparation Method

| *Cmpd. No. | Structure | Prepared According to Example | Colorless Semi-Solid |
|---|---|---|---|
| 207 | 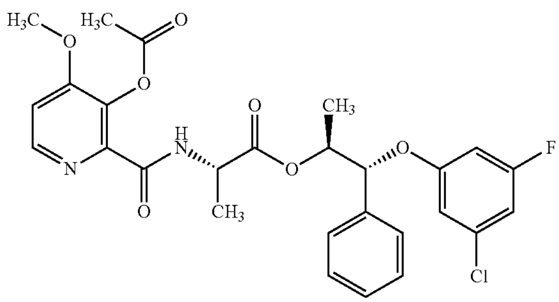 [SMILES: COc1ccnc(C(=O)N[C@@H](C)C(=O)O[C@@H](C)[C@H](Oc2cc(F)cc(Cl)c2)c2ccccc2)c1OC(C)=O] | Example 8B | White Powder |
| 208 | 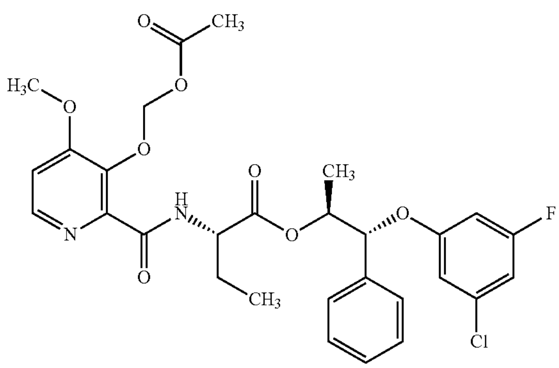 [SMILES: CC[C@H](NC(=O)c1nccc(OC)c1OCOC(C)=O)C(=O)O[C@@H](C)[C@H](Oc1cc(F)cc(Cl)c1)c1ccccc1] | Example 8A | Sticky White Solid |
| 209 | 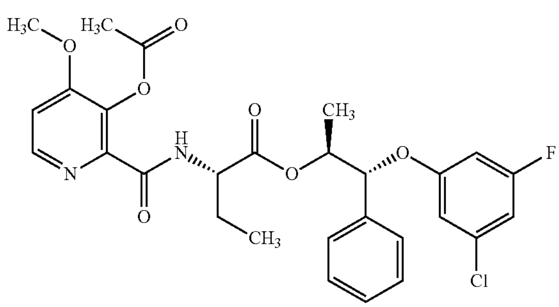 [SMILES: CC[C@H](NC(=O)c1nccc(OC)c1OC(C)=O)C(=O)O[C@@H](C)[C@H](Oc1cc(F)cc(Cl)c1)c1ccccc1] | Example 8B | White Powder |
| 210 | 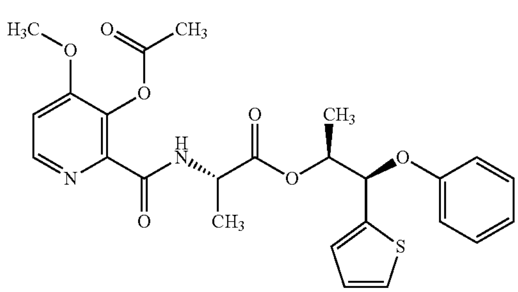 [SMILES: COc1ccnc(C(=O)N[C@@H](C)C(=O)O[C@@H](C)[C@@H](Oc2ccccc2)c2cccs2)c1OC(C)=O] | Example 8B | Colorless Oil |

TABLE 1-continued

Compound Structure, Appearance, and Preparation Method

| *Cmpd. No. | Structure | Prepared According to Example | Colorless Semi-Solid |
|---|---|---|---|
| 211 | (structure) | Example 8B | Colorless Oil |
| 212 | (structure) | Example 8B | Colorless Foam/Oil |
| 213 | (structure) | Example 8A | Colorless Foam/Oil |
| 214 | (structure) | Example 8B | Colorless Oil |

TABLE 1-continued

Compound Structure, Appearance, and Preparation Method

| *Cmpd. No. | Structure | Prepared According to Example | Colorless Semi-Solid |
|---|---|---|---|
| 215 | 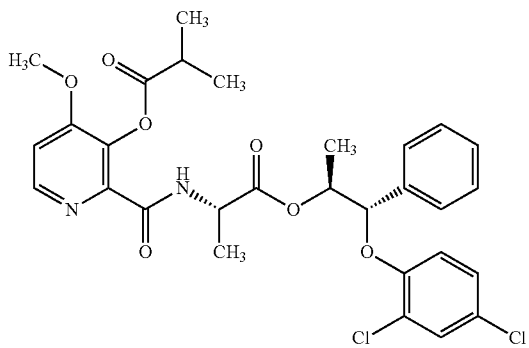 [SMILES: COc1ccnc(C(=O)N[C@@H](C)C(=O)O[C@@H](C)[C@@H](Oc2ccc(Cl)cc2Cl)c2ccccc2)c1OC(=O)C(C)C] | Example 8B | Colorless Oil |
| 216 | 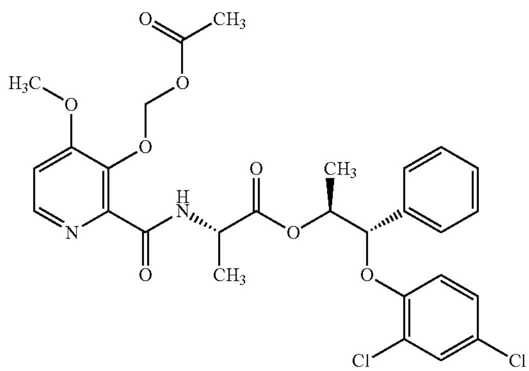 [SMILES: COc1ccnc(C(=O)N[C@@H](C)C(=O)O[C@@H](C)[C@@H](Oc2ccc(Cl)cc2Cl)c2ccccc2)c1OCOC(C)=O] | Example 8A | Colorless Oil |
| 217 | 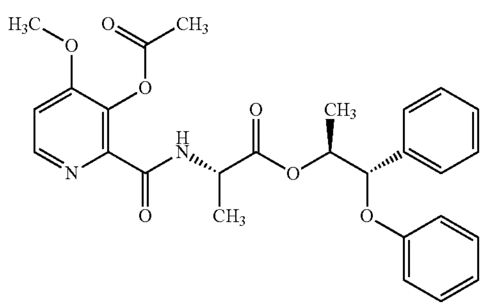 [SMILES: COc1ccnc(C(=O)N[C@@H](C)C(=O)O[C@@H](C)[C@@H](Oc2ccccc2)c2ccccc2)c1OC(C)=O] | Example 8B | Colorless Oil |
| 218 | 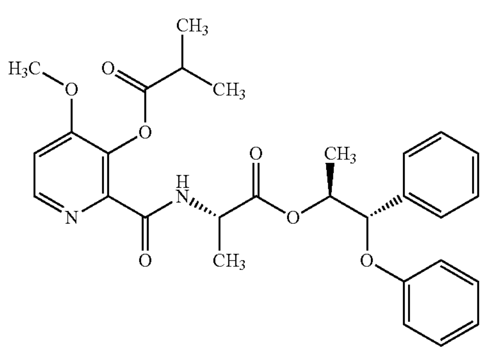 [SMILES: COc1ccnc(C(=O)N[C@@H](C)C(=O)O[C@@H](C)[C@@H](Oc2ccccc2)c2ccccc2)c1OC(=O)C(C)C] | Example 8B | Colorless Oil |

TABLE 1-continued

Compound Structure, Appearance, and Preparation Method

| *Cmpd. No. | Structure | Prepared According to Example | Colorless Semi-Solid |
|---|---|---|---|
| 219 | 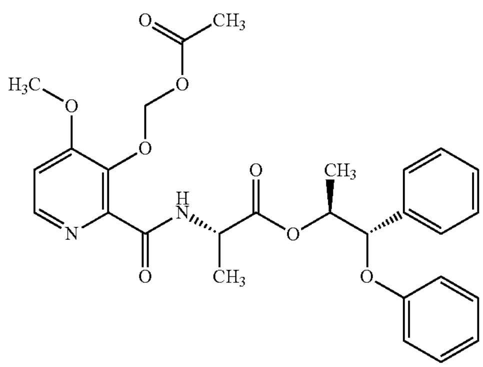 [SMILES: COc1ccnc(C(=O)N[C@@H](C)C(=O)O[C@@H](C)[C@@H](Oc2ccccc2)c2ccccc2)c1OCOC(C)=O] | Example 8A | Colorless Oil |
| 220 | 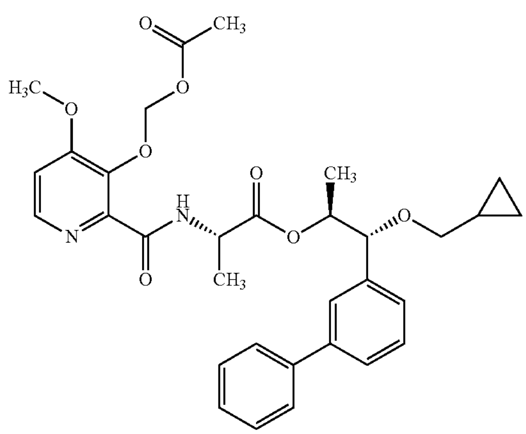 [SMILES: COc1ccnc(C(=O)N[C@@H](C)C(=O)O[C@@H](C)[C@H](OCC2CC2)c2cccc(-c3ccccc3)c2)c1OCOC(C)=O] | Example 8A | Colorless Oil |
| 221 | 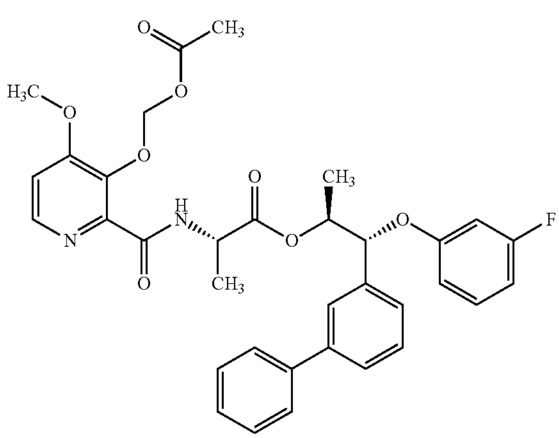 [SMILES: COc1ccnc(C(=O)N[C@@H](C)C(=O)O[C@@H](C)[C@H](Oc2cccc(F)c2)c2cccc(-c3ccccc3)c2)c1OCOC(C)=O] | Example 8A | Colorless Oil |

TABLE 1-continued

Compound Structure, Appearance, and Preparation Method

| *Cmpd. No. | Structure | Prepared According to Example | Colorless Semi-Solid |
|---|---|---|---|
| 222 | 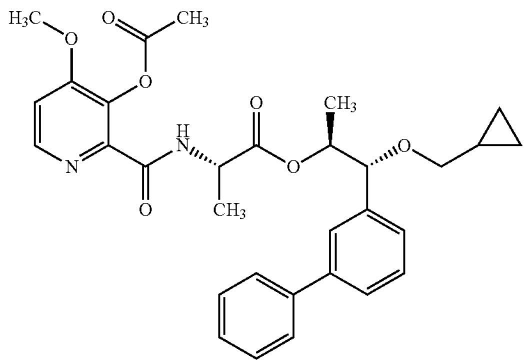 [SMILES: COc1ccnc(C(=O)N[C@@H](C)C(=O)O[C@@H](C)[C@H](OCC2CC2)c2cccc(-c3ccccc3)c2)c1OC(C)=O] | Example 8B | Colorless Oil |
| 223 | 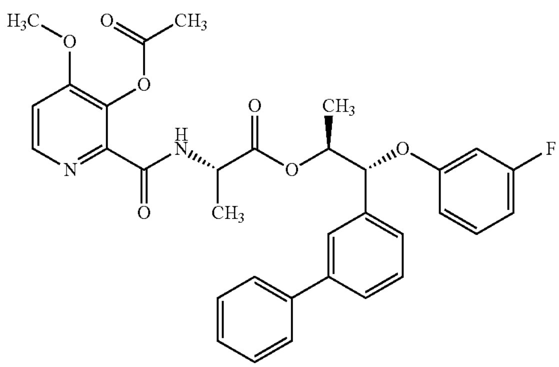 [SMILES: COc1ccnc(C(=O)N[C@@H](C)C(=O)O[C@@H](C)[C@H](Oc2cccc(F)c2)c2cccc(-c3ccccc3)c2)c1OC(C)=O] | Example 8B | Off White Foam |
| 224 | 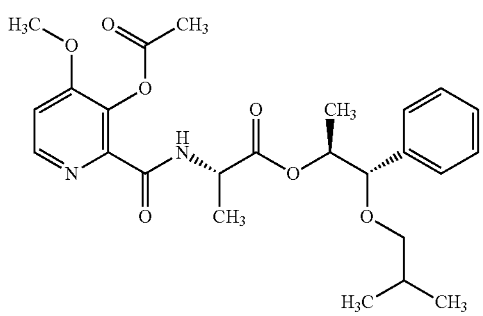 [SMILES: COc1ccnc(C(=O)N[C@@H](C)C(=O)O[C@@H](C)[C@@H](OCC(C)C)c2ccccc2)c1OC(C)=O] | Example 8B | Colorless Oil |
| 225 | 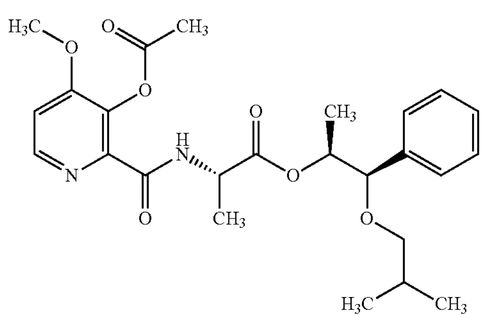 [SMILES: COc1ccnc(C(=O)N[C@@H](C)C(=O)O[C@@H](C)[C@H](OCC(C)C)c2ccccc2)c1OC(C)=O] | Example 8B | Colorless Oil |

TABLE 1-continued
Compound Structure, Appearance, and Preparation Method
| *Cmpd. No. | Structure | Prepared According to Example | Colorless Semi-Solid |
|---|---|---|---|
| 226 | 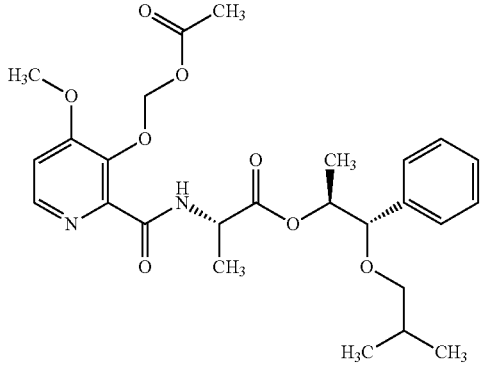 [SMILES: COc1ccnc(C(=O)N[C@@H](C)C(=O)O[C@@H](C)[C@@H](OCC(C)C)c2ccccc2)c1OCOC(C)=O] | Example 8A | Colorless Oil |
| 227 | 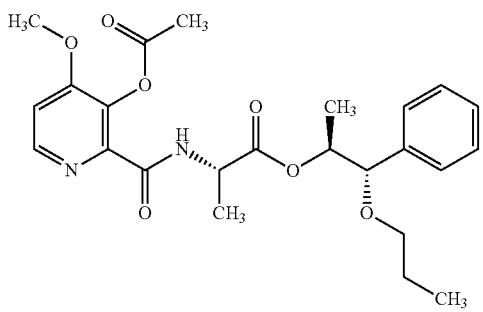 [SMILES: CCCO[C@@H](c1ccccc1)[C@H](C)OC(=O)[C@H](C)NC(=O)c1nccc(OC)c1OC(C)=O] | Example 8B | Colorless Oil |
| 228 | 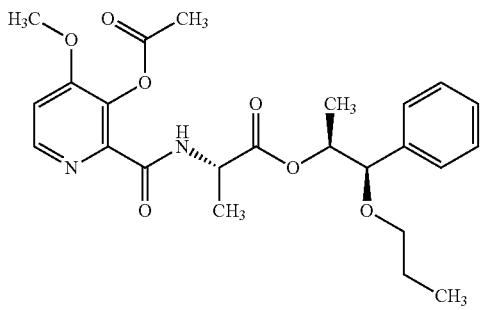 [SMILES: CCCO[C@H](c1ccccc1)[C@H](C)OC(=O)[C@H](C)NC(=O)c1nccc(OC)c1OC(C)=O] | Example 8B | Colorless Oil |
| 229 | 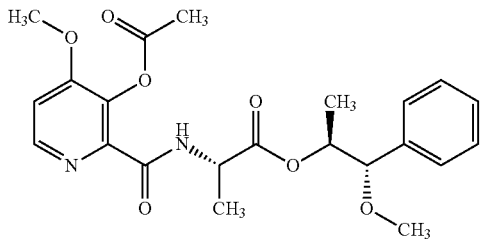 [SMILES: COc1ccnc(C(=O)N[C@@H](C)C(=O)O[C@@H](C)[C@@H](OC)c2ccccc2)c1OC(C)=O] | Example 8B | Colorless Oil |

TABLE 1-continued

Compound Structure, Appearance, and Preparation Method

| *Cmpd. No. | Structure | Prepared According to Example | Colorless Semi-Solid |
|---|---|---|---|
| 230 | 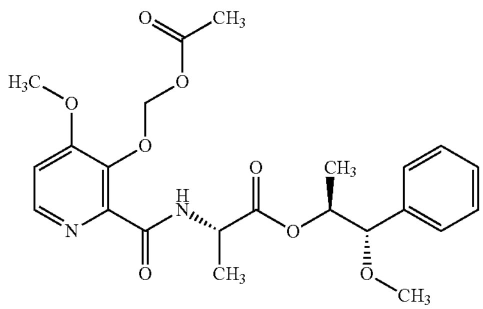 [SMILES: COc1ccnc(C(=O)N[C@@H](C)C(=O)O[C@@H](C)[C@@H](OC)c2ccccc2)c1OCOC(C)=O] | Example 8A | Colorless Oil |
| 231 | 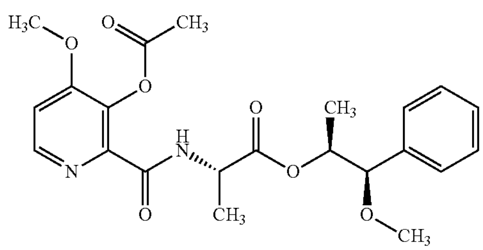 [SMILES: COc1ccnc(C(=O)N[C@@H](C)C(=O)O[C@@H](C)[C@H](OC)c2ccccc2)c1OC(C)=O] | Example 8B | Colorless Oil |
| 232 | 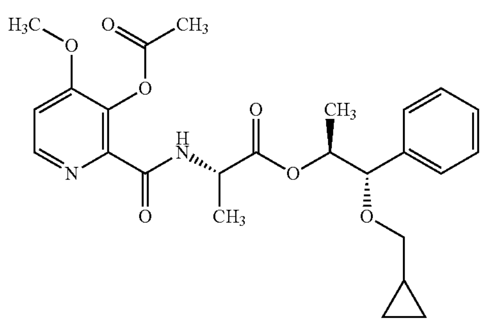 [SMILES: COc1ccnc(C(=O)N[C@@H](C)C(=O)O[C@@H](C)[C@@H](OCC2CC2)c2ccccc2)c1OC(C)=O] | Example 8B | Colorless Oil |
| 233 | 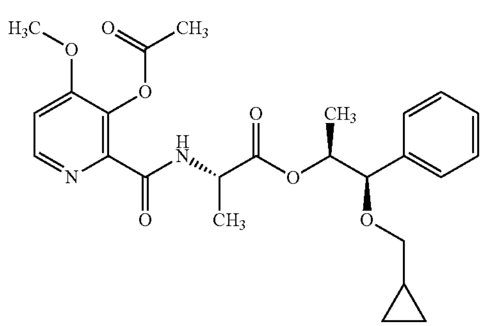 [SMILES: COc1ccnc(C(=O)N[C@@H](C)C(=O)O[C@@H](C)[C@H](OCC2CC2)c2ccccc2)c1OC(C)=O] | Example 8B | Colorless Oil |

141
TABLE 1-continued
Compound Structure, Appearance, and Preparation Method
| *Cmpd. No. | Structure | Prepared According to Example | Colorless Semi-Solid |
|---|---|---|---|
| 234 | 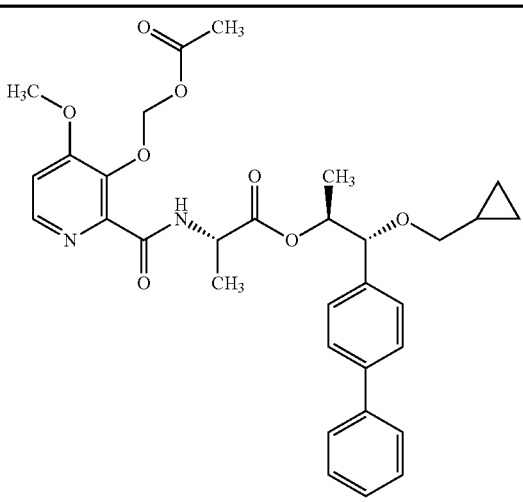 | Example 8A | Colorless Oil |
| 235 | 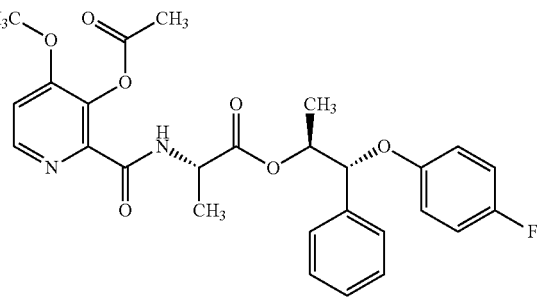 | Example 8B | Colorless Oil |
| 236 | 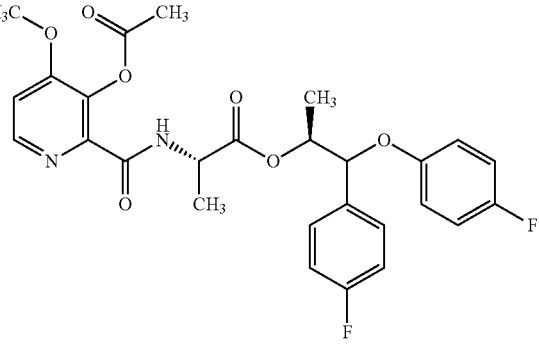 | Example 8B | Colorless Oil |
| 237 | 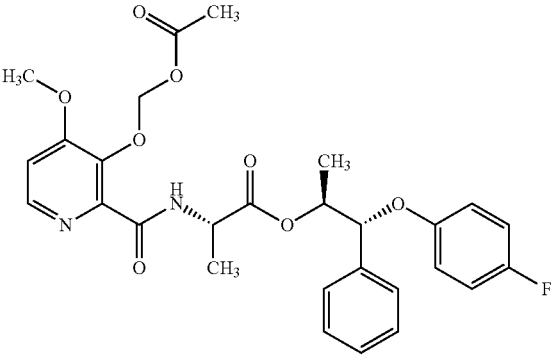 [SMILES: COc1ccnc(C(=O)N[C@@H](C)C(=O)O[C@@H](C)[C@H](Oc2ccc(F)cc2)c2ccccc2)c1OCOC(C)=O] | Example 8A | Colorless Oil |

TABLE 1-continued

Compound Structure, Appearance, and Preparation Method

| *Cmpd. No. | Structure | Prepared According to Example | Colorless Semi-Solid |
|---|---|---|---|
| 238 | 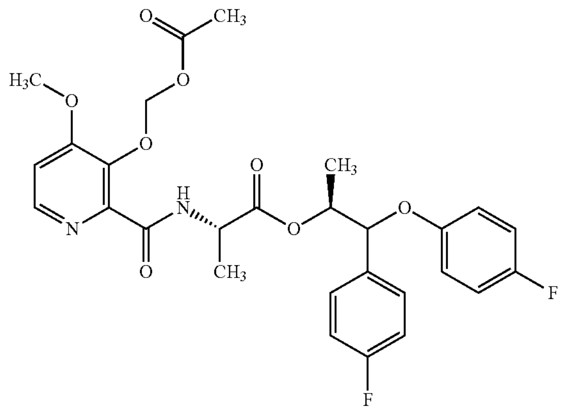 [SMILES: COc1ccnc(C(=O)N[C@@H](C)C(=O)O[C@@H](C)C(Oc2ccc(F)cc2)c2ccc(F)cc2)c1OCOC(C)=O] | Example 8A | Colorless Oil |
| 239 | 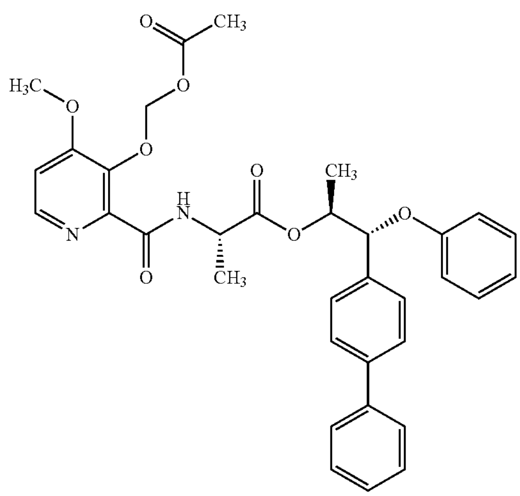 [SMILES: COc1ccnc(C(=O)N[C@@H](C)C(=O)O[C@@H](C)[C@H](Oc2ccccc2)c2ccc(-c3ccccc3)cc2)c1OCOC(C)=O] | Example 8A | Colorless Oil |
| 240 | 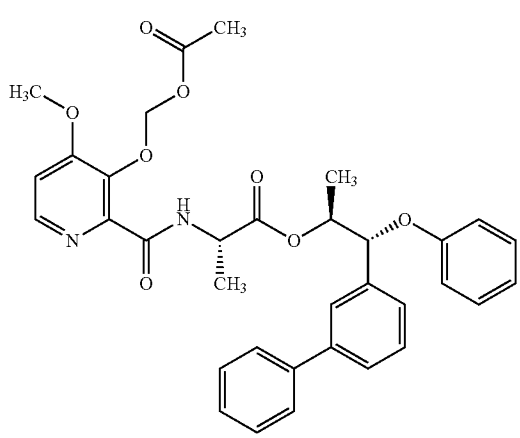 [SMILES: COc1ccnc(C(=O)N[C@@H](C)C(=O)O[C@@H](C)[C@H](Oc2ccccc2)c2cccc(-c3ccccc3)c2)c1OCOC(C)=O] | Example 8A | Colorless Oil |

TABLE 1-continued

Compound Structure, Appearance, and Preparation Method

| *Cmpd. No. | Structure | Prepared According to Example | Colorless Semi-Solid |
|---|---|---|---|
| 241 | 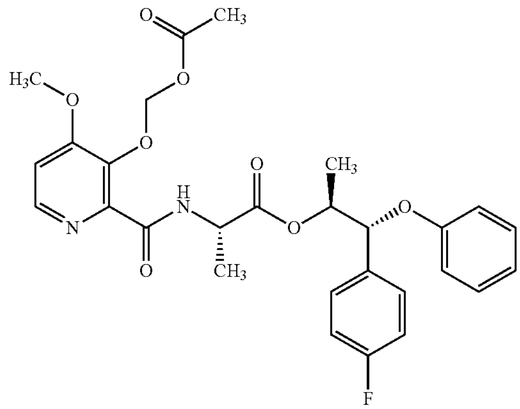 [SMILES: COc1ccnc(C(=O)N[C@@H](C)C(=O)O[C@@H](C)[C@H](Oc2ccccc2)c2ccc(F)cc2)c1OCOC(C)=O] | Example 8A | Colorless Oil |
| 242 | 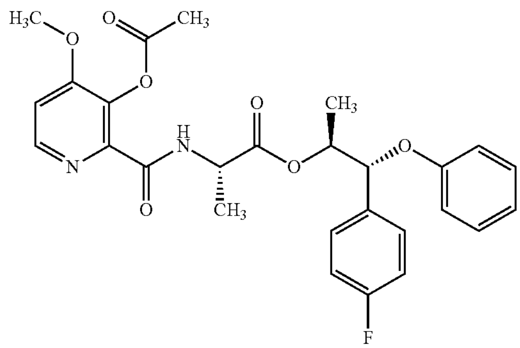 [SMILES: COc1ccnc(C(=O)N[C@@H](C)C(=O)O[C@@H](C)[C@H](Oc2ccccc2)c2ccc(F)cc2)c1OC(C)=O] | Example 8B | Light Yellow Oil |
| 243 | 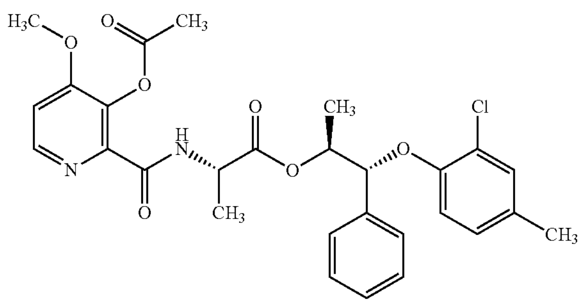 [SMILES: COc1ccnc(C(=O)N[C@@H](C)C(=O)O[C@@H](C)[C@H](Oc2ccc(C)cc2Cl)c2ccccc2)c1OC(C)=O] | Example 8B | Colorless Oil |
| 244 | 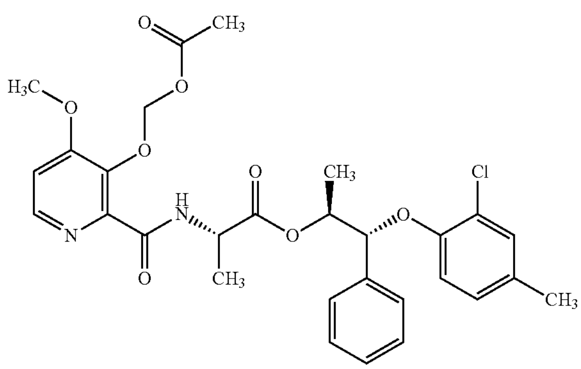 [SMILES: COc1ccnc(C(=O)N[C@@H](C)C(=O)O[C@@H](C)[C@H](Oc2ccc(C)cc2Cl)c2ccccc2)c1OCOC(C)=O] | Example 8A | Colorless Oil |

TABLE 1-continued

Compound Structure, Appearance, and Preparation Method

| *Cmpd. No. | Structure | Prepared According to Example | Colorless Semi-Solid |
|---|---|---|---|
| 245 | 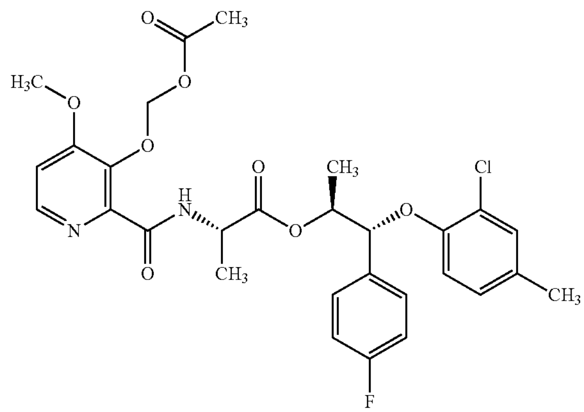 [SMILES: COc1ccnc(C(=O)N[C@@H](C)C(=O)O[C@@H](C)[C@H](Oc2ccc(C)cc2Cl)c2ccc(F)cc2)c1OCOC(C)=O] | Example 8A | Colorless Oil |
| 246 | 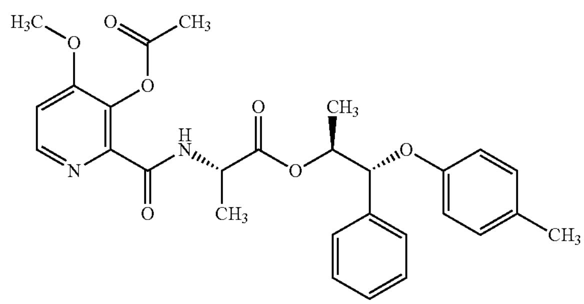 [SMILES: COc1ccnc(C(=O)N[C@@H](C)C(=O)O[C@@H](C)[C@H](Oc2ccc(C)cc2)c2ccccc2)c1OC(C)=O] | Example 8B | Colorless Oil |
| 247 | 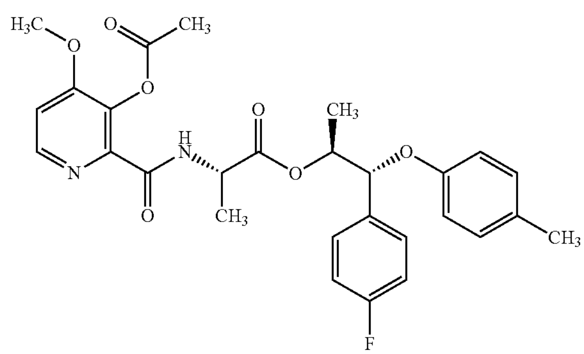 [SMILES: COc1ccnc(C(=O)N[C@@H](C)C(=O)O[C@@H](C)[C@H](Oc2ccc(C)cc2)c2ccc(F)cc2)c1OC(C)=O] | Example 8B | Colorless Oil |
| 248 | 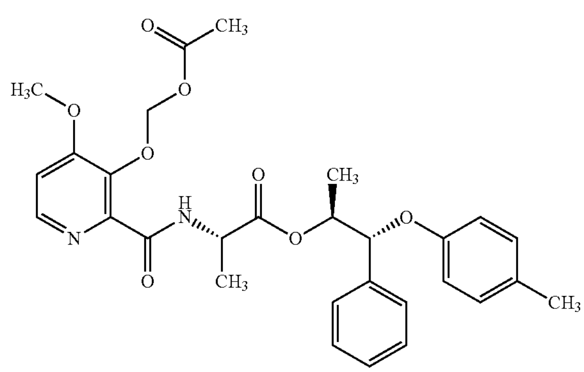 [SMILES: COc1ccnc(C(=O)N[C@@H](C)C(=O)O[C@@H](C)[C@H](Oc2ccc(C)cc2)c2ccccc2)c1OCOC(C)=O] | Example 8A | Colorless Oil |

TABLE 1-continued

Compound Structure, Appearance, and Preparation Method

| *Cmpd. No. | Structure | Prepared According to Example | Colorless Semi-Solid |
|---|---|---|---|
| 249 | 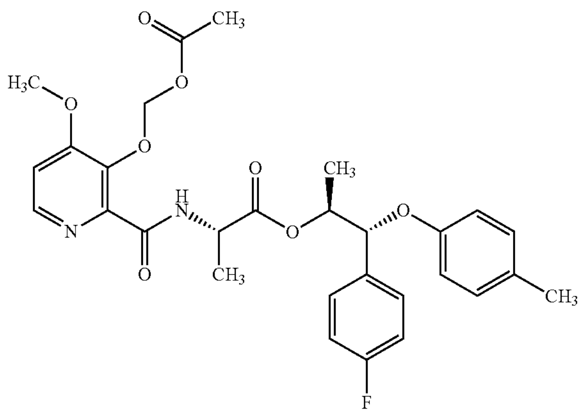 [SMILES: COc1ccnc(C(=O)N[C@@H](C)C(=O)O[C@@H](C)[C@H](Oc2ccc(C)cc2)c2ccc(F)cc2)c1OCOC(C)=O] | Example 8A | Colorless Oil |
| 250 | 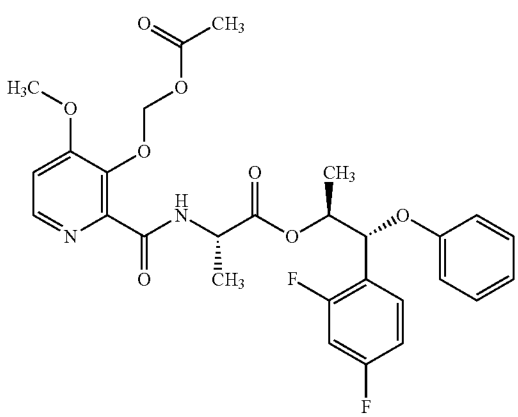 [SMILES: COc1ccnc(C(=O)N[C@@H](C)C(=O)O[C@@H](C)[C@H](Oc2ccccc2)c2ccc(F)cc2F)c1OCOC(C)=O] | Example 8A | Colorless Oil |
| 251 | 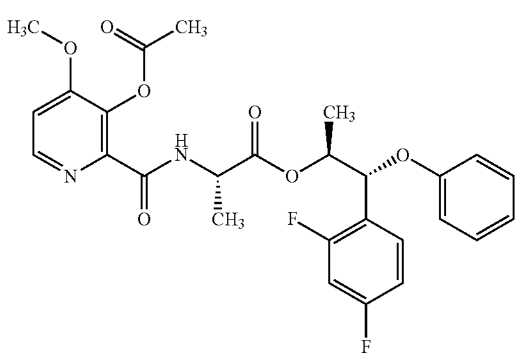 [SMILES: COc1ccnc(C(=O)N[C@@H](C)C(=O)O[C@@H](C)[C@H](Oc2ccccc2)c2ccc(F)cc2F)c1OC(C)=O] | Example 8B | Faint Yellow Oil |

TABLE 1-continued

Compound Structure, Appearance, and Preparation Method

| *Cmpd. No. | Structure | Prepared According to Example | Colorless Semi-Solid |
|---|---|---|---|
| 252 | 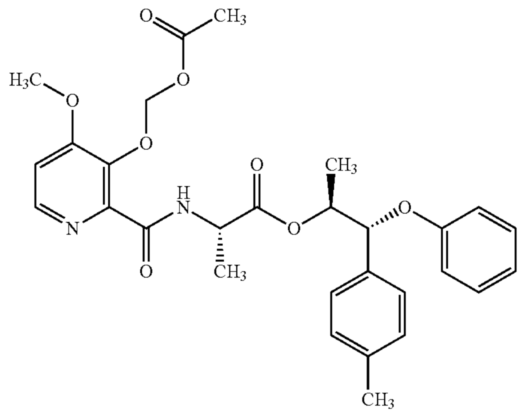 [SMILES: COc1ccnc(C(=O)N[C@@H](C)C(=O)O[C@@H](C)[C@H](Oc2ccccc2)c2ccc(C)cc2)c1OCOC(C)=O] | Example 8A | Colorless Oil |
| 253 | 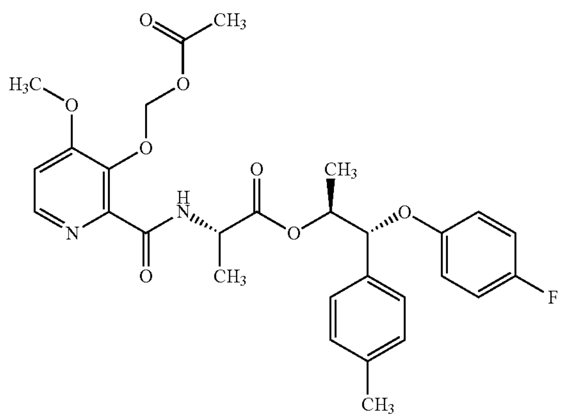 [SMILES: COc1ccnc(C(=O)N[C@@H](C)C(=O)O[C@@H](C)[C@H](Oc2ccc(F)cc2)c2ccc(C)cc2)c1OCOC(C)=O] | Example 8A | Colorless Oil |
| 254 | 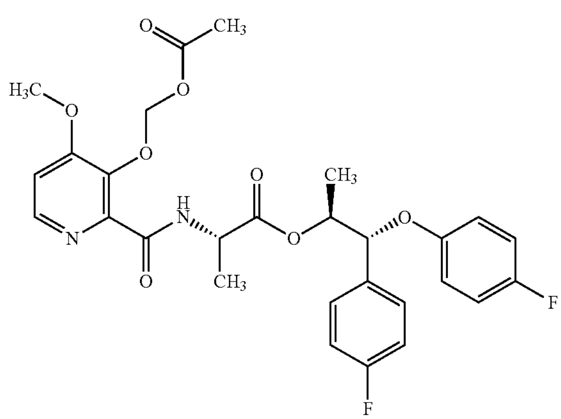 [SMILES: COc1ccnc(C(=O)N[C@@H](C)C(=O)O[C@@H](C)[C@H](Oc2ccc(F)cc2)c2ccc(F)cc2)c1OCOC(C)=O] | Example 8A | Colorless Oil |

TABLE 1-continued

Compound Structure, Appearance, and Preparation Method

| *Cmpd. No. | Structure | Prepared According to Example | Colorless Semi-Solid |
|---|---|---|---|
| 255 | 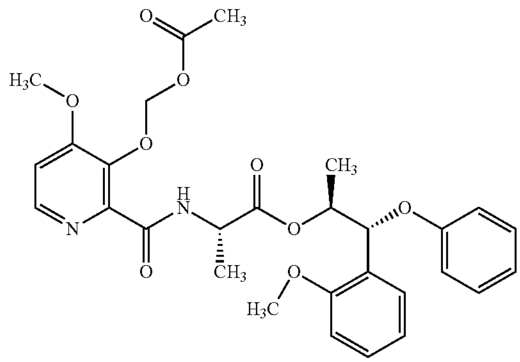 [SMILES: COc1ccccc1[C@@H](Oc1ccccc1)[C@H](C)OC(=O)[C@H](C)NC(=O)c1nccc(OC)c1OCOC(C)=O] | Example 8A | Colorless Oil |
| 256 | 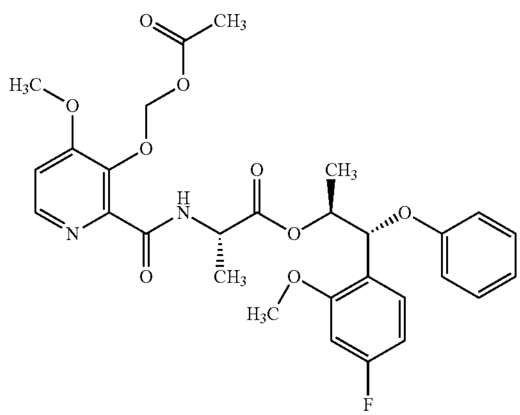 [SMILES: COc1cc(F)ccc1[C@@H](Oc1ccccc1)[C@H](C)OC(=O)[C@H](C)NC(=O)c1nccc(OC)c1OCOC(C)=O] | Example 8A | Faint Yellow Oil |
| 257 | 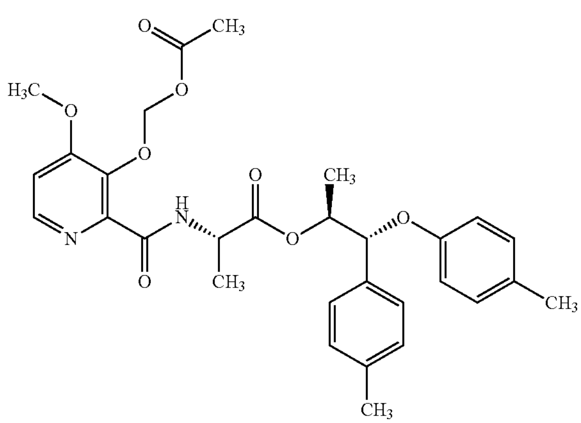 [SMILES: COc1ccnc(C(=O)N[C@@H](C)C(=O)O[C@@H](C)[C@H](Oc2ccc(C)cc2)c2ccc(C)cc2)c1OCOC(C)=O] | Example 8A | Colorless Oil |

TABLE 1-continued
Compound Structure, Appearance, and Preparation Method
| *Cmpd. No. | Structure | Prepared According to Example | Colorless Semi-Solid |
|---|---|---|---|
| 258 | 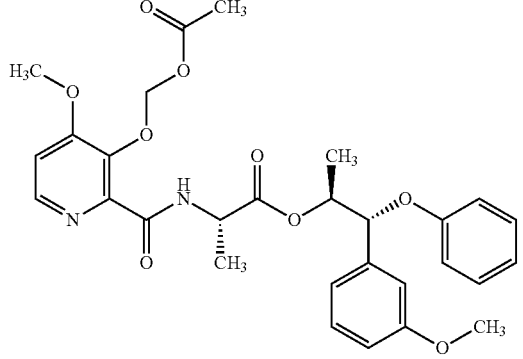 [SMILES: COc1cccc([C@@H](Oc2ccccc2)[C@H](C)OC(=O)[C@H](C)NC(=O)c2nccc(OC)c2OCOC(C)=O)c1] | Example 8A | Colorless Oil |
| 259 | 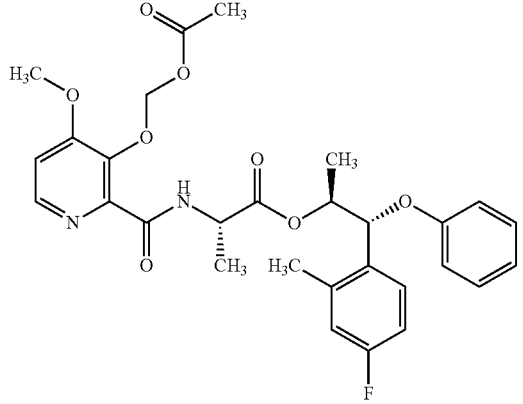 [SMILES: COc1ccnc(C(=O)N[C@@H](C)C(=O)O[C@@H](C)[C@H](Oc2ccccc2)c2ccc(F)cc2C)c1OCOC(C)=O] | Example 8A | Colorless Oil |
| 260 | 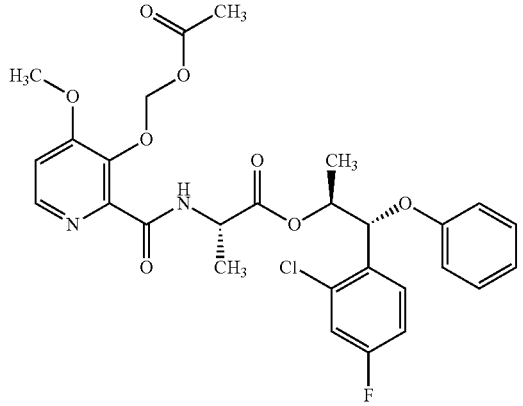 [SMILES: COc1ccnc(C(=O)N[C@@H](C)C(=O)O[C@@H](C)[C@H](Oc2ccccc2)c2ccc(F)cc2Cl)c1OCOC(C)=O] | Example 8A | Colorless Oil |

TABLE 1-continued

Compound Structure, Appearance, and Preparation Method

| *Cmpd. No. | Structure | Prepared According to Example | Colorless Semi-Solid |
|---|---|---|---|
| 261 | 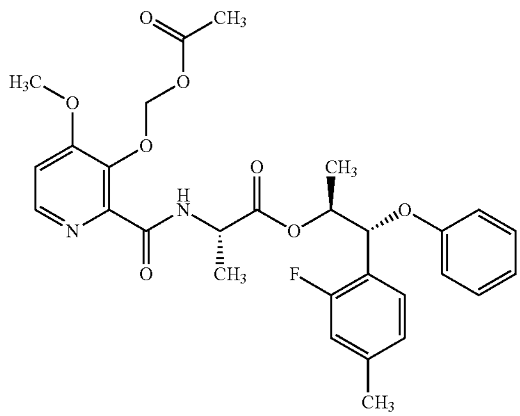 [SMILES: COc1ccnc(C(=O)N[C@@H](C)C(=O)O[C@@H](C)[C@H](Oc2ccccc2)c2ccc(C)cc2F)c1OCOC(C)=O] | Example 8A | White Foam |
| 262 | 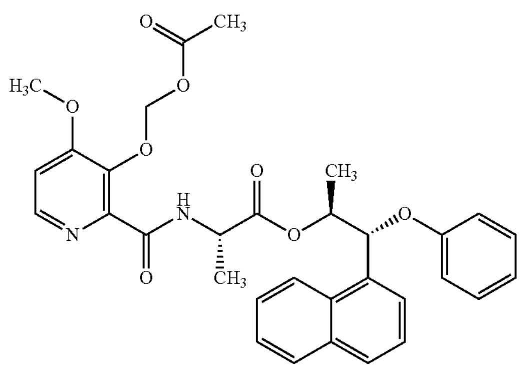 [SMILES: COc1ccnc(C(=O)N[C@@H](C)C(=O)O[C@@H](C)[C@H](Oc2ccccc2)c2cccc3ccccc23)c1OCOC(C)=O] | Example 8A | White Foam |
| 263 | 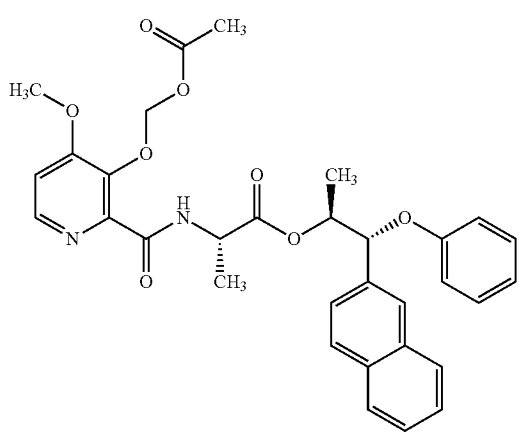 [SMILES: COc1ccnc(C(=O)N[C@@H](C)C(=O)O[C@@H](C)[C@H](Oc2ccccc2)c2ccc3ccccc3c2)c1OCOC(C)=O] | Example 8A | White Foam |

TABLE 1-continued

Compound Structure, Appearance, and Preparation Method

| *Cmpd. No. | Structure | Prepared According to Example | Colorless Semi-Solid |
|---|---|---|---|
| 264 | 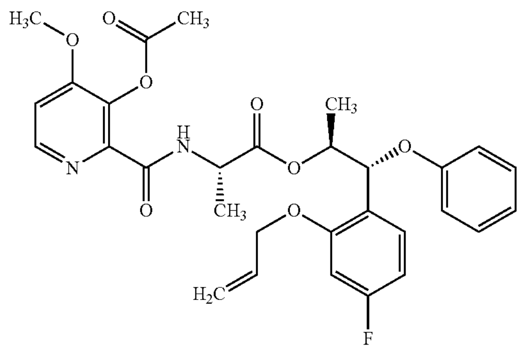 [SMILES: C=CCOc1cc(F)ccc1[C@@H](Oc1ccccc1)[C@H](C)OC(=O)[C@H](C)NC(=O)c1nccc(OC)c1OC(C)=O] | Example 8B | White Foam |
| 265 | 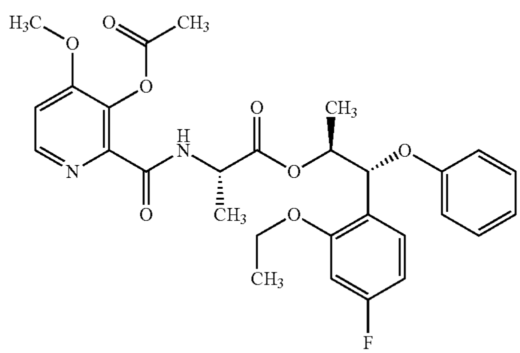 [SMILES: CCOc1cc(F)ccc1[C@@H](Oc1ccccc1)[C@H](C)OC(=O)[C@H](C)NC(=O)c1nccc(OC)c1OC(C)=O] | Example 8B | White Foam |
| 266 | 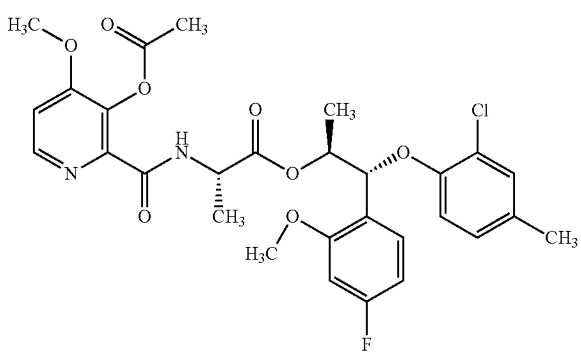 [SMILES: COc1cc(F)ccc1[C@@H](Oc1ccc(C)cc1Cl)[C@H](C)OC(=O)[C@H](C)NC(=O)c1nccc(OC)c1OC(C)=O] | Example 8B | White Foam |
| 267 | 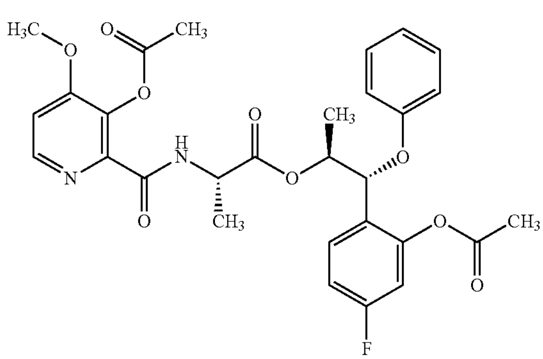 [SMILES: COc1ccnc(C(=O)N[C@@H](C)C(=O)O[C@@H](C)[C@H](Oc2ccccc2)c2ccc(F)cc2OC(C)=O)c1OC(C)=O] | Example 8B | White Foam |

TABLE 1-continued

Compound Structure, Appearance, and Preparation Method

| *Cmpd. No. | Structure | Prepared According to Example | Colorless Semi-Solid |
|---|---|---|---|
| 268 | 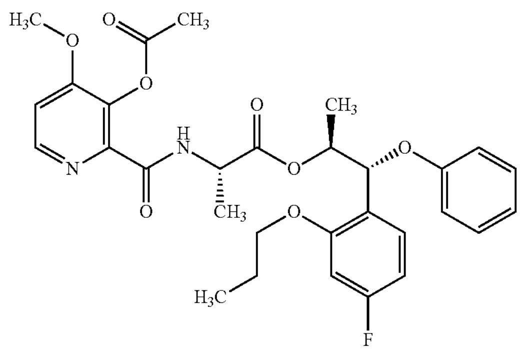 [SMILES: CCCOc1cc(F)ccc1[C@@H](Oc1ccccc1)[C@H](C)OC(=O)[C@H](C)NC(=O)c1nccc(OC)c1OC(C)=O] | Example 8B | White Foam |
| 269 | 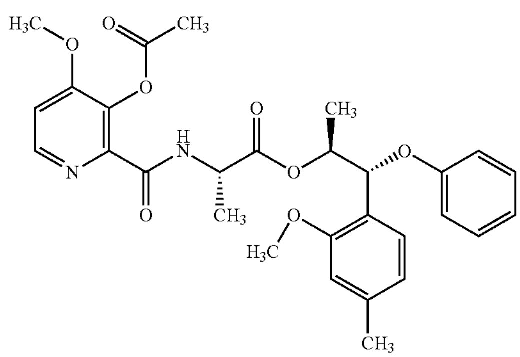 [SMILES: COc1cc(C)ccc1[C@@H](Oc1ccccc1)[C@H](C)OC(=O)[C@H](C)NC(=O)c1nccc(OC)c1OC(C)=O] | Example 8B | Off White Foam |
| 270 | 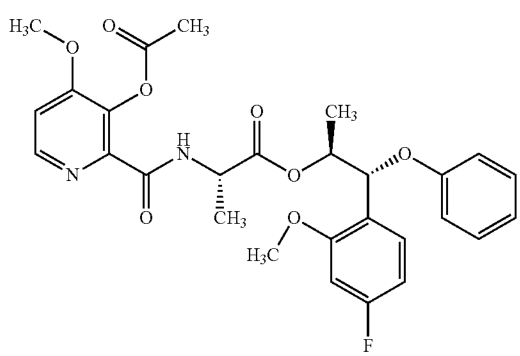 [SMILES: COc1cc(F)ccc1[C@@H](Oc1ccccc1)[C@H](C)OC(=O)[C@H](C)NC(=O)c1nccc(OC)c1OC(C)=O] | Example 8B | White Foam |
| 271 | 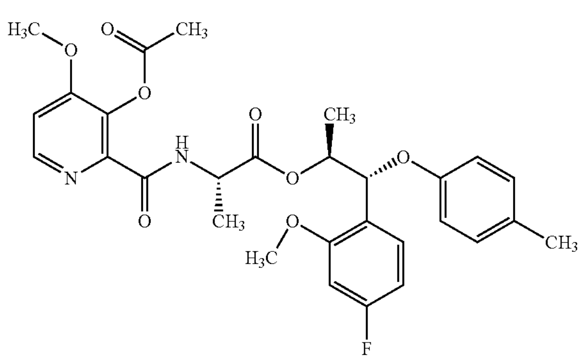 [SMILES: COc1cc(F)ccc1[C@@H](Oc1ccc(C)cc1)[C@H](C)OC(=O)[C@H](C)NC(=O)c1nccc(OC)c1OC(C)=O] | Example 8B | White Foam |

TABLE 1-continued

Compound Structure, Appearance, and Preparation Method

| *Cmpd. No. | Structure | Prepared According to Example | Colorless Semi-Solid |
|---|---|---|---|
| 272 | 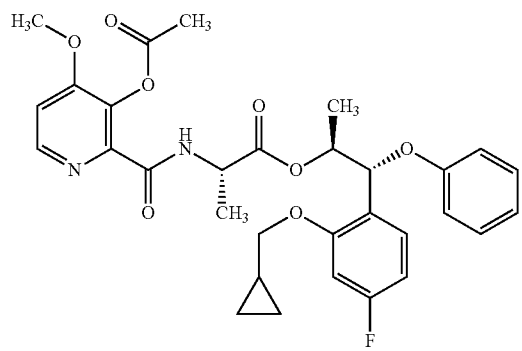 [SMILES: COc1ccnc(C(=O)N[C@@H](C)C(=O)O[C@@H](C)[C@H](Oc2ccccc2)c2ccc(F)cc2OCC2CC2)c1OC(C)=O] | Example 8B | Colorless Oil |
| 273 | 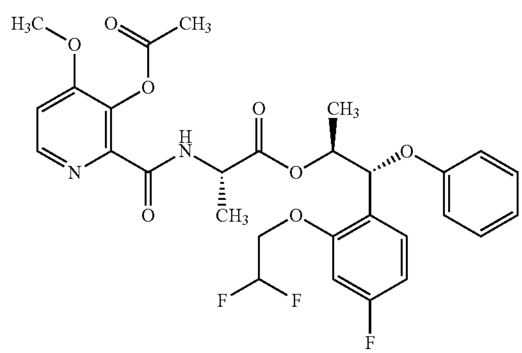 [SMILES: COc1ccnc(C(=O)N[C@@H](C)C(=O)O[C@@H](C)[C@H](Oc2ccccc2)c2ccc(F)cc2OCC(F)F)c1OC(C)=O] | Example 8B | Colorless Oil |
| 274 | 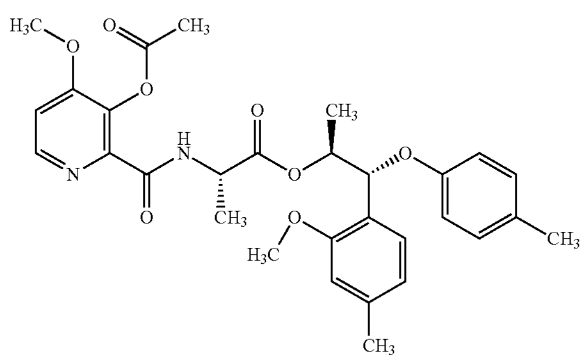 [SMILES: COc1cc(C)ccc1[C@@H](Oc1ccc(C)cc1)[C@H](C)OC(=O)[C@H](C)NC(=O)c1nccc(OC)c1OC(C)=O] | Example 8B | White Foam |
| 275 | 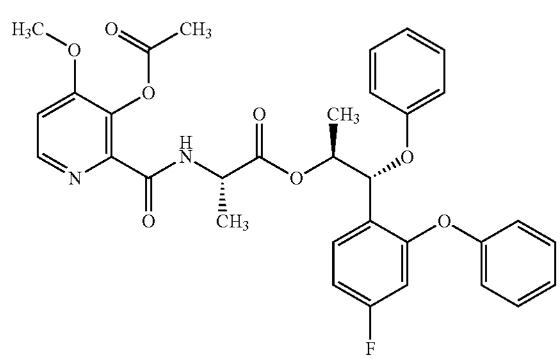 [SMILES: COc1ccnc(C(=O)N[C@@H](C)C(=O)O[C@@H](C)[C@H](Oc2ccccc2)c2ccc(F)cc2Oc2ccccc2)c1OC(C)=O] | Example 8B | White Foam |

TABLE 1-continued

Compound Structure, Appearance, and Preparation Method

| *Cmpd. No. | Structure | Prepared According to Example | Colorless Semi-Solid |
|---|---|---|---|
| 276 | 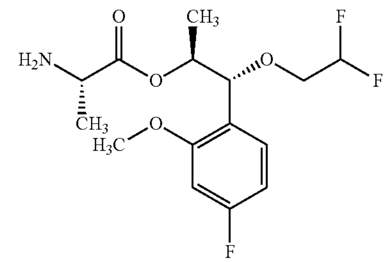 [SMILES: COc1cc(F)ccc1[C@@H](OCC(F)F)[C@H](C)OC(=O)[C@H](C)N] | Example 6A | White Oily Solid |
| 277 | 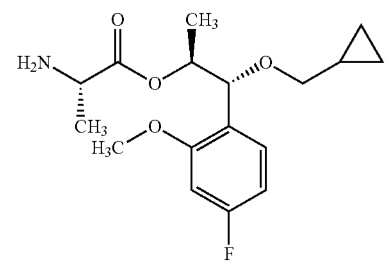 [SMILES: COc1cc(F)ccc1[C@@H](OCC1CC1)[C@H](C)OC(=O)[C@H](C)N] | Example 6A | Colorless Oil |
| 278 | 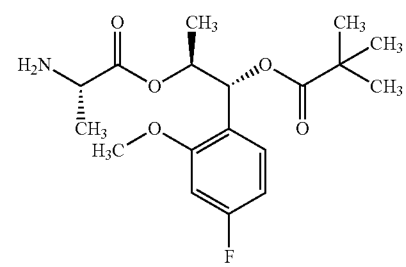 [SMILES: COc1cc(F)ccc1[C@@H](OC(=O)C(C)(C)C)[C@H](C)OC(=O)[C@H](C)N] | Example 6A | Colorless Oil |
| 279 | 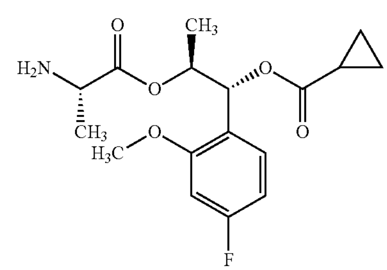 [SMILES: COc1cc(F)ccc1[C@@H](OC(=O)C1CC1)[C@H](C)OC(=O)[C@H](C)N] | Example 6A | Colorless Oil |
| 280 | 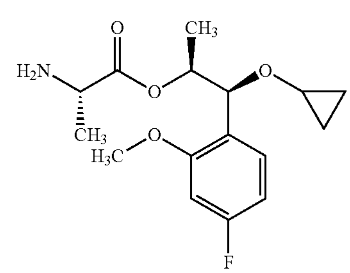 [SMILES: COc1cc(F)ccc1[C@H](OC1CC1)[C@H](C)OC(=O)[C@H](C)N] | Example 6A | Colorless Oil |

TABLE 1-continued

Compound Structure, Appearance, and Preparation Method

| *Cmpd. No. | Structure | Prepared According to Example | Colorless Semi-Solid |
|---|---|---|---|
| 281 | 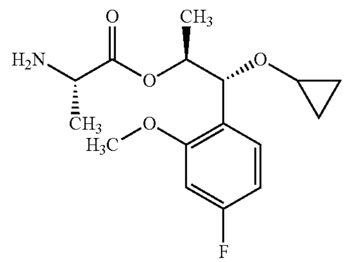 [SMILES: COc1cc(F)ccc1[C@@H](OC1CC1)[C@H](C)OC(=O)[C@H](C)N] | Example 6A | Colorless Oil |
| 282 | 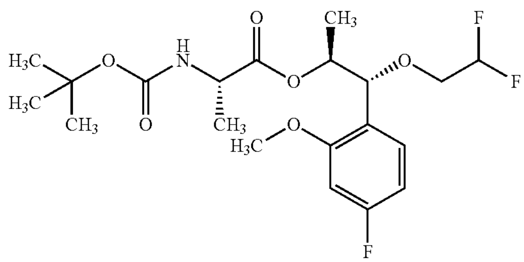 [SMILES: COc1cc(F)ccc1[C@@H](OCC(F)F)[C@H](C)OC(=O)[C@H](C)NC(=O)OC(C)(C)C] | Example 1E; Example 2C; Example 4B; Example 5 | Colorless Oil |
| 283 | 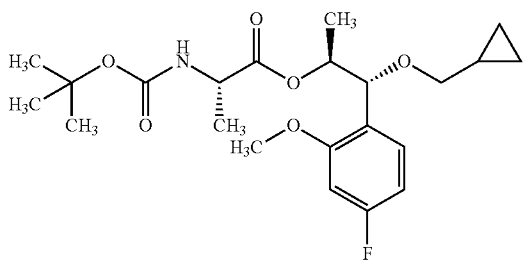 [SMILES: COc1cc(F)ccc1[C@@H](OCC1CC1)[C@H](C)OC(=O)[C@H](C)NC(=O)OC(C)(C)C] | Example 1E; Example 2C; Example 4B; Example 5 | Colorless Oil |
| 284 | 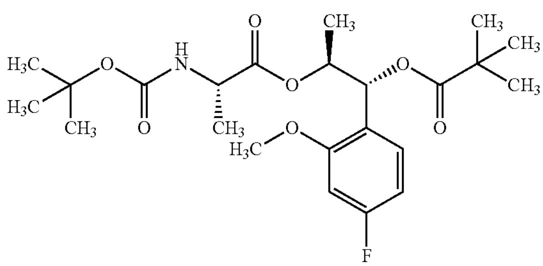 [SMILES: COc1cc(F)ccc1[C@@H](OC(=O)C(C)(C)C)[C@H](C)OC(=O)[C@H](C)NC(=O)OC(C)(C)C] | Example 1E; Example 2D; Example 4B; Example 5 | Colorless Oil |
| 285 | 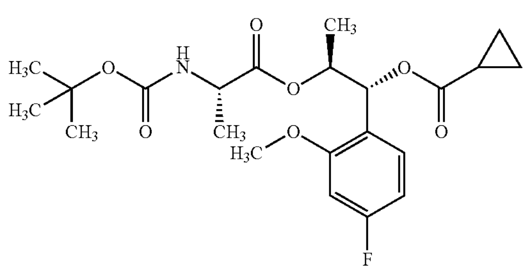 [SMILES: COc1cc(F)ccc1[C@@H](OC(=O)C1CC1)[C@H](C)OC(=O)[C@H](C)NC(=O)OC(C)(C)C] | Example 1E; Example 2D; Example 4B; Example 5 | Colorless Oil |

TABLE 1-continued

Compound Structure, Appearance, and Preparation Method

| *Cmpd. No. | Structure | Prepared According to Example | Colorless Semi-Solid |
|---|---|---|---|
| 286 | 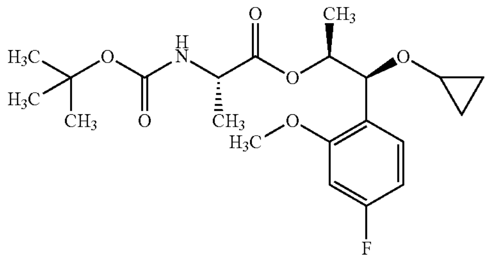 [SMILES: COc1cc(F)ccc1[C@H](OC1CC1)[C@H](C)OC(=O)[C@H](C)NC(=O)OC(C)(C)C] | Examples 10A-C; Example 5 | Colorless Oil |
| 287 | 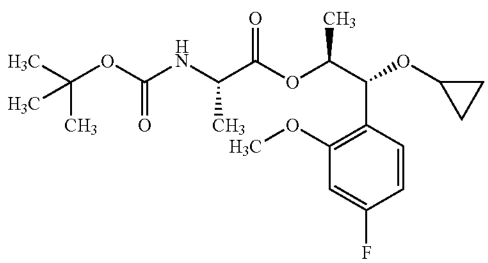 [SMILES: COc1cc(F)ccc1[C@@H](OC1CC1)[C@H](C)OC(=O)[C@H](C)NC(=O)OC(C)(C)C] | Examples 10A-C; Example 5 | Colorless Oil |
| 288 | 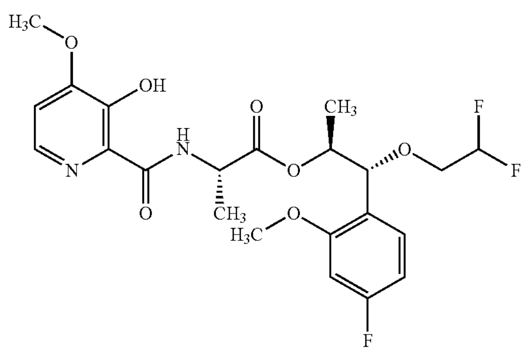 [SMILES: COc1cc(F)ccc1[C@@H](OCC(F)F)[C@H](C)OC(=O)[C@H](C)NC(=O)c1nccc(OC)c1O] | Example 6B | Colorless Oil |
| 289 | 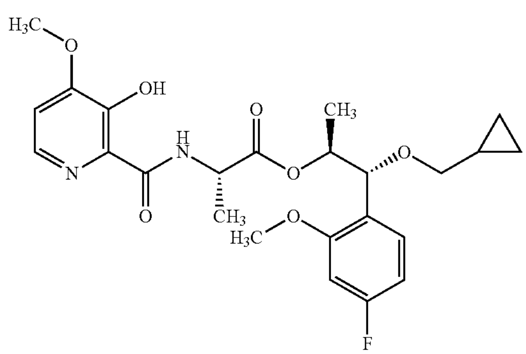 [SMILES: COc1cc(F)ccc1[C@@H](OCC1CC1)[C@H](C)OC(=O)[C@H](C)NC(=O)c1nccc(OC)c1O] | Example 6B | Colorless Oil |

TABLE 1-continued

Compound Structure, Appearance, and Preparation Method

| *Cmpd. No. | Structure | Prepared According to Example | Colorless Semi-Solid |
|---|---|---|---|
| 290 | 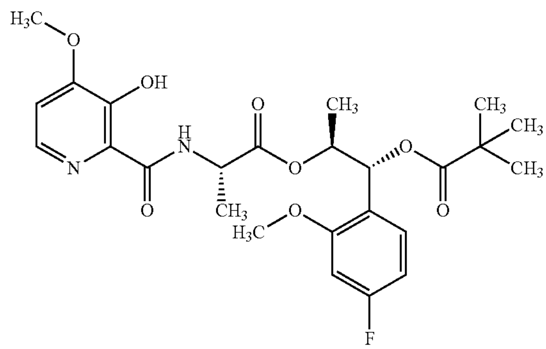 [SMILES: COc1cc(F)ccc1[C@@H](OC(=O)C(C)(C)C)[C@H](C)OC(=O)[C@H](C)NC(=O)c1nccc(OC)c1O] | Example 6B | Colorless Oil |
| 291 | 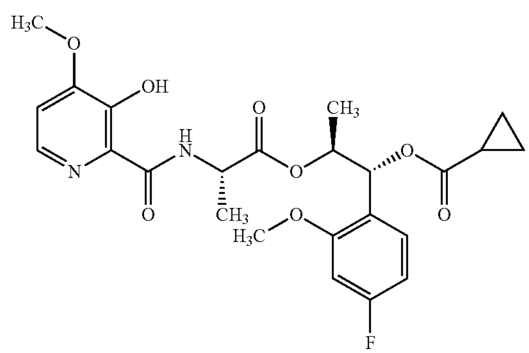 [SMILES: COc1cc(F)ccc1[C@@H](OC(=O)C1CC1)[C@H](C)OC(=O)[C@H](C)NC(=O)c1nccc(OC)c1O] | Example 6B | Oily White Solid |
| 292 | 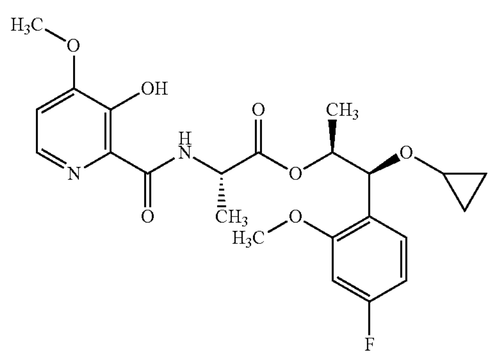 [SMILES: COc1cc(F)ccc1[C@H](OC1CC1)[C@H](C)OC(=O)[C@H](C)NC(=O)c1nccc(OC)c1O] | Example 6B | White Wax |
| 293 | 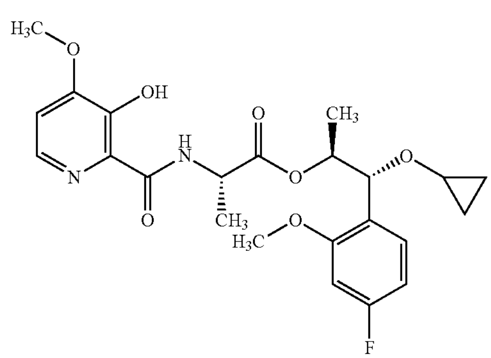 [SMILES: COc1cc(F)ccc1[C@@H](OC1CC1)[C@H](C)OC(=O)[C@H](C)NC(=O)c1nccc(OC)c1O] | Example 6B | Colorless Oil |

TABLE 1-continued

Compound Structure, Appearance, and Preparation Method

| *Cmpd. No. | Structure | Prepared According to Example | Colorless Semi-Solid |
|---|---|---|---|
| 294 | 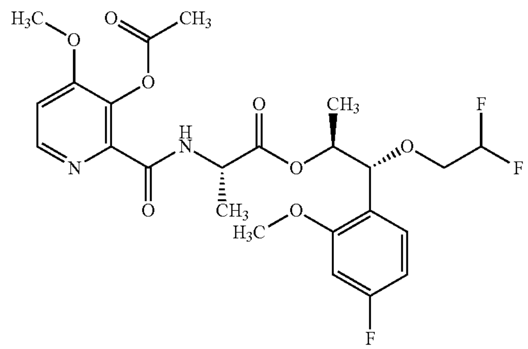 [SMILES: COc1cc(F)ccc1[C@@H](OCC(F)F)[C@H](C)OC(=O)[C@H](C)NC(=O)c1nccc(OC)c1OC(C)=O] | Example 8B | White Foam |
| 295 | 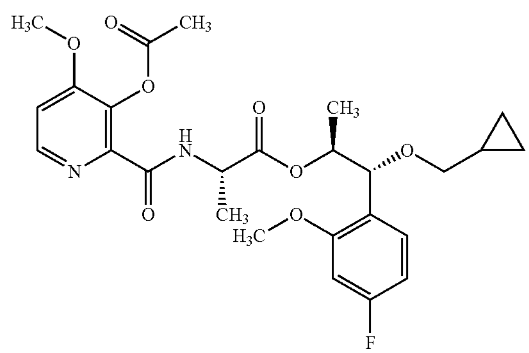 [SMILES: COc1cc(F)ccc1[C@@H](OCC1CC1)[C@H](C)OC(=O)[C@H](C)NC(=O)c1nccc(OC)c1OC(C)=O] | Example 8B | White Foam |
| 296 | 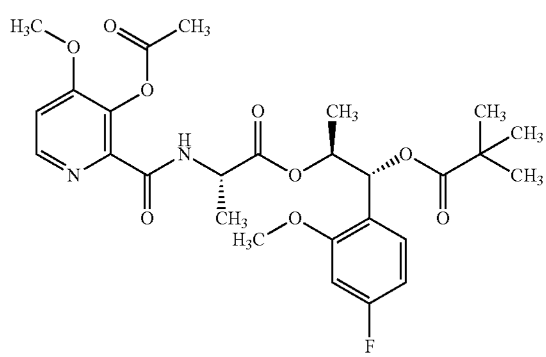 [SMILES: COc1cc(F)ccc1[C@@H](OC(=O)C(C)(C)C)[C@H](C)OC(=O)[C@H](C)NC(=O)c1nccc(OC)c1OC(C)=O] | Example 8B | White Foam |
| 297 | 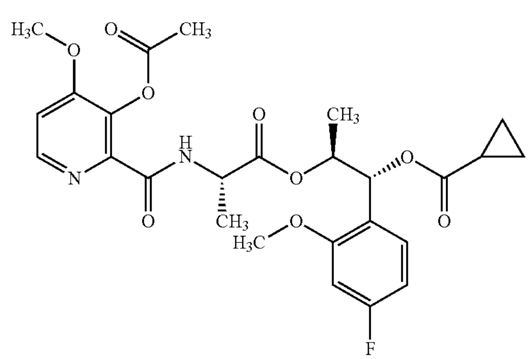 [SMILES: COc1cc(F)ccc1[C@@H](OC(=O)C1CC1)[C@H](C)OC(=O)[C@H](C)NC(=O)c1nccc(OC)c1OC(C)=O] | Example 8B | White Foam |

TABLE 1-continued

Compound Structure, Appearance, and Preparation Method

| *Cmpd. No. | Structure | Prepared According to Example | Colorless Semi-Solid |
|---|---|---|---|
| 298 | 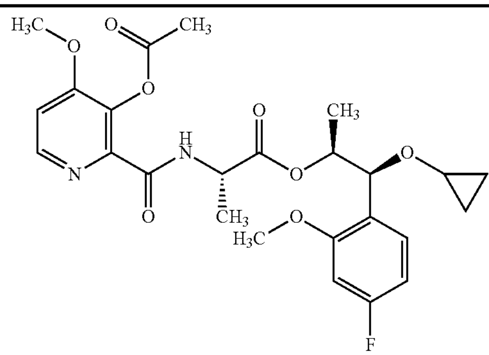 | Example 8B | Off White Foam |
| 299 | 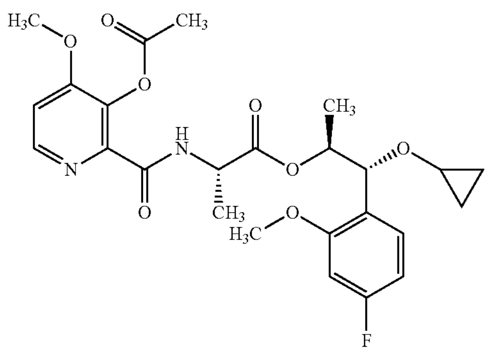 [SMILES: COc1cc(F)ccc1[C@@H](OC1CC1)[C@H](C)OC(=O)[C@H](C)NC(=O)c1nccc(OC)c1OC(C)=O] | Example 8B | Colorless Oil |

TABLE 2

Analytical Data

| *Cmpd. No. | IR (cm$^{-1}$) | MASS | NMR ($^{1}$H, $^{13}$C or $^{19}$F) |
|---|---|---|---|
| 1 | | HRMS-ESI (m/z) [M]$^{+}$ calcd for C$_{21}$H$_{31}$NO$_{5}$, 377.2202; found, 377.2206 | $^{1}$H NMR (500 MHz, CDCl$_{3}$) δ 7.36-7.22 (m, 5H), 5.09 (p, J = 6.3 Hz, 1H), 5.01-4.93 (m, 1H), 4.31 (d, J = 6.2 Hz, 1H), 4.23-4.13 (m, 1H), 3.19 (d, J = 6.8 Hz, 2H), 1.42 (s, 9H), 1.32 (d, J = 6.4 Hz, 3H), 1.04 (d, J = 7.2 Hz, 3H), 1.03-0.96 (m, 1H), 0.54-0.40 (m, 2H), 0.19-0.04 (m, 2H). $^{13}$C NMR (126 MHz, CDCl$_{3}$) δ 172.47, 154.95, 138.76, 128.21, 127.95, 127.59, 83.05, 79.63, 74.05, 73.71, 49.19, 28.32, 18.43, 16.01, 10.58, 3.19, 2.71. |
| 2 | | ESIMS m/z 400 ([M + H]$^{+}$) | $^{1}$H NMR (400 MHz, CDCl$_{3}$) δ 7.43-7.22 (m, 5H), 7.23-7.12 (m, 2H), 6.93-6.78 (m, 3H), 5.26 (qd, J = 6.3, 4.8 Hz, 1H), 5.18 (d, J = 5.0 Hz, 1H), 4.97 (d, J = 8.2 Hz, 1H), 4.24 (h, J = 7.4, 6.8 Hz, 1H), 1.42 (s, 9H), 1.37 (d, J = 6.4 Hz, 3H), 1.12 (d, J = 7.2 Hz, 3H). $^{13}$C NMR (101 MHz, CDCl$_{3}$) δ 172.72, 157.90, 137.59, 129.37, 128.52, 128.15, 126.97, 126.80, 121.20, 115.98, 81.23, 79.75, 74.16, 49.28, 28.32, 18.45, 15.04. |
| 3 | | ESIMS m/z 456 ([M + Na]$^{+}$) | $^{1}$H NMR (400 MHz, CDCl$_{3}$) δ 7.39-7.30 (m, 5H), 7.16-7.09 (m, 2H), 6.79-6.71 (m, 2H), 5.25 (qd, J = |

TABLE 2-continued

Analytical Data

| *Cmpd. No. | IR (cm⁻¹) | MASS | NMR ($^1$H, $^{13}$C or $^{19}$F) |
|---|---|---|---|
| | | | 6.5, 4.8 Hz, 1H), 5.13 (d, J = 4.9 Hz, 1H), 4.94 (d, J = 8.0 Hz, 1H), 4.24 (t, J = 7.6 Hz, 1H), 1.42 (s, 9H), 1.35 (d, J = 6.4 Hz, 3H), 1.13 (d, J = 7.2 Hz, 3H). $^{13}$C NMR (101 MHz, CDCl$_3$) δ 172.71, 156.42, 155.02, 137.00, 129.28, 128.62, 128.36, 126.90, 126.13, 117.25, 81.62, 79.82, 73.96, 49.25, 28.30, 18.46, 14.90. |
| 4 | | ESIMS m/z 434 ([M + H]⁺) | $^1$H NMR (400 MHz, CDCl$_3$) δ 7.41-7.26 (m, 5H), 7.08 (ddd, J = 8.4, 7.7, 0.6 Hz, 1H), 6.91-6.82 (m, 2H), 6.70 (ddd, J = 8.4, 2.4, 1.0 Hz, 1H), 5.30-5.19 (m, 1H), 5.16 (d, J = 4.9 Hz, 1H), 4.95 (d, J = 8.3 Hz, 1H), 4.28-4.19 (m, 1H), 1.42 (s, 9H), 1.35 (d, J = 6.5 Hz, 3H), 1.14 (d, J = 7.2 Hz, 3H). $^{13}$C NMR (101 MHz, CDCl$_3$) δ 172.71, 158.54, 155.01, 136.85, 134.75, 130.15, 128.65, 128.40, 126.87, 121.47, 116.59, 114.09, 81.48, 79.81, 73.95, 49.26, 28.30, 18.44, 14.89. |
| 5 | | ESIMS m/z 456 ([M + Na])⁺ | $^1$H NMR (400 MHz, CDCl$_3$) δ 7.44-7.26 (m, 6H), 7.00 (ddd, J = 8.3, 7.5, 1.7 Hz, 1H), 6.82 (td, J = 7.7, 1.4 Hz, 1H), 6.66 (dd, J = 8.3, 1.4 Hz, 1H), 5.36-5.22 (m, 2H), 4.97 (d, J = 8.2 Hz, 1H), 4.29-4.20 (m, 1H), 1.45-1.39 (m, 12H), 1.15 (d, J = 7.2 Hz, 3H). $^{13}$C NMR (101 MHz, CDCl$_3$) δ 172.71, 155.00, 153.31, 136.81, 130.34, 128.61, 128.39, 127.44, 126.90, 123.54, 121.78, 115.14, 82.01, 79.75, 74.19, 49.30, 28.30, 18.43, 14.86. |
| 6 | | ESIMS m/z 436 ([M + H]⁺) | $^1$H NMR (500 MHz, CDCl$_3$) δ 7.42-7.27 (m, 5H), 6.98 (ddd, J = 10.6, 9.0, 5.3 Hz, 1H), 6.58-6.44 (m, 2H), 5.30 (qd, J = 6.4, 5.0 Hz, 1H), 5.17 (d, J = 5.0 Hz, 1H), 4.95 (d, J = 8.0 Hz, 1H), 4.24 (t, J = 7.7 Hz, 1H), 1.42 (s, 9H), 1.39 (d, J = 6.4 Hz, 3H), 1.14 (d, J = 7.2 Hz, 3H). $^{13}$C NMR (126 MHz, CDCl$_3$) δ 172.66, 158.32 (dd, J = 242.4, 2.5 Hz), 155.00, 149.47 (dd, J = 242.1, 3.4 Hz), 146.24 (dd, J = 12.1, 10.8 Hz), 136.27, 128.69, 128.66, 126.99, 116.41 (dd, J = 20.8, 10.1 Hz), 107.68 (dd, J = 24.0, 6.9 Hz), 105.12 (dd, J = 27.2, 1.7 Hz), 83.04, 79.80, 73.72, 49.25, 28.29, 18.35, 15.03. |
| 7 | | ESIMS m/z 468 ([M + H]⁺) | $^1$H NMR (500 MHz, CDCl$_3$) δ 7.40-7.28 (m, 6H), 6.97 (dd, J = 8.8, 2.6 Hz, 1H), 6.57 (d, J = 8.9 Hz, 1H), 5.30 (qd, J = 6.4, 4.6 Hz, 1H), 5.21 (d, J = 4.6 Hz, 1H), 4.96 (d, J = 8.1 Hz, 1H), 4.29-4.22 (m, 1H), 1.43-1.39 (m, 12H), 1.16 (d, J = 7.2 Hz, 3H). $^{13}$C NMR (126 MHz, CDCl$_3$) δ 172.70, 155.00, 152.06, 136.27, 130.04, 128.71, 128.59, 127.36, 126.86, 126.20, 124.35, 115.83, 82.37, 79.80, 73.97, 49.27, 28.29, 18.43, 14.82. |
| 8 | | ESIMS m/z 452 ([M + H]⁺) | $^1$H NMR (500 MHz, CDCl$_3$) δ 7.38-7.30 (m, 5H), 6.68-6.60 (m, 2H), 6.48-6.40 (m, 1H), 5.29-5.20 (m, 1H), 5.14 (d, J = 4.7 Hz, 1H), 4.94 |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | (d, J = 8.2 Hz, 1H), 4.28-4.21 (m, 1H), 1.42 (s, 9H), 1.34 (d, J = 6.5 Hz, 3H), 1.15 (d, J = 7.3 Hz, 3H). $^1$H NMR (500 MHz, CDCl$_3$) δ 7.38-7.30 (m, 5H), 6.68-6.60 (m, 2H), 6.48-6.40 (m, 1H), 5.29-5.20 (m, 1H), 5.14 (d, J = 4.7 Hz, 1H), 4.94 (d, J = 8.2 Hz, 1H), 4.28-4.21 (m, 1H), 1.42 (s, 9H), 1.34 (d, J = 6.5 Hz, 3H), 1.15 (d, J = 7.3 Hz, 3H). $^{13}$C NMR (126 MHz, CDCl$_3$) δ 172.69, 163.12 (d, J = 248.4 Hz), 159.25 (d, J = 12.4 Hz), 155.00, 136.22, 135.29 (d, J = 13.3 Hz), 128.78, 128.62, 126.80, 112.55 (d, J = 3.3 Hz), 109.25 (d, J = 25.2 Hz), 102.25 (d, J = 25.0 Hz), 81.78, 79.86, 73.72, 49.24, 28.29, 18.43, 14.82. |
| 9 | (Thin film) 3364.14, 2978.73, 1709.99, 1492.42, 1235.09, 1160.57 | HRMS-ESI (m/z) ([M + Na]$^+$) calcd for C$_{23}$H$_{29}$NNaO$_5$, 422.1938; found, 422.1940 | $^1$H NMR (400 MHz, CDCl$_3$) δ 7.42-7.37 (m, 2H), 7.37-7.30 (m, 2H), 7.31-7.22 (m, 1H), 7.22-7.14 (m, 2H), 6.92-6.81 (m, 3H), 5.29-5.20 (m, 2H), 4.93 (d, J = 8.0 Hz, 1H), 4.31-4.16 (m, 1H), 1.43 (s, 9H), 1.37-1.31 (m, 3H), 1.28 (d, J = 7.2 Hz, 3H). |
| 10 | (Thin film) 3366.73, 1708.90, 1492.33, 1236.49, 1159.90 | HRMS-ESI (m/z) ([M + Na]$^+$) calcd for C$_{23}$H$_{29}$NNaO$_5$, 422.1938; found, 422.1939 | $^1$H NMR (400 MHz, CDCl$_3$) δ 7.41-7.37 (m, 2H), 7.36-7.30 (m, 2H), 7.29-7.23 (m, 1H), 7.21-7.12 (m, 2H), 6.90-6.85 (m, 1H), 6.85-6.80 (m, 2H), 5.26 (dq, J = 6.2, 4.8 Hz, 1H), 5.18 (d, J = 5.0 Hz, 1H), 4.97 (d, J = 8.3 Hz, 1H), 4.31-4.16 (m, 1H), 1.42 (s, 9H), 1.37 (d, J = 6.4 Hz, 3H), 1.12 (d, J = 7.2 Hz, 3H). $^{13}$C NMR (101 MHz, CDCl$_3$) δ 172.72, 157.90, 155.00, 137.59, 129.37, 128.53, 128.16, 126.97, 121.20, 115.98, 81.23, 79.76, 74.17, 49.28, 28.32, 18.45, 15.04. |
| 11 | | ESIMS m/z 467 ([M + H]$^+$) | $^1$H NMR (400 MHz, CDCl$_3$) δ 7.41-7.27 (m, 5H), 6.68-6.59 (m, 2H), 6.43 (dt, J = 10.4, 2.3 Hz, 1H), 5.29-5.18 (m, 1H), 5.14 (d, J = 4.7 Hz, 1H), 4.96 (d, J = 8.2 Hz, 1H), 4.22 (q, J = 6.8 Hz, 1H), 1.73-1.61 (m, 1H), 1.54-1.40 (m, 10H), 1.33 (d, J = 6.4 Hz, 3H), 0.72 (t, J = 7.5 Hz, 3H). $^{13}$C NMR (101 MHz, CDCl$_3$) δ 172.06, 163.12 (d, J = 248.2 Hz), 159.24 (d, J = 12.4 Hz), 155.27, 136.21, 135.29 (d, J = 13.3 Hz), 128.80, 128.63, 126.78, 112.54 (d, J = 3.3 Hz), 109.24 (d, J = 25.2 Hz), 102.23 (d, J = 25.1 Hz), 81.77, 79.80, 73.79, 54.48, 28.30, 25.65, 14.81, 9.14. $^{19}$F NMR (376 MHz, CDCl$_3$) δ -109.89. |
| 12 | | ESIMS m/z 473 ([M + Na]$^+$) | $^1$H NMR (400 MHz, CDCl$_3$) δ 7.43-7.28 (m, 5H), 6.98 (ddd, J = 10.6, 9.0, 5.3 Hz, 1H), 6.59-6.42 (m, 2H), 5.29 (qd, J = 6.4, 4.8 Hz, 1H), 5.17 (d, J = 4.9 Hz, 1H), 4.97 (d, J = 8.3 Hz, 1H), 4.22 (q, J = 6.8 Hz, 1H), 1.72-1.58 (m, 1H), 1.48-1.36 (m, 13H), 0.69 (t, J = 7.5 Hz, 3H). $^{13}$C NMR (101 MHz, CDCl$_3$) δ 172.01, 158.32 (dd, J = 242.4, 2.5 Hz), 155.25, 149.44 (dd, J = 242.0, 3.3 Hz), 146.24 (dd, J = 12.3, 10.6 Hz), 136.29, 128.71, 128.66, 126.94, |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 116.38 (dd, J = 20.8, 10.2 Hz), 107.66 (d, J = 24.0 Hz), 105.03 (dd, J = 27.3, 1.4 Hz), 83.01, 79.74, 73.84, 54.48, 28.30, 25.61, 15.03, 9.05. $^{19}$F NMR (376 MHz, CDCl$_3$) δ-116.68 (d, J = 15.0 Hz), −138.71 (d, J = 15.0 Hz). |
| 13 | | ESIMS m/z 469 ([M + H]$^+$) | $^1$H NMR (500 MHz, CDCl$_3$) δ 7.47-7.41 (m, 2H), 7.40-7.27 (m, 5H), 6.92-6.86 (m, 2H), 5.32-5.21 (m, 2H), 4.94 (d, J = 8.1 Hz, 1H), 4.25 (t, J = 7.6 Hz, 1H), 1.41 (s, 9H), 1.37 (d, J = 6.3 Hz, 3H), 1.14 (d, J = 7.2 Hz, 3H). $^{13}$C NMR (126 MHz, CDCl$_3$) δ 172.72, 160.16, 155.00, 136.58, 128.73, 128.51, 126.85 (q, J = 3.7 Hz), 126.83, 124.25 (q, J = 271.2 Hz), 123.34 (q, J = 32.6 Hz), 115.78, 81.32, 79.85, 73.87, 49.26, 28.29, 18.43, 14.84. $^{19}$F NMR (471 MHz, CDCl$_3$) δ-61.67. |
| 14 | | ESIMS m/z 497 ([M + H]$^+$) | $^1$H NMR (500 MHz, CDCl$_3$) δ 7.47-7.40 (m, 2H), 7.40-7.28 (m, 5H), 6.91-6.84 (m, 2H), 5.32-5.23 (m, 2H), 4.93 (d, J = 9.3 Hz, 1H), 4.19 (dd, J = 9.2, 4.5 Hz, 1H), 2.01-1.90 (m, 1H), 1.42 (s, 9H), 1.36 (d, J = 6.2 Hz, 3H), 0.84 (d, J = 6.8 Hz, 3H), 0.62 (d, J = 6.8 Hz, 3H). $^{13}$C NMR (126 MHz, CDCl$_3$) δ 171.85, 160.12, 155.66, 136.53, 128.78, 128.50, 126.82 (q, J = 4.1 Hz), 126.78, 124.25 (q, J = 271.5 Hz), 123.30 (q, J = 32.9 Hz), 115.72, 81.20, 79.77, 73.97, 58.46, 31.11, 28.28, 18.97, 16.93, 14.69. $^{19}$F NMR (471 MHz, CDCl$_3$) δ-61.67. |
| 15 | | ESIMS m/z 418 ([M + H]$^+$) | $^1$H NMR (500 MHz, CDCl$_3$) δ 7.40-7.25 (m, 5H), 7.11 (td, J = 8.3, 6.8 Hz, 1H), 6.64-6.51 (m, 3H), 5.25 (qd, J = 6.4, 4.8 Hz, 1H), 5.16 (d, J = 4.9 Hz, 1H), 4.95 (d, J = 8.2 Hz, 1H), 4.28-4.21 (m, 1H), 1.42 (s, 9H), 1.36 (d, J = 6.4 Hz, 3H), 1.14 (d, J = 7.2 Hz, 3H). $^{13}$C NMR (126 MHz, CDCl$_3$) δ 172.71, 163.39 (d, J = 245.6 Hz), 159.11 (d, J = 10.8 Hz), 155.00, 136.93, 130.13 (d, J = 10.0 Hz), 128.64, 128.37, 126.87, 111.57 (d, J = 2.9 Hz), 108.08 (d, J = 21.3 Hz), 103.73 (d, J = 24.8 Hz), 81.50, 79.80, 73.93, 49.25, 28.30, 18.44, 14.91. |
| 16 | | ESIMS m/z 495 ([M + H]$^+$) | $^1$H NMR (500 MHz, CDCl$_3$) δ 7.40-7.26 (m, 5H), 7.19-7.08 (m, 4H), 6.97-6.92 (m, 2H), 6.65-6.50 (m, 3H), 5.17 (qd, J = 6.4, 3.8 Hz, 1H), 5.12 (d, J = 4.4 Hz, 1H), 4.88 (d, J = 8.5 Hz, 1H), 4.59-4.51 (m, 1H), 2.97 (dd, J = 13.9, 5.8 Hz, 1H), 2.90 (dd, J = 13.9, 5.9 Hz, 1H), 1.40 (s, 9H), 1.34 (d, J = 6.4 Hz, 3H). $^{13}$C NMR (126 MHz, CDCl$_3$) δ 171.29, 163.41 (d, J = 245.4 Hz), 158.96 (d, J = 10.9 Hz), 155.00, 136.91, 135.75, 130.14 (d, J = 10.0 Hz), 129.33, 128.73, 128.43, 126.93, 126.80, 111.63 (d, J = 2.9 Hz), 108.07 (d, J = 21.2 Hz), 103.75 (d, J = 24.9 Hz), 81.24, 79.86, 74.68, 54.31, 37.92, 28.27, 14.49. |

TABLE 2-continued

Analytical Data

| *Cmpd. No. | IR (cm$^{-1}$) | MASS | NMR ($^1$H, $^{13}$C or $^{19}$F) |
|---|---|---|---|
| 17 | | ESIMS m/z 454 ([M + Na]$^+$) | |
| 18 | | ESIMS m/z 454 ([M + H]$^+$) | $^1$H NMR (400 MHz, CDCl$_3$) δ 7.59-7.54 (m, 3H), 7.51 (dd, J = 7.6, 1.2 Hz, 1H), 7.47-7.29 (m, 6H), 5.15 (p, J = 6.4 Hz, 1H), 4.96 (d, J = 7.2 Hz, 1H), 4.39 (d, J = 6.3 Hz, 1H), 4.26-4.13 (m, 1H), 3.28-3.20 (m, 2H), 1.42 (s, 9H), 1.36 (d, J = 6.3 Hz, 3H), 1.09-0.99 (m, 4H), 0.56-0.44 (m, 2H), 0.20-0.08 (m, 2H). $^{13}$C NMR (126 MHz, CDCl$_3$) δ 172.56, 154.96, 141.18, 140.86, 139.40, 128.81, 128.71, 127.41, 127.09, 126.76, 126.51, 126.33, 83.14, 79.68, 74.08, 73.85, 49.18, 30.94, 28.31, 16.04, 10.62, 3.24, 2.75. |
| 19 | (Thin film) 3356, 2923, 2850, 1712 | ESIMS m/z 428 ([M + Na]$^+$) | $^1$H NMR (400 MHz, CDCl$_3$) δ 7.28 (dd, J = 5.1, 1.2 Hz, 1H), 7.24-7.17 (m, 2H), 7.07 (dd, J = 3.5, 1.2 Hz, 1H), 6.97 (dd, J = 5.0, 3.5 Hz, 1H), 6.95-6.85 (m, 3H), 5.46-5.34 (m, 2H), 5.06 (d, J = 7.0 Hz, 1H), 4.41-4.22 (m, 1H), 1.44 (s, 9H), 1.29 (d, J = 7.2 Hz, 3H), 1.25 (d, J = 6.0 Hz, 3H). |
| 20 | (Thin film) 3358, 2979, 2929, 1712 | ESIMS m/z 428 ([M + Na]$^+$) | $^1$H NMR (400 MHz, CDCl$_3$) δ 7.31-7.17 (m, 3H), 7.07 (dt, J = 3.4, 1.0 Hz, 1H), 7.00-6.85 (m, 4H), 5.42 (d, J = 5.1 Hz, 1H), 5.39-5.31 (m, 1H), 5.06-4.93 (m, 1H), 4.40-4.21 (m, 1H), 1.43 (s, 9H), 1.39 (d, J = 6.4 Hz, 3H), 1.21 (d, J = 7.2 Hz, 3H). |
| 21 | | ESIMS m/z 491 [(M + Na)$^+$] | $^1$H NMR (400 MHz, CDCl$_3$) δ 7.40-7.29 (m, 6H), 6.97 (dd, J = 8.8, 2.6 Hz, 1H), 6.64 (d, J = 8.9 Hz, 1H), 5.50-5.37 (m, 1H), 5.14 (d, J = 6.8 Hz, 1H), 5.07 (d, J = 8.1 Hz, 1H), 4.37-4.24 (m, 1H), 1.44 (s, 9H), 1.29 (d, J = 7.2 Hz, 3H), 1.21 (d, J = 6.5 Hz, 3H). $^{13}$C NMR (101 MHz, CDCl$_3$) δ 206.90, 172.67, 155.04, 151.85, 136.01, 130.07, 128.88, 128.81, 127.30, 127.18, 125.99, 124.11, 115.42, 82.78, 79.76, 73.14, 49.33, 28.33, 18.68, 16.21. |
| 22 | | ESIMS m/z 401 ([M + H]$^+$) | $^1$H NMR (400 MHz, CDCl$_3$) δ 8.66 (d, J = 2.2 Hz, 1H), 8.55 (dd, J = 4.8, 1.7 Hz, 1H), 7.74 (dt, J = 7.9, 2.0 Hz, 1H), 7.33-7.27 (m, 1H), 7.24-7.10 (m, 2H), 6.92 (tt, J = 7.3, 1.1 Hz, 1H), 6.87-6.74 (m, 2H), 5.32-5.24 (m, 1H), 5.21 (d, J = 5.4 Hz, 1H), 4.95 (d, J = 7.4 Hz, 1H), 4.31-4.14 (m, 1H), 1.42 (s, 9H), 1.40 (d, J = 6.3 Hz, 3H), 1.14 (d, J = 7.2 Hz, 3H). |
| 23 | (Thin film) 3351, 2979, 1704, 1491 | ESIMS m/z 407 ([M + H]$^+$) | $^1$H NMR (400 MHz, CDCl$_3$) δ 7.80 (dd, J = 3.2, 1.3 Hz, 1H), 7.35 (t, J = 3.2 Hz, 1H), 7.25-7.16 (m, 2H), 7.03-6.89 (m, 3H), 5.66-5.54 (m, 1H), 5.54-5.45 (m, 1H), 5.18-5.01 (m, 1H), 4.38-4.22 (m, 1H), 1.44 (s, 9H), 1.35 (d, J = 6.4 Hz, 3H), 1.25 (d, J = 7.8 Hz, 3H). |
| 24 | | ESIMS m/z 494 ([M + H]$^+$) | $^1$H NMR (400 MHz, CDCl$_3$) δ 7.59-7.51 (m, 4H), 7.46-7.40 (m, 3H), 7.35 (ddd, J = 4.9, 4.1, 2.6 Hz, 2H), 7.16-7.09 (m, 1H), 6.61 (ddt, J = 13.3, 4.6, 2.3 Hz, 3H), 5.33-5.27 (m, 2H), 5.23 (d, J = 4.9 Hz, 1H), 4.95 (d, J = 7.2 Hz, 1H), 4.30-4.20 |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | (m, 1H), 1.42 (s, 9H), 1.40 (d, J = 6.4 Hz, 3H), 1.11 (d, J = 7.2 Hz, 3H). $^{13}$C NMR (101 MHz, CDCl$_3$) δ 164.64, 141.66, 140.57, 137.60, 130.24, 129.12, 128.84, 127.58, 127.20, 127.14, 125.75, 125.53, 111.62, 108.30, 108.09, 103.94, 103.69, 99.99, 81.63, 74.01, 60.39, 28.29, 18.39, 14.90, 14.20. |
| 25 | | ESIMS m/z 380.6 ([M + H]$^+$) | $^1$H NMR (400 MHz, CDCl$_3$) δ 7.38-7.27 (m, 5H), 5.26-4.89 (m, 2H), 4.39-4.26 (m, 1H), 4.22 (d, J = 6.8 Hz, 1H), 3.15-2.97 (m, 2H), 1.92-1.74 (m, 1H), 1.44 (s, 9H), 1.35 (dd, J = 7.0, 2.6 Hz, 3H), 1.06 (d, J = 6.5 Hz, 3H), 0.86 (d, J = 6.7 Hz, 6H). |
| 26 | | ESIMS m/z 380.6 ([M + H]$^+$) | $^1$H NMR (400 MHz, CDCl$_3$) δ 7.37-7.27 (m, 5H), 5.11-5.03 (m, 1H), 4.97 (d, J = 7.9 Hz, 1H), 4.22 (d, J = 6.1 Hz, 1H), 4.18 (d, J = 8.1 Hz, 1H), 3.14 (dd, J = 8.8, 6.5 Hz, 1H), 3.04 (dd, J = 8.8, 6.4 Hz, 1H), 1.92-1.76 (m, 1H), 1.43 (s, 9H), 1.30 (d, J = 6.3 Hz, 3H), 1.06 (d, J = 7.2 Hz, 3H), 0.90 (d, J = 3.9 Hz, 3H), 0.88 (d, J = 3.9 Hz, 3H). |
| 27 | | ESIMS m/z 388 ([M + Na]$^+$) | $^1$H NMR (400 MHz, CDCl$_3$) δ 7.39-7.27 (m, 5H), 5.22-5.10 (m, 1H), 5.09 (d, J = 7.8 Hz, 1H), 4.40-4.27 (m, 1H), 4.22 (d, J = 6.9 Hz, 1H), 3.36-3.16 (m, 2H), 1.60-1.48 (m, 2H), 1.44 (s, 9H), 1.35 (d, J = 7.1 Hz, 3H), 1.06 (d, J = 6.5 Hz, 3H), 0.87 (t, J = 7.4 Hz, 3H). |
| 28 | | ESIMS m/z 388 ([M + Na]$^+$) | $^1$H NMR (400 MHz, CDCl$_3$) δ 7.39-7.27 (m, 5H), 5.18-5.02 (m, 1H), 4.98 (d, J = 8.0 Hz, 1H), 4.24 (d, J = 6.1 Hz, 1H), 4.23-4.12 (m, 1H), 3.33 (dt, J = 9.1, 6.6 Hz, 1H), 3.25 (dt, J = 9.1, 6.4 Hz, 1H), 1.57 (dtd, J = 13.8, 7.4, 6.5 Hz, 2H), 1.43 (s, 9H), 1.29 (d, J = 6.4 Hz, 3H), 1.06 (d, J = 7.2 Hz, 3H), 0.90 (t, J = 7.4 Hz, 3H). |
| 29 | | ESIMS m/z 360 ([M + Na]$^+$) | $^1$H NMR (400 MHz, CDCl$_3$) δ 7.41-7.28 (m, 5H), 5.24-5.12 (m, 1H), 5.08 (d, J = 5.5 Hz, 1H), 4.40-4.24 (m, 1H), 4.11 (d, J = 6.9 Hz, 1H), 3.90 (s, 3H), 1.44 (s, 9H), 1.36 (d, J = 7.0 Hz, 3H), 1.07 (d, J = 6.5 Hz, 3H). |
| 30 | | ESIMS m/z 360 ([M + Na]$^+$) | $^1$H NMR (400 MHz, CDCl$_3$) δ 7.38-7.28 (m, 5H), 5.16-5.05 (m, 1H), 4.97 (d, J = 7.7 Hz, 1H), 4.31-4.18 (m, 1H), 4.17 (d, J = 5.9 Hz, 1H), 3.26 (s, 3H), 1.43 (s, 9H), 1.28 (d, J = 6.4 Hz, 3H), 1.08 (d, J = 7.2 Hz, 3H). |
| 31 | | ESIMS m/z 400 ([M + Na]$^+$) | $^1$H NMR (400 MHz, CDCl$_3$) δ 7.36-7.28 (m, 5H), 5.22-5.11 (m, 1H), 5.10 (d, J = 5.1 Hz, 1H), 4.37-4.27 (m, 2H), 3.90 (s, 3H), 3.21-3.08 (m, 2H), 1.44 (s, 9H), 1.37 (d, J = 7.1 Hz, 3H), 1.08 (d, J = 6.5 Hz, 3H), 1.01-0.94 (m, 1H), 0.54-0.39 (m, 2H), 0.17-0.02 (m, 2H). |
| 32 | | ESIMS m/z 476 ([M + H]$^+$) | $^1$H NMR (400 MHz, CDCl$_3$) δ 7.62 (s, 1H), 7.55 (d, J = 7.4 Hz, 2H), 7.51 (dd, J = 7.0, 1.7 Hz, 1H), 7.46-7.32 (m, 5H), 7.19 (dd, J = 8.2, 7.6 Hz, 2H), 6.88 (dd, J = 13.9, 7.9 Hz, 3H), 5.34-5.28 (m, 1H), 5.25 (d, J = 5.0 Hz, 1H), 4.96 (d, J = 7.3 Hz, 1H), 4.29-4.17 (m, 1H), 1.44-1.39 |

TABLE 2-continued

| | | Analytical Data | |
|---|---|---|---|
| *Cmpd. No. | IR (cm$^{-1}$) | MASS | NMR ($^1$H, $^{13}$C or $^{19}$F) |
| | | | (m, 12H), 1.09 (d, J = 7.2 Hz, 3H). $^{13}$C NMR (101 MHz, CDCl$_3$) δ 172.80, 157.95, 154.98, 141.49, 140.68, 138.25, 129.41, 129.01, 128.81, 127.50, 127.13, 126.97, 125.86, 125.65, 121.29, 116.04, 81.38, 74.23, 49.24, 28.30, 18.39, 15.03. |
| 33 | | ESIMS m/z 498 ([M + Na]$^+$) | $^1$H NMR (400 MHz, CDCl$_3$) δ 7.58-7.54 (m, 4H), 7.48-7.40 (m, 4H), 7.36-7.31 (m, 1H), 7.23-7.17 (m, 2H), 6.93-6.84 (m, 3H), 5.29 (p, J = 6.3 Hz, 1H), 5.23 (d, J = 4.9 Hz, 1H), 4.96 (d, J = 7.1 Hz, 1H), 4.31-4.20 (m, 1H), 1.42 (s, 9H), 1.40 (d, J = 6.4 Hz, 3H), 1.14 (d, J = 7.2 Hz, 3H). $^{13}$C NMR (101 MHz, CDCl$_3$) δ 172.77, 157.90, 141.05, 140.53, 136.56, 129.40, 128.77, 127.42, 127.39, 127.24, 127.04, 121.25, 116.00, 81.03, 74.17, 49.29, 28.30, 18.47, 15.03. |
| 34 | | ESIMS m/z 418 ([M + H]$^+$) | $^1$H NMR (400 MHz, CDCl$_3$) δ 7.40-7.34 (m, 2H), 7.22-7.15 (m, 2H), 7.02 (dd, J = 14.6, 5.9 Hz, 2H), 6.90 (t, J = 7.4 Hz, 1H), 6.83-6.78 (m, 2H), 5.26-5.19 (m, 1H), 5.15 (d, J = 5.1 Hz, 1H), 4.94 (d, J = 7.2 Hz, 1H), 4.24 (dt, J = 13.4, 6.8 Hz, 1H), 1.42 (s, 9H), 1.37 (d, J = 6.4 Hz, 3H), 1.13 (d, J = 7.2 Hz, 3H). $^{19}$F NMR (376 MHz, CDCl$_3$) δ-113.75 (s, 1F). |
| 35 | | ESIMS m/z 419 ([M + H]$^+$) | $^1$H NMR (400 MHz, CDCl$_3$) δ 7.39-7.27 (m, 5H), 6.90-6.81 (m, 2H), 6.81-6.68 (m, 2H), 5.24 (qd, J = 6.4, 4.8 Hz, 1H), 5.09 (d, J = 4.9 Hz, 1H), 5.00-4.89 (m, 1H), 4.32-4.16 (m, 1H), 1.42 (s, 9H), 1.36 (d, J = 6.5 Hz, 3H), 1.12 (d, J = 7.2 Hz, 3H). $^{19}$F NMR (376 MHz, CDCl$_3$) δ-123.15. |
| 36 | | ESIMS m/z 437 ([M + H]$^+$) | $^1$H NMR (400 MHz, CDCl$_3$) δ 7.39-7.29 (m, 2H), 7.11-6.98 (m, 2H), 6.92-6.81 (m, 2H), 6.79-6.68 (m, 2H), 5.39-5.27 (m, 1H), 5.05-4.98 (m, 2H), 4.38-4.25 (m, 1H), 1.44 (s, 9H), 1.27 (d, J = 7.3 Hz, 3H), 1.19 (d, J = 6.5 Hz, 3H). $^{19}$F NMR (376 MHz, CDCl$_3$) δ-113.06, −122.98. |
| 37 | | ESIMS m/z 449 ([M + H]$^+$) | $^1$H NMR (300 MHz, CDCl$_3$) δ 7.44-7.27 (m, 5H), 7.19-7.12 (m, 1H), 6.78 (ddd, J = 8.4, 2.2, 0.8 Hz, 1H), 6.54 (d, J = 8.4 Hz, 1H), 5.35-5.27 (m, 1H), 5.20 (d, J = 4.8 Hz, 1H), 4.97 (d, J = 7.2 Hz, 1H), 4.37-4.15 (m, 1H), 2.19 (s, 3H), 1.46-1.32 (m, 12H), 1.15 (d, J = 7.2 Hz, 3H). $^{13}$C NMR (126 MHz, CDCl$_3$) δ 172.71, 151.07, 137.00, 131.53, 130.75, 128.57, 128.54, 128.31, 127.84, 126.97, 123.12, 115.12, 82.12, 79.73, 74.17, 28.30, 20.24, 18.45. |
| 38 | | ESIMS m/z 467 ([M + H]$^+$) | $^1$H NMR (300 MHz, CDCl$_3$) δ 7.44-7.32 (m, 2H), 7.15 (dd, J = 2.2, 0.8 Hz, 1H), 7.10-6.96 (m, 2H), 6.80 (ddd, J = 8.5, 2.1, 0.8 Hz, 1H), 6.53 (d, J = 8.4 Hz, 1H), 5.27 (qd, J = 6.4, 4.8 Hz, 1H), 5.18 (d, J = 4.9 Hz, 1H), 4.96 (d, J = 8.2 Hz, 1H), 4.36-4.12 (m, 1H), 2.20 (s, 3H), 1.42 (s, 9H), 1.41 (d, J = 8.0 Hz, 3H), 1.16 |

TABLE 2-continued

Analytical Data

| *Cmpd. No. | IR (cm$^{-1}$) | MASS | NMR ($^1$H, $^{13}$C or $^{19}$F) |
|---|---|---|---|
| 39 | | ESIMS m/z 436 ([M + H]$^+$) | (d, J = 7.2 Hz, 3H). $^{19}$F NMR (471 MHz, CDCl$_3$) δ-113.45. $^1$H NMR (400 MHz, CDCl$_3$) δ 7.43 (td, J = 8.7, 6.5 Hz, 1H), 7.25-7.16 (m, 2H), 6.95-6.89 (m, 1H), 6.89-6.78 (m, 4H), 5.47 (d, J = 5.8 Hz, 1H), 5.33 (p, J = 6.1 Hz, 1H), 4.97 (d, J = 7.2 Hz, 1H), 4.32-4.18 (m, 1H), 1.43 (s, 9H), 1.39 (d, J = 6.4 Hz, 3H), 1.17 (d, J = 7.2 Hz, 3H). $^{19}$F NMR (471 MHz, CDCl$_3$) δ-109.59 (d, J = 6.7 Hz), -113.96 (s). |
| 40 | | ESIMS m/z 414 ([M + H]$^+$) | $^1$H NMR (400 MHz, CDCl$_3$) δ 7.27 (d, J = 6.8 Hz, 3H), 7.19-7.11 (m, 4H), 6.87 (t, J = 7.4 Hz, 1H), 6.82 (d, J = 7.8 Hz, 2H), 5.28-5.21 (m, 1H), 5.15 (d, J = 4.8 Hz, 1H), 4.96 (d, J = 7.2 Hz, 1H), 4.29-4.19 (m, 1H), 2.31 (s, 3H), 1.42 (s, 9H), 1.35 (d, J = 6.4 Hz, 3H), 1.14 (d, J = 7.2 Hz, 3H). $^{13}$C NMR (101 MHz, CDCl$_3$) δ 172.73, 157.95, 137.83, 134.48, 129.33, 129.19, 126.87, 121.09, 115.96, 81.07, 74.22, 28.31, 21.15, 18.51, 14.93. |
| 41 | | ESIMS m/z 452 ([M + Na]$^+$). | $^1$H NMR (400 MHz, CDCl$_3$) δ 7.37 (d, J = 7.6 Hz, 1H), 7.26-7.21 (m, 1H), 7.16 (t, J = 7.8 Hz, 2H), 6.86 (dt, J = 18.3, 8.1 Hz, 5H), 5.66 (d, J = 4.6 Hz, 1H), 5.39-5.31 (m, 1H), 5.01 (s, 1H), 4.25 (s, 1H), 3.91 (s, 3H), 1.42 (s, 9H), 1.33 (d, J = 6.5 Hz, 3H), 1.17 (d, J = 7.2 Hz, 3H). $^{13}$C NMR (376 MHz, CDCl$_3$) δ 172.50, 157.92, 156.64, 154.95, 129.29, 129.11, 127.82, 125.54, 120.89, 120.85, 115.65, 110.22, 79.63, 74.92, 73.02, 55.48, 49.36, 28.32, 18.60, 15.02. |
| 42 | | ESIMS m/z 470 ([M + Na]$^+$) | $^1$H NMR (400 MHz, CDCl$_3$) δ 7.33 (t, J = 7.7 Hz, 1H), 7.17 (t, J = 7.9 Hz, 2H), 6.87 (t, J = 7.3 Hz, 1H), 6.80 (d, J = 8.2 Hz, 2H), 6.60 (dd, J = 13.0, 5.7 Hz, 2H), 5.58 (d, J = 4.7 Hz, 1H), 5.33 (dd, J = 11.9, 5.7 Hz, 1H), 4.99 (s, 1H), 4.25 (s, 1H), 3.90 (s, 3H), 1.42 (s, 9H), 1.32 (d, J = 6.5 Hz, 3H), 1.18 (d, J = 7.2 Hz, 3H). $^{13}$C NMR (101 MHz, CDCl$_3$) δ 172.46, 163.39 (d, J = 246.4 Hz), 157.82 (d, J = 9.7 Hz), 157.68, 154.95, 129.34, 128.98 (d, J = 10.1 Hz), 121.31 (d, J = 3.2 Hz), 121.07, 115.60, 107.38 (d, J = 21.3 Hz), 98.70 (d, J = 25.8 Hz), 79.70, 74.55, 72.89, 55.78, 49.36, 28.31, 18.59, 15.08. $^{19}$F NMR (376 MHz, CDCl$_3$) δ-111.26 (s, 1F). |
| 43 | | ESIMS m/z 462 ([M + H]$^+$) | $^1$H NMR (400 MHz, CDCl$_3$) δ 7.27 (d, J = 6.6 Hz, 2H), 7.19-7.08 (m, 3H), 6.78 (ddd, J = 8.6, 2.1, 0.9 Hz, 1H), 6.54 (d, J = 8.4 Hz, 1H), 5.33-5.23 (m, 1H), 5.17 (d, J = 4.6 Hz, 1H), 4.98 (d, J = 8.0 Hz, 1H), 4.37-4.15 (m, 1H), 2.31 (s, 3H), 2.19 (s, 3H), 1.42 (s, 9H), 1.39 (d, J = 6.5 Hz, 3H), 1.17 (d, J = 7.2 Hz, 3H). |
| 44 | | ESIMS m/z 432 ([M + H]$^+$) | $^1$H NMR (400 MHz, CDCl$_3$) δ 7.28-7.21 (m, 2H), 7.14 (d, J = 7.8 Hz, 2H), 6.89-6.80 (m, 2H), 6.80-6.72 (m, 2H), 5.23 (qd, J = 6.4, 4.7 Hz, 1H), 5.06 (d, J = 4.8 Hz, 1H), 5.02-4.92 (m, 1H), 4.33-4.17 (m, 1H), |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 2.31 (s, 3H), 1.42 (s, 9H), 1.35 (d, J = 6.4 Hz, 3H), 1.15 (d, J = 7.2 Hz, 3H). $^{19}$F NMR (376 MHz, CDCl$_3$) δ-123.28. |
| 45 | | ESIMS m/z 436 ([M + H]$^+$) | $^1$H NMR (400 MHz, CDCl$_3$) δ 7.41-7.30 (m, 2H), 7.09-6.97 (m, 2H), 6.90-6.81 (m, 2H), 6.80-6.66 (m, 2H), 5.22 (qd, J = 6.4, 4.9 Hz, 1H), 5.08 (d, J = 5.1 Hz, 1H), 5.04-4.91 (m, 1H), 4.31-4.18 (m, 1H), 1.42 (s, 9H), 1.36 (d, J = 6.4 Hz, 3H), 1.14 (d, J = 7.2 Hz, 3H). $^{19}$F NMR (376 MHz, CDCl$_3$) δ-113.44, -122.75. |
| 46 | | ESIMS m/z 430 ([M + H]$^+$) | $^1$H NMR (400 MHz, CDCl$_3$) δ 7.24 (t, J = 7.9 Hz, 1H), 7.20-7.15 (m, 2H), 6.98 (d, J = 7.6 Hz, 1H), 6.94-6.92 (m, 1H), 6.89 (t, J = 7.4 Hz, 1H), 6.85-6.78 (m, 3H), 5.28-5.21 (m, 1H), 5.15 (d, J = 4.9 Hz, 1H), 4.97 (d, J = 5.5 Hz, 1H), 4.31-4.17 (m, 1H), 3.77 (s, 3H), 1.42 (s, 9H), 1.37 (d, J = 6.4 Hz, 3H), 1.14 (d, J = 7.2 Hz, 3H). $^{13}$C NMR (101 MHz, CDCl$_3$) δ 172.72, 159.79, 157.98, 154.99, 139.27, 129.54, 129.35, 121.23, 119.32, 115.98, 113.49, 112.51, 81.16, 79.76, 74.18, 55.20, 49.30, 28.30, 18.44, 14.92. |
| 47 | | ESIMS m/z 432 ([M + H]$^+$) | $^1$H NMR (400 MHz, CDCl$_3$) δ 7.36 (dd, J = 8.6, 5.9 Hz, 1H), 7.20-7.15 (m, 2H), 6.85 (ddd, J = 12.0, 11.1, 5.0 Hz, 3H), 6.76-6.71 (m, 2H), 5.36 (d, J = 5.0 Hz, 1H), 5.21-5.13 (m, 1H), 4.93 (d, J = 7.0 Hz, 1H), 4.24 (s, 1H), 2.50 (s, 3H), 1.43-1.39 (m, 12H), 1.09 (d, J = 7.2 Hz, 3H). $^{19}$F NMR (101 MHz, CDCl$_3$) δ-114.88 (s, 1F). |
| 48 | | ESIMS m/z 474 ([M + Na]$^+$) | $^1$H NMR (400 MHz, CDCl$_3$) δ 7.48 (dd, J = 8.8, 6.1 Hz, 1H), 7.24-7.17 (m, 2H), 7.13 (dd, J = 8.4, 2.6 Hz, 1H), 6.94 (ddd, J = 18.0, 11.6, 4.9 Hz, 2H), 6.82-6.77 (m, 2H), 5.61 (d, J = 5.4 Hz, 1H), 5.35-5.28 (m, 1H), 4.97 (d, J = 5.8 Hz, 1H), 4.32-4.21 (m, 1H), 1.42 (s, 9H), 1.39 (d, J = 6.4 Hz, 3H), 1.17 (d, J = 7.2 Hz, 3H). $^{19}$F NMR (376 MHz, CDCl$_3$) δ-111.26 (s, 1F). |
| 49 | | ESIMS m/z 432 ([M + H]$^+$) | $^1$H NMR (400 MHz, CDCl$_3$) δ 7.30 (t, J = 7.7 Hz, 1H), 7.22-7.16 (m, 2H), 6.92-6.81 (m, 5H), 5.48 (d, J = 5.6 Hz, 1H), 5.34 (p, J = 6.3 Hz, 1H), 4.99 (d, J = 6.4 Hz, 1H), 4.31-4.18 (m, 1H), 2.30 (s, 3H), 1.42 (s, 9H), 1.38 (d, J = 6.4 Hz, 3H), 1.16 (d, J = 7.1 Hz, 3H). $^{19}$F NMR (376 MHz, CDCl$_3$) δ-119.17 (s, 1F). |
| 50 | | ESIMS m/z 450 ([M + H]$^+$) | $^1$H NMR (400 MHz, CDCl$_3$) δ 8.40 (d, J = 8.5 Hz, 1H), 7.89 (d, J = 8.1 Hz, 1H), 7.79 (d, J = 8.2 Hz, 1H), 7.64 (t, J = 8.0 Hz, 2H), 7.54 (t, J = 7.5 Hz, 1H), 7.44-7.38 (m, 1H), 7.12 (dd, J = 8.5, 7.5 Hz, 2H), 6.85 (t, J = 7.3 Hz, 1H), 6.79 (d, J = 8.5 Hz, 2H), 6.07 (d, J = 4.0 Hz, 1H), 5.46-5.39 (m, 1H), 4.96 (d, J = 5.1 Hz, 1H), 4.31-4.18 (m, 1H), 1.44-1.38 (m, 12H), 1.00 (d, J = 7.2 Hz, 3H). |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | $^{13}$C NMR (101 MHz, CDCl$_3$) δ 173.23, 158.01, 155.02, 133.75, 133.03, 130.60, 129.39, 129.02, 128.66, 126.78, 125.85, 125.47, 124.72, 122.88, 121.13, 115.68, 79.78, 77.52, 73.84, 49.25, 28.31, 18.25, 14.36. |
| 51 | | ESIMS m/z 467 ([M + NH$_4$]$^+$) | $^1$H NMR (400 MHz, CDCl$_3$) δ 7.87-7.77 (m, 4H), 7.53 (dd, J = 8.5, 1.6 Hz, 1H), 7.50-7.44 (m, 2H), 7.16 (dd, J = 9.6, 6.5 Hz, 2H), 6.90-6.84 (m, 3H), 5.40-5.31 (m, 2H), 4.94 (d, J = 5.8 Hz, 1H), 4.31-4.18 (m, 1H), 1.43-1.38 (m, 12H), 1.09 (d, J = 7.2 Hz, 3H). $^{13}$C NMR (101 MHz, CDCl$_3$) δ 172.74, 157.99, 154.99, 135.15, 133.18, 133.10, 129.38, 128.44, 127.94, 127.73, 126.32, 126.28, 126.20, 124.37, 121.28, 116.07, 81.46, 79.77, 74.22, 49.27, 28.30, 18.43, 14.95. |
| 52 | | ESIMS m/z 491 ([M + NH$_4$]$^+$) | $^1$H NMR (400 MHz, CDCl$_3$) δ 7.34 (dd, J = 9.2, 6.1 Hz, 1H), 7.21-7.15 (m, 2H), 6.88 (t, J = 7.4 Hz, 1H), 6.81 (d, J = 7.9 Hz, 2H), 6.61 (ddd, J = 10.9, 5.1, 2.4 Hz, 2H), 6.09 (ddt, J = 17.2, 10.4, 5.1 Hz, 1H), 5.63 (d, J = 4.6 Hz, 1H), 5.47 (ddd, J = 17.3, 3.0, 1.5 Hz, 1H), 5.39-5.31 (m, 2H), 5.02 (d, J = 6.1 Hz, 1H), 4.67-4.56 (m, 2H), 4.32-4.19 (m, 1H), 1.42 (s, 9H), 1.32 (d, J = 6.5 Hz, 3H), 1.19 (d, J = 7.2 Hz, 3H). $^{19}$F NMR (376 MHz, CDCl$_3$) δ-111.28 (s, 1F). |
| 53 | | ESIMS m/z 504 ([M + Na]$^+$) | $^1$H NMR (400 MHz, CDCl$_3$) δ 7.34 (ddd, J = 9.5, 8.5, 4.1 Hz, 2H), 7.05-7.00 (m, 1H), 6.82 (td, J = 7.7, 1.3 Hz, 1H), 6.67-6.60 (m, 3H), 5.66 (d, J = 4.4 Hz, 1H), 5.41-5.32 (m, 1H), 5.01 (d, J = 6.6 Hz, 1H), 4.33-4.21 (m, 1H), 3.90 (s, 3H), 1.42 (s, 9H), 1.36 (d, J = 6.5 Hz, 3H), 1.22 (d, J = 7.2 Hz, 3H). $^{19}$F NMR (376 MHz, CDCl$_3$) δ-110.78 (s). |
| 54 | | ESIMS m/z 484 ([M + Na]$^+$) | $^1$H NMR (400 MHz, CDCl$_3$) δ 7.35-7.29 (m, 1H), 7.21-7.14 (m, 2H), 6.88 (t, J = 7.3 Hz, 1H), 6.81 (d, J = 7.9 Hz, 2H), 6.62-6.55 (m, 2H), 5.60 (d, J = 4.4 Hz, 1H), 5.39-5.31 (m, 1H), 5.03 (d, J = 5.3 Hz, 1H), 4.33-4.20 (m, 1H), 4.10 (q, J = 7.0 Hz, 2H), 1.49 (t, J = 7.0 Hz, 3H), 1.42 (s, 9H), 1.31 (d, J = 6.5 Hz, 3H), 1.20 (d, J = 7.2 Hz, 3H). $^{19}$F NMR (376 MHz, CDCl$_3$) δ-111.52 (s, 1F). |
| 56 | | ESIMS m/z 461 ([M + NH$_4$]$^+$) | $^1$H NMR (400 MHz, CDCl$_3$) δ 7.23 (d, J = 7.6 Hz, 1H), 7.19-7.13 (m, 2H), 6.88-6.79 (m, 3H), 6.70 (d, J = 7.8 Hz, 2H), 5.61 (d, J = 4.5 Hz, 1H), 5.37-5.30 (m, 1H), 5.04 (d, J = 5.9 Hz, 1H), 4.32-4.20 (m, 1H), 3.89 (s, 3H), 2.31 (s, 3H), 1.42 (s, 9H), 1.31 (d, J = 6.5 Hz, 3H), 1.19 (d, J = 7.2 Hz, 3H). $^{13}$C NMR (101 MHz, CDCl$_3$) δ 172.50, 157.97, 156.56, 154.98, 139.18, 129.26, 127.66, 122.44, 121.53, 120.79, 115.64, 111.13, 79.64, 74.88, 73.09, 55.42, 49.39, 28.33, 21.56, 18.64, 14.97. |

TABLE 2-continued

Analytical Data

| *Cmpd. No. | IR (cm$^{-1}$) | MASS | NMR ($^1$H, $^{13}$C or $^{19}$F) |
|---|---|---|---|
| 57 | | ESIMS m/z 518 ([M + Na]$^+$) | $^1$H NMR (400 MHz, CDCl$_3$) δ 7.36 (dd, J = 8.7, 6.7 Hz, 1H), 7.14 (d, J = 1.7 Hz, 1H), 6.81 (dd, J = 8.4, 1.6 Hz, 1H), 6.63 (dd, J = 12.8, 5.8 Hz, 2H), 6.54 (d, J = 8.4 Hz, 1H), 5.61 (d, J = 4.4 Hz, 1H), 5.39-5.32 (m, 1H), 5.02 (d, J = 6.1 Hz, 1H), 4.32-4.19 (m, 1H), 3.89 (s, 3H), 2.20 (s, 3H), 1.42 (s, 9H), 1.35 (d, J = 6.5 Hz, 3H), 1.22 (d, J = 7.2 Hz, 3H). $^{19}$F NMR (376 MHz, CDCl$_3$) δ-110.94 (s). |
| 58 | | ESIMS m/z 514 ([M + Na]$^+$) | $^1$H NMR (400 MHz, CDCl$_3$) δ 7.26 (d, J = 7.7 Hz, 1H), 7.12 (d, J = 1.8 Hz, 1H), 6.79 (dd, J = 8.4, 1.6 Hz, 1H), 6.72 (d, J = 7.9 Hz, 1H), 6.69 (s, 1H), 6.56 (d, J = 8.4 Hz, 1H), 5.63 (d, J = 4.2 Hz, 1H), 5.37 (qd, J = 6.5, 4.4 Hz, 1H), 5.05 (d, J = 7.1 Hz, 1H), 4.32-4.20 (m, 1H), 3.88 (s, 3H), 2.31 (s, 3H), 2.18 (s, 3H), 1.42 (s, 9H), 1.35 (d, J = 6.5 Hz, 3H), 1.22 (d, J = 7.2 Hz, 3H). $^{13}$C NMR (101 MHz, CDCl$_3$) δ 172.46, 156.52, 154.99, 151.15, 139.39, 130.93, 130.58, 127.85, 127.70, 122.80, 121.86, 121.61, 114.38, 111.08, 79.60, 75.69, 73.10, 55.41, 49.41, 28.31, 21.58, 20.20, 18.65, 14.85. |
| 59 | | ESIMS m/z 510 ([M + Na]$^+$) | $^1$H NMR (400 MHz, CDCl$_3$) δ 7.35-7.30 (m, 1H), 7.21-7.16 (m, 2H), 6.88 (t, J = 7.3 Hz, 1H), 6.83 (d, J = 7.8 Hz, 2H), 6.62-6.54 (m, 2H), 5.63 (d, J = 4.7 Hz, 1H), 5.39-5.32 (m, 1H), 5.02 (d, J = 8.5 Hz, 1H), 4.31-4.21 (m, 1H), 3.89 (d, J = 6.8 Hz, 2H), 1.42 (s, 9H), 1.36-1.27 (m, 4H), 1.21 (d, J = 7.2 Hz, 3H), 0.71-0.65 (m, 2H), 0.40 (q, J = 4.6 Hz, 2H). $^{19}$F NMR (376 MHz, CDCl$_3$) δ-111.48 (s). |
| 60 | | ESIMS m/z 498 ([M + H]$^+$) | $^1$H NMR (400 MHz, CDCl$_3$) δ 7.37 (dd, J = 8.6, 6.6 Hz, 1H), 7.22-7.15 (m, 2H), 6.89 (t, J = 7.4 Hz, 1H), 6.82-6.77 (m, 2H), 6.69 (td, J = 8.3, 2.3 Hz, 1H), 6.59 (dd, J = 10.2, 2.3 Hz, 1H), 6.24 (tt, J = 54.8, 4.0 Hz, 1H), 5.59 (d, J = 4.3 Hz, 1H), 5.35-5.29 (m, 1H), 5.00 (d, J = 6.3 Hz, 1H), 4.34-4.18 (m, 3H), 1.42 (s, 9H), 1.32 (d, J = 6.5 Hz, 3H), 1.19 (d, J = 7.2 Hz, 3H). $^{19}$F NMR (376 MHz, CDCl$_3$) δ-110.58 (s), −124.95 (d, J = 296.8 Hz), −125.95 (d, J = 296.7 Hz). |
| 61 | | ESIMS m/z 566 ([M + Na]$^+$) | $^1$H NMR (400 MHz, CDCl$_3$) δ 7.53 (dd, J = 8.7, 6.5 Hz, 1H), 7.45-7.39 (m, 2H), 7.33 (d, J = 7.9, 1.6 Hz, 1H), 7.22 (t, J = 7.4 Hz, 1H), 7.09-7.01 (m, 3H), 6.85 (td, J = 7.7, 1.2 Hz, 1H), 6.76 (dd, J = 13.8, 5.4 Hz, 2H), 6.50 (dd, J = 10.1, 2.4 Hz, 1H), 5.78 (d, J = 4.6 Hz, 1H), 5.53-5.46 (m, 1H), 5.05 (d, J = 6.2 Hz, 1H), 4.36-4.22 (m, 1H), 1.43 (d, J = 6.6 Hz, 3H), 1.42 (s, 9H), 1.25 (d, J = 6.8 Hz, 3H). $^{19}$F NMR (376 MHz, CDCl$_3$) δ-110.21 (s). |
| 62 | | ESIMS m/z 278 ([M + H]$^+$) | |
| 63 | | ESIMS m/z 301 ([M + H]$^+$) | |
| 64 | | ESIMS m/z 300 ([M + H]$^+$) | |

TABLE 2-continued

| | | Analytical Data | |
|---|---|---|---|
| *Cmpd. No. | IR (cm$^{-1}$) | MASS | NMR ($^1$H, $^{13}$C or $^{19}$F) |
| 65 | | ESIMS m/z 300 ([M + H]$^+$) | |
| 66 | | ESIMS m/z 334 ([M + H]$^+$) | |
| 67 | | ESIMS m/z 334 ([M + H]$^+$) | |
| 68 | | ESIMS m/z 334 ([M + H]$^+$) | |
| 69 | | ESIMS m/z 368 ([M + H]$^+$) | |
| 70 | | ESIMS m/z 336 ([M + H]$^+$) | |
| 71 | | ESIMS m/z 352 ([M + H]$^+$) | |
| 72 | | ESIMS m/z 350 ([M + H]$^+$) | |
| 73 | | ESIMS m/z 366 ([M + H]$^+$) | |
| 74 | | ESIMS m/z 368 ([M + H]$^+$) | |
| 75 | | ESIMS m/z 396 ([M + H]$^+$) | |
| 76 | | ESIMS m/z 318 ([M + H]$^+$) | |
| 77 | | ESIMS m/z 394 ([M + H]$^+$) | |
| 78 | | ESIMS m/z 354 ([M + H]$^+$) | |
| 79 | | ESIMS m/z 354 ([M + H]$^+$) | |
| 80 | | ESIMS m/z 368 ([M + H]$^+$) | |
| 81 | | ESIMS m/z 394 ([M + H]$^+$) | |
| 82 | | ESIMS m/z 280 ([M + H]$^+$) | |
| 83 | | ESIMS m/z 280 ([M + H]$^+$) | |
| 84 | | ESIMS m/z 376 ([M + H]$^+$) | |
| 85 | | ESIMS m/z 376 ([M + H]$^+$) | |
| 86 | | ESIMS m/z 319 ([M + H]$^+$) | |
| 87 | | ESIMS m/z 337 ([M + H]$^+$) | |
| 88 | | ESIMS m/z 348 ([M + H]$^+$) | |
| 89 | | ESIMS m/z 366 ([M + H]$^+$) | |
| 90 | | ESIMS m/z 318 ([M + H]$^+$) | |
| 91 | | ESIMS m/z 336 ([M + H]$^+$) | |
| 92 | | ESIMS m/z 314 ([M + H]$^+$) | |
| 93 | | ESIMS m/z 330 ([M + H]$^+$) | |
| 94 | | ESIMS m/z 348 ([M + H]$^+$) | |
| 95 | | ESIMS m/z 362 ([M + H]$^+$) | |
| 96 | | ESIMS m/z 332 ([M + H]$^+$) | |
| 97 | | ESIMS m/z 336 ([M + H]$^+$) | |
| 98 | | ESIMS m/z 330 ([M + H]$^+$) | |
| 99 | | ESIMS m/z 332 ([M + H]$^+$) | |
| 100 | | ESIMS m/z 352 ([M + H]$^+$) | |
| 101 | | ESIMS m/z 332 ([M + H]$^+$) | |

TABLE 2-continued

Analytical Data

| *Cmpd. No. | IR (cm$^{-1}$) | MASS | NMR ($^1$H, $^{13}$C or $^{19}$F) |
|---|---|---|---|
| 102 | | ESIMS m/z 350 ([M + H]$^+$) | |
| 103 | | ESIMS m/z 350 ([M + H]$^+$) | |
| 104 | | ESIMS m/z 374 ([M + H]$^+$) | |
| 105 | | ESIMS m/z 382 ([M + H]$^+$) | |
| 106 | | ESIMS m/z 362 ([M + H]$^+$) | |
| 107 | | ESIMS m/z 344 ([M + H]$^+$) | |
| 108 | | ESIMS m/z 396 ([M + H]$^+$) | |
| 109 | | ESIMS m/z 392 ([M + H]$^+$) | |
| 110 | | ESIMS m/z 388 ([M + H]$^+$) | |
| 111 | | ESIMS m/z 398 ([M + H]$^+$) | |
| 112 | | ESIMS m/z 444 ([M + H]$^+$) | |
| 113 | | HRMS-ESI (m/z) [M]$^+$ calcd for C$_{23}$H$_{28}$N$_2$O$_6$, 428.1947; found, 428.1953 | $^1$H NMR (500 MHz, CDCl$_3$) δ 12.12 (d, J = 0.6 Hz, 1H), 8.40 (d, J = 8.1 Hz, 1H), 7.97 (d, J = 5.2 Hz, 1H), 7.36-7.19 (m, 5H), 6.86 (d, J = 5.2 Hz, 1H), 5.14 (h, J = 6.3 Hz, 1H), 4.66-4.52 (m, 1H), 4.33 (d, J = 6.4 Hz, 1H), 3.94 (s, 3H), 3.26-3.12 (m, 2H), 1.35 (d, J = 6.3 Hz, 3H), 1.22 (d, J = 7.2 Hz, 3H), 1.01 (ttt, J = 8.1, 6.7, 4.8 Hz, 1H), 0.54-0.40 (m, 2H), 0.19-0.04 (m, 2H). |
| 114 | | HRMS-ESI (m/z) [M]$^+$ calcd for C$_{25}$H$_{26}$N$_2$O$_6$, 450.1791; found, 450.1795 | $^1$H NMR (500 MHz, CDCl$_3$) δ 12.08 (s, 1H), 8.40 (d, J = 7.9 Hz, 1H), 7.97 (d, J = 5.2 Hz, 1H), 7.42-7.34 (m, 2H), 7.35-7.20 (m, 3H), 7.21-7.08 (m, 2H), 6.91-6.75 (m, 4H), 5.30 (qd, J = 6.5, 5.2 Hz, 1H), 5.20 (d, J = 5.1 Hz, 1H), 4.64 (p, J = 7.3 Hz, 1H), 3.93 (s, 3H), 1.40 (d, J = 6.4 Hz, 3H), 1.30 (d, J = 7.2 Hz, 3H). $^{13}$C NMR (126 MHz, CDCl$_3$) δ 171.55, 168.65, 157.83, 155.34, 148.72, 140.44, 137.48, 130.40, 129.34, 128.53, 128.19, 126.95, 121.19, 115.92, 109.42, 81.18, 74.52, 56.06, 47.93, 18.02, 15.09. |
| 115 | (Thin film) 3367.32, 2984.27, 1737.93, 1648.90, 1527.87, 1480.95, 1237.99 | HRMS-ESI (m/z) ([M + H]$^+$) calcd for C$_{25}$H$_{27}$N$_2$O$_6$, 451.1864; found, 451.1869 | $^1$H NMR (400 MHz, CDCl$_3$) δ 12.12 (d, J = 0.6 Hz, 1H), 8.39 (d, J = 7.9 Hz, 1H), 7.99 (d, J = 5.2 Hz, 1H), 7.42-7.37 (m, 2H), 7.35-7.28 (m, 2H), 7.20-7.11 (m, 2H), 6.90-6.80 (m, 5H), 5.32-5.22 (m, 2H), 4.73-4.49 (m, 1H), 3.95 (s, 3H), 1.45 (d, J = 7.2 Hz, 3H), 1.37 (d, J = 6.3 Hz, 3H). $^{13}$C NMR (101 MHz, CDCl$_3$) δ 171.45, 168.64, 157.85, 155.38, 148.76, 140.45, 137.46, 130.48, 129.35, 128.54, 128.12, 126.83, 121.22, 116.05, 109.44, 81.10, 74.75, 56.08, 47.92, 18.13, 14.56. |
| 116 | (Thin film) 3367.65, 2984.35, 1738.51, 1648.67, 1528.19, 1480.80, 1238.38 | HRMS-ESI (m/z) ([M + H]$^+$) calcd for C$_{25}$H$_{27}$N$_2$O$_6$, 451.1864; found, 451.1872 | $^1$H NMR (400 MHz, CDCl$_3$) δ 12.08 (d, J = 0.6 Hz, 1H), 8.40 (d, J = 7.9 Hz, 1H), 7.97 (d, J = 5.2 Hz, 1H), 7.43-7.37 (m, 2H), 7.34-7.27 (m, 2H), 7.20-7.11 (m, 2H), 6.93-6.78 (m, 5H), 5.30 (qd, J = 6.4, 5.1 Hz, 1H), 5.20 (d, J = 5.1 Hz, 1H), 4.69-4.58 (m, 1H), 3.94 (s, 3H), 1.40 (d, J = 6.4 Hz, 3H), 1.30 (d, J = 7.2 Hz, 3H). |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | $^{13}$C NMR (101 MHz, CDCl$_3$) δ 171.55, 168.66, 157.85, 155.36, 148.74, 140.44, 137.50, 130.43, 129.35, 128.54, 128.20, 126.96, 121.20, 115.94, 109.44, 81.21, 74.53, 56.06, 47.94, 18.02, 15.10. |
| 117 | (Thin film) 3368, 2939, 1739, 1648, 1577, 1528, 1480, 1446, 1242, 1059 | HRMS-ESI (m/z) ([M + H]$^+$) calcd for C$_{25}$H$_{26}$ClN$_2$O$_6$, 485.1474; found, 485.1476 | $^1$H NMR (400 MHz, CDCl$_3$) δ 12.05 (d, J = 0.6 Hz, 1H), 8.40 (d, J = 7.9 Hz, 1H), 7.97 (d, J = 5.2 Hz, 1H), 7.44-7.38 (m, 2H), 7.36-7.28 (m, 4H), 7.00 (ddd, J = 8.3, 7.5, 1.7 Hz, 1H), 6.89-6.77 (m, 2H), 6.66 (dd, J = 8.3, 1.4 Hz, 1H), 5.40-5.30 (m, 1H), 5.28 (d, J = 4.7 Hz, 1H), 4.70-4.59 (m, 1H), 3.94 (s, 3H), 1.45 (d, J = 6.4 Hz, 3H), 1.34 (d, J = 7.2 Hz, 3H). $^{13}$C NMR (101 MHz, CDCl$_3$) δ 171.59, 168.69, 155.34, 153.24, 148.72, 140.45, 136.73, 130.41, 130.30, 128.63, 128.43, 127.44, 126.89, 123.48, 121.77, 115.06, 109.43, 81.93, 74.57, 56.06, 47.97, 17.97, 14.86. |
| 118 | (Thin film) 3368, 2939, 1739, 1648, 1576, 1528, 1476, 1452, 1241 | HRMS-ESI (m/z) ([M + H]$^+$) calcd for C$_{25}$H$_{26}$ClN$_2$O$_6$, 485.1474; found, 485.1474 | $^1$H NMR (400 MHz, CDCl$_3$) δ 12.04 (d, J = 0.6 Hz, 1H), 8.39 (d, J = 7.9 Hz, 1H), 7.96 (d, J = 5.2 Hz, 1H), 7.38-7.27 (m, 5H), 7.11-7.02 (m, 1H), 6.89-6.80 (m, 3H), 6.67 (ddd, J = 8.3, 2.3, 1.1 Hz, 1H), 5.35-5.24 (m, 1H), 5.19 (d, J = 4.9 Hz, 1H), 4.64 (dq, J = 8.4, 7.3 Hz, 1H), 3.93 (s, 3H), 1.38 (d, J = 6.4 Hz, 3H), 1.33 (d, J = 7.2 Hz, 3H). $^{13}$C NMR (101 MHz, CDCl$_3$) δ 171.51, 168.71, 158.47, 155.35, 148.73, 140.47, 136.75, 134.71, 130.35, 130.15, 128.68, 128.43, 126.85, 121.46, 116.56, 113.93, 109.47, 81.40, 74.29, 56.06, 47.99, 17.98, 14.87. |
| 119 | (Thin film) 3368, 2939, 1739, 1649, 1577, 1529, 1488, 1452, 1240 | HRMS-ESI (m/z) ([M + H]$^+$) calcd for C$_{25}$H$_{26}$ClN$_2$O$_6$, 485.1474; found, 485.1465 | $^1$H NMR (400 MHz, CDCl$_3$) δ 12.04 (d, J = 0.6 Hz, 1H), 8.37 (d, J = 8.0 Hz, 1H), 7.96 (d, J = 5.2 Hz, 1H), 7.37-7.27 (m, 5H), 7.13-7.05 (m, 2H), 6.89-6.82 (m, 1H), 6.76-6.69 (m, 2H), 5.35-5.24 (m, 1H), 5.15 (d, J = 4.8 Hz, 1H), 4.70-4.57 (m, 1H), 3.94 (s, 3H), 1.37 (d, J = 6.4 Hz, 3H), 1.34 (d, J = 7.2 Hz, 3H). $^{13}$C NMR (101 MHz, CDCl$_3$) δ 171.50, 168.74, 156.35, 155.37, 148.74, 140.45, 136.88, 130.33, 129.24, 128.65, 128.39, 126.86, 126.09, 117.14, 109.43, 81.55, 74.31, 56.08, 48.03, 17.95, 14.81. |
| 120 | (Thin film) 3368, 2939, 1739, 1648, 1576, 1528, 1478, 1452, 1262, 1243, 1058 | HRMS-ESI (m/z) ([M + H]$^+$) calcd for C$_{25}$H$_{25}$Cl$_2$N$_2$O$_6$, 519.1084; found, 519.1067 | $^1$H NMR (400 MHz, CDCl$_3$) δ 12.00 (d, J = 0.6 Hz, 1H), 8.37 (d, J = 7.8 Hz, 1H), 7.96 (d, J = 5.2 Hz, 1H), 7.40-7.25 (m, 6H), 6.94 (dd, J = 8.8, 2.5 Hz, 1H), 6.89-6.82 (m, 1H), 6.55 (d, J = 8.8 Hz, 1H), 5.38-5.30 (m, 1H), 5.23 (d, J = 4.5 Hz, 1H), 4.71-4.58 (m, 1H), 3.94 (s, 3H), 1.42 (d, J = 6.4 Hz, 3H), 1.37 (d, J = 7.2 Hz, 3H). $^{13}$C NMR (101 MHz, CDCl$_3$) δ 171.51, 168.77, 155.34, 151.97, 148.72, 140.46, 136.16, 130.31, 129.97, 128.75, 128.62, 127.35, 126.80, 126.14, 124.24, 115.67, 109.42, 82.26, 74.33, 56.08, 48.08, 17.90, 14.64. |

TABLE 2-continued

Analytical Data

| *Cmpd. No. | IR (cm$^{-1}$) | MASS | NMR ($^1$H, $^{13}$C or $^{19}$F) |
|---|---|---|---|
| 121 | | HRMS-ESI (m/z) ([M + H]$^+$) calcd for C$_{25}$H$_{25}$F$_2$N$_2$O$_6$, 487.1675; found, 487.1675 | $^1$H NMR (400 MHz, CDCl$_3$) δ 12.05 (d, J = 0.6 Hz, 1H), 8.39 (d, J = 7.9 Hz, 1H), 7.97 (d, J = 5.2 Hz, 1H), 7.43-7.27 (m, 5H), 6.96 (ddd, J = 10.6, 8.9, 5.3 Hz, 1H), 6.86 (dd, J = 5.3, 0.7 Hz, 1H), 6.58-6.43 (m, 2H), 5.35 (qd, J = 6.4, 5.1 Hz, 1H), 5.18 (d, J = 5.1 Hz, 1H), 4.70-4.58 (m, 1H), 3.94 (s, 3H), 1.42 (d, J = 6.4 Hz, 3H), 1.32 (d, J = 7.2 Hz, 3H). $^{13}$C NMR (101 MHz, CDCl$_3$) δ 171.48, 168.67, 158.31 (dd, J = 242.3, 2.6 Hz), 155.36, 149.45 (d, J = 239.0 Hz), 148.74, 146.17 (dd, J = 12.6, 10.5 Hz), 140.46, 136.19, 130.39, 128.71, 126.99, 116.40 (dd, J = 20.9, 10.1 Hz), 109.45, 107.72 (dd, J = 23.7, 6.9 Hz), 105.13 (dd, J = 27.3, 1.5 Hz), 83.03, 74.07, 56.07, 47.91, 17.93, 15.13. $^{19}$F NMR (376 MHz, CDCl$_3$) δ-116.63 (d, J = 15.0 Hz), −138.72 (d, J = 15.0 Hz). |
| 122 | | HRMS-ESI (m/z) ([M + H]$^+$) calcd for C$_{25}$H$_{25}$ClFN$_2$O$_6$, 503.1380; found, 503.1361 | $^1$H NMR (400 MHz, CDCl$_3$) δ 12.01 (d, J = 0.6 Hz, 1H), 8.38 (d, J = 7.8 Hz, 1H), 7.97 (d, J = 5.2 Hz, 1H), 7.38-7.27 (m, 5H), 6.86 (dd, J = 5.3, 0.7 Hz, 1H), 6.66-6.58 (m, 2H), 6.41 (dt, J = 10.5, 2.3 Hz, 1H), 5.29 (qd, J = 6.4, 4.7 Hz, 1H), 5.16 (d, J = 4.8 Hz, 1H), 4.70-4.58 (m, 1H), 3.94 (s, 3H), 1.36 (app dd, J = 6.8, 2.3 Hz, 6H). $^{13}$C NMR (101 MHz, CDCl$_3$) δ 171.45, 168.74, 163.09 (d, J = 248.1 Hz), 159.18 (d, J = 12.3 Hz), 155.37, 148.74, 140.47, 136.11, 135.26 (d, J = 13.4 Hz), 130.30, 128.80, 128.65, 126.76, 112.46 (d, J = 3.2 Hz), 109.48, 109.24 (d, J = 25.1 Hz), 102.15 (d, J = 25.0 Hz), 81.71, 74.04, 56.06, 48.02, 17.95, 14.76. $^{19}$F NMR (376 MHz, CDCl$_3$) δ-109.82. |
| 123 | (Thin film) 3371, 2972, 2939, 1739, 1650, 1577, 1509, 1432, 1251, 1203, 1146 | HRMS-ESI (m/z) ([M + H]$^+$) calcd for C$_{26}$H$_{27}$F$_2$N$_2$O$_6$, 501.1832; found, 501.1831 | $^1$H NMR (500 MHz, CDCl$_3$) δ 12.08 (d, J = 0.6 Hz, 1H), 8.43 (d, J = 8.4 Hz, 1H), 7.98 (d, J = 5.2 Hz, 1H), 7.42-7.36 (m, 2H), 7.36-7.28 (m, 3H), 6.96 (ddd, J = 10.5, 9.0, 5.3 Hz, 1H), 6.87 (d, J = 5.3 Hz, 1H), 6.57-6.49 (m, 1H), 6.46 (ddd, J = 9.7, 6.6, 3.0 Hz, 1H), 5.34 (qd, J = 6.4, 5.0 Hz, 1H), 5.18 (d, J = 5.1 Hz, 1H), 4.62 (ddd, J = 8.4, 6.8, 5.2 Hz, 1H), 3.94 (s, 3H), 1.89-1.78 (m, 1H), 1.67 (dt, J = 14.2, 7.2 Hz, 1H), 1.42 (d, J = 6.4 Hz, 3H), 0.79 (t, J = 7.4 Hz, 3H). $^{13}$C NMR (126 MHz, CDCl$_3$) δ 170.84, 168.86, 158.31 (dd, J = 242.4, 2.6 Hz), 155.36, 149.41 (dd, J = 242.1, 3.3 Hz), 148.71, 146.16 (dd, J = 12.5, 10.7 Hz), 140.48, 136.20, 130.43, 128.73, 128.71, 126.96, 116.37 (dd, J = 20.9, 10.0 Hz), 109.43, 107.65 (dd, J = 23.9, 6.9 Hz), 105.00 (dd, J = 27.2, 1.7 Hz), 82.95, 74.15, 56.07, 53.08, 25.36, 15.15, 9.28. |

TABLE 2-continued

Analytical Data

| *Cmpd. No. | IR (cm⁻¹) | MASS | NMR ($^1$H, $^{13}$C or $^{19}$F) |
|---|---|---|---|
| 124 | | HRMS-ESI (m/z) ([M + H]⁺) calcd for $C_{26}H_{27}ClFN_2O_6$, 517.1536; found, 517.1534 | $^1$H NMR (500 MHz, CDCl$_3$) δ 12.04 (d, J = 0.7 Hz, 1H), 8.41 (d, J = 8.3 Hz, 1H), 7.98 (d, J = 5.2 Hz, 1H), 7.37-7.28 (m, 5H), 6.87 (dd, J = 5.2, 0.7 Hz, 1H), 6.65-6.58 (m, 2H), 6.40 (dt, J = 10.4, 2.3 Hz, 1H), 5.29 (qd, J = 6.4, 4.7 Hz, 1H), 5.16 (d, J = 4.7 Hz, 1H), 4.61 (ddd, J = 8.3, 6.9, 5.3 Hz, 1H), 3.94 (s, 3H), 1.92-1.80 (m, 1H), 1.71 (dt, J = 14.2, 7.2 Hz, 1H), 1.36 (d, J = 6.4 Hz, 3H), 0.83 (t, J = 7.5 Hz, 3H). $^{13}$C NMR (126 MHz, CDCl$_3$) δ 170.82, 168.91, 163.07 (d, J = 248.1 Hz), 159.14 (d, J = 12.3 Hz), 155.36, 148.71, 140.49, 136.08, 135.24 (d, J = 13.3 Hz), 130.34, 128.81, 128.65, 126.74, 112.44 (d, J = 3.3 Hz), 109.47, 109.21 (d, J = 25.1 Hz), 102.12 (d, J = 25.0 Hz), 81.66, 74.07, 56.07, 53.21, 25.38, 14.78, 9.41. $^{19}$F NMR (471 MHz, CDCl$_3$) δ-109.83. |
| 125 | | HRMS-ESI (m/z) ([M + H]⁺) calcd for $C_{26}H_{26}F_3N_2O_6$, 519.1737; found, 519.1739 | $^1$H NMR (500 MHz, CDCl$_3$) δ 12.03 (d, J = 0.7 Hz, 1H), 8.37 (d, J = 7.8 Hz, 1H), 7.95 (d, J = 5.2 Hz, 1H), 7.44-7.27 (m, 7H), 6.90-6.82 (m, 3H), 5.36-5.27 (m, 1H), 5.25 (d, J = 4.8 Hz, 1H), 4.69-4.60 (m, 1H), 3.94 (s, 3H), 1.39 (d, J = 6.4 Hz, 3H), 1.35 (d, J = 7.2 Hz, 3H). $^{13}$C NMR (126 MHz, CDCl$_3$) δ 171.49, 168.74, 160.08, 155.36, 148.74, 140.45, 136.46, 130.31, 128.75, 128.53, 126.80 (q, J = 3.8 Hz), 126.80, 124.25 (q, J = 271.7 Hz), 123.29 (q, J = 32.8 Hz), 115.71, 109.44, 81.26, 74.20, 56.06, 48.02, 17.95, 14.81. $^{19}$F NMR (471 MHz, CDCl$_3$) δ-61.64. |
| 126 | | HRMS-ESI (m/z) ([M + H]⁺) calcd for $C_{28}H_{30}F_3N_2O_6$, 547.2050; found, 547.2059 | $^1$H NMR (500 MHz, CDCl$_3$) δ 12.07 (d, J = 0.6 Hz, 1H), 8.43 (d, J = 9.2 Hz, 1H), 7.95 (d, J = 5.2 Hz, 1H), 7.43-7.26 (m, 7H), 6.88-6.82 (m, 3H), 5.35-5.25 (m, 2H), 4.59 (dd, J = 9.2, 4.9 Hz, 1H), 3.94 (s, 3H), 2.21-2.10 (m, 1H), 1.38 (d, J = 6.4 Hz, 3H), 0.92 (d, J = 6.9 Hz, 3H), 0.80 (d, J = 6.9 Hz, 3H). $^{13}$C NMR (126 MHz, CDCl$_3$) δ 170.52, 169.07, 160.05, 155.37, 148.69, 140.48, 136.40, 130.39, 128.76, 128.52, 126.77 (q, J = 3.8 Hz), 126.76, 124.25 (q, J = 271.4 Hz), 123.24 (q, J = 32.7 Hz), 115.67, 109.42, 81.15, 74.25, 57.08, 56.06, 31.17, 19.11, 17.38, 14.69. $^{19}$F NMR (471 MHz, CDCl$_3$) δ-61.64. |
| 127 | (Thin film) 3369, 2940, 1740, 1649, 1529, 1482, 1450, 1262, 1132 | HRMS-ESI (m/z) ([M + H]⁺) calcd for $C_{25}H_{26}FN_2O_6$, 469.1769; found, 469.1784 | $^1$H NMR (500 MHz, CDCl$_3$) δ 12.04 (d, J = 0.6 Hz, 1H), 8.39 (d, J = 7.8 Hz, 1H), 7.97 (d, J = 5.2 Hz, 1H), 7.40-7.26 (m, 5H), 7.10 (td, J = 8.3, 6.9 Hz, 1H), 6.86 (dd, J = 5.2, 0.7 Hz, 1H), 6.62-6.49 (m, 3H), 5.29 (qd, J = 6.5, 5.0 Hz, 1H), 5.18 (d, J = 4.9 Hz, 1H), 4.69-4.59 (m, 1H), 3.94 (s, 3H), 1.38 (d, J = 6.4 Hz, 3H), 1.33 (d, J = 7.2 Hz, 3H). $^{13}$C NMR (126 MHz, CDCl$_3$) δ 171.51, 168.70, 163.35 (d, J = 245.3 Hz), 159.04 (d, J = 10.8 Hz), 155.35, 148.73, 140.46, 136.83, 130.35, 130.12 (d, J = 10.0 Hz), 128.66, 128.41, 126.85, 111.44 (d, J = 2.9 Hz), 109.45, 108.08 (d, J = |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 21.4 Hz), 103.69 (d, J = 24.8 Hz), 81.45, 74.28, 56.06, 47.97, 17.99, 14.91. |
| 128 | | HRMS-ESI (m/z) ([M + H]$^+$) calcd for C$_{31}$H$_{30}$FN$_2$O$_6$, 545.2082; found, 545.2090 | $^1$H NMR (500 MHz, CDCl$_3$) δ 11.98 (d, J = 0.6 Hz, 1H), 8.40 (d, J = 8.4 Hz, 1H), 7.94 (d, J = 5.3 Hz, 1H), 7.38-7.25 (m, 5H), 7.20-7.07 (m, 4H), 7.07-7.00 (m, 2H), 6.85 (d, J = 5.3 Hz, 1H), 6.63-6.54 (m, 2H), 6.50 (dt, J = 10.8, 2.4 Hz, 1H), 5.20 (qd, J = 6.4, 4.3 Hz, 1H), 5.12 (d, J = 4.3 Hz, 1H), 4.94 (ddd, J = 8.5, 6.4, 5.7 Hz, 1H), 3.94 (s, 3H), 3.12 (dd, J = 14.0, 5.8 Hz, 1H), 3.06 (dd, J = 14.0, 6.4 Hz, 1H), 1.35 (d, J = 6.4 Hz, 3H). $^{13}$C NMR (126 MHz, CDCl$_3$) δ 170.23, 168.73, 163.37 (d, J = 245.4 Hz), 158.91 (d, J = 10.9 Hz), 155.29, 148.67, 140.56, 136.79, 135.42, 130.30, 130.12 (d, J = 10.0 Hz), 129.25, 128.72, 128.59, 128.42, 127.16, 126.75, 111.52 (d, J = 2.9 Hz), 109.44, 108.05 (d, J = 21.2 Hz), 103.72 (d, J = 24.9 Hz), 81.17, 74.95, 56.06, 53.08, 37.82, 14.43. |
| 129 | | HRMS-ESI (m/z) ([M + Na]$^+$) calcd for C$_{23}$H$_{24}$N$_2$O$_6$SNa, 479.1253; found, 479.1244. | $^1$H NMR (400 MHz, CDCl$_3$) δ 12.11 (s, 1H), 8.49 (d, J = 8.0 Hz, 1H), 7.98 (d, J = 5.2 Hz, 1H), 7.32-7.26 (m, 1H), 7.24-7.15 (m, 2H), 7.07 (dd, J = 3.5, 1.2 Hz, 1H), 6.96 (dd, J = 5.1, 3.5 Hz, 1H), 6.93-6.88 (m, 3H), 6.86 (d, J = 5.2 Hz, 1H), 5.50-5.35 (m, 2H), 4.79-4.65 (m, 1H), 3.94 (s, 3H), 1.47 (d, J = 7.2 Hz, 3H), 1.34-1.22 (m, 3H). $^{13}$C NMR (101 MHz, CDCl$_3$) δ 171.68, 168.70, 157.64, 155.36, 148.75, 140.46, 140.15, 129.41, 126.78, 126.28, 125.92, 121.59, 115.96, 109.44, 78.29, 77.22, 73.83, 56.07, 48.02, 18.38, 16.14. |
| 130 | | HRMS-ESI (m/z) ([M + H]$^+$) calcd for C$_{24}$H$_{26}$N$_3$O$_6$, 452.1821; found, 452.1814. | $^1$H NMR (400 MHz, CDCl$_3$) δ 12.06 (s, 1H), 8.66 (d, J = 2.2 Hz, 1H), 8.53 (td, J = 5.0, 1.7 Hz, 1H), 8.38 (s, 1H), 7.97 (d, J = 5.3 Hz, 1H), 7.78 (dt, J = 7.9, 2.0 Hz, 1H), 7.31-7.27 (m, 1H), 7.23-7.14 (m, 2H), 6.92 (ddt, J = 8.5, 7.3, 1.1 Hz, 1H), 6.88-6.85 (m, 1H), 6.84-6.78 (m, 2H), 5.36-5.28 (m, 1H), 5.24 (d, J = 5.4 Hz, 1H), 4.62 (q, J = 7.4 Hz, 1H), 3.94 (s, 3H), 1.41 (d, J = 6.3 Hz, 3H), 1.32 (d, J = 7.2 Hz, 3H). $^{13}$C NMR (101 MHz, CDCl$_3$) δ 171.41, 157.15, 149.21, 148.33, 135.34, 133.62, 129.58, 123.91, 121.85, 115.97, 109.47, 79.13, 77.22, 73.82, 56.09, 47.90, 17.90, 15.49. |
| 131 | | HRMS-ESI (m/z) ([M + H]$^+$) calcd for C$_{29}$H$_{33}$N$_2$O$_6$, 505.2333; found, 505.2333. | $^1$H NMR (400 MHz, CDCl$_3$) δ 12.10 (s, 1H), 8.40 (d, J = 7.8 Hz, 1H), 7.96 (d, J = 5.1 Hz, 1H), 7.57 (dd, J = 10.0, 2.0 Hz, 3H), 7.53-7.49 (m, 1H), 7.46-7.40 (m, 3H), 7.39-7.30 (m, 3H), 6.87-6.82 (m, 1H), 5.20 (p, J = 6.3 Hz, 1H), 4.63-4.54 (m, 1H), 4.42 (d, J = 6.3 Hz, 1H), 3.93 (s, 3H), 3.28-3.20 (m, 2H), 1.39 (d, J = 6.3 Hz, 3H), 1.21 (d, J = 7.2 Hz, 3H), 1.08-0.98 (m, 1H), 0.54-0.44 (m, 2H), 0.18-0.07 (m, 2H). $^{13}$C NMR (126 MHz, CDCl$_3$) δ 171.42, 168.59, 155.32, 148.70, 141.20, 140.81, 140.44, 139.33, |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 130.43, 128.80, 128.75, 127.40, 127.09, 126.81, 126.46, 126.29, 109.40, 83.10, 74.50, 73.89, 56.05, 47.89, 17.94, 16.03, 10.61, 3.22, 2.75. |
| 132 | (Thin film) 3369, 2985, 2939, 1742 | HRMS-ESI (m/z) ([M + H]$^+$) calcd for C$_{22}$H$_{24}$N$_3$O$_6$S, 458.1379; found, 458.1374 | $^1$H NMR (400 MHz, CDCl$_3$) δ 12.19-12.04 (m, 1H), 8.56-8.39 (m, 1H), 8.09-7.95 (m, 1H), 7.87-7.74 (m, 1H), 7.45-7.30 (m, 1H), 7.23 (t, J = 8.0 Hz, 2H), 6.98-6.92 (m, 3H), 6.86 (d, J = 5.2 Hz, 1H), 5.66-5.42 (m, 2H), 4.81-4.56 (m, 1H), 3.95 (s, 3H), 1.42 (d, J = 7.2 Hz, 3H), 1.38 (d, J = 6.4 Hz, 3H). $^{13}$C NMR (126 MHz, CDCl$_3$) δ 168.69, 168.08, 157.49, 155.36, 148.74, 142.82, 142.50, 140.46, 129.60, 122.04, 120.24, 115.92, 115.57, 109.44, 79.67, 73.19, 56.08, 47.97, 18.28, 16.05. |
| 133 | | HRMS-ESI (m/z) ([M + H]$^+$) calcd for C$_{31}$H$_{30}$FN$_2$O$_6$, 545.2082; found, 545.2098. | $^1$H NMR (400 MHz, CDCl$_3$) δ 12.02 (s, 1H), 8.39 (d, J = 8.0 Hz, 1H), 7.96 (d, J = 5.2 Hz, 1H), 7.60-7.50 (m, 4H), 7.47-7.33 (m, 5H), 7.11 (dd, J = 15.1, 8.2 Hz, 1H), 6.85 (d, J = 5.3 Hz, 1H), 6.64-6.55 (m, 3H), 5.34 (dt, J = 11.6, 6.6 Hz, 1H), 5.26 (d, J = 4.9 Hz, 1H), 4.69-4.60 (m, 1H), 3.94 (s, 3H), 1.42 (d, J = 6.4 Hz, 3H), 1.32 (d, J = 7.2 Hz, 3H). $^{13}$C NMR (126 MHz, CDCl$_3$) δ 171.60, 168.72, 159.13, 155.34, 148.72, 141.69, 140.46, 137.50, 130.33, 130.23, 130.15, 129.16, 128.83, 127.58, 127.23, 127.13, 125.70, 125.46, 111.44, 109.44, 108.11, 103.87, 103.67, 81.54, 74.39, 56.06, 47.98, 31.87, 17.95, 14.83. |
| 134 | | HRMS-ESI (m/z) ([M + H]$^+$) calcd for C$_{25}$H$_{25}$Cl$_2$N$_2$O$_6$, 519.1089; found, 519.1077 | $^1$H NMR (400 MHz, CDCl$_3$) δ 12.13 (s, 1H), 8.47 (d, J = 8.2 Hz, 1H), 7.95 (d, J = 5.1 Hz, 1H), 7.43-7.22 (m, 6H), 6.95 (dd, J = 8.8, 2.6 Hz, 1H), 6.86 (d, J = 5.3 Hz, 1H), 6.63 (d, J = 8.9 Hz, 1H), 5.53-5.39 (m, 1H), 5.16 (d, J = 6.8 Hz, 1H), 4.81-4.63 (m, 1H), 3.94 (s, 3H), 1.47 (d, J = 7.2 Hz, 3H), 1.24 (d, J = 6.4 Hz, 3H). $^{13}$C NMR (101 MHz, CDCl$_3$) δ 171.43, 168.67, 155.34, 151.86, 148.74, 140.44, 135.93, 130.42, 130.01, 128.91, 128.82, 127.27, 127.16, 125.98, 124.14, 115.40, 109.44, 82.80, 73.57, 56.08, 48.02, 18.26, 16.18. |
| 135 | | HRMS-ESI (m/z) ([M + H]$^+$) calcd for C$_{25}$H$_{27}$N$_2$O$_6$, 451.1869; found, 451.1868 | $^1$H NMR (400 MHz, CDCl$_3$) δ 12.13 (d, J = 0.6 Hz, 1H), 8.48 (d, J = 8.0 Hz, 1H), 7.97 (d, J = 5.2 Hz, 1H), 7.42-7.35 (m, 2H), 7.36-7.24 (m, 3H), 7.22-7.08 (m, 2H), 6.93-6.79 (m, 4H), 5.53-5.33 (m, 1H), 5.13 (d, J = 6.5 Hz, 1H), 4.79-4.61 (m, 1H), 3.93 (s, 3H), 1.42 (d, J = 7.2 Hz, 3H), 1.24 (d, J = 6.5 Hz, 3H). $^{13}$C NMR (101 MHz, CDCl$_3$) δ 171.71, 168.67, 157.82, 155.35, 148.75, 140.46, 137.30, 130.49, 129.35, 128.64, 128.41, 127.12, 121.09, 115.75, 109.44, 81.86, 74.06, 56.07, 48.01, 18.41, 16.35. |

TABLE 2-continued

Analytical Data

| *Cmpd. No. | IR (cm⁻¹) | MASS | NMR ($^1$H, $^{13}$C or $^{19}$F) |
|---|---|---|---|
| 136 | | HRMS-ESI (m/z) ([M + H]⁺) calcd for C$_{23}$H$_{31}$N$_2$O$_6$, 431.2182; found, 431.2192 | $^1$H NMR (400 MHz, CDCl$_3$) δ 12.18 (s, 1H), 8.50 (d, J = 8.0 Hz, 1H), 8.00 (d, J = 5.2 Hz, 1H), 7.39-7.27 (m, 5H), 6.87 (d, J = 5.2 Hz, 1H), 5.19 (p, J = 6.5 Hz, 1H), 4.72 (dq, J = 8.6, 7.2 Hz, 1H), 4.25 (d, J = 6.7 Hz, 1H), 3.95 (s, 3H), 3.18-2.99 (m, 2H), 1.89-1.75 (m, 1H), 1.50 (d, J = 7.2 Hz, 3H), 1.10 (d, J = 6.5 Hz, 3H), 0.89-0.81 (m, 6H). $^{13}$C NMR (101 MHz, CDCl$_3$) δ 171.63, 168.62, 155.36, 148.75, 140.45, 138.47, 130.57, 128.31, 128.10, 127.62, 109.41, 84.00, 76.10, 74.45, 56.07, 48.04, 28.63, 19.41, 19.36, 18.47, 16.34. |
| 137 | | HRMS-ESI (m/z) ([M + H]⁺) calcd for C$_{23}$H$_{31}$N$_2$O$_6$, 431.2182; found, 431.2187 | $^1$H NMR (400 MHz, CDCl$_3$) δ 12.13 (s, 1H), 8.40 (d, J = 7.9 Hz, 1H), 7.98 (d, J = 5.2 Hz, 1H), 7.43-7.21 (m, 5H), 6.86 (d, J = 5.3 Hz, 1H), 5.13 (p, J = 6.3 Hz, 1H), 4.67-4.49 (m, 1H), 4.25 (d, J = 6.1 Hz, 1H), 3.94 (s, 3H), 3.14 (dd, J = 8.8, 6.5 Hz, 1H), 3.05 (dd, J = 8.8, 6.4 Hz, 1H), 1.92-1.76 (m, 1H), 1.33 (d, J = 6.3 Hz, 3H), 1.25 (d, J = 7.2 Hz, 3H), 0.89 (d, J = 3.1 Hz, 3H), 0.87 (d, J = 3.2 Hz, 3H). $^{13}$C NMR (101 MHz, CDCl$_3$) δ 171.40, 168.58, 155.36, 148.73, 140.44, 138.80, 130.49, 128.21, 127.94, 127.54, 109.42, 83.71, 76.27, 74.67, 56.07, 47.89, 28.63, 19.33, 18.00, 15.85. |
| 138 | (Thin film) 3372, 2964, 2875, 1650 | HRMS-ESI (m/z) ([M + H]⁺) calcd for C$_{22}$H$_{29}$N$_2$O$_6$, 417.2025; found, 417.2016. | $^1$H NMR (400 MHz, CDCl$_3$) δ 12.18 (d, J = 0.6 Hz, 1H), 8.50 (d, J = 7.8 Hz, 1H), 8.00 (d, J = 5.2 Hz, 1H), 7.40-7.27 (m, 5H), 6.87 (d, J = 5.3 Hz, 1H), 5.27-5.11 (m, 1H), 4.80-4.67 (m, 1H), 4.26 (d, J = 6.7 Hz, 1H), 3.95 (s, 3H), 3.30 (dt, J = 9.0, 6.8 Hz, 1H), 3.23 (dt, J = 9.1, 6.5 Hz, 1H), 1.60-1.53 (m, 2H), 1.50 (d, J = 7.2 Hz, 3H), 1.10 (d, J = 6.5 Hz, 3H), 0.87 (t, J = 7.4 Hz, 3H). |
| 139 | (Thin film) 3370, 2964, 2876, 1734 | HRMS-ESI (m/z) ([M + H]⁺) calcd for C$_{22}$H$_{29}$N$_2$O$_6$, 417.2025; found, 417.2018. | $^1$H NMR (400 MHz, CDCl$_3$) δ 12.12 (s, 1H), 8.40 (d, J = 8.0 Hz, 1H), 7.98 (d, J = 5.2 Hz, 1H), 7.37-7.26 (m, 5H), 6.86 (d, J = 5.2 Hz, 1H), 5.20-5.06 (m, 1H), 4.66-4.51 (m, 1H), 4.27 (d, J = 6.1 Hz, 1H), 3.94 (s, 3H), 3.33 (dt, J = 9.1, 6.5 Hz, 1H), 3.25 (dt, J = 9.2, 6.5 Hz, 1H), 1.55 (dtd, J = 13.8, 7.4, 6.5 Hz, 2H), 1.32 (d, J = 6.3 Hz, 3H), 1.24 (d, J = 7.2 Hz, 3H), 0.89 (t, J = 7.4 Hz, 3H). $^{13}$C NMR (126 MHz, CDCl$_3$) δ 171.40, 168.58, 155.35, 148.73, 140.44, 138.84, 130.50, 128.23, 127.97, 127.53, 109.41, 83.51, 74.57, 71.13, 56.08, 47.90, 23.00, 18.01, 15.87, 10.65. |
| 140 | (Thin film) 3367, 2984, 2938, 1739 | HRMS-ESI (m/z) ([M + H]⁺) calcd for C$_{20}$H$_{25}$N$_2$O$_6$, 389.1712; found, 389.1713. | $^1$H NMR (400 MHz, CDCl$_3$) δ 12.17 (d, J = 0.6 Hz, 1H), 8.50 (d, J = 8.0 Hz, 1H), 8.00 (d, J = 5.2 Hz, 1H), 7.40-7.28 (m, 5H), 6.87 (d, J = 5.1 Hz, 1H), 5.28-5.15 (m, 1H), 4.80-4.64 (m, 1H), 4.14 (d, J = 6.8 Hz, 1H), 3.95 (s, 3H), 3.24 (s, 3H), 1.51 (d, J = 7.2 Hz, 3H), 1.11 (d, J = 6.5 Hz, 3H). |

TABLE 2-continued

Analytical Data

| *Cmpd. No. | IR (cm$^{-1}$) | MASS | NMR ($^1$H, $^{13}$C or $^{19}$F) |
|---|---|---|---|
| 141 | (Thin film) 3366, 2938, 1737, 1648 | HRMS-ESI (m/z) ([M + H]$^+$) calcd for C$_{20}$H$_{25}$N$_2$O$_6$, 389.1712; found, 389.1709. | $^1$H NMR (400 MHz, CDCl$_3$) δ 12.12 (s, 1H), 8.40 (d, J = 8.0 Hz, 1H), 7.98 (d, J = 5.2 Hz, 1H), 7.37-7.28 (m, 5H), 6.86 (d, J = 5.2 Hz, 1H), 5.14 (p, J = 6.4 Hz, 1H), 4.66-4.54 (m, 1H), 4.19 (d, J = 5.9 Hz, 1H), 3.94 (s, 3H), 3.26 (s, 3H), 1.31 (d, J = 6.4 Hz, 3H), 1.26 (d, J = 7.2 Hz, 3H). |
| 142 | (Thin film) 3367, 2985, 2872, 1738 | HRMS-ESI (m/z) ([M + H]$^+$) calcd for C$_{23}$H$_{29}$N$_2$O$_6$, 429.2025; found, 429.2009. | $^1$H NMR (400 MHz, CDCl$_3$) δ 12.18 (d, J = 0.6 Hz, 1H), 8.51 (d, J = 8.3 Hz, 1H), 8.00 (d, J = 5.2 Hz, 1H), 7.36-7.26 (m, 5H), 6.87 (d, J = 5.3 Hz, 1H), 5.27-5.15 (m, 1H), 4.80-4.65 (m, 1H), 4.34 (d, J = 6.8 Hz, 1H), 3.95 (s, 3H), 3.17 (dd, J = 6.8, 3.2 Hz, 2H), 1.52 (d, J = 7.2 Hz, 3H), 1.12 (d, J = 6.5 Hz, 3H), 1.03-0.93 (m, 1H), 0.53-0.34 (m, 2H), 0.16-0.05 (m, 2H). |
| 143 | | HRMS-ESI (m/z) ([M + H]$^+$) calcd for C$_{29}$H$_{33}$N$_2$O$_6$, 505.2330; found, 505.2347. | $^1$H NMR (400 MHz, CDCl$_3$) δ 12.12 (s, 1H), 8.40 (d, J = 7.9 Hz, 1H), 7.97 (d, J = 5.2 Hz, 1H), 7.59-7.52 (m, 4H), 7.46-7.38 (m, 4H), 7.38-7.32 (m, 1H), 6.84 (d, J = 5.2 Hz, 1H), 5.23-5.14 (m, 1H), 4.66-4.57 (m, 1H), 4.40 (d, J = 6.2 Hz, 1H), 3.93 (s, 3H), 3.23 (d, J = 6.8 Hz, 2H), 1.38 (d, J = 6.3 Hz, 3H), 1.26 (d, J = 7.2 Hz, 3H), 1.09-0.98 (m, 1H), 0.55-0.44 (m, 2H), 0.19-0.09 (m, 2H). $^{13}$C NMR (126 MHz, CDCl$_3$) δ 171.42, 168.61, 155.35, 148.73, 140.91, 140.70, 140.45, 137.70, 130.47, 128.77, 128.02, 127.34, 127.05, 126.98, 109.40, 82.77, 74.48, 73.84, 56.06, 47.90, 18.00, 16.02, 10.60, 3.21, 2.74. |
| 144 | | HRMS-ESI (m/z) ([M + H]$^+$) calcd for C$_{31}$H$_{31}$N$_2$O$_6$, 527.2177; found, 527.2184. | $^1$H NMR (400 MHz, CDCl$_3$) δ 12.08 (s, 1H), 8.41 (d, J = 7.9 Hz, 1H), 7.96 (d, J = 5.2 Hz, 1H), 7.57-7.52 (m, 4H), 7.48-7.40 (m, 4H), 7.34 (ddd, J = 7.3, 3.8, 1.2 Hz, 1H), 7.21-7.16 (m, 2H), 6.91-6.83 (m, 4H), 5.38-5.31 (m, 1H), 5.26 (d, J = 4.9 Hz, 1H), 4.67 (p, J = 7.2 Hz, 1H), 3.93 (s, 3H), 1.43 (d, J = 6.4 Hz, 3H), 1.33 (d, J = 7.2 Hz, 3H). $^{13}$C NMR (101 MHz, CDCl$_3$) δ 171.61, 168.69, 157.86, 155.36, 148.75, 141.08, 140.52, 140.45, 136.45, 130.42, 129.40, 128.77, 127.42, 127.40, 127.26, 127.05, 121.27, 115.97, 109.43, 81.01, 74.54, 56.06, 47.96, 18.05, 15.10. |
| 145 | | HRMS-ESI (m/z) ([M + H]$^+$) calcd for C$_{31}$H$_{31}$N$_2$O$_6$, 527.2177; found, 527.2187. | $^1$H NMR (400 MHz, CDCl$_3$) δ 12.06 (s, 1H), 8.40 (d, J = 7.8 Hz, 1H), 7.95 (d, J = 5.2 Hz, 1H), 7.63 (s, 1H), 7.56 (dd, J = 5.2, 3.3 Hz, 2H), 7.52-7.49 (m, 1H), 7.46-7.32 (m, 6H), 7.20-7.15 (m, 2H), 6.90-6.83 (m, 4H), 5.36 (dt, J = 12.2, 6.1 Hz, 1H), 5.28 (s, 1H), 4.64 (p, J = 7.2 Hz, 1H), 3.93 (s, 3H), 1.44 (d, J = 6.4 Hz, 3H), 1.28 (d, J = 7.2 Hz, 3H). $^{13}$C NMR (101 MHz, CDCl$_3$) δ 171.65, 168.69, 157.92, 155.35, 148.73, 141.53, 140.65, 140.46, 138.18, 130.40, 129.41, 129.05, 128.81, 127.51, 127.13, 127.03, 125.85, 125.62, 121.31, 116.01, 109.43, 81.35, 74.63, 56.06, 47.95, 17.98, 15.04. |

TABLE 2-continued

Analytical Data

| *Cmpd. No. | IR (cm$^{-1}$) | MASS | NMR ($^1$H, $^{13}$C or $^{19}$F) |
|---|---|---|---|
| 146 | | HRMS-ESI (m/z) ([M + H]$^+$) calcd for C$_{25}$H$_{26}$FN$_2$O$_6$, 469.1775; found, 469.1778 | $^1$H NMR (400 MHz, CDCl$_3$) δ 12.05 (s, 1H), 8.38 (d, J = 7.9 Hz, 1H), 7.96 (d, J = 5.2 Hz, 1H), 7.41-7.18 (m, 5H), 6.91-6.77 (m, 3H), 6.77-6.60 (m, 2H), 5.29 (qd, J = 6.4, 4.9 Hz, 1H), 5.11 (d, J = 4.9 Hz, 1H), 4.76-4.55 (m, 1H), 3.94 (s, 3H), 1.38 (d, J = 6.4 Hz, 3H), 1.33 (d, J = 7.2 Hz, 3H). $^{19}$F NMR (376 MHz, CDCl$_3$) δ-123.13. |
| 147 | | HRMS-ESI (m/z) ([M + H]$^+$) calcd for C$_{25}$H$_{25}$F$_2$N$_2$O$_6$, 487.1680; found, 487.1678 | $^1$H NMR (400 MHz, CDCl$_3$) δ 12.10 (s, 1H), 8.44 (d, J = 8.0 Hz, 1H), 7.97 (d, J = 5.2 Hz, 1H), 7.41-7.29 (m, 2H), 7.16-6.95 (m, 2H), 6.91-6.78 (m, 3H), 6.78-6.60 (m, 2H), 5.42-5.30 (m, 1H), 5.03 (d, J = 6.6 Hz, 1H), 4.79-4.66 (m, 1H), 3.94 (s, 3H) 1.45 (d, J = 7.2 Hz, 3H), 1.21 (d, J = 6.4 Hz, 3H). $^{19}$F NMR (376 MHz, CDCl$_3$) δ-113.00, −122.95. |
| 148 | | HRMS-ESI (m/z) ([M + H]$^+$) calcd for C$_{25}$H$_{26}$FN$_2$O$_6$, 469.1769; found, 469.1777. | $^1$H NMR (400 MHz, CDCl$_3$) δ 12.06 (s, 1H), 8.39 (d, J = 7.7 Hz, 1H), 7.97 (d, J = 5.2 Hz, 1H), 7.40-7.34 (m, 2H), 7.20-7.13 (m, 2H), 7.03-6.96 (m, 2H), 6.88 (dd, J = 15.2, 6.3 Hz, 2H), 6.82-6.78 (m, 2H), 5.31-5.24 (m, 1H), 5.18 (d, J = 5.2 Hz, 1H), 4.64 (p, J = 7.2 Hz, 1H), 3.93 (s, 3H), 1.39 (d, J = 6.4 Hz, 3H), 1.33 (d, J = 7.2 Hz, 3H). $^{19}$F NMR (376 MHz, CDCl$_3$) δ-113.62. |
| 149 | | HRMS-ESI (m/z) ([M + Na]$^+$) calcd for C$_{26}$H$_{27}$ClN$_2$O$_6$Na, 521.1456; found, 521.1450 | $^1$H NMR (300 MHz, CDCl$_3$) δ 12.06 (s, 1H), 8.40 (d, J = 7.6 Hz, 1H), 7.97 (d, J = 5.3 Hz, 1H), 7.45-7.26 (m, 5H), 7.12 (dd, J = 2.2, 0.8 Hz, 1H), 6.86 (d, J = 5.2 Hz, 1H), 6.78 (ddd, J = 8.4, 2.2, 0.8 Hz, 1H), 6.54 (d, J = 8.3 Hz, 1H), 5.41-5.30 (m, 1H), 5.23 (d, J = 4.8 Hz, 1H), 4.78-4.57 (m, 1H), 3.94 (s, 3H), 2.19 (s, 3H), 1.44 (d, J = 6.4 Hz, 3H), 1.33 (d, J = 7.2 Hz, 3H). $^{13}$C NMR (75 MHz, CDCl$_3$) δ 171.60, 168.67, 155.33, 151.00, 148.71, 140.46, 136.91, 131.54, 130.72, 130.41, 128.58, 128.37, 127.85, 126.96, 123.06, 115.04, 109.41, 82.02, 74.56, 56.08, 47.97, 20.25, 18.00, 14.97. |
| 150 | | HRMS-ESI (m/z) ([M + H]$^+$) calcd for C$_{26}$H$_{27}$ClFN$_2$O$_6$, 517.1541; found, 517.1537 | $^1$H NMR (300 MHz, CDCl$_3$) δ 12.04 (s, 1H), 8.39 (d, J = 7.9 Hz, 1H), 7.98 (d, J = 5.2 Hz, 1H), 7.46-7.31 (m, 2H), 7.12 (dd, J = 2.1, 0.8 Hz, 1H), 7.08-6.92 (m, 2H), 6.86 (d, J = 5.2 Hz, 1H), 6.79 (ddd, J = 8.4, 2.2, 0.9 Hz, 1H), 6.52 (d, J = 8.4 Hz, 1H), 5.32 (qd, J = 6.4, 4.8 Hz, 1H), 5.20 (d, J = 4.9 Hz, 1H), 4.80-4.53 (m, 1H), 3.94 (s, 3H), 2.20 (s, 3H), 1.43 (d, J = 6.4 Hz, 3H), 1.35 (d, J = 7.2 Hz, 3H). $^{19}$F NMR (471 MHz, CDCl$_3$) δ-113.34. |
| 151 | | HRMS-ESI (m/z) ([M + H]$^+$) calcd for C$_{26}$H$_{29}$N$_2$O$_6$, 465.2025; found, 465.2012 | $^1$H NMR (300 MHz, CDCl$_3$) δ 12.09 (d, J = 0.7 Hz, 1H), 8.41 (d, J = 8.0 Hz, 1H), 7.97 (d, J = 5.2 Hz, 1H), 7.47-7.34 (m, 2H), 7.34-7.19 (m, 3H), 7.00-6.91 (m, 2H), 6.90-6.81 (m, 1H), 6.78-6.65 (m, 2H), 5.29 (qd, J = 6.4, 5.2 Hz, 1H), 5.15 (d, J = 5.2 Hz, 1H), 4.75-4.56 (m, 1H), 3.94 (s, 3H), 2.21 (s, 3H), 1.39 (d, J = 6.4 Hz, 3H), 1.30 (d, J = 7.2 Hz, 3H). |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | $^{13}$C NMR (75 MHz, CDCl$_3$) δ 171.57, 168.65, 155.71, 155.35, 148.73, 140.46, 137.67, 130.46, 130.42, 129.80, 128.50, 128.14, 126.99, 115.81, 109.42, 81.36, 74.55, 56.10, 56.06, 47.93, 20.44, 18.05, 15.14. |
| 152 | | HRMS-ESI (m/z) ([M + H]$^+$) calcd for C$_{26}$H$_{28}$FN$_2$O$_6$, 483.1931; found, 483.1918 | $^1$H NMR (300 MHz, CDCl$_3$) δ 12.07 (d, J = 0.6 Hz, 1H), 8.39 (d, J = 7.9 Hz, 1H), 7.97 (d, J = 5.2 Hz, 1H), 7.47-7.31 (m, 2H), 7.05-6.93 (m, 4H), 6.86 (dd, J = 5.3, 0.7 Hz, 1H), 6.75-6.62 (m, 2H), 5.26 (qd, J = 6.4, 5.2 Hz, 1H), 5.13 (d, J = 5.3 Hz, 1H), 4.74-4.57 (m, 1H), 3.94 (s, 3H), 2.22 (s, 3H), 1.39 (d, J = 6.4 Hz, 3H), 1.33 (d, J = 7.2 Hz, 3H). $^{13}$C NMR (75 MHz, CDCl$_3$) δ 171.51, 168.67, 162.46 (d, J = 246.8 Hz), 155.41 (d, J = 5.7 Hz), 148.75, 140.48, 133.42 (d, J = 3.3 Hz), 130.70, 130.37, 129.85, 128.73 (d, J = 8.1 Hz), 115.82, 115.64, 115.36, 109.45, 80.76, 74.34, 56.10, 47.93, 20.44, 18.05, 15.24. |
| 153 | | HRMS-ESI (m/z) ([M + H]$^+$) calcd for C$_{25}$H$_{25}$F$_2$N$_2$O$_6$, 487.1675; found, 487.1690. | $^1$H NMR (300 MHz, CDCl$_3$) δ 12.07 (d, J = 0.6 Hz, 1H), 8.39 (d, J = 7.9 Hz, 1H), 7.97 (d, J = 5.2 Hz, 1H), (td, J = 8.7, 6.4 Hz, 1H), 7.23-7.42 7.16 (m, 2H), 6.94-6.88 (m, 1H), 6.87 (d, J = 5.1 Hz, 1H), 6.85-6.74 (m, 4H), 5.49 (d, J = 5.7 Hz, 1H), 5.38 (p, J = 6.1 Hz, 1H), 4.66 (dq, J = 14.5, 7.2 Hz, 1H), 3.94 (s, 3H), 1.41 (d, J = 6.3 Hz, 3H), 1.36 (d, J = 7.2 Hz, 3H). $^{19}$F NMR (471 MHz, CDCl$_3$) δ-109.47 (dt, J = 15.4, 7.9 Hz), −113.95 (dd, J = 17.3, 8.3 Hz). |
| 154 | | ESIMS m/z 465 ([M + H]$^+$) | $^1$H NMR (400 MHz, CDCl$_3$) δ 12.09 (s, 1H), 8.41 (d, J = 7.8 Hz, 1H), 7.97 (d, J = 5.2 Hz, 1H), 7.27 (d, J = 8.0 Hz, 2H), 7.18-7.09 (m, 4H), 6.89-6.79 (m, 4H), 5.29 (dq, J = 12.9, 6.4 Hz, 1H), 5.17 (d, J = 5.0 Hz, 1H), 4.64 (p, J = 7.3 Hz, 1H), 3.94 (s, 3H), 2.31 (s, 3H), 1.39 (d, J = 6.4 Hz, 3H), 1.33 (d, J = 7.2 Hz, 3H). $^{13}$C NMR (101 MHz, CDCl$_3$) δ 171.57, 168.66, 157.90, 155.36, 148.74, 140.44, 137.89, 134.39, 130.45, 129.32, 129.21, 126.87, 121.10, 115.93, 109.43, 81.06, 74.59, 56.06, 47.96, 21.15, 18.06, 15.03. |
| 155 | | HRMS-ESI (m/z) ([M + H]$^+$) calcd for C$_{26}$H$_{28}$FN$_2$O$_6$, 483.1931; found, 483.1928 | $^1$H NMR (300 MHz, CDCl$_3$) δ 12.07 (d, J = 0.6 Hz, 1H), 8.39 (d, J = 7.8 Hz, 1H), 7.96 (d, J = 5.2 Hz, 1H), 7.34-7.19 (m, 2H), 7.19-7.05 (m, 2H), 6.92-6.65 (m, 5H), 5.28 (qd, J = 6.4, 4.8 Hz, 1H), 5.08 (d, J = 4.8 Hz, 1H), 4.74-4.57 (m, 1H), 3.93 (s, 3H), 1.37 (d, J = 6.4 Hz, 3H), 1.35 (d, J = 7.2 Hz, 3H). $^{19}$F NMR (471 MHz, CDCl$_3$) δ-123.34. |
| 156 | | HRMS-ESI (m/z) ([M + H]$^+$) calcd for C$_{25}$H$_{25}$F$_2$N$_2$O$_6$, 487.1680; found, 487.1678 | $^1$H NMR (300 MHz, CDCl$_3$) δ 12.04 (s, 1H), 8.36 (d, J = 7.8 Hz, 1H), 7.97 (d, J = 5.2 Hz, 1H), 7.41-7.28 (m, 2H), 7.11-6.92 (m, 2H), 6.93-6.78 (m, 3H), 6.78-6.62 (m, 2H), 5.26 (qd, J = 6.4, 4.9 Hz, 1H), 5.09 (d, J = 5.0 Hz, 1H), 4.72-4.57 (m, 1H), 3.94 (s, 3H), 1.37 (d, J = 6.6 |

TABLE 2-continued

Analytical Data

| *Cmpd. No. | IR (cm⁻¹) | MASS | NMR ($^1$H, $^{13}$C or $^{19}$F) |
|---|---|---|---|
| | | | Hz, 3H), 1.35 (d, J = 7.6 Hz, 3H). $^{19}$F NMR (471 MHz, CDCl$_3$) δ-113.40, −122.82. |
| 157 | | HRMS-ESI (m/z) ([M + H]$^+$) calcd for C$_{27}$H$_{31}$N$_2$O$_6$, 479.2182; found, 479.2180 | $^1$H NMR (400 MHz, CDCl$_3$) δ 12.09 (s, 1H), 8.41 (d, J = 8.0 Hz, 1H), 7.96 (d, J = 5.2 Hz, 1H), 7.41-7.16 (m, 2H), 7.10 (d, J = 7.8 Hz, 2H), 6.94 (d, J = 8.1 Hz, 2H), 6.85 (d, J = 5.2 Hz, 1H), 6.75-6.64 (m, 2H), 5.33-5.23 (m, 1H), 5.12 (d, J = 5.0 Hz, 1H), 4.64 (p, J = 7.3 Hz, 1H), 3.93 (s, 3H), 2.30 (s, 3H), 2.20 (s, 3H), 1.38 (d, J = 6.4 Hz, 3H), 1.32 (d, J = 7.2 Hz, 3H). $^{13}$C NMR (101 MHz, CDCl$_3$) δ 171.55, 168.66, 155.82, 155.37, 148.78, 140.41, 137.80, 134.60, 130.51, 130.35, 129.75, 129.16, 126.90, 115.84, 109.42, 81.29, 74.60, 56.04, 47.96, 21.11, 20.41, 18.07, 15.06. |
| 158 | | HRMS-ESI (m/z) ([M + H]$^+$) calcd for C$_{26}$H$_{29}$N$_2$O$_7$, 481.1969; found, 481.1958. | $^1$H NMR (400 MHz, CDCl$_3$) δ 12.11 (s, 1H), 8.44 (d, J = 7.7 Hz, 1H), 7.94 (d, J = 5.2 Hz, 1H), 7.38 (d, J = 7.5 Hz, 1H), 7.26-7.21 (m, 1H), 7.15 (t, J = 7.8 Hz, 2H), 6.91-6.80 (m, 6H), 5.69 (d, J = 4.5 Hz, 1H), 5.45-5.38 (m, 1H), 4.66 (p, J = 7.2 Hz, 1H), 3.93 (s, 3H), 3.91 (s, 3H), 1.37-1.32 (m, 6H). $^{13}$C NMR (101 MHz, CDCl$_3$) δ 171.46, 168.67, 157.89, 156.63, 155.34, 148.75, 140.38, 130.54, 129.27, 129.14, 127.84, 125.40, 120.88, 120.86, 115.61, 110.21, 109.40, 74.91, 73.33, 56.03, 55.47, 48.01, 18.07, 14.94. |
| 159 | | HRMS-ESI (m/z) ([M + H]$^+$) calcd for C$_{26}$H$_{28}$FN$_2$O$_7$, 499.1875; found, 499.1876. | $^1$H NMR (400 MHz, CDCl$_3$) δ 12.10 (s, 1H), 8.42 (d, J = 7.7 Hz, 1H), 7.95 (d, J = 5.2 Hz, 1H), 7.37-7.29 (m, 1H), 7.16 (t, J = 7.9 Hz, 2H), 6.86 (dd, J = 11.0, 6.2 Hz, 2H), 6.79 (d, J = 8.0 Hz, 2H), 6.64-6.54 (m, 2H), 5.61 (d, J = 4.5 Hz, 1H), 5.42-5.34 (m, 1H), 4.66 (p, J = 7.2 Hz, 1H), 3.93 (s, 3H), 3.89 (s, 3H), 1.37 (d, J = 7.2 Hz, 3H), 1.34 (d, J = 6.5 Hz, 3H). $^{13}$C NMR (101 MHz, CDCl$_3$) δ 171.41, 168.69, 163.41 (d, J = 246.4 Hz), 157.81 (d, J = 9.7 Hz), 157.65, 155.37, 148.76, 140.40, 130.49, 129.32, 129.02 (d, J = 10.0 Hz), 121.15 (d, J = 3.3 Hz), 121.05, 115.57, 109.43, 107.39 (d, J = 21.4 Hz), 98.69 (d, J = 25.8 Hz), 74.53, 73.20, 56.04, 55.78, 48.01, 18.06, 14.98. $^{19}$F NMR (376 MHz, CDCl$_3$) δ-111.20 (s, 1F). |
| 160 | | | $^1$H NMR (300 MHz, CDCl$_3$) δ 12.08 (s, 1H), 8.42 (d, J = 7.9 Hz, 1H), 7.97 (d, J = 5.2 Hz, 1H), 7.37-7.23 (m, 2H), 7.20-7.06 (m, 3H), 6.85 (d, J = 5.2 Hz, 1H), 6.77 (ddd, J = 8.4, 2.2, 0.8 Hz, 1H), 6.54 (d, J = 8.4 Hz, 1H), 5.33 (qd, J = 6.4, 4.7 Hz, 1H), 5.20 (d, J = 4.7 Hz, 1H), 4.77-4.53 (m, 1H), 3.93 (s, 3H), 2.31 (s, 3H), 2.18 (s, 3H), 1.43 (d, J = 6.4 Hz, 3H), 1.36 (d, J = 7.2 Hz, 3H). |

TABLE 2-continued

Analytical Data

| *Cmpd. No. | IR (cm$^{-1}$) | MASS | NMR ($^1$H, $^{13}$C or $^{19}$F) |
|---|---|---|---|
| 161 | | HRMS-ESI (m/z) ([M + H]$^+$) calcd for C$_{26}$H$_{29}$N$_2$O$_7$, 481.1969; found, 481.1971. | $^1$H NMR (400 MHz, CDCl$_3$) δ 12.07 (s, 1H), 8.41 (d, J = 7.8 Hz, 1H), 7.96 (d, J = 5.2 Hz, 1H), 7.23 (t, J = 7.9 Hz, 1H), 7.16 (dd, J = 8.4, 7.5 Hz, 2H), 7.00-6.92 (m, 2H), 6.91-6.78 (m, 5H), 5.33-5.26 (m, 1H), 5.18 (d, J = 5.0 Hz, 1H), 4.65 (p, J = 7.3 Hz, 1H), 3.93 (s, 3H), 3.77 (s, 3H), 1.40 (d, J = 6.4 Hz, 3H), 1.33 (d, J = 7.2 Hz, 3H). $^{13}$C NMR (101 MHz, CDCl$_3$) δ 171.58, 168.69, 159.80, 157.93, 155.36, 148.76, 140.43, 139.19, 130.45, 129.57, 129.34, 121.24, 119.31, 115.94, 113.49, 112.53, 109.44, 81.13, 74.55, 56.05, 55.21, 47.95, 18.02, 14.97. |
| 162 | | HRMS-ESI (m/z) ([M + H]$^+$) calcd for C$_{26}$H$_{28}$FN$_2$O$_6$, 483.1926; found, 483.1936. | $^1$H NMR (400 MHz, CDCl$_3$) δ 12.04 (s, 1H), 8.37 (d, J = 7.7 Hz, 1H), 7.96 (d, J = 5.2 Hz, 1H), 7.37 (dd, J = 8.5, 5.9 Hz, 1H), 7.19-7.13 (m, 2H), 6.90-6.80 (m, 4H), 6.76-6.70 (m, 2H), 5.39 (d, J = 4.9 Hz, 1H), 5.26-5.18 (m, 1H), 4.63 (p, J = 7.2 Hz, 1H), 3.93 (s, 3H), 2.50 (s, 3H), 1.43 (d, J = 6.4 Hz, 3H), 1.29 (d, J = 7.2 Hz, 3H). $^{13}$C NMR (101 MHz, CDCl$_3$) δ 171.66, 168.74, 162.19 (d, J = 246.5 Hz), 157.70, 155.38, 148.77, 140.44, 137.84 (d, J = 7.8 Hz), 131.39 (d, J = 3.1 Hz), 130.38, 129.42, 128.68 (d, J = 8.5 Hz), 121.32, 115.70, 117.18 (d, J = 21.2 Hz), 113.25 (d, J = 21.1 Hz), 109.48, 77.73, 73.55, 56.05, 47.95, 19.26 (d, J = 1.2 Hz), 17.86, 14.75. $^{19}$F NMR (376 MHz, CDCl$_3$) δ-114.75 (d, J = 2.1 Hz, 1F). |
| 163 | | HRMS-ESI (m/z) ([M + H]$^+$) calcd for C$_{25}$H$_{25}$ClFN$_2$O$_6$, 503.1380; found, 503.1386. | $^1$H NMR (400 MHz, CDCl$_3$) δ 12.06 (s, 1H), 8.39 (d, J = 7.7 Hz, 1H), 7.96 (dd, J = 5.1, 0.9 Hz, 1H), 7.48 (dd, J = 8.7, 6.1 Hz, 1H), 7.19 (t, J = 7.7 Hz, 2H), 7.09 (dd, J = 8.4, 2.4 Hz, 1H), 6.96-6.82 (m, 3H), 6.78 (d, J = 8.0 Hz, 2H), 5.63 (d, J = 5.4 Hz, 1H), 5.37 (p, J = 6.3 Hz, 1H), 4.66 (p, J = 7.3 Hz, 1H), 3.93 (d, J = 1.3 Hz, 3H), 1.42 (d, J = 6.4 Hz, 3H), 1.37 (d, J = 7.2 Hz, 3H). $^{13}$C NMR (101 MHz, CDCl$_3$) δ 171.29, 168.71, 162.08 (d, J = 251.1 Hz), 157.07, 155.39, 148.78, 140.42, 133.93 (d, J = 10.2 Hz), 130.42, 131.14 (d, J = 3.6 Hz), 129.99 (d, J = 9.0 Hz), 129.52, 121.54, 116.71 (d, J = 24.8 Hz), 115.51, 114.83 (d, J = 21.2 Hz), 109.48, 76.63, 73.19, 56.05, 47.98, 17.95, 15.56. $^{19}$F NMR (376 MHz, CDCl$_3$) δ-111.13 (d, J = 3.2 Hz). |
| 164 | | HRMS-ESI (m/z) ([M + H]$^+$) calcd for C$_{26}$H$_{28}$FN$_2$O$_6$, 483.1926; found, 483.1935. | $^1$H NMR (400 MHz, CDCl$_3$) δ 12.10 (s, 1H), 8.41 (d, J = 7.9 Hz, 1H), 7.97 (d, J = 5.2 Hz, 1H), 7.30 (t, J = 7.7 Hz, 1H), 7.18 (dd, J = 8.5, 7.5 Hz, 2H), 6.85 (ddd, J = 12.2, 11.0, 7.5 Hz, 6H), 5.50 (d, J = 5.7 Hz, 1H), 5.39 (p, J = 6.2 Hz, 1H), 4.66 (p, J = 7.2 Hz, 1H), 3.94 (s, 3H), 2.29 (s, 3H), 1.41 (d, J = 6.4 Hz, 3H), 1.35 (d, J = 7.2 Hz, 3H). $^{13}$C NMR (101 MHz, CDCl$_3$) δ 171.32, 168.64, 160.23 (d, J = 245.5 Hz), 157.37, 155.36, 148.76, 140.51 (d, J = 8.0 Hz), 140.40, 130.51, |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 129.42, 128.21 (d, J = 4.2 Hz), 125.34 (d, J = 2.9 Hz), 121.33, 121.31 (d, J = 13.6 Hz), 115.78, 115.58, 74.30, 73.35, 56.04, 47.93, 21.04, 18.01, 15.84. $^{19}$F NMR (376 MHz, CDCl$_3$) δ-119.17 (s, 1F). |
| 165 | | HRMS-ESI (m/z) ([M + H]$^+$) calcd for C$_{29}$H$_{29}$N$_2$O$_6$, 501.2020; found, 501.2031. | $^1$H NMR (400 MHz, CDCl$_3$) δ 12.05 (s, 1H), 8.41 (t, J = 6.4 Hz, 2H), 7.97 (d, J = 5.2 Hz, 1H), 7.89 (d, J = 8.1 Hz, 1H), 7.80 (d, J = 8.2 Hz, 1H), 7.64 (t, J = 6.1 Hz, 2H), 7.53 (t, J = 7.5 Hz, 1H), 7.41 (t, J = 7.7 Hz, 1H), 7.11 (t, J = 8.0 Hz, 2H), 6.87-6.82 (m, 2H), 6.78 (d, J = 8.1 Hz, 2H), 6.11 (d, J = 4.0 Hz, 1H), 5.52-5.44 (m, 1H), 4.64 (p, J = 7.3 Hz, 1H), 3.93 (s, 3H), 1.43 (d, J = 6.5 Hz, 3H), 1.19 (d, J = 7.2 Hz, 3H). $^{13}$C NMR (101 MHz, CDCl$_3$) δ 172.08, 168.73, 157.99, 155.37, 148.77, 140.45, 133.75, 132.92, 130.57, 130.44, 129.38, 129.03, 128.71, 126.85, 125.87, 125.47, 124.73, 122.84, 121.15, 115.63, 109.46, 77.48, 74.16, 56.05, 47.94, 17.80, 14.35. |
| 166 | | HRMS-ESI (m/z) ([M + H]$^+$) calcd for C$_{29}$H$_{29}$N$_2$O$_6$, 501.2020; found, 501.2027. | $^1$H NMR (400 MHz, CDCl$_3$) δ 12.06 (s, 1H), 8.39 (d, J = 7.8 Hz, 1H), 7.95 (d, J = 5.2 Hz, 1H), 7.85 (s, 1H), 7.83-7.76 (m, 3H), 7.53 (dd, J = 8.5, 1.5 Hz, 1H), 7.49-7.43 (m, 2H), 7.18-7.11 (m, 2H), 6.89-6.83 (m, 4H), 5.44-5.36 (m, 2H), 4.65 (p, J = 7.3 Hz, 1H), 3.93 (s, 3H), 1.44 (d, J = 6.1 Hz, 3H), 1.28 (d, J = 7.2 Hz, 3H). $^{13}$C NMR (101 MHz, CDCl$_3$) δ 171.60, 168.69, 157.94, 155.37, 148.76, 140.43, 135.05, 133.19, 133.10, 130.44, 129.38, 128.48, 127.92, 127.73, 126.33, 126.29, 126.22, 124.33, 121.29, 116.04, 109.45, 81.43, 74.60, 56.05, 47.96, 18.00, 14.99. |
| 167 | | HRMS-ESI (m/z) ([M + H]$^+$) calcd for C$_{28}$H$_{30}$FN$_2$O$_7$, 525.2032; found, 525.2022. | $^1$H NMR (400 MHz, CDCl$_3$) δ 12.11 (s, 1H), 8.43 (d, J = 7.8 Hz, 1H), 7.96 (d, J = 5.2 Hz, 1H), 7.34 (t, J = 7.6 Hz, 1H), 7.21-7.11 (m, 2H), 6.84 (ddd, J = 20.4, 10.4, 7.6 Hz, 4H), 6.63-6.54 (m, 2H), 6.09 (ddt, J = 17.2, 10.4, 5.1 Hz, 1H), 5.65 (d, J = 4.5 Hz, 1H), 5.47 (ddd, J = 17.4, 3.0, 1.6 Hz, 1H), 5.44-5.38 (m, 1H), 5.35 (dd, J = 10.6, 1.3 Hz, 1H), 4.71-4.63 (m, 1H), 4.63-4.59 (m, 2H), 3.93 (s, 3H), 1.38 (d, J = 7.2 Hz, 3H), 1.34 (d, J = 6.5 Hz, 3H). $^{13}$C NMR (101 MHz, CDCl$_3$) δ 171.38, 168.68, 163.23 (d, J = 246.5 Hz), 157.61, 156.70 (d, J = 9.8 Hz), 155.37, 148.77, 140.40, 132.39, 130.49, 129.32, 129.16 (d, J = 10.2 Hz), 121.38 (d, J = 3.3 Hz), 121.06, 117.99, 115.59, 109.43, 107.62 (d, J = 21.3 Hz), 99.83 (d, J = 25.8 Hz), 74.57, 73.20, 69.23, 56.04, 48.01, 18.12, 15.11. $^{19}$F NMR (376 MHz, CDCl$_3$) δ-111.20. |

TABLE 2-continued

Analytical Data

| *Cmpd. No. | IR (cm⁻¹) | MASS | NMR ($^1$H, $^{13}$C or $^{19}$F) |
|---|---|---|---|
| 168 | | HRMS-ESI (m/z) ([M + H]⁺) calcd for $C_{27}H_{30}FN_2O_7$, 513.2032; found, 513.1999. | $^1$H NMR (400 MHz, CDCl$_3$) δ 12.12 (s, 1H), 8.44 (d, J = 7.8 Hz, 1H), 7.95 (d, J = 5.2 Hz, 1H), 7.31 (dd, J = 8.4, 6.8 Hz, 1H), 7.19-7.13 (m, 2H), 6.89-6.83 (m, 2H), 6.81-6.77 (m, 2H), 6.61-6.53 (m, 2H), 5.62 (d, J = 4.3 Hz, 1H), 5.45-5.38 (m, 1H), 4.67 (p, J = 7.2 Hz, 1H), 4.09 (q, J = 7.0 Hz, 2H), 3.93 (s, 3H), 1.50 (t, J = 7.0 Hz, 3H), 1.38 (d, J = 7.2 Hz, 3H), 1.33 (d, J = 6.5 Hz, 3H). $^{13}$C NMR (101 MHz, CDCl$_3$) δ 171.38, 168.69, 163.32 (d, J = 246.1 Hz), 157.70, 157.07 (d, J = 9.9 Hz), 155.36, 148.76, 140.40, 130.49, 129.30, 128.97 (d, J = 10.1 Hz), 121.10 (d, J = 3.2 Hz), 121.01, 115.57, 109.43, 107.19 (d, J = 21.4 Hz), 99.31 (d, J = 25.7 Hz), 74.70, 73.15, 64.11, 56.04, 48.03, 18.12, 14.95, 14.65. $^{19}$F NMR (376 MHz, CDCl$_3$) δ-111.45 (d, J = 3.1 Hz). |
| 169 | | HRMS-ESI (m/z) ([M + H]⁺) calcd for $C_{27}H_{29}ClFN_2O_7$, 547.1642; found, 547.1642. | $^1$H NMR (400 MHz, CDCl$_3$) δ 12.10 (s, 1H), 8.44 (d, J = 7.9 Hz, 1H), 7.95 (dd, J = 5.2, 0.7 Hz, 1H), 7.37 (dd, J = 9.2, 6.6 Hz, 1H), 7.10 (d, J = 1.9 Hz, 1H), 6.85 (d, J = 5.2 Hz, 1H), 6.79 (dd, J = 8.4, 1.9 Hz, 1H), 6.64-6.57 (m, 2H), 6.54 (d, J = 8.4 Hz, 1H), 5.65 (d, J = 4.3 Hz, 1H), 5.45-5.38 (m, 1H), 4.68 (p, J = 7.2 Hz, 1H), 3.93 (d, J = 0.6 Hz, 3H), 3.89 (s, 3H), 2.19 (s, 3H), 1.40 (d, J = 7.2 Hz, 3H), 1.37 (d, J = 6.5 Hz, 3H). $^{13}$C NMR (101 MHz, CDCl$_3$) δ 171.40, 168.68, 163.49 (d, J = 246.8 Hz), 157.80 (d, J = 9.7 Hz), 155.33, 150.82, 148.73, 140.40, 131.29, 130.67, 130.47, 129.13 (d, J = 10.1 Hz), 127.86, 122.88, 120.59 (d, J = 3.0 Hz), 114.31, 109.40, 107.47 (d, J = 21.2 Hz), 98.68 (d, J = 25.9 Hz), 75.29, 73.17, 56.03, 55.79, 48.01, 20.20, 18.06, 14.87. $^{19}$F NMR (376 MHz, CDCl$_3$) δ-110.85 (d, J = 2.9 Hz). |
| 170 | | HRMS-ESI (m/z) ([M + H]⁺) calcd for $C_{25}H_{26}FN_2O_7$, 485.1719; found, 485.1717. | $^1$H NMR (400 MHz, CDCl$_3$) δ 12.44 (s, 1H), 9.00 (s, 1H), 8.35 (d, J = 7.6 Hz, 1H), 8.09 (d, J = 5.3 Hz, 1H), 7.22 (ddd, J = 8.4, 7.0, 3.6 Hz, 3H), 6.97 (d, J = 5.3 Hz, 1H), 6.94 (t, J = 7.3 Hz, 1H), 6.88 (d, J = 7.8 Hz, 2H), 6.54 (td, J = 8.4, 2.5 Hz, 1H), 6.32 (dd, J = 10.0, 2.2 Hz, 1H), 5.50 (d, J = 6.9 Hz, 1H), 5.20 (p, J = 6.1 Hz, 1H), 4.65 (p, J = 7.1 Hz, 1H), 3.99 (s, 3H), 1.51 (d, J = 6.3 Hz, 3H), 1.45 (d, J = 7.1 Hz, 3H). $^{13}$C NMR (101 MHz, CDCl$_3$) δ 170.47, 168.33, 163.09 (d, J = 246.5 Hz), 157.25, 156.26, 155.47 (d, J = 11.1 Hz), 149.58, 140.15, 130.12, 129.54, 128.71 (d, J = 10.3 Hz), 121.77, 119.93 (d, J = 3.4 Hz), 115.76, 109.65, 107.75 (d, J = 21.7 Hz), 103.82 (d, J = 24.0 Hz), 74.78, 56.25, 48.98, 29.26, 18.55, 16.20. $^{19}$F NMR (376 MHz, CDCl$_3$) δ-112.15. |

TABLE 2-continued

Analytical Data

| *Cmpd. No. | IR (cm$^{-1}$) | MASS | NMR ($^1$H, $^{13}$C or $^{19}$F) |
|---|---|---|---|
| 171 | | HRMS-ESI (m/z) ([M + H]$^+$) calcd for C$_{28}$H$_{32}$FN$_2$O$_7$, 527.2188; found, 527.2188 | $^1$H NMR (400 MHz, CDCl$_3$) δ 12.12 (s, 1H), 8.43 (d, J = 7.8 Hz, 1H), 7.96 (d, J = 5.2 Hz, 1H), 7.32 (dd, J = 8.3, 6.8 Hz, 1H), 7.20-7.13 (m, 2H), 6.86 (dd, J = 10.0, 6.2 Hz, 2H), 6.82-6.77 (m, 2H), 6.61-6.53 (m, 2H), 5.62 (d, J = 4.5 Hz, 1H), 5.43-5.36 (m, 1H), 4.66 (p, J = 7.2 Hz, 1H), 3.98 (t, J = 6.4 Hz, 2H), 3.94 (s, 3H), 1.96-1.86 (m, 2H), 1.37 (d, J = 7.2 Hz, 3H), 1.34 (d, J = 6.5 Hz, 3H), 1.11 (t, J = 7.4 Hz, 3H). $^{13}$C NMR (101 MHz, CDCl$_3$) δ 171.38, 168.68, 163.33 (d, J = 246.1 Hz), 157.68, 157.21 (d, J = 10.0 Hz), 155.36, 148.76, 140.40, 130.49, 129.30, 128.95 (d, J = 10.2 Hz), 121.10 (d, J = 3.2 Hz), 120.99, 115.53, 109.42, 107.16 (d, J = 21.5 Hz), 99.24 (d, J = 25.9 Hz), 74.64, 73.25, 70.01, 56.04, 48.01, 22.49, 18.13, 15.03, 10.67. $^{19}$F NMR (376 MHz, CDCl$_3$) δ-111.41 (s, 1F). |
| 172 | | HRMS-ESI (m/z) ([M + H]$^+$) calcd for C$_{27}$H$_{31}$N$_2$O$_7$, 495.2126; found, 495.2123. | $^1$H NMR (400 MHz, CDCl$_3$) δ 12.13 (s, 1H), 8.46 (d, J = 7.8 Hz, 1H), 7.94 (d, J = 5.2 Hz, 1H), 7.24 (d, J = 8.1 Hz, 1H), 7.17-7.12 (m, 2H), 6.83 (ddd, J = 11.1, 8.0, 6.7 Hz, 4H), 6.70 (d, J = 6.4 Hz, 2H), 5.64 (d, J = 4.4 Hz, 1H), 5.43-5.36 (m, 1H), 4.67 (p, J = 7.2 Hz, 1H), 3.93 (s, 3H), 3.89 (s, 3H), 2.31 (s, 3H), 1.36 (d, J = 7.2 Hz, 3H), 1.34 (d, J = 6.5 Hz, 3H). $^{13}$C NMR (101 MHz, CDCl$_3$) δ 171.48, 168.66, 157.92, 156.54, 155.33, 148.74, 140.39, 139.23, 130.54, 129.25, 127.68, 122.28, 121.53, 120.78, 115.59, 111.11, 109.39, 74.84, 73.41, 56.03, 55.41, 48.03, 21.57, 18.11, 14.89. |
| 173 | | HRMS-ESI (m/z) ([M + H]$^+$) calcd for C$_{27}$H$_{30}$FN$_2$O$_7$, 513.2032; found, 513.2027. | $^1$H NMR (400 MHz, CDCl$_3$) δ 12.11 (s, 1H), 8.44 (d, J = 7.8 Hz, 1H), 7.95 (d, J = 5.2 Hz, 1H), 7.33 (dd, J = 8.2, 6.8 Hz, 1H), 6.95 (d, J = 8.3 Hz, 2H), 6.85 (d, J = 5.2 Hz, 1H), 6.69 (t, J = 5.7 Hz, 2H), 6.63-6.55 (m, 2H), 5.57 (d, J = 4.6 Hz, 1H), 5.40-5.33 (m, 1H), 4.66 (p, J = 7.2 Hz, 1H), 3.93 (s, 3H), 3.88 (s, 3H), 2.21 (s, 3H), 1.37 (d, J = 7.2 Hz, 3H), 1.33 (d, J = 6.5 Hz, 3H). $^{13}$C NMR (101 MHz, CDCl$_3$) δ 171.43, 168.68, 163.36 (d, J = 246.2 Hz), 157.81 (d, J = 9.8 Hz), 155.53, 155.36, 148.76, 140.41, 130.49, 130.27, 129.77, 129.04 (d, J = 10.1 Hz), 121.33 (d, J = 3.2 Hz), 115.43, 109.42, 107.35 (d, J = 21.3 Hz), 98.66 (d, J = 25.9 Hz), 74.65, 73.23, 56.04, 55.77, 48.01, 20.42, 18.09, 15.00. $^{19}$F NMR (376 MHz, CDCl$_3$) δ-111.31 (s). |
| 174 | | ESIMS m/z 533 ([M + H]$^+$) | $^1$H NMR (400 MHz, CDCl$_3$) δ 12.08 (s, 1H), 8.43 (d, J = 7.9 Hz, 1H), 7.95 (d, J = 5.2 Hz, 1H), 7.36 (dd, J = 9.1, 6.7 Hz, 1H), 7.29 (dd, J = 7.9, 1.5 Hz, 1H), 7.04-6.98 (m, 1H), 6.85 (d, J = 5.2 Hz, 1H), 6.80 (td, J = 7.7, 1.1 Hz, 1H), 6.66-6.58 (m, 3H), 5.69 (d, J = 4.3 Hz, 1H), 5.43 (qd, J = 6.5, 4.4 Hz, 1H), 4.68 (p, J = 7.3 Hz, 1H), 3.94 (s, 3H), 3.90 (s, 3H), 1.40 (d, J = 7.2 Hz, 3H), 1.38 |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | (d, J = 6.5 Hz, 3H). $^{13}$C NMR (101 MHz, CDCl$_3$) δ 171.39, 168.69, 163.54 (d, J = 246.9 Hz), 157.78 (d, J = 9.7 Hz), 155.34, 153.03, 148.73, 140.40, 130.47, 130.25, 129.07 (d, J = 10.1 Hz), 127.44, 123.32, 121.58, 120.39 (d, J = 3.3 Hz), 114.39, 109.42, 107.53 (d, J = 21.3 Hz), 98.72 (d, J = 25.9 Hz), 75.25, 73.14, 56.04, 55.82, 48.01, 18.05, 14.81. $^{19}$F NMR (376 MHz, CDCl$_3$) δ-110.71 (s, 1F). |
| 175 | | HRMS-ESI (m/z) ([M + H]$^+$) calcd for C$_{29}$H$_{32}$FN$_2$O$_7$, 539.2188; found, 539.2194. | $^1$H NMR (400 MHz, CDCl$_3$) δ 12.13 (s, 1H), 8.44 (d, J = 7.8 Hz, 1H), 7.96 (d, J = 5.2 Hz, 1H), 7.33 (dd, J = 9.2, 6.7 Hz, 1H), 7.20-7.14 (m, 2H), 6.85 (ddd, J = 13.7, 10.5, 7.6 Hz, 4H), 6.56 (ddd, J = 11.1, 5.1, 2.5 Hz, 2H), 5.66 (d, J = 4.5 Hz, 1H), 5.47-5.39 (m, 1H), 4.67 (p, J = 7.2 Hz, 1H), 3.94 (s, 3H), 3.89 (d, J = 6.8 Hz, 2H), 1.39 (d, J = 7.2 Hz, 3H), 1.37-1.30 (m, 4H), 0.72-0.66 (m, 2H), 0.41 (q, J = 5.1 Hz, 2H). $^{13}$C NMR (101 MHz, CDCl$_3$) δ 171.37, 168.67, 163.28 (d, J = 246.4 Hz), 157.67, 157.10 (d, J = 9.9 Hz), 155.36, 148.77, 140.40, 130.50, 129.29, 129.08 (d, J = 10.1 Hz), 121.24 (d, J = 3.4 Hz), 120.98, 115.55, 109.42, 107.25 (d, J = 21.3 Hz), 99.41 (d, J = 25.6 Hz), 74.53, 73.30, 72.96, 56.04, 48.02, 18.17, 15.18, 10.08, 3.26, 3.12. $^{19}$F NMR (376 MHz, CDCl$_3$) δ-111.40 (s). |
| 176 | | HRMS-ESI (m/z) ([M + H]$^+$) calcd for C$_{27}$H$_{28}$F$_3$N$_2$O$_7$, 549.1843; found, 549.1844 | $^1$H NMR (400 MHz, CDCl$_3$) δ 12.09 (s, 1H), 8.40 (d, J = 7.8 Hz, 1H), 7.97 (d, J = 5.2 Hz, 1H), 7.37 (dd, J = 8.5, 6.6 Hz, 1H), 7.20-7.13 (m, 2H), 6.91-6.84 (m, 2H), 6.81-6.75 (m, 2H), 6.67 (td, J = 8.3, 2.3 Hz, 1H), 6.57 (dd, J = 10.2, 2.3 Hz, 1H), 6.23 (tt, J = 54.8, 4.0 Hz, 1H), 5.60 (d, J = 4.2 Hz, 1H), 5.42-5.35 (m, 1H), 4.65 (p, J = 7.2 Hz, 1H), 4.29-4.19 (m, 2H), 3.94 (s, 3H), 1.38 (d, J = 7.2 Hz, 3H), 1.34 (d, J = 6.5 Hz, 3H). $^{13}$C NMR (101 MHz, CDCl$_3$) δ 171.42, 168.69, 163.14 (d, J = 247.8 Hz), 157.52, 155.56 (d, J = 9.8 Hz), 155.39, 148.77, 140.42, 130.43, 129.51 (d, J = 9.9 Hz), 129.40, 121.72 (d, J = 3.4 Hz), 121.26, 115.55, 113.24 (t, J = 241.4 Hz), 109.46, 108.86 (d, J = 21.2 Hz), 99.64 (d, J = 26.1 Hz), 74.59, 73.00, 67.61 (t, J = 29.7 Hz), 56.05, 48.01, 18.05, 14.73. $^{19}$F NMR (376 MHz, CDCl$_3$) δ-110.47 (s), -124.95 (d, J = 296.7 Hz), -125.91 (d, J = 296.7 Hz). |
| 177 | | HRMS-ESI (m/z) ([M + H]$^+$) calcd for C$_{28}$H$_{33}$N$_2$O$_7$, 509.2282; found, 509.2284. | $^1$H NMR (400 MHz, CDCl$_3$) δ 12.14 (s, 1H), 8.46 (d, J = 7.9 Hz, 1H), 7.95 (d, J = 5.2 Hz, 1H), 7.24 (d, J = 7.5 Hz, 1H), 6.94 (d, J = 8.2 Hz, 2H), 6.85 (d, J = 5.2 Hz, 1H), 6.73-6.67 (m, 4H), 5.59 (d, J = 4.4 Hz, 1H), 5.42-5.35 (m, 1H), 4.66 (p, J = 7.2 Hz, 1H), 3.93 (s, 3H), 3.88 (s, 3H), 2.31 (s, 3H), 2.20 (s, 3H), 1.36 (d, J = 7.2 Hz, 3H), 1.33 (d, J = 6.5 Hz, 3H). |

TABLE 2-continued

Analytical Data

| *Cmpd. No. | IR (cm$^{-1}$) | MASS | NMR ($^1$H, $^{13}$C or $^{19}$F) |
|---|---|---|---|
| 178 | | HRMS-ESI (m/z) ([M + H]$^+$) calcd for C$_{27}$H$_{30}$FN$_2$O$_7$, 561.2032; found, 561.2030. | $^{13}$C NMR (101 MHz, CDCl$_3$) δ 171.49, 168.65, 156.56, 155.81, 155.34, 148.74, 140.38, 139.13, 130.57, 129.94, 129.70, 127.70, 122.47, 121.52, 115.44, 111.09, 109.37, 74.98, 73.45, 56.03, 55.39, 48.02, 21.56, 20.41, 18.13, 14.89. $^1$H NMR (400 MHz, CDCl$_3$) δ 12.10 (s, 1H), 8.43 (d, J = 7.8 Hz, 1H), 7.95 (d, J = 5.2 Hz, 1H), 7.47 (dd, J = 8.7, 6.5 Hz, 1H), 7.45-7.39 (m, 2H), 7.24-7.15 (m, 3H), 7.11-7.06 (m, 2H), 6.87 (ddd, J = 11.6, 9.4, 6.2 Hz, 4H), 6.71 (td, J = 8.3, 2.5 Hz, 1H), 6.48 (dd, J = 10.1, 2.5 Hz, 1H), 5.72 (d, J = 4.9 Hz, 1H), 5.54-5.47 (m, 1H), 4.70 (p, J = 7.2 Hz, 1H), 3.93 (s, 3H), 1.44-1.38 (m, 6H). $^{19}$F NMR (376 MHz, CDCl$_3$) δ-110.54--110.75 (m). |
| 179 | | ESIMS m/z 595 ([M + H]$^+$) | $^1$H NMR (300 MHz, CDCl$_3$) δ 12.08 (s, 1H), 8.43 (d, J = 7.9 Hz, 1H), 7.96 (d, J = 5.2 Hz, 1H), 7.53 (dd, J = 8.7, 6.5 Hz, 1H), 7.45-7.38 (m, 2H), 7.31 (dd, J = 7.9, 1.6 Hz, 1H), 7.22 (dt, J = 8.4, 1.0 Hz, 1H), 7.09-7.00 (m, 3H), 6.87-6.81 (m, 2H), 6.79-6.71 (m, 2H), 6.49 (dd, J = 10.1, 2.5 Hz, 1H), 5.80 (d, J = 4.5 Hz, 1H), 5.59-5.52 (m, 1H), 4.71 (p, J = 7.2 Hz, 1H), 3.93 (s, 3H), 1.45 (d, J = 6.5 Hz, 3H), 1.43 (d, J = 7.3 Hz, 3H). $^{19}$F NMR (376 MHz, CDCl$_3$) δ-110.16 (s). |
| 180 | | | $^1$H NMR (300 MHz, CDCl$_3$) δ 12.24 (s, 1H), 8.51 (d, J = 7.9 Hz, 1H), 7.98 (d, J = 5.2 Hz, 1H), 7.39-7.27 (m, 5H), 6.87 (d, J = 5.2 Hz, 1H), 5.07 (dd, J = 6.8, 4.8 Hz, 1H), 4.85-4.69 (m, 1H), 4.26 (d, J = 6.8 Hz, 1H), 3.95 (s, 3H), 3.19 (s, 3H), 1.83-1.66 (m, 1H), 1.56 (d, J = 7.1 Hz, 3H), 0.90 (d, J = 6.9 Hz, 3H), 0.89 (d, J = 6.8 Hz, 3H). $^{13}$C NMR (75 MHz, CDCl$_3$) δ 171.86, 168.59, 155.30, 148.70, 140.42, 137.92, 130.58, 128.59, 128.30, 127.51, 109.37, 83.45, 81.46, 57.02, 48.05, 28.26, 19.78, 18.62, 16.72 |
| 181 | | ESIMS m/z 543 ([M + H]$^+$) | $^1$H NMR (400 MHz, CDCl$_3$) δ 12.12 (s, 1H), 8.46 (d, J = 7.9 Hz, 1H), 7.95 (d, J = 5.2 Hz, 1H), 7.26 (d, J = 7.7 Hz, 1H), 7.10 (d, J = 1.9 Hz, 1H), 6.84 (d, J = 5.2 Hz, 1H), 6.78 (dd, J = 8.4, 1.6 Hz, 1H), 6.73-6.68 (m, 2H), 6.55 (d, J = 8.4 Hz, 1H), 5.67 (d, J = 4.2 Hz, 1H), 5.43 (qd, J = 6.4, 4.3 Hz, 1H), 4.68 (p, J = 7.2 Hz, 1H), 3.93 (s, 3H), 3.88 (s, 3H), 2.31 (s, 3H), 2.18 (s, 3H), 1.39 (d, J = 7.2 Hz, 3H), 1.37 (d, J = 6.5 Hz, 3H). $^{13}$C NMR (101 MHz, CDCl$_3$) δ 171.46, 168.66, 156.53, 155.31, 151.08, 148.72, 140.38, 139.44, 130.90, 130.55, 127.84, 127.71, 122.75, 121.72, 121.61, 114.28, 111.08, 109.36, 75.59, 73.42, 56.02, 55.41, 48.03, 21.58, 20.20, 18.10, 14.78. |

TABLE 2-continued

Analytical Data

| *Cmpd. No. | IR (cm$^{-1}$) | MASS | NMR ($^1$H, $^{13}$C or $^{19}$F) |
|---|---|---|---|
| 182 | | HRMS-ESI (m/z) [M]$^+$ calcd for C$_{26}$H$_{32}$N$_2$O$_8$, 500.2159; found, 500.2165 | $^1$H NMR (500 MHz, CDCl$_3$) δ 8.31-8.22 (m, 2H), 7.36-7.20 (m, 5H), 6.94 (d, J = 5.4 Hz, 1H), 5.78-5.68 (m, 2H), 5.12 (h, J = 6.4 Hz, 1H), 4.68-4.55 (m, 1H), 4.33 (d, J = 6.4 Hz, 1H), 3.90 (s, 3H), 3.19 (dd, J = 6.8, 2.4 Hz, 2H), 2.06 (s, 3H), 1.35 (d, J = 6.3 Hz, 3H), 1.17 (d, J = 7.1 Hz, 3H), 1.01 (ttt, J = 8.0, 6.7, 4.9 Hz, 1H), 0.54-0.41 (m, 2H), 0.19-0.04 (m, 2H). $^{13}$C NMR (126 MHz, CDCl$_3$) δ 172.03, 170.27, 162.86, 160.26, 145.68, 143.97, 142.51, 138.81, 128.21, 127.95, 127.60, 109.52, 89.56, 83.08, 74.22, 73.75, 56.17, 48.08, 20.87, 18.13, 16.07, 10.59, 3.17, 2.71. |
| 183 | | HRMS-ESI (m/z) [M]$^+$ calcd for C$_{28}$H$_{30}$N$_2$O$_8$, 522.2002; found, 522.2005 | $^1$H NMR (500 MHz, CDCl$_3$) δ 8.32-8.26 (m, 1H), 8.24 (d, J = 5.4 Hz, 1H), 7.44-7.21 (m, 5H), 7.22-7.08 (m, 2H), 6.94-6.89 (m, 1H), 6.89-6.78 (m, 3H), 5.77-5.67 (m, 2H), 5.33-5.25 (m, 1H), 5.21 (d, J = 5.1 Hz, 1H), 4.66 (p, J = 7.2 Hz, 1H), 3.90 (s, 3H), 2.06 (s, 3H), 1.39 (d, J = 6.4 Hz, 3H), 1.26 (d, J = 7.2 Hz, 3H). $^{13}$C NMR (126 MHz, CDCl$_3$) δ 172.22, 170.27, 162.94, 160.26, 157.88, 145.68, 144.00, 142.41, 137.59, 129.33, 128.50, 128.14, 126.98, 121.15, 115.97, 109.55, 89.55, 81.23, 74.29, 56.17, 48.12, 20.87, 18.18, 15.10. |
| 184 | | HRMS-ESI (m/z) [M]$^+$ calcd for C$_{27}$H$_{28}$N$_2$O$_7$, 492.1897; found, 492.1900 | $^1$H NMR (500 MHz, CDCl$_3$) δ 8.50-8.42 (m, 1H), 8.33-8.23 (m, 1H), 7.42-7.35 (m, 2H), 7.34-7.20 (m, 3H), 7.20-7.11 (m, 2H), 7.01-6.92 (m, 1H), 6.90-6.76 (m, 3H), 5.32-5.16 (m, 2H), 4.64 (tt, J = 10.1, 5.1 Hz, 1H), 3.86 (s, 3H), 2.38 (s, 3H), 1.38 (d, J = 6.3 Hz, 3H), 1.24 (d, J = 7.2 Hz, 3H). $^{13}$C NMR (126 MHz, CDCl$_3$) δ 172.08, 168.87, 162.36, 159.40, 157.85, 146.63, 141.41, 137.54, 137.45, 129.32, 128.49, 128.13, 126.97, 121.15, 115.96, 109.76, 81.19, 74.29, 56.24, 47.89, 20.74, 18.32, 15.09. |
| 185 | (Thin film) 3376.11, 2985.22, 1739.53, 1675.70, 1493.93, 1200.10 | HRMS-ESI (m/z) ([M + H]$^+$) calcd for C$_{28}$H$_{31}$N$_2$O$_8$, 523.2075; found, 523.2075 | $^1$H NMR (400 MHz, CDCl$_3$) δ 8.31-8.26 (m, 2H), 7.43-7.36 (m, 2H), 7.34-7.28 (m, 2H), 7.26-7.21 (m, 1H), 7.20-7.13 (m, 2H), 6.95 (d, J = 5.4 Hz, 1H), 6.91-6.80 (m, 3H), 5.75-5.71 (m, 2H), 5.32-5.18 (m, 2H), 4.74-4.60 (m, 1H), 3.91 (s, 3H), 2.05 (s, 3H), 1.43 (d, J = 7.1 Hz, 3H), 1.36 (d, J = 6.2 Hz, 3H). $^{13}$C NMR (101 MHz, CDCl$_3$) δ 172.07, 170.27, 162.88, 160.30, 157.87, 145.67, 144.08, 142.45, 137.56, 129.33, 128.50, 128.06, 126.83, 121.16, 116.07, 109.55, 89.61, 81.11, 74.54, 56.19, 48.16, 20.87, 18.37, 14.52. |
| 186 | (Thin film) 3378.15, 2984.35, 1740.49, 1674.69, 1493.07, 1199.65 | HRMS-ESI (m/z) ([M + H]$^+$) calcd for C$_{28}$H$_{31}$N$_2$O$_8$, 523.2075; found, 523.2087 | $^1$H NMR (400 MHz, CDCl$_3$) δ 8.28 (d, J = 7.8 Hz, 1H), 8.24 (d, J = 5.4 Hz, 1H), 7.43-7.37 (m, 2H), 7.36-7.21 (m, 3H), 7.20-7.13 (m, 2H), 6.93 (d, J = 5.4 Hz, 1H), 6.90-6.79 (m, 3H), 5.74 (d, J = 6.4 Hz, 1H), 5.71 (d, J = 6.4 Hz, 1H), 5.33-5.18 (m, 2H), 4.67 (dq, J = 11.0, 7.2 Hz, |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 1H), 3.90 (s, 3H), 2.06 (s, 3H), 1.39 (d, J = 6.4 Hz, 3H), 1.26 (d, J = 7.2 Hz, 3H). $^{13}$C NMR (101 MHz, CDCl$_3$) δ 172.22, 170.27, 162.95, 160.27, 157.90, 145.68, 144.01, 142.44, 137.61, 129.34, 128.51, 128.14, 126.99, 121.16, 115.99, 109.55, 89.57, 81.26, 74.31, 56.18, 48.14, 20.88, 18.20, 15.11. |
| 187 | (Thin film) 3380, 2970, 1740, 1675, 1504, 1488, 1202, 1132 | HRMS-ESI (m/z) ([M + H]$^+$) calcd for C$_{28}$H$_{30}$FN$_2$O$_8$, 541.1981; found, 541.1990 | $^1$H NMR (500 MHz, CDCl$_3$) δ 8.30-8.22 (m, 2H), 7.41-7.24 (m, 5H), 7.10 (td, J = 8.3, 6.7 Hz, 1H), 6.93 (d, J = 5.4 Hz, 1H), 6.64-6.50 (m, 3H), 5.76-5.68 (m, 2H), 5.32-5.21 (m, 1H), 5.19 (d, J = 4.9 Hz, 1H), 4.67 (p, J = 7.2 Hz, 1H), 3.90 (s, 3H), 2.06 (s, 3H), 1.38 (d, J = 6.4 Hz, 3H), 1.28 (d, J = 7.2 Hz, 3H). $^{13}$C NMR (126 MHz, CDCl$_3$) δ 172.19, 170.29, 163.36 (d, J = 245.4 Hz), 162.98, 160.27, 159.11 (d, J = 10.9 Hz), 145.68, 144.03, 142.37, 136.95, 130.10 (d, J = 10.0 Hz), 128.63, 128.35, 126.88, 111.55 (d, J = 3.0 Hz), 109.57, 108.03 (d, J = 21.3 Hz), 103.73 (d, J = 24.8 Hz), 89.56, 81.50, 74.07, 56.17, 48.15, 20.88, 18.16, 14.93. $^{19}$F NMR (471 MHz, CDCl$_3$) δ-111.61 (dt, J = 10.9, 7.7 Hz). |
| 188 | (Thin film) 3380, 2970, 2941, 1768, 1738, 1676, 1507, 1488, 1199, 1132 | HRMS-ESI (m/z) ([M + H]$^+$) calcd for C$_{27}$H$_{28}$FN$_2$O$_7$, 511.1875; found, 511.1883 | $^1$H NMR (500 MHz, CDCl$_3$) δ 8.45 (br s, 1H), 8.29 (d, J = 5.4 Hz, 1H), 7.40-7.26 (m, 5H), 7.10 (td, J = 8.3, 6.8 Hz, 1H), 6.99 (d, J = 5.5 Hz, 1H), 6.63-6.50 (m, 3H), 5.26 (qd, J = 6.4, 4.7 Hz, 1H), 5.18 (d, J = 4.9 Hz, 1H), 4.65 (p, J = 7.4 Hz, 1H), 3.90 (s, 3H), 2.39 (s, 3H), 1.36 (d, J = 6.4 Hz, 3H), 1.27 (d, J = 7.1 Hz, 3H). $^{13}$C NMR (126 MHz, CDCl$_3$) δ 172.08, 168.91, 163.36 (d, J = 245.5 Hz), 162.41, 159.43, 159.10 (d, J = 11.0 Hz), 146.63, 141.41, 137.49, 136.92, 130.08 (d, J = 10.0 Hz), 128.62, 128.35, 126.89, 111.56 (d, J = 2.9 Hz), 109.76, 108.02 (d, J = 21.2 Hz), 103.73 (d, J = 24.9 Hz), 81.47, 74.09, 56.27, 47.93, 20.75, 18.31, 14.91. $^{19}$F NMR (471 MHz, CDCl$_3$) δ-111.63 (dt, J = 10.9, 7.7 Hz). |
| 189 | (Thin film) 3379, 2970, 1740, 1676, 1488, 1200 | HRMS-ESI (m/z) ([M + H]$^+$) calcd for C$_{34}$H$_{34}$FN$_2$O$_8$, 617.2294; found, 617.2304 | $^1$H NMR (500 MHz, CDCl$_3$) δ 8.29 (d, J = 8.3 Hz, 1H), 8.22 (d, J = 5.4 Hz, 1H), 7.39-7.25 (m, 5H), 7.18-7.06 (m, 4H), 7.05-6.99 (m, 2H), 6.92 (d, J = 5.4 Hz, 1H), 6.64-6.56 (m, 2H), 6.52 (dt, J = 10.8, 2.4 Hz, 1H), 5.71-5.64 (m, 2H), 5.21-5.10 (m, 2H), 4.99 (dt, J = 8.5, 5.9 Hz, 1H), 3.90 (s, 3H), 3.07 (qd, J = 13.9, 6.0 Hz, 2H), 2.04 (d, J = 2.0 Hz, 3H), 1.34 (d, J = 6.4 Hz, 3H). $^{13}$C NMR (126 MHz, CDCl$_3$) δ 170.84, 170.27, 163.38 (d, J = 245.4 Hz), 163.01, 160.23, 158.97 (d, J = 10.9 Hz), 145.72, 144.01, 142.22, 136.91, 135.85, 130.10 (d, J = 10.0 Hz), 129.37, 128.70, 128.42, 128.37, 126.92, 126.77, 111.62 (d, J = 2.9 Hz), 109.56, 107.99 (d, J = 21.3 Hz), 103.75 (d, J = 24.9 Hz), 89.54, 81.19, 74.80, 56.16, 53.30, 37.83, 20.87, 14.34. |

TABLE 2-continued

Analytical Data

| *Cmpd. No. | IR (cm⁻¹) | MASS | NMR (¹H, ¹³C or ¹⁹F) |
|---|---|---|---|
| 190 | | HRMS-ESI (m/z) ([M + H]⁺) calcd for $C_{33}H_{32}FN_2O_7$, 587.2188; found, 587.2184 | $^{19}F$ NMR (471 MHz, CDCl$_3$) δ -111.61 (dt, J = 10.8, 7.6 Hz). $^{1}H$ NMR (400 MHz, CDCl$_3$) δ 8.45 (d, J = 8.4 Hz, 1H), 8.25 (d, J = 5.5 Hz, 1H), 7.39-7.24 (m, 5H), 7.17-7.03 (m, 4H), 7.02-6.94 (m, 3H), 6.65-6.55 (m, 2H), 6.52 (dt, J = 10.9, 2.4 Hz, 1H), 5.19-5.08 (m, 2H), 4.97 (dt, J = 8.5, 5.6 Hz, 1H), 3.89 (s, 3H), 3.09 (app d, J = 5.7 Hz, 2H), 2.39 (s, 3H), 1.32 (d, J = 6.3 Hz, 3H). $^{13}C$ NMR (101 MHz, CDCl$_3$) δ 170.67, 168.88, 163.40 (d, J = 245.3 Hz), 162.47, 159.39, 158.97 (d, J = 10.9 Hz), 146.72, 141.37, 137.49, 136.88, 135.69, 130.10 (d, J = 9.9 Hz), 129.43, 128.71, 128.42, 128.37, 126.95, 126.77, 111.64 (d, J = 2.9 Hz), 109.79, 107.98 (d, J = 21.3 Hz), 103.76 (d, J = 24.8 Hz), 81.14, 74.87, 56.27, 53.09, 37.85, 20.77, 14.26. |
| 191 | | HRMS-ESI (m/z) ([M + H]⁺) calcd for $C_{28}H_{29}F_2N_2O_8$, 559.1886; found, 559.1909 | $^{19}F$ NMR (376 MHz, CDCl$_3$) δ -111.61. $^{1}H$ NMR (400 MHz, CDCl$_3$) δ 8.31-8.22 (m, 2H), 7.44-7.27 (m, 5H), 7.02-6.91 (m, 2H), 6.58-6.44 (m, 2H), 5.77-5.68 (m, 2H), 5.33 (qd, J = 6.4, 5.0 Hz, 1H), 5.20 (d, J = 5.1 Hz, 1H), 4.73-4.60 (m, 1H), 3.90 (s, 3H), 2.06 (s, 3H), 1.41 (d, J = 6.4 Hz, 3H), 1.28 (d, J = 7.2 Hz, 3H). $^{13}C$ NMR (101 MHz, CDCl$_3$) δ 172.15, 170.28, 162.99, 160.27, 158.32 (dd, J = 242.3, 2.7 Hz), 149.47 (dd, J = 242.0, 3.2 Hz), 146.24 (dd, J = 12.5, 10.5 Hz), 145.69, 144.00, 142.41, 136.31, 128.68, 128.65, 127.01, 116.38 (dd, J = 21.0, 10.2 Hz), 109.58, 107.65 (dd, J = 23.8, 6.9 Hz), 105.13 (dd, J = 27.2, 1.4 Hz), 89.53, 83.05, 73.87, 56.18, 48.14, 20.86, 18.06, 15.10. $^{19}F$ NMR (376 MHz, CDCl$_3$) δ -116.68 (d, J = 15.0 Hz), -138.67 (d, J = 15.0 Hz). |
| 192 | | HRMS-ESI (m/z) ([M + H]⁺) calcd for $C_{27}H_{27}F_2N_2O_7$, 529.1781; found, 529.1784 | $^{1}H$ NMR (400 MHz, CDCl$_3$) δ 8.46 (d, J = 8.0 Hz, 1H), 8.29 (d, J = 5.4 Hz, 1H), 7.43-7.25 (m, 5H), 7.04-6.91 (m, 2H), 6.57-6.43 (m, 2H), 5.31 (qd, J = 6.5, 5.1 Hz, 1H), 5.18 (d, J = 5.1 Hz, 1H), 4.65 (dq, J = 8.3, 7.2 Hz, 1H), 3.89 (s, 3H), 2.39 (s, 3H), 1.40 (d, J = 6.4 Hz, 3H), 1.27 (d, J = 7.2 Hz, 3H). $^{13}C$ NMR (101 MHz, CDCl$_3$) δ 172.04, 168.90, 162.43, 159.44, 158.32 (dd, J = 242.3, 2.5 Hz), 149.46 (dd, J = 242.1, 3.2 Hz), 146.63, 146.23 (dd, J = 12.3, 10.8 Hz), 141.42, 137.50, 136.28, 128.67, 128.65, 127.00, 116.35 (dd, J = 20.9, 10.1 Hz), 109.77, 107.62 (dd, J = 23.8, 7.0 Hz), 105.11 (dd, J = 27.3, 1.3 Hz), 82.99, 73.90, 56.27, 47.94, 20.75, 18.19, 15.03. $^{19}F$ NMR (376 MHz, CDCl$_3$) δ -116.69 (d, J = 15.0 Hz), -138.71 (d, J = 14.9 Hz). |
| 193 | | HRMS-ESI (m/z) ([M + H]⁺) calcd for $C_{29}H_{31}F_2N_2O_8$, 573.2043; found, 573.2058 | $^{1}H$ NMR (400 MHz, CDCl$_3$) δ 8.35-8.22 (m, 2H), 7.44-7.27 (m, 5H), 7.02-6.91 (m, 2H), 6.58-6.42 (m, 2H), 5.78-5.68 (m, 2H), 5.32 (qd, J = 6.4, 5.0 Hz, 1H), 5.19 (d, J = 5.0 Hz, 1H), 4.66 (ddd, J = 8.3, 6.6, 5.2 |

TABLE 2-continued

Analytical Data

| *Cmpd. No. | IR (cm⁻¹) | MASS | NMR (¹H, ¹³C or ¹⁹F) |
|---|---|---|---|
| | | | Hz, 1H), 3.91 (s, 3H), 2.06 (s, 3H), 1.87-1.75 (m, 1H), 1.69-1.57 (m, 1H), 1.41 (d, J = 6.4 Hz, 3H), 0.75 (t, J = 7.4 Hz, 3H). ¹³C NMR (101 MHz, CDCl₃) δ 171.51, 170.28, 163.14, 160.30, 158.33 (dd, J = 239.9, 2.6 Hz), 149.43 (dd, J = 241.9, 3.2 Hz), 146.24 (dd, J = 12.4, 10.6 Hz), 145.69, 144.04, 142.42, 136.32, 128.71, 128.66, 126.98, 116.35 (dd, J = 21.0, 10.0 Hz), 109.55, 107.58 (dd, J = 23.9, 7.0 Hz), 105.00 (dd, J = 27.3, 1.4 Hz), 89.60, 82.99, 73.97, 56.18, 53.27, 25.41, 20.87, 15.09, 9.21. ¹⁹F NMR (376 MHz, CDCl₃) δ-116.70 (d, J = 15.0 Hz), -138.70 (d, J = 14.9 Hz). |
| 194 | | HRMS-ESI (m/z) ([M + H]⁺) calcd for C₂₈H₂₉F₂N₂O₇, 543.1937; found, 543.1948 | ¹H NMR (400 MHz, CDCl₃) δ 8.49 (d, J = 8.6 Hz, 1H), 8.30 (d, J = 5.4 Hz, 1H), 7.43-7.27 (m, 5H), 7.02-6.91 (m, 2H), 6.57-6.42 (m, 2H), 5.30 (qd, J = 6.4, 4.9 Hz, 1H), 5.19 (d, J = 5.0 Hz, 1H), 4.64 (ddd, J = 8.5, 6.5, 5.2 Hz, 1H), 3.89 (s, 3H), 2.39 (s, 3H), 1.86-1.72 (m, 1H), 1.68-1.56 (m, 1H), 1.40 (d, J = 6.4 Hz, 3H), 0.74 (t, J = 7.4 Hz, 3H). ¹³C NMR (101 MHz, CDCl₃) δ 171.38, 168.89, 162.60, 159.44, 158.31 (dd, J = 242.3, 2.6 Hz), 149.42 (dd, J = 242.0, 3.4 Hz), 146.65, 146.23 (dd, J = 12.4, 10.6 Hz), 141.47, 137.49, 136.29, 128.70, 128.65, 126.96, 116.32 (dd, J = 20.9, 10.2 Hz), 109.75, 107.54 (dd, J = 23.8, 6.8 Hz), 104.98 (dd, J = 27.2, 1.7 Hz), 82.92, 73.99, 56.27, 53.07, 25.48, 20.75, 15.02, 9.13. ¹⁹F NMR (376 MHz, CDCl₃) δ-116.69 (d, J = 15.0 Hz), -138.73 (d, J = 15.0 Hz). |
| 195 | | HRMS-ESI (m/z) ([M + H]⁺) calcd for C₂₉H₃₀F₃N₂O₈, 591.1949; found, 591.1953 | ¹H NMR (400 MHz, CDCl₃) δ 8.26 (d, J = 7.8 Hz, 1H), 8.22 (d, J = 5.4 Hz, 1H), 7.45-7.26 (m, 7H), 6.96-6.84 (m, 3H), 5.76-5.67 (m, 2H), 5.34-5.24 (m, 2H), 4.67 (p, J = 7.3 Hz, 1H), 3.90 (s, 3H), 2.06 (s, 3H), 1.39 (d, J = 6.1 Hz, 3H), 1.30 (d, J = 7.2 Hz, 3H). ¹³C NMR (101 MHz, CDCl₃) δ 172.15, 170.28, 163.04, 160.28, 160.18, 145.66, 144.02, 142.32, 136.59, 128.72, 128.47, 126.82, 126.75 (q, J = 3.9 Hz), 124.33 (q, J = 259.5 Hz), 123.21 (q, J = 32.7 Hz), 115.78, 109.58, 89.54, 81.31, 73.99, 56.16, 48.23, 20.86, 18.09, 14.76. ¹⁹F NMR (376 MHz, CDCl₃) δ-61.61. |
| 196 | | HRMS-ESI (m/z) ([M + H]⁺) calcd for C₂₈H₂₈F₃N₂O₇, 561.1843; found, 561.1853 | ¹H NMR (400 MHz, CDCl₃) δ 8.44 (d, J = 8.2 Hz, 1H), 8.25 (d, J = 5.4 Hz, 1H), 7.43-7.28 (m, 7H), 6.97 (d, J = 5.5 Hz, 1H), 6.90-6.86 (m, 2H), 5.33-5.22 (m, 2H), 4.72-4.59 (m, 1H), 3.89 (s, 3H), 2.39 (s, 3H), 1.37 (d, J = 6.0 Hz, 3H), 1.29 (d, J = 7.2 Hz, 3H). ¹³C NMR (101 MHz, CDCl₃) δ 172.03, 168.88, 162.48, 160.16, 159.43, 146.59, 141.35, 137.51, 136.57, 128.71, 128.46, 126.82, 126.77 (q, J = 4.2 Hz), 124.29 (q, J = 271.2 Hz), 123.19 (q, J = 32.6 |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | Hz), 115.79, 109.77, 81.27, 74.04, 56.26, 48.02, 20.75, 18.24, 14.71. $^{19}$F NMR (376 MHz, CDCl$_3$) δ-61.60. |
| 197 | | HRMS-ESI (m/z) ([M + H]$^+$) calcd for C$_{31}$H$_{34}$F$_3$N$_2$O$_8$, 619.2262; found, 619.2266 | $^1$H NMR (400 MHz, CDCl$_3$) δ 8.34 (d, J = 9.2 Hz, 1H), 8.21 (d, J = 5.3 Hz, 1H), 7.44-7.27 (m, 7H), 6.93 (d, J = 5.4 Hz, 1H), 6.90-6.83 (m, 2H), 5.77-5.67 (m, 2H), 5.29 (q, J = 2.4, 1.9 Hz, 2H), 4.64 (dd, J = 9.1, 4.8 Hz, 1H), 3.90 (s, 3H), 2.20-2.08 (m, 1H), 2.06 (s, 3H), 1.40-1.34 (m, 3H), 0.90 (d, J = 6.8 Hz, 3H), 0.77 (d, J = 6.8 Hz, 3H). $^{13}$C NMR (101 MHz, CDCl$_3$) δ 171.20, 170.26, 163.35, 160.36, 160.16, 145.63, 144.13, 142.28, 136.52, 128.74, 128.45, 126.77, 126.72 (q, J = 3.9 Hz), 124.28 (q, J = 271.3 Hz), 123.16 (q, J = 32.9 Hz), 115.72, 109.55, 89.64, 81.19, 74.05, 57.21, 56.16, 31.25, 20.86, 19.10, 17.46, 14.55. $^{19}$F NMR (376 MHz, CDCl$_3$) δ-61.61. |
| 198 | | HRMS-ESI (m/z) ([M + H]$^+$) calcd for C$_{30}$H$_{32}$F$_3$N$_2$O$_7$, 589.2156; found, 589.2158 | $^1$H NMR (400 MHz, CDCl$_3$) δ 8.48 (d, J = 9.4 Hz, 1H), 8.24 (d, J = 5.4 Hz, 1H), 7.43-7.29 (m, 7H), 6.97 (d, J = 5.5 Hz, 1H), 6.89-6.82 (m, 2H), 5.31-5.23 (m, 2H), 4.60 (dd, J = 9.4, 4.8 Hz, 1H), 3.89 (s, 3H), 2.39 (s, 3H), 2.17-2.04 (m, 1H), 1.35 (d, J = 6.1 Hz, 3H), 0.89 (d, J = 6.8 Hz, 3H), 0.77 (d, J = 6.8 Hz, 3H). $^{13}$C NMR (101 MHz, CDCl$_3$) δ 171.04, 168.87, 162.80, 160.15, 159.43, 146.60, 141.48, 137.50, 136.50, 128.73, 128.44, 126.76, 126.70 (q, J = 3.7 Hz), 124.30 (q, J = 269.7 Hz), 123.13 (q, J = 33.0 Hz), 115.73, 109.72, 81.14, 74.08, 57.04, 56.25, 31.31, 20.76, 19.00, 17.48, 14.46. $^{19}$F NMR (376 MHz, CDCl$_3$) δ-61.60. |
| 199 | (Thin film) 3382, 2987, 2941, 1742, 1674, 1574, 1504, 1478, 1200, 729 | HRMS-ESI (m/z) ([M + H]$^+$) calcd for C$_{28}$H$_{29}$Cl$_2$N$_2$O$_8$, 591.1295; found, 591.1301 | $^1$H NMR (500 MHz, CDCl$_3$) δ 8.28-8.21 (m, 2H), 7.40-7.27 (m, 6H), 6.97-6.91 (m, 2H), 6.57 (d, J = 8.9 Hz, 1H), 5.75-5.67 (m, 2H), 5.32 (qd, J = 6.4, 4.6 Hz, 1H), 5.24 (d, J = 4.6 Hz, 1H), 4.67 (p, J = 7.3 Hz, 1H), 3.91 (s, 3H), 2.07 (s, 3H), 1.42 (d, J = 6.4 Hz, 3H), 1.32 (d, J = 7.2 Hz, 3H). $^{13}$C NMR (126 MHz, CDCl$_3$) δ 172.17, 170.29, 163.04, 160.25, 152.05, 145.67, 144.00, 142.33, 136.30, 129.96, 128.71, 128.56, 127.34, 126.83, 126.04, 124.28, 115.75, 109.54, 89.55, 82.31, 74.15, 56.18, 48.24, 20.88, 18.08, 14.69. |
| 200 | | HRMS-ESI (m/z) ([M + H]$^+$) calcd for C$_{27}$H$_{27}$Cl$_2$N$_2$O$_7$, 561.1190; found, 561.1207 | $^1$H NMR (500 MHz, CDCl$_3$) δ 8.43 (s, 1H), 8.28 (d, J = 5.5 Hz, 1H), 7.40-7.27 (m, 6H), 6.98 (d, J = 5.5 Hz, 1H), 6.92 (dd, J = 8.9, 2.5 Hz, 1H), 6.56 (d, J = 8.9 Hz, 1H), 5.33-5.25 (m, 1H), 5.23 (d, J = 4.5 Hz, 1H), 4.65 (p, J = 7.4 Hz, 1H), 3.91 (s, 3H), 2.38 (s, 3H), 1.40 (d, J = 6.5 Hz, 3H), 1.31 (d, J = 7.2 Hz, 3H). $^{13}$C NMR (126 MHz, CDCl$_3$) δ 172.06, 168.90, 162.48, 159.40, 152.04, 146.60, 141.34, 137.47, 136.28, 129.92, 128.70, 128.55, 127.33, 126.80, 126.01, 124.26, 115.76, 109.73, 82.25, 74.19, 56.28, 48.03, 20.75, 18.20, 14.59. |

TABLE 2-continued

Analytical Data

| *Cmpd. No. | IR (cm$^{-1}$) | MASS | NMR ($^{1}$H, $^{13}$C or $^{19}$F) |
|---|---|---|---|
| 201 | | HRMS-ESI (m/z) ([M + H]$^{+}$) calcd for C$_{28}$H$_{30}$ClN$_{2}$O$_{8}$, 557.1685; found, 557.1702 | $^{1}$H NMR (500 MHz, CDCl$_{3}$) δ 8.28-8.21 (m, 2H), 7.39-7.25 (m, 5H), 7.12-7.07 (m, 2H), 6.93 (d, J = 5.4 Hz, 1H), 6.77-6.71 (m, 2H), 5.72 (app q, J = 6.5 Hz, 2H), 5.27 (qd, J = 6.5, 4.8 Hz, 1H), 5.16 (d, J = 4.9 Hz, 1H), 4.66 (p, J = 7.3 Hz, 1H), 3.91 (s, 3H), 2.06 (s, 3H), 1.37 (d, J = 6.4 Hz, 3H), 1.29 (d, J = 7.2 Hz, 3H). $^{13}$C NMR (126 MHz, CDCl$_{3}$) δ 172.17, 170.29, 163.00, 160.27, 156.41, 145.66, 144.03, 142.33, 137.00, 129.23, 128.62, 128.33, 126.88, 126.02, 117.21, 109.56, 89.56, 81.58, 74.11, 56.18, 48.20, 20.88, 18.13, 14.81. |
| 202 | (Thin film) 3379, 2986, 2940, 1742, 1675, 1593, 1578, 1504, 1201, 1002 | HRMS-ESI (m/z) ([M + H]$^{+}$) calcd for C$_{28}$H$_{30}$ClN$_{2}$O$_{8}$, 557.1685; found, 557.1688 | $^{1}$H NMR (500 MHz, CDCl$_{3}$) δ 8.30-8.22 (m, 2H), 7.41-7.26 (m, 5H), 7.11-7.03 (m, 1H), 6.93 (d, J = 5.4 Hz, 1H), 6.89-6.83 (m, 2H), 6.72-6.66 (m, 1H), 5.76-5.68 (m, 2H), 5.32-5.22 (m, 1H), 5.19 (d, J = 4.9 Hz, 1H), 4.66 (p, J = 7.4 Hz, 1H), 3.90 (s, 3H), 2.06 (s, 3H), 1.37 (d, J = 6.4 Hz, 3H), 1.28 (d, J = 7.2 Hz, 3H). $^{13}$C NMR (126 MHz, CDCl$_{3}$) δ 172.18, 170.28, 162.98, 160.26, 158.52, 145.68, 144.02, 142.35, 136.86, 134.68, 130.13, 128.64, 128.37, 126.88, 121.41, 116.58, 114.03, 109.57, 89.56, 81.44, 74.08, 56.17, 48.16, 20.88, 18.16, 14.89. |
| 203 | (Thin film) 3380, 2985, 2940, 1769, 1737, 1676, 1592, 1507, 1197, 1174 | HRMS-ESI (m/z) ([M + H]$^{+}$) calcd for C$_{27}$H$_{28}$ClN$_{2}$O$_{7}$, 527.1580; found, 527.1590 | $^{1}$H NMR (500 MHz, CDCl$_{3}$) δ 8.45 (br s, 1H), 8.29 (d, J = 5.4 Hz, 1H), 7.40-7.26 (m, 5H), 7.10-7.03 (m, 1H), 6.98 (d, J = 5.5 Hz, 1H), 6.88-6.82 (m, 2H), 6.72-6.66 (m, 1H), 5.30-5.22 (m, 1H), 5.18 (d, J = 4.9 Hz, 1H), 4.65 (p, J = 7.4 Hz, 1H), 3.90 (s, 3H), 2.39 (s, 3H), 1.36 (d, J = 6.4 Hz, 3H), 1.27 (d, J = 7.2 Hz, 3H). $^{13}$C NMR (126 MHz, CDCl$_{3}$) δ 172.06, 168.90, 162.41, 159.42, 158.51, 146.63, 141.40, 137.48, 136.83, 134.68, 130.11, 128.64, 128.37, 126.88, 121.39, 116.58, 114.04, 109.76, 81.41, 74.10, 56.27, 47.93, 20.76, 18.31, 14.87. |
| 204 | | HRMS-ESI (m/z) ([M + H]$^{+}$) calcd for C$_{28}$H$_{30}$ClN$_{2}$O$_{8}$, 557.1685; found, 557.1691 | $^{1}$H NMR (500 MHz, CDCl$_{3}$) δ 8.30-8.22 (m, 2H), 7.44-7.38 (m, 2H), 7.37-7.26 (m, 4H), 6.99 (ddd, J = 8.2, 7.4, 1.7 Hz, 1H), 6.93 (d, J = 5.4 Hz, 1H), 6.81 (td, J = 7.7, 1.5 Hz, 1H), 6.67 (dd, J = 8.4, 1.4 Hz, 1H), 5.76-5.69 (m, 2H), 5.37-5.26 (m, 2H), 4.67 (p, J = 7.3 Hz, 1H), 3.90 (s, 3H), 2.06 (s, 3H), 1.44 (d, J = 6.4 Hz, 3H), 1.29 (d, J = 7.2 Hz, 3H). $^{13}$C NMR (126 MHz, CDCl$_{3}$) δ 172.24, 170.28, 162.97, 160.25, 153.29, 145.68, 144.00, 142.42, 136.85, 130.30, 128.60, 128.38, 127.42, 126.92, 123.50, 121.72, 115.11, 109.53, 89.56, 81.98, 74.35, 56.17, 48.15, 20.88, 18.14, 14.93. |
| 205 | (Thin film) 3379, 2985, 2940, 1769, 1739, 1674, 1589, 1507, 1481, 1195, | HRMS-ESI (m/z) ([M + H]$^{+}$) calcd for C$_{27}$H$_{28}$ClN$_{2}$O$_{7}$, 527.1580; found, 527.1585 | $^{1}$H NMR (500 MHz, CDCl$_{3}$) δ 8.46 (br s, 1H), 8.29 (d, J = 5.4 Hz, 1H), 7.44-7.38 (m, 2H), 7.37-7.24 (m, 4H), 7.02-6.95 (m, 2H), 6.81 (td, J = 7.7, 1.4 Hz, 1H), 6.66 (dd, J = 8.3, 1.5 Hz, 1H), 5.36-5.25 (m, 2H), |

TABLE 2-continued

Analytical Data

| *Cmpd. No. | IR (cm$^{-1}$) | MASS | NMR ($^1$H, $^{13}$C or $^{19}$F) |
|---|---|---|---|
| | 1174, 1059, 729 | | 4.66 (p, J = 7.4 Hz, 1H), 3.90 (s, 3H), 2.38 (s, 3H), 1.43 (d, J = 6.4 Hz, 3H), 1.27 (d, J = 7.2 Hz, 3H). $^{13}$C NMR (126 MHz, CDCl$_3$) δ 172.13, 168.91, 162.39, 159.41, 153.29, 146.63, 141.46, 137.47, 136.82, 130.29, 128.59, 128.38, 127.41, 126.91, 123.50, 121.72, 115.11, 109.72, 81.96, 74.38, 56.27, 47.93, 20.76, 18.30, 14.90. |
| 206 | | HRMS-ESI (m/z) ([M + H]$^+$) calcd for C$_{28}$H$_{29}$ClFN$_2$O$_8$, 575.1591; found, 575.1597 | $^1$H NMR (500 MHz, CDCl$_3$) δ 8.29-8.22 (m, 2H), 7.38-7.27 (m, 5H), 6.94 (d, J = 5.4 Hz, 1H), 6.67-6.59 (m, 2H), 6.43 (dt, J = 10.5, 2.3 Hz, 1H), 5.72 (app q, J = 6.4 Hz, 2H), 5.30-5.22 (m, 1H), 5.17 (d, J = 4.8 Hz, 1H), 4.66 (p, J = 7.3 Hz, 1H), 3.91 (s, 3H), 2.07 (s, 3H), 1.36 (d, J = 6.4 Hz, 3H), 1.30 (d, J = 7.2 Hz, 3H). $^{13}$C NMR (126 MHz, CDCl$_3$) δ 172.14, 170.30, 163.09 (d, J = 248.2 Hz), 163.02, 160.28, 159.25 (d, J = 12.3 Hz), 145.67, 144.04, 142.31, 136.23, 135.22 (d, J = 13.4 Hz), 128.77, 128.60, 126.79, 112.53 (d, J = 3.3 Hz), 109.59, 109.18 (d, J = 25.2 Hz), 102.22 (d, J = 25.0 Hz), 89.54, 81.75, 73.84, 56.18, 48.18, 20.88, 18.13, 14.79. $^{19}$F NMR (471 MHz, CDCl$_3$) δ-109.91 (dd, J = 10.3, 8.4 Hz). |
| 207 | | HRMS-ESI (m/z) ([M + H]$^+$) calcd for C$_{27}$H$_{27}$ClFN$_2$O$_7$, 545.1485; found, 545.1485 | $^1$H NMR (500 MHz, CDCl$_3$) δ 8.44 (br s, 1H), 8.29 (d, J = 5.4 Hz, 1H), 7.37-7.27 (m, 5H), 6.99 (d, J = 5.5 Hz, 1H), 6.67-6.58 (m, 2H), 6.42 (dt, J = 10.6, 2.3 Hz, 1H), 5.25 (qd, J = 6.4, 4.5 Hz, 1H), 5.15 (d, J = 4.7 Hz, 1H), 4.64 (p, J = 7.4 Hz, 1H), 3.90 (s, 3H), 2.39 (s, 3H), 1.34 (d, J = 6.4 Hz, 3H), 1.30 (d, J = 7.2 Hz, 3H). $^{13}$C NMR (126 MHz, CDCl$_3$) δ 172.02, 168.92, 163.08 (d, J = 248.5 Hz), 162.47, 159.43, 159.23 (d, J = 12.3 Hz), 146.60, 141.33, 137.50, 136.19, 135.19 (d, J = 13.5 Hz), 128.76, 128.58, 126.79, 112.51 (d, J = 3.2 Hz), 109.79, 109.14 (d, J = 25.1 Hz), 102.20 (d, J = 25.1 Hz), 81.68, 73.86, 56.27, 48.01, 20.76, 18.23, 14.70. $^{19}$F NMR (471 MHz, CDCl$_3$) δ-109.96 (dd, J = 10.3, 8.5 Hz). |
| 208 | | HRMS-ESI (m/z) ([M + H]$^+$) calcd for C$_{29}$H$_{31}$ClFN$_2$O$_8$, 589.1747; found, 589.1752 | $^1$H NMR (500 MHz, CDCl$_3$) δ 8.31 (d, J = 8.3 Hz, 1H), 8.25 (d, J = 5.4 Hz, 1H), 7.38-7.28 (m, 5H), 6.94 (d, J = 5.4 Hz, 1H), 6.66-6.58 (m, 2H), 6.42 (dt, J = 10.5, 2.2 Hz, 1H), 5.76-5.68 (m, 2H), 5.26 (td, J = 6.4, 4.7 Hz, 1H), 5.17 (d, J = 4.7 Hz, 1H), 4.66 (ddd, J = 8.3, 6.6, 5.2 Hz, 1H), 3.91 (s, 3H), 2.06 (s, 3H), 1.88-1.77 (m, 1H), 1.71-1.62 (m, 1H), 1.35 (d, J = 6.4 Hz, 3H), 0.79 (t, J = 7.5 Hz, 3H). $^{13}$C NMR (126 MHz, CDCl$_3$) δ 171.51, 170.29, 163.08 (d, J = 248.3 Hz), 163.18, 160.31, 159.23 (d, J = 12.3 Hz), 145.68, 144.06, 142.33, 136.20, 135.22 (d, J = 13.4 Hz), 128.79, 128.60, 126.78, 112.51 (d, J = 3.2 Hz), 109.58, 109.16 (d, J = 25.2 Hz), 102.19 (d, J = 25.0 Hz), 89.59, 81.71, 73.89, 56.18, 53.34, |

TABLE 2-continued

Analytical Data

| *Cmpd. No. | IR (cm$^{-1}$) | MASS | NMR ($^1$H, $^{13}$C or $^{19}$F) |
|---|---|---|---|
| 209 | | HRMS-ESI (m/z) ([M + H]$^+$) calcd for C$_{28}$H$_{29}$ClFN$_2$O$_7$, 559.1642; found, 559.1646 | 25.45, 20.88, 14.77, 9.34. $^{19}$F NMR (471 MHz, CDCl$_3$) δ-109.92 (dd, J = 10.4, 8.3 Hz). $^1$H NMR (500 MHz, CDCl$_3$) δ 8.50-8.45 (m, 1H), 8.30 (d, J = 5.4 Hz, 1H), 7.37-7.27 (m, 5H), 6.99 (d, J = 5.5 Hz, 1H), 6.65-6.58 (m, 2H), 6.41 (dt, J = 10.6, 2.3 Hz, 1H), 5.25 (qd, J = 6.3, 4.4 Hz, 1H), 5.16 (d, J = 4.6 Hz, 1H), 4.67-4.59 (m, 1H), 3.90 (s, 3H), 2.39 (s, 3H), 1.87-1.77 (m, 1H), 1.71-1.61 (m, 1H), 1.33 (d, J = 6.4 Hz, 3H), 0.78 (t, J = 7.4 Hz, 3H). $^{13}$C NMR (126 MHz, CDCl$_3$) δ 171.38, 168.91, 163.07 (d, J = 248.1 Hz), 162.63, 159.43, 159.21 (d, J = 12.3 Hz), 146.62, 141.38, 137.49, 136.16, 135.18 (d, J = 13.5 Hz), 128.77, 128.58, 126.77, 112.49 (d, J = 3.2 Hz), 109.77, 109.12 (d, J = 25.3 Hz), 102.16 (d, J = 25.1 Hz), 81.65, 73.89, 56.27, 53.16, 25.51, 20.76, 14.69, 9.27. $^{19}$F NMR (471 MHz, CDCl$_3$) δ-109.96 (dd, J = 10.3, 8.3 Hz). |
| 210 | | HRMS-ESI (m/z) ([M + Na]$^+$) calcd for C$_{25}$H$_{26}$N$_2$O$_7$SNa, 521.1359; found, 521.1354. | $^1$H NMR (400 MHz, CDCl$_3$) δ 8.54 (d, J = 8.1 Hz, 1H), 8.32 (d, J = 5.4 Hz, 1H), 7.30-7.23 (m, 1H), 7.24-7.16 (m, 2H), 7.06 (dd, J = 3.7, 1.2 Hz, 1H), 7.00 (d, J = 5.5 Hz, 1H), 6.95 (dd, J = 5.0, 3.5 Hz, 1H), 6.94-6.86 (m, 3H), 5.50-5.34 (m, 2H), 4.73 (dq, J = 8.2, 7.1 Hz, 1H), 3.91 (s, 3H), 2.40 (s, 3H), 1.42 (d, J = 7.1 Hz, 3H), 1.25 (d, J = 6.2 Hz, 3H). $^{13}$C NMR (101 MHz, CDCl$_3$) δ 172.20, 168.92, 162.40, 159.44, 157.67, 146.65, 141.54, 140.20, 137.51, 129.39, 126.74, 126.26, 125.85, 121.54, 115.99, 109.74, 78.23, 73.49, 56.28, 48.03, 20.76, 18.70, 16.04. |
| 211 | (Thin film) 3380, 2938, 1770, 1509 | HRMS-ESI (m/z) ([M + H]$^+$) calcd for C$_{26}$H$_{28}$N$_3$O$_7$, 494.1936; found, 494.1931 | $^1$H NMR (400 MHz, CDCl$_3$) δ 8.66 (d, J = 2.2 Hz, 1H), 8.54 (dd, J = 4.8, 1.7 Hz, 1H), 8.44 (d, J = 7.9 Hz, 1H), 8.30 (d, J = 5.5 Hz, 1H), 7.74 (dt, J = 7.9, 2.0 Hz, 1H), 7.24 (dd, J = 4.9, 0.8 Hz, 1H), 7.22-7.13 (m, 2H), 6.99 (d, J = 5.5 Hz, 1H), 6.91 (tt, J = 7.2, 1.1 Hz, 1H), 6.82 (dt, J = 7.8, 1.1 Hz, 2H), 5.35-5.26 (m, 1H), 5.23 (d, J = 5.4 Hz, 1H), 4.72-4.61 (m, 1H), 3.91 (s, 3H), 2.39 (s, 3H), 1.40 (d, J = 6.4 Hz, 3H), 1.27 (d, J = 7.2 Hz, 3H). $^{13}$C NMR (101 MHz, CDCl$_3$) δ 171.99, 168.91, 162.41, 159.46, 157.31, 149.74, 148.94, 146.65, 141.39, 134.73, 133.23, 129.53, 123.58, 121.71, 116.04, 109.79, 79.29, 77.22, 73.70, 56.29, 47.86, 20.75, 18.29, 15.48. |
| 212 | (Thin film) 3376, 2928, 1770, 1676 | HRMS-ESI (m/z) ([M + H]$^+$) calcd for C$_{24}$H$_{26}$N$_3$O$_7$S, 500.1483; found, 500.1478 | $^1$H NMR (500 MHz, CDCl$_3$) δ 8.52 (s, 1H), 8.36-8.29 (m, 1H), 7.84-7.74 (m, 1H), 7.38-7.31 (m, 1H), 7.26-7.18 (m, 2H), 7.05-6.91 (m, 4H), 5.67-5.56 (m, 1H), 5.58-5.47 (m, 1H), 4.78-4.67 (m, 1H), 3.91 (s, 3H), 1.44-1.34 (m, 6H). |
| 213 | (Thin film) 3378, 2986, 1747, 1674 | HRMS-ESI (m/z) ([M + H]$^+$) calcd for C$_{25}$H$_{28}$N$_3$O$_8$S, 530.1591; found, 530.1585 | $^1$H NMR (500 MHz, CDCl$_3$) δ 8.40-8.24 (m, 2H), 7.80-7.77 (m, 1H), 7.39-7.31 (m, 1H), 7.25-7.18 (m, 2H), 7.00-6.87 (m, 4H), 5.73 (d, J = 1.9 Hz, 2H), 5.66-5.46 (m, 2H), |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 4.79-4.65 (m, 1H), 3.91 (s, 3H), 2.07 (d, J = 1.8 Hz, 3H), 1.45-1.31 (m, 6H). $^{13}$C NMR (126 MHz, CDCl$_3$) δ 207.06, 170.35, 168.21, 163.00, 160.27, 157.52, 145.71, 142.76, 142.45, 129.59, 129.58, 122.13, 122.00, 120.25, 115.96, 115.60, 109.57, 89.54, 79.70, 72.94, 56.19, 53.77, 48.19, 20.88, 16.06. |
| 214 | | HRMS-ESI (m/z) ([M + H]$^+$) calcd for C$_{27}$H$_{27}$Cl$_2$N$_2$O$_7$, 561.1195; found, 561.1179 | $^1$H NMR (400 MHz, CDCl$_3$) δ 8.53 (d, J = 5.5 Hz, 1H), 8.29 (d, J = 5.4 Hz, 1H), 7.43-7.23 (m, 6H), 7.05-6.87 (m, 2H), 6.65 (d, J = 8.9 Hz, 1H), 5.50-5.36 (m, 1H), 5.17 (d, J = 6.6 Hz, 1H), 4.79-4.65 (m, 1H), 3.89 (s, 3H), 2.39 (s, 3H), 1.41 (d, J = 7.2 Hz, 3H), 1.21 (d, J = 6.5 Hz, 3H). $^{13}$C NMR (101 MHz, CDCl$_3$) δ 171.96, 168.90, 162.39, 159.45, 151.89, 146.64, 141.45, 137.51, 135.96, 130.00, 128.82, 128.75, 127.28, 127.21, 125.92, 124.14, 115.46, 109.80, 82.63, 73.24, 56.29, 48.04, 20.76, 18.53, 16.07. |
| 215 | | HRMS-ESI (m/z) ([M + H]$^+$) calcd for C$_{29}$H$_{31}$Cl$_2$N$_2$O$_7$, 589.1508; found, 589.1495 | $^1$H NMR (400 MHz, CDCl$_3$) δ 8.47 (d, J = 7.9 Hz, 1H), 8.29 (d, J = 5.4 Hz, 1H), 7.45-7.27 (m, 6H), 7.05-6.91 (m, H), 6.65 (d, J = 8.9 Hz, 1H), 5.54-5.35 (m, 1H), 5.17 (d, J = 6.5 Hz, 1H), 4.81-4.62 (m, 1H), 3.88 (s, 3H), 3.03-2.87 (m, 1H), 1.40 (d, J = 7.2 Hz, 3H), 1.36 (d, J = 7.0 Hz, 6H), 1.21 (d, J = 6.6 Hz, 3H). $^{13}$C NMR (101 MHz, CDCl$_3$) δ 174.71, 172.05, 162.37, 159.43, 151.90, 146.54, 141.84, 137.68, 135.96, 130.01, 128.79, 128.73, 127.28, 127.22, 125.92, 124.16, 115.46, 109.63, 82.58, 73.18, 56.30, 48.03, 33.96, 18.83, 18.57, 16.04. |
| 216 | | HRMS-ESI (m/z) ([M + H]$^+$) calcd for C$_{28}$H$_{29}$Cl$_2$N$_2$O$_8$, 591.1301; found, 591.1289 | $^1$H NMR (400 MHz, CDCl$_3$) δ 8.36 (d, J = 7.9 Hz, 1H), 8.24 (d, J = 5.4 Hz, 1H), 7.40-7.27 (m, 6H), 7.02-6.90 (m, 2H), 6.66 (d, J = 8.9 Hz, 1H), 5.75 (s, 2H), 5.51-5.39 (m, 1H), 5.18 (d, J = 6.8 Hz, 1H), 4.84-4.63 (m, 1H), 3.91 (s, 3H), 2.07 (s, 3H), 1.44 (d, J = 7.2 Hz, 3H), 1.23 (d, J = 6.5 Hz, 3H). $^{13}$C NMR (101 MHz, CDCl$_3$) δ 172.08, 170.26, 162.94, 160.28, 151.90, 145.67, 144.00, 142.38, 135.99, 129.99, 128.84, 128.77, 127.28, 127.20, 125.91, 124.11, 115.43, 109.59, 89.53, 82.75, 73.26, 56.19, 48.25, 20.87, 18.41, 16.13. |
| 217 | | HRMS-ESI (m/z) ([M + H]$^+$) calcd for C$_{27}$H$_{29}$N$_2$O$_7$, 493.1975; found, 493.1969 | $^1$H NMR (400 MHz, CDCl$_3$) δ 8.53 (d, J = 7.0 Hz, 1H), 8.30 (d, J = 5.4 Hz, 1H), 7.43-7.35 (m, 2H), 7.34-7.23 (m, 3H), 7.21-7.08 (m, 2H), 6.98 (d, J = 5.5 Hz, 1H), 6.91-6.74 (m, 3H), 5.50-5.32 (m, 1H), 5.12 (d, J = 6.4 Hz, 1H), 4.79-4.62 (m, 1H), 3.88 (s, 3H), 2.39 (s, 3H), 1.37 (d, J = 7.1 Hz, 3H), 1.21 (d, J = 6.5 Hz, 3H). $^{13}$C NMR (101 MHz, CDCl$_3$) δ 172.24, 168.92, 162.40, 159.45, 157.85, 146.69, 141.54, 137.50, 137.36, 129.35, 128.60, 128.36, |

TABLE 2-continued

Analytical Data

| *Cmpd. No. | IR (cm$^{-1}$) | MASS | NMR ($^1$H, $^{13}$C or $^{19}$F) |
|---|---|---|---|
| 218 | | HRMS-ESI (m/z) ([M + H]$^+$) calcd for C$_{29}$H$_{33}$N$_2$O$_7$, 521.2288; found, 521.2285 | 127.18, 121.05, 115.79, 109.78, 81.81, 73.75, 56.29, 48.03, 20.77, 18.71, 16.27. $^1$H NMR (400 MHz, CDCl$_3$) 8.47 (d, J = 6.6 Hz, 1H), 8.29 (d, J = 5.4 Hz, 1H), 7.41-7.35 (m, 2H), 7.35-7.21 (m, 3H), 7.19-7.11 (m, 2H), 6.96 (d, J = 5.5 Hz, 1H), 6.91-6.72 (m, 3H), 5.49-5.28 (m, 1H), 5.12 (d, J = 6.4 Hz, 1H), 4.80-4.60 (m, 1H), 3.86 (s, 3H), 3.09-2.82 (m, 1H), 1.41-1.32 (m, 9H), 1.21 (d, J = 6.5 Hz, 3H). $^{13}$C NMR (101 MHz, CDCl$_3$) δ 174.72, 172.32, 162.39, 159.42, 157.86, 146.59, 141.93, 137.66, 137.37, 129.34, 128.59, 128.34, 127.18, 121.04, 115.79, 109.63, 81.78, 73.70, 56.29, 48.02, 33.96, 18.83, 18.74, 16.25. |
| 219 | | HRMS-ESI (m/z) ([M + H]$^+$) calcd for C$_{28}$H$_{31}$N$_2$O$_8$, 523.2080; found, 523.2081 | $^1$H NMR (400 MHz, CDCl$_3$) δ 8.35 (d, J = 7.9 Hz, 1H), 8.26 (d, J = 5.4 Hz, 1H), 7.45-7.36 (m, 2H), 7.36-7.22 (m, 3H), 7.21-7.09 (m, 2H), 6.94 (d, J = 5.4 Hz, 1H), 6.91-6.75 (m, 3H), 5.74 (s, 2H), 5.48-5.34 (m, 1H), 5.13 (d, J = 6.5 Hz, 1H), 4.82-4.64 (m, 1H), 3.89 (s, 3H), 2.06 (s, 3H), 1.39 (d, J = 7.2 Hz, 3H), 1.23 (d, J = 6.5 Hz, 3H). $^{13}$C NMR (101 MHz, CDCl$_3$) δ 172.36, 170.28, 162.97, 160.27, 157.86, 145.72, 143.98, 142.50, 137.38, 129.34, 128.61, 128.36, 127.16, 121.04, 115.78, 109.59, 89.54, 81.87, 73.76, 56.19, 48.25, 20.88, 18.55, 16.32. |
| 220 | | HRMS-ESI (m/z) ([M + H]$^+$) calcd for C$_{32}$H$_{37}$N$_2$O$_8$, 577.2544; found, 577.2557. | $^1$H NMR (400 MHz, CDCl$_3$) δ 8.26 (t, J = 7.2 Hz, 2H), 7.60-7.56 (m, 3H), 7.52-7.49 (m, 1H), 7.46-7.31 (m, 6H), 6.92 (d, J = 5.4 Hz, 1H), 5.72 (s, 2H), 5.18 (p, J = 6.4 Hz, 1H), 4.61 (p, J = 7.2 Hz, 1H), 4.42 (d, J = 6.4 Hz, 1H), 3.89 (s, 3H), 3.24 (d, J = 6.7 Hz, 2H), 2.05 (s, 3H), 1.38 (d, J = 6.3 Hz, 3H), 1.16 (d, J = 7.2 Hz, 3H), 1.08-1.00 (m, 1H), 0.55-0.43 (m, 2H), 0.19-0.08 (m, 2H). $^{13}$C NMR (101 MHz, CDCl$_3$) δ 172.11, 170.26, 162.89, 160.25, 145.68, 143.97, 142.50, 141.19, 140.88, 139.47, 128.79, 128.72, 127.38, 127.11, 126.76, 126.50, 126.32, 109.51, 89.57, 83.15, 74.28, 73.90, 56.16, 48.09, 20.86, 18.09, 16.03, 10.63, 3.22, 2.75. |
| 221 | | HRMS-ESI (m/z) ([M + H]$^+$) calcd for C$_{34}$H$_{34}$FN$_2$O$_8$, 617.2294; found, 617.2312. | $^1$H NMR (400 MHz, CDCl$_3$) δ 8.28 (d, J = 7.8 Hz, 1H), 8.24 (d, J = 5.4 Hz, 1H), 7.60 (s, 1H), 7.57-7.51 (m, 3H), 7.46-7.40 (m, 3H), 7.39-7.34 (m, 2H), 7.11 (dd, J = 15.1, 8.2 Hz, 1H), 6.93 (d, J = 5.4 Hz, 1H), 6.66-6.56 (m, 3H), 5.74-5.69 (m, 2H), 5.32 (dd, J = 6.3, 5.0 Hz, 1H), 5.27 (d, J = 4.9 Hz, 1H), 4.67 (p, J = 7.2 Hz, 1H), 3.90 (s, 3H), 2.06 (s, 3H), 1.42 (d, J = 6.4 Hz, 3H), 1.26 (d, J = 7.1 Hz, 3H). $^{13}$C NMR (101 MHz, CDCl$_3$) δ 172.27, 170.27, 163.00, 160.27, 145.67, 144.03, 142.36, 141.66, 140.58, 137.63, 130.21, 130.11, 129.12, 128.83, 127.55, 127.14, 125.76, 125.51, 111.56, 109.56, |

TABLE 2-continued

Analytical Data

| *Cmpd. No. | IR (cm$^{-1}$) | MASS | NMR ($^1$H, $^{13}$C or $^{19}$F) |
|---|---|---|---|
| 222 | | HRMS-ESI (m/z) ([M + H]$^+$) calcd for C$_{31}$H$_{35}$N$_2$O$_7$, 547.2439; found, 547.2447. | 108.25, 108.04, 103.94, 103.69, 56.17, 48.16, 20.87, 18.11, 14.86. $^{19}$F NMR (376 MHz, CDCl$_3$) δ -111.52. $^1$H NMR (400 MHz, CDCl$_3$) δ 8.45 (s, 1H), 8.30 (d, J = 5.4 Hz, 1H), 7.60-7.55 (m, 3H), 7.52-7.48 (m, 1H), 7.47-7.30 (m, 5H), 6.98 (d, J = 5.5 Hz, 1H), 5.17 (p, J = 6.4 Hz, 1H), 4.64-4.55 (m, 1H), 4.41 (d, J = 6.3 Hz, 1H), 3.89 (s, 3H), 3.24 (d, J = 6.8 Hz, 2H), 2.38 (s, 3H), 1.37 (d, J = 6.3 Hz, 3H), 1.14 (d, J = 7.2 Hz, 3H), 1.03 (tdd, J = 8.0, 7.4, 1.9 Hz, 1H), 0.55-0.43 (m, 2H), 0.19-0.07 (m, 2H). $^{13}$C NMR (101 MHz, CDCl$_3$) δ 172.00, 168.89, 162.30, 159.41, 146.63, 141.53, 141.19, 140.88, 139.45, 128.79, 128.72, 127.37, 127.12, 126.75, 126.46, 126.31, 109.69, 83.11, 74.34, 73.91, 56.26, 47.88, 20.75, 18.27, 15.96, 10.63, 3.21, 2.75. |
| 223 | | HRMS-ESI (m/z) ([M + H]$^+$) calcd for C$_{33}$H$_{32}$FN$_2$O$_7$, 587.2188; found, 587.2196. | $^1$H NMR (400 MHz, CDCl$_3$) δ 8.45 (s, 1H), 8.28 (d, J = 5.4 Hz, 1H), 7.59 (s, 1H), 7.57-7.50 (m, 3H), 7.46-7.34 (m, 5H), 7.11 (dd, J = 15.2, 8.2 Hz, 1H), 6.98 (d, J = 5.5 Hz, 1H), 6.66-6.55 (m, 3H), 5.32 (dd, J = 8.8, 3.9 Hz, 1H), 5.26 (d, J = 4.8 Hz, 1H), 4.65 (p, J = 7.3 Hz, 1H), 3.90 (s, 3H), 2.38 (s, 3H), 1.40 (d, J = 6.3 Hz, 3H), 1.25 (d, J = 7.2 Hz, 3H). $^{13}$C NMR (101 MHz, CDCl$_3$) δ 172.16, 168.90, 162.44, 159.43, 146.62, 141.65, 141.40, 140.58, 137.61, 130.19, 130.09, 129.12, 128.82, 127.54, 127.18, 127.15, 125.75, 125.51, 111.60, 111.57, 109.75, 108.23, 104.03, 103.93, 103.69, 81.59, 74.21, 56.27, 47.95, 20.75, 18.25, 14.83. |
| 224 | | HRMS-ESI (m/z) ([M + H]$^+$) calcd for C$_{25}$H$_{33}$N$_2$O$_7$, 473.2288; found, 473.2290 | $^1$H NMR (400 MHz, CDCl$_3$) δ 8.55 (d, J = 5.9 Hz, 1H), 8.33 (d, J = 5.4 Hz, 1H), 7.38-7.22 (m, 5H), 7.00 (d, J = 5.5 Hz, 1H), 5.25-5.11 (m, 1H), 4.82-4.63 (m, 1H), 4.24 (d, J = 6.7 Hz, 1H), 3.89 (s, 3H), 3.14-2.97 (m, 2H), 2.40 (s, 3H), 1.46 (d, J = 7.2 Hz, 3H), 1.07 (d, J = 6.5 Hz, 3H), 0.90-0.81 (m, 6H). $^{13}$C NMR (101 MHz, CDCl$_3$) δ 172.17, 168.89, 162.34, 159.44, 146.67, 146.65, 141.61, 138.52, 137.48, 128.27, 128.04, 127.66, 109.75, 83.96, 76.05, 74.13, 56.28, 48.06, 28.62, 20.76, 19.41, 19.36, 18.75, 16.27. |
| 225 | | HRMS-ESI (m/z) ([M + H]$^+$) calcd for C$_{25}$H$_{33}$N$_2$O$_7$, 473.2288; found, 473.2288 | $^1$H NMR (400 MHz, CDCl$_3$) δ 8.46 (d, J = 7.9 Hz, 1H), 8.31 (d, J = 5.4 Hz, 1H), 7.35-7.18 (m, 5H), 6.99 (d, J = 5.4 Hz, 1H), 5.18-5.01 (m, 1H), 4.70-4.52 (m, 1H), 4.35-4.14 (m, 1H), 3.88 (d, J = 1.6 Hz, 3H), 3.19-3.10 (m, 1H), 3.09-3.00 (m, 1H), 2.38 (d, J = 1.4 Hz, 3H), 1.30 (d, J = 6.5, 3H), 1.19 (d, J = 7.1 Hz, 3H), 0.93-0.80 (m, 6H). $^{13}$C NMR (101 MHz, CDCl$_3$) δ 171.96, 168.88, 162.31, 159.43, 146.65, 141.53, 138.89, 137.46, 128.18, 127.89, 127.53, 109.75, |

TABLE 2-continued

Analytical Data

| *Cmpd. No. | IR (cm⁻¹) | MASS | NMR (¹H, ¹³C or ¹⁹F) |
|---|---|---|---|
| 226 | | HRMS-ESI (m/z) ([M + H]⁺) calcd for $C_{26}H_{35}N_2O_8$, 503.2393; found, 503.2401 | 83.70, 76.28, 74.48, 56.27, 47.89, 28.64, 20.74, 19.36, 19.34, 18.32, 15.79.<br>¹H NMR (400 MHz, CDCl₃) δ 8.37 (d, J = 7.8 Hz, 1H), 8.28 (d, J = 5.4 Hz, 1H), 7.43-7.25 (m, 5H), 6.96 (d, J = 5.4 Hz, 1H), 5.75 (s, 2H), 5.19 (p, J = 6.5 Hz, 1H), 4.74 (p, J = 7.2 Hz, 1H), 4.25 (d, J = 6.7 Hz, 1H), 3.91 (s, 3H), 3.17-2.97 (m, 2H), 2.07 (s, 3H), 1.48 (d, J = 7.1 Hz, 3H), 1.09 (d, J = 6.5 Hz, 3H), 0.92-0.81 (m, 6H).<br>¹³C NMR (101 MHz, CDCl₃) δ 172.29, 170.26, 162.92, 160.26, 145.72, 143.94, 142.61, 138.53, 128.27, 128.05, 127.65, 109.55, 89.54, 84.01, 76.06, 74.13, 56.18, 48.27, 28.62, 20.86, 19.40, 19.36, 18.60, 16.32. |
| 227 | (Thin film) 3381, 2963, 2876, 1676 | HRMS-ESI (m/z) ([M + H]⁺) calcd for $C_{24}H_{31}N_2O_7$, 459.2131; found, 459.2124. | ¹H NMR (400 MHz, CDCl₃) δ 8.55 (d, J = 7.7 Hz, 1H), 8.34 (d, J = 5.5 Hz, 1H), 7.41-7.27 (m, 5H), 7.00 (d, J = 5.5 Hz, 1H), 5.24-5.11 (m, 1H), 4.78-4.65 (m, 1H), 4.25 (d, J = 6.8 Hz, 1H), 3.91 (s, 3H), 3.29 (dt, J = 9.1, 6.8 Hz, 1H), 3.23 (dt, J = 9.1, 6.5 Hz, 1H), 2.40 (s, 3H), 1.59-1.49 (m, 2H), 1.46 (d, J = 7.2 Hz, 3H), 1.07 (d, J = 6.5 Hz, 3H), 0.87 (t, J = 7.3 Hz, 3H). |
| 228 | (Thin film) 3379, 2963, 2937, 1771 | HRMS-FAB (m/z) ([M + H]⁺) calcd for $C_{24}H_{31}N_2O_7$, 459.2131; found, 459.2125. | ¹H NMR (400 MHz, CDCl₃) δ 8.46 (s, 1H), 8.32 (d, J = 5.4 Hz, 1H), 7.36-7.27 (m, 5H), 6.99 (d, J = 5.5 Hz, 1H), 5.10 (p, J = 6.3 Hz, 1H), 4.60 (dq, J = 8.2, 7.2 Hz, 1H), 4.27 (d, J = 6.1 Hz, 1H), 3.90 (s, 3H), 3.33 (dt, J = 9.1, 6.6 Hz, 1H), 3.25 (dt, J = 9.1, 6.5 Hz, 1H), 2.39 (s, 3H), 1.60-1.50 (m, 2H), 1.30 (d, J = 6.3 Hz, 3H), 1.18 (d, J = 7.1 Hz, 3H), 0.89 (t, J = 7.4 Hz, 3H). |
| 229 | (Thin film) 3379, 2984, 2939, 1770 | HRMS-FAB (m/z) ([M + H]⁺) calcd for $C_{22}H_{27}N_2O_7$, 431.1818; found, 431.1818. | ¹H NMR (400 MHz, CDCl₃) δ 8.56 (d, J = 7.8 Hz, 1H), 8.33 (d, J = 5.4 Hz, 1H), 7.40-7.26 (m, 5H), 7.00 (d, J = 5.5 Hz, 1H), 5.27-5.14 (m, 1H), 4.83-4.66 (m, 1H), 4.14 (d, J = 6.9 Hz, 1H), 3.90 (s, 3H), 3.23 (s, 3H), 2.40 (s, 3H), 1.47 (d, J = 7.1 Hz, 3H), 1.08 (d, J = 6.5 Hz, 3H). |
| 230 | (Thin film) 3377, 2985, 2938, 1740 | HRMS-FAB (m/z) ([M + H]⁺) calcd for $C_{23}H_{29}N_2O_8$, 461.1924; found, 461.1922. | ¹H NMR (400 MHz, CDCl₃) δ 8.37 (d, J = 7.8 Hz, 1H), 8.28 (d, J = 5.3 Hz, 1H), 7.39-7.27 (m, 5H), 6.95 (d, J = 5.4 Hz, 1H), 5.75 (s, 2H), 5.28-5.15 (m, 1H), 4.75 (p, J = 7.2 Hz, 1H), 4.14 (d, J = 6.9 Hz, 1H), 3.91 (s, 3H), 3.24 (s, 3H), 2.07 (s, 3H), 1.49 (d, J = 7.2 Hz, 3H), 1.10 (d, J = 6.5 Hz, 3H). |
| 231 | (Thin film) 3377, 2984, 1770, 1675 | HRMS-FAB (m/z) ([M + H]⁺) calcd for $C_{22}H_{27}N_2O_7$, 431.1818; found, 431.1808. | ¹H NMR (400 MHz, CDCl₃) δ 8.46 (d, J = 7.1 Hz, 1H), 8.32 (d, J = 5.5 Hz, 1H), 7.39-7.26 (m, 5H), 6.99 (d, J = 5.5 Hz, 1H), 5.17-4.99 (m, 1H), 4.60 (dq, J = 8.1, 7.1 Hz, 1H), 4.18 (d, J = 5.9 Hz, 1H), 3.90 (s, 3H), 3.26 (s, 3H), 2.39 (s, 3H), 1.29 (d, J = 6.4 Hz, 3H), 1.20 (d, J = 7.2 Hz, 3H). |
| 232 | (Thin film) 3378, 2986, 1771, 1676 | HRMS-ESI (m/z) ([M + H]⁺) calcd for $C_{25}H_{31}N_2O_7$, 471.2131; found, 471.2123. | ¹H NMR (400 MHz, CDCl₃) δ 8.56 (d, J = 7.9 Hz, 1H), 8.33 (d, J = 5.5 Hz, 1H), 7.37-7.28 (m, 5H), 7.00 (d, J = 5.5 Hz, 1H), 5.25-5.13 (m, 1H), 4.80-4.67 (m, 1H), 4.32 (d, J = 6.8 Hz, 1H), 3.90 (s, 3H), 3.16 (dd, J = 6.8, 1.2 Hz, 2H), 2.40 (s, |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 3H), 1.48 (d, J = 7.2 Hz, 3H), 1.08 (d, J = 6.5 Hz, 3H), 1.04-0.94 (m, 1H), 0.53-0.39 (m, 2H), 0.17-0.02 (m, 2H). |
| 233 | (Thin film) 3385, 2986, 1771, 1676 | HRMS-FAB (m/z) ([M + H]$^+$) calcd for C$_{25}$H$_{31}$N$_2$O$_7$, 471.2131; found, 471.2126. | $^1$H NMR (400 MHz, CDCl$_3$) δ 8.53-8.40 (m, 1H), 8.32 (d, J = 5.5 Hz, 1H), 7.36-7.27 (m, 5H), 6.99 (d, J = 5.5 Hz, 1H), 5.20-5.05 (m, 1H), 4.71-4.48 (m, 1H), 4.33 (d, J = 6.3 Hz, 1H), 3.90 (s, 3H), 3.19 (dd, J = 6.8, 1.3 Hz, 2H), 2.39 (s, 3H), 1.33 (d, J = 6.3 Hz, 3H), 1.16 (d, J = 7.2 Hz, 3H), 1.06-0.90 (m, 1H), 0.53-0.38 (m, 2H), 0.22-0.04 (m, 2H). |
| 234 | | HRMS-ESI (m/z) ([M + H]$^+$) calcd for C$_{32}$H$_{37}$N$_2$O$_8$, 577.2544; found, 577.2553. | $^1$H NMR (400 MHz, CDCl$_3$) δ 8.26 (t, J = 7.7 Hz, 2H), 7.59-7.51 (m, 4H), 7.46-7.38 (m, 4H), 7.34 (dd, J = 8.3, 6.3 Hz, 1H), 6.92 (d, J = 5.5 Hz, 1H), 5.73 (s, 2H), 5.17 (p, J = 6.3 Hz, 1H), 4.63 (dd, J = 14.8, 7.3 Hz, 1H), 4.39 (d, J = 6.2 Hz, 1H), 3.89 (s, 3H), 3.24 (d, J = 6.8 Hz, 2H), 2.06 (s, 3H), 1.37 (d, J = 6.3 Hz, 3H), 1.21 (d, J = 7.2 Hz, 3H), 1.04 (tdd, J = 8.0, 7.4, 2.5 Hz, 1H), 0.55-0.43 (m, 2H), 0.20-0.09 (m, 2H). $^{13}$C NMR (101 MHz, CDCl$_3$) δ 172.08, 170.27, 162.89, 160.26, 145.68, 143.98, 142.53, 140.86, 140.76, 137.84, 128.75, 128.03, 127.31, 127.06, 126.95, 109.51, 89.57, 82.83, 74.25, 73.85, 56.16, 48.11, 20.87, 18.17, 16.03, 10.62, 3.21, 2.74. |
| 235 | | HRMS-ESI (m/z) ([M + H]$^+$) calcd for C$_{27}$H$_{28}$FN$_2$O$_7$, 511.1880; found, 511.1879 | $^1$H NMR (400 MHz, CDCl$_3$) δ 8.45 (d, J = 6.4 Hz, 1H), 8.29 (d, J = 5.4 Hz, 1H), 7.43-7.27 (m, 5H), 6.98 (d, J = 5.5 Hz, 1H), 6.92-6.80 (m, 2H), 6.81-6.66 (m, 2H), 5.26 (qd, J = 6.5, 5.0 Hz, 1H), 5.11 (d, J = 4.9 Hz, 1H), 4.65 (dq, J = 8.1, 7.2 Hz, 1H), 3.90 (s, 3H), 2.39 (s, 3H), 1.36 (d, J = 6.4 Hz, 3H), 1.26 (d, J = 7.2 Hz, 3H). $^{19}$F NMR (376 MHz, CDCl$_3$) δ-123.24. |
| 236 | | HRMS-ESI (m/z) ([M + H]$^+$) calcd for C$_{27}$H$_{27}$F$_2$N$_2$O$_7$, 529.1786; found, 529.1788 | $^1$H NMR (400 MHz, CDCl$_3$) δ 8.49 (d, J = 7.9 Hz, 1H), 8.31 (d, J = 5.4 Hz, 1H), 7.38-7.28 (m, 2H), 7.09-6.93 (m, 3H), 6.92-6.79 (m, 2H), 6.79-6.64 (m, 2H), 5.40-5.28 (m, 1H), 5.03 (d, J = 6.5 Hz, 1H), 4.72 (dq, J = 8.2, 7.2 Hz, 1H), 3.92 (s, 3H), 2.40 (s, 3H), 1.40 (d, J = 7.2 Hz, 3H), 1.19 (d, J = 6.5 Hz, 3H). $^{19}$F NMR (376 MHz, CDCl$_3$) δ-113.21, −123.09. |
| 237 | | HRMS-ESI (m/z) ([M + H]$^+$) calcd for C$_{28}$H$_{30}$FN$_2$O$_8$, 541.1986; found, 541.1992 | $^1$H NMR (400 MHz, CDCl$_3$) δ 8.27 (d, J = 5.1 Hz, 1H), 8.25 (d, J = 5.5 Hz, 1H), 7.45-7.25 (m, 5H), 6.93 (d, J = 5.5 Hz, 1H), 6.90-6.80 (m, 2H), 6.80-6.68 (m, 2H), 5.78-5.61 (m, 2H), 5.27 (qd, J = 6.4, 4.9 Hz, 1H), 5.12 (d, J = 4.9 Hz, 1H), 4.66 (p, J = 7.2 Hz, 1H), 3.91 (s, 3H), 2.07 (s, 3H), 1.38 (d, J = 6.4 Hz, 3H), 1.27 (d, J = 7.2 Hz, 3H). $^{19}$F NMR (376 MHz, CDCl$_3$) δ-123.22. |
| 238 | | HRMS-ESI (m/z) ([M + H]$^+$) calcd for C$_{28}$H$_{29}$F$_2$N$_2$O$_8$, 559.1892; found, 559.1889 | $^1$H NMR (400 MHz, CDCl$_3$) δ 8.32 (d, J = 7.9 Hz, 1H), 8.26 (d, J = 4.9 Hz, 1H), 7.40-7.30 (m, 2H), 7.04-6.98 (m, 2H), 6.95 (d, J = 5.1 Hz, 1H), 6.90-6.81 (m, 2H), 6.78-6.71 (m, 2H), 5.74 (s, 2H), 5.42-5.29 (m, 1H), 5.03 (d, J = 6.5 Hz, 1H), |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 4.82-4.70 (m, 1H), 3.92 (s, 3H), 2.07 (s, 3H), 1.42 (d, J = 7.2 Hz, 3H), 1.20 (d, J = 6.5 Hz, 3H). $^{19}$F NMR (376 MHz, CDCl$_3$) δ -113.16, -123.06. double check |
| 239 | | HRMS-ESI (m/z) ([M + H]$^+$) calcd for C$_{34}$H$_{35}$N$_2$O$_8$, 599.2388; found, 599.2395. | $^1$H NMR (400 MHz, CDCl$_3$) δ 8.28 (d, J = 7.8 Hz, 1H), 8.24 (d, J = 5.4 Hz, 1H), 7.57-7.52 (m, 4H), 7.49-7.39 (m, 4H), 7.34 (dd, J = 8.3, 6.3 Hz, 1H), 7.19 (dd, J = 8.6, 7.4 Hz, 2H), 6.93-6.85 (m, 4H), 5.72 (t, J = 3.6 Hz, 2H), 5.35-5.29 (m, 1H), 5.26 (d, J = 5.0 Hz, 1H), 4.69 (p, J = 7.2 Hz, 1H), 3.90 (s, 3H), 2.06 (s, 3H), 1.42 (d, J = 6.4 Hz, 3H), 1.28 (d, J = 7.2 Hz, 3H). |
| 240 | | HRMS-ESI (m/z) ([M + H]$^+$) calcd for C$_{34}$H$_{35}$N$_2$O$_8$, 599.2388; found, 599.2393. | $^1$H NMR (400 MHz, CDCl$_3$) δ 8.28 (d, J = 7.8 Hz, 1H), 8.24 (d, J = 5.4 Hz, 1H), 7.63 (s, 1H), 7.56 (dd, J = 5.1, 3.4 Hz, 2H), 7.52-7.49 (m, 1H), 7.45-7.38 (m, 4H), 7.35 (ddd, J = 7.3, 3.8, 1.2 Hz, 1H), 7.21-7.15 (m, 2H), 6.93-6.86 (m, 4H), 5.74-5.70 (m, 2H), 5.37-5.30 (m, 1H), 5.29 (d, J = 1.8 Hz, 1H), 4.67 (p, J = 7.2 Hz, 1H), 3.90 (s, 3H), 2.06 (s, 3H), 1.43 (d, J = 6.3 Hz, 3H), 1.23 (d, J = 7.2 Hz, 3H). $^{13}$C NMR (101 MHz, CDCl$_3$) δ 172.31, 170.28, 162.98, 160.27, 157.97, 145.69, 144.01, 142.43, 141.50, 140.69, 138.29, 129.39, 129.01, 128.80, 127.48, 127.14, 126.97, 125.88, 125.65, 121.26, 116.06, 109.54, 89.57, 81.39, 74.40, 56.17, 48.14, 20.87, 18.13, 15.05. |
| 241 | | ESIMS m/z 541 ([M + H]$^+$) | $^1$H NMR (400 MHz, CDCl$_3$) δ 8.26 (t, J = 6.2 Hz, 2H), 7.40-7.35 (m, 2H), 7.17 (dd, J = 8.4, 7.6 Hz, 2H), 7.01 (t, J = 8.6 Hz, 2H), 6.94 (d, J = 5.4 Hz, 1H), 6.89 (t, J = 7.3 Hz, 1H), 6.83-6.79 (m, 2H), 5.74-5.70 (m, 2H), 5.29-5.22 (m, 1H), 5.18 (d, J = 5.3 Hz, 1H), 4.66 (p, J = 7.2 Hz, 1H), 3.91 (s, 3H), 2.06 (s, 3H), 1.39 (d, J = 6.4 Hz, 3H), 1.28 (d, J = 7.2 Hz, 3H). $^{13}$C NMR (151 MHz, CDCl$_3$) δ 172.16, 170.29, 163.30, 162.97, 161.67, 160.29, 157.64, 145.70, 144.04, 142.39, 133.40, 133.38, 129.40, 128.76, 128.71, 121.37, 116.00, 115.59, 115.44, 109.59, 89.56, 80.67, 74.11, 56.19, 48.13, 20.88, 18.20, 15.23. |
| 242 | | ESIMS m/z 511 ([M + H]$^+$) | $^1$H NMR (400 MHz, CDCl$_3$) δ 8.45 (d, J = 6.7 Hz, 1H), 8.29 (d, J = 5.4 Hz, 1H), 7.40-7.33 (m, 2H), 7.20-7.14 (m, 2H), 7.03-6.97 (m, 3H), 6.89 (t, J = 7.4 Hz, 1H), 6.83-6.78 (m, 2H), 5.28-5.21 (m, 1H), 5.17 (d, J = 5.2 Hz, 1H), 4.65 (dq, J = 14.5, 7.2 Hz, 1H), 3.90 (s, 3H), 2.39 (s, 3H), 1.37 (d, J = 6.4 Hz, 3H), 1.27 (d, J = 7.2 Hz, 3H). $^{13}$C NMR (151 MHz, CDCl$_3$) δ 172.04, 168.91, 163.30, 162.40, 161.67, 159.47, 157.64, 146.66, 141.43, 137.52, 133.36, 133.34, 129.40, 128.77, 128.72, 121.37, 116.01, 115.58, 115.44, 109.81, 80.64, 74.12, 56.30, 47.90, 20.76, 15.24. |

TABLE 2-continued

Analytical Data

| *Cmpd. No. | IR (cm$^{-1}$) | MASS | NMR ($^1$H, $^{13}$C or $^{19}$F) |
|---|---|---|---|
| 243 | | HRMS-ESI (m/z) ([M + H]$^+$) calcd for C$_{28}$H$_{30}$ClN$_2$O$_7$, 541.1741; found, 541.1733 | $^1$H NMR (300 MHz, CDCl$_3$) δ 8.47 (d, J = 8.0 Hz, 1H), 8.29 (d, J = 5.4 Hz, 1H), 7.43-7.36 (m, 2H), 7.36-7.22 (m, 3H), 7.13 (dd, J = 2.2, 0.8 Hz, 1H), 6.97 (d, J = 5.5 Hz, 1H), 6.77 (ddd, J = 8.4, 2.2, 0.9 Hz, 1H), 6.55 (d, J = 8.4 Hz, 1H), 5.41-5.24 (m, 1H), 5.22 (d, J = 4.8 Hz, 1H), 4.65 (dq, J = 8.3, 7.2 Hz, 1H), 3.88 (s, 3H), 2.38 (s, 3H), 2.18 (s, 3H), 1.42 (d, J = 6.4 Hz, 3H), 1.27 (d, J = 7.2 Hz, 3H). $^{13}$C NMR (75 MHz, CDCl$_3$) δ 172.15, 168.93, 162.40, 159.41, 151.06, 146.67, 141.44, 137.46, 137.01, 131.47, 130.71, 128.55, 128.33, 127.85, 126.99, 123.08, 115.10, 109.76, 82.07, 74.36, 56.30, 47.94, 20.77, 20.23, 18.32, 15.00. |
| 244 | | HRMS-ESI (m/z) ([M + H]$^+$) calcd for C$_{29}$H$_{32}$ClN$_2$O$_8$, 571.1847; found, 571.1834 | $^1$H NMR (300 MHz, CDCl$_3$) δ 8.28 (d, J = 8.8 Hz, 1H), 8.25 (d, J = 5.4 Hz, 1H), 7.45-7.37 (m, 2H), 7.37-7.22 (m, 3H), 7.13 (dd, J = 2.1, 0.8 Hz, 1H), 6.93 (d, J = 5.4 Hz, 1H), 6.77 (ddd, J = 8.3, 2.2, 0.8 Hz, 1H), 6.56 (d, J = 8.3 Hz, 1H), 5.72 (d, J = 1.4 Hz, 2H), 5.33 (qd, J = 6.4, 4.0 Hz, 1H), 5.23 (d, J = 4.9 Hz, 1H), 4.78-4.58 (m, 1H), 3.90 (s, 3H), 2.18 (s, 3H), 2.06 (s, 3H), 1.43 (d, J = 6.4 Hz, 3H), 1.28 (d, J = 7.2 Hz, 3H). $^{13}$C NMR (75 MHz, CDCl$_3$) δ 172.24, 170.29, 162.97, 160.25, 151.05, 145.71, 143.97, 142.42, 137.03, 131.48, 130.71, 128.54, 128.32, 127.84, 127.00, 123.07, 115.09, 109.56, 89.54, 82.08, 74.32, 56.20, 48.16, 20.90, 20.23, 18.14, 15.02. |
| 245 | | HRMS-ESI (m/z) ([M + H]$^+$) calcd for C$_{29}$H$_{31}$ClFN$_2$O$_8$, 589.1753; found, 589.1746 | $^1$H NMR (300 MHz, CDCl$_3$) δ 8.32-8.24 (m, 2H), 7.48-7.34 (m, 2H), 7.13 (dd, J = 2.1, 0.8 Hz, 1H), 7.07-6.98 (m, 2H), 6.94 (d, J = 5.4 Hz, 1H), 6.79 (ddd, J = 8.4, 2.2, 0.9 Hz, 1H), 6.54 (d, J = 8.3 Hz, 1H), 5.72 (d, J = 0.9 Hz, 2H), 5.31 (qd, J = 6.4, 5.0 Hz, 1H), 5.21 (d, J = 5.0 Hz, 1H), 4.80-4.56 (m, 1H), 3.90 (s, 3H), 2.19 (s, 3H), 2.06 (s, 3H), 1.43 (d, J = 6.4 Hz, 3H), 1.30 (d, J = 7.2 Hz, 3H). $^{13}$C NMR (75 MHz, CDCl$_3$) δ 172.17, 170.29, 162.98, 162.56 (d, J = 247.0 Hz), 160.26, 150.79, 145.71, 143.98, 142.36, 132.80 (d, J = 3.2 Hz), 131.77, 130.79, 128.81 (d, J = 8.2 Hz), 127.86, 123.20, 115.53 (d, J = 21.6 Hz), 115.22, 109.59, 89.51, 81.53, 74.08, 56.18 (d, J = 3.1 Hz), 48.13, 20.87 (d, J = 2.1 Hz), 20.24 (d, J = 1.8 Hz), 18.14, 15.15. |
| 246 | | HRMS-ESI (m/z) ([M + H]$^+$) calcd for C$_{28}$H$_{31}$N$_2$O$_7$, 507.2131; found, 507.2120 | $^1$H NMR (300 MHz, CDCl$_3$) δ 8.48 (d, J = 7.9 Hz, 1H), 8.27 (d, J = 5.4 Hz, 1H), 7.44-7.35 (m, 2H), 7.35-7.18 (m, 3H), 6.99-6.90 (m, 3H), 6.79-6.68 (m, 2H), 5.27 (qd, J = 6.4, 5.0 Hz, 1H), 5.15 (d, J = 5.2 Hz, 1H), 4.65 (dq, J = 8.1, 7.1 Hz, 1H), 3.86 (s, 3H), 2.38 (s, 3H), 2.20 (s, 3H), 1.37 (d, J = 6.5 Hz, 3H), 1.24 (d, J = 7.2 Hz, 3H). $^{13}$C NMR (75 MHz, CDCl$_3$) δ 172.13, 168.93, 162.40, 159.44, |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 155.77, 146.69, 141.44, 137.75, 137.48, 130.41, 129.80, 128.49, 128.12, 127.04, 115.88, 109.80, 81.40, 74.34, 56.29, 47.93, 20.78, 20.46, 18.38, 15.16. |
| 247 | | HRMS-ESI (m/z) ([M + H]$^+$) calcd for C$_{28}$H$_{30}$FN$_2$O$_7$, 525.2037; found, 525.2021 | $^1$H NMR (300 MHz, CDCl$_3$) δ 8.46 (d, J = 8.2 Hz, 1H), 8.28 (d, J = 5.4 Hz, 1H), 7.45-7.30 (m, 2H), 7.06-6.91 (m, 5H), 6.76-6.63 (m, 2H), 5.24 (qd, J = 6.4, 5.2 Hz, 1H), 5.12 (d, J = 5.3 Hz, 1H), 4.65 (dq, J = 8.3, 7.2 Hz, 1H), 3.88 (s, 3H), 2.39 (s, 3H), 2.21 (s, 3H), 1.37 (d, J = 6.3 Hz, 3H), 1.27 (d, J = 7.1 Hz, 3H). $^{13}$C NMR (75 MHz, CDCl$_3$) δ 172.04, 168.93, 162.44 (d, J = 246.6 Hz), 162.40, 159.45, 155.49, 146.68, 141.39, 137.50, 133.52 (d, J = 3.2 Hz), 130.63, 129.84, 128.78 (d, J = 8.2 Hz), 115.88, 115.46 (d, J = 21.5 Hz), 109.82, 80.79, 74.12, 56.28 (d, J = 1.9 Hz), 47.89, 20.77 (d, J = 1.5 Hz), 20.45 (d, J = 1.8 Hz), 18.37, 15.29. |
| 248 | | HRMS-ESI (m/z) ([M + H]$^+$) calcd for C$_{29}$H$_{33}$N$_2$O$_8$, 537.2237; found, 537.2229 | $^1$H NMR (300 MHz, CDCl$_3$) δ 8.29 (d, J = 8.5 Hz, 1H), 8.24 (d, J = 5.4 Hz, 1H), 7.46-7.35 (m, 2H), 7.35-7.18 (m, 3H), 6.99-6.88 (m, 3H), 6.80-6.66 (m, 2H), 5.72 (d, J = 1.6 Hz, 2H), 5.27 (qd, J = 6.4, 4.9 Hz, 1H), 5.16 (d, J = 5.1 Hz, 1H), 4.75-4.57 (m, 1H), 3.88 (s, 3H), 2.20 (s, 3H), 2.06 (s, 3H), 1.39 (d, J = 6.4 Hz, 3H), 1.26 (d, J = 7.2 Hz, 3H). $^{13}$C NMR (75 MHz, CDCl$_3$) δ 172.23, 170.29, 162.97, 160.27, 155.76, 145.72, 143.97, 142.40, 137.77, 130.40, 129.79, 128.48, 128.09, 127.02, 115.85, 109.60, 89.52, 81.40, 74.30, 56.20, 56.17, 48.15, 20.88 (d, J = 2.0 Hz), 20.44 (d, J = 1.8 Hz), 18.18, 15.15.z |
| 249 | | HRMS-ESI (m/z) ([M + H]$^+$) calcd for C$_{29}$H$_{32}$FN$_2$O$_8$, 555.2142; found, 555.2133 | $^1$H NMR (300 MHz, CDCl$_3$) δ 8.28 (d, J = 7.9 Hz, 1H), 8.25 (d, J = 5.4 Hz, 1H), 7.45-7.31 (m, 2H), 7.08-6.86 (m, 5H), 6.77-6.65 (m, 2H), 5.73 (d, J = 1.0 Hz, 2H), 5.33-5.19 (m, 1H), 5.13 (d, J = 5.3 Hz, 1H), 4.76-4.51 (m, 1H), 3.90 (s, 3H), 2.21 (s, 3H), 2.06 (s, 3H), 1.38 (d, J = 6.3 Hz, 3H), 1.28 (d, J = 7.2 Hz, 3H). $^{13}$C NMR (75 MHz, CDCl$_3$) δ 172.15, 170.29, 162.97, 162.43 (d, J = 246.6 Hz), 160.28, 155.49, 145.72, 143.99, 142.35, 133.54 (d, J = 3.2 Hz), 130.63, 129.83, 128.77 (d, J = 8.2 Hz), 115.86, 115.45 (d, J = 21.6 Hz), 109.62, 89.50, 80.80, 74.09, 56.19 (d, J = 2.6 Hz), 48.12, 20.87 (d, J = 2.2 Hz), 20.44 (d, J = 1.9 Hz), 18.19, 15.27. |
| 250 | | HRMS-ESI (m/z) ([M + H]$^+$) calcd for C$_{28}$H$_{29}$F$_2$N$_2$O$_8$, 559.1886; found, 559.1883. | $^1$H NMR (400 MHz, CDCl$_3$) δ 8.28 (d, J = 7.8 Hz, 1H), 8.25 (dd, J = 5.4, 1.0 Hz, 1H), 7.44 (dt, J = 14.6, 7.3 Hz, 1H), 7.20 (t, J = 7.7 Hz, 2H), 6.96-6.88 (m, 2H), 6.86-6.77 (m, 4H), 5.77-5.69 (m, 2H), 5.49 (d, J = 5.7 Hz, 1H), 5.37 (p, J = 6.2 Hz, 1H), 4.69 (p, J = 7.3 Hz, 1H), 3.90 (d, J = 0.9 Hz, 3H), 2.06 (s, 3H), 1.40 (d, J = 6.4 Hz, 3H), 1.31 (d, J = 7.2 Hz, 3H). $^{13}$C NMR (101 MHz, CDCl$_3$) δ 171.94, 170.27, 162.93, 160.28, |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 157.09, 145.67, 144.03, 142.39, 129.68 (dd, J = 14.7, 10.2 Hz), 129.52, 121.60, 120.60 (d, J = 7.0 Hz), 115.58, 112.00 (d, J = 21.2 Hz), 109.58, 103.61 (t, J = 25.6 Hz), 89.54, 74.01, 72.91, 56.18, 48.10, 20.86, 18.17, 15.96. $^{19}$F NMR (376 MHz, CDCl$_3$) δ-109.61 (d, J = 7.6 Hz), −113.91 (d, J = 7.6 Hz). |
| 251 | | HRMS-ESI (m/z) ([M + H]$^+$) calcd for C$_{27}$H$_{27}$F$_2$N$_2$O$_7$, 529.1781; found, 529.1777. | $^1$H NMR (400 MHz, CDCl$_3$) δ 8.46 (d, J = 6.2 Hz, 1H), 8.30 (d, J = 5.4 Hz, 1H), 7.44 (dt, J = 14.6, 7.2 Hz, 1H), 7.23-7.16 (m, 2H), 6.99 (d, J = 5.5 Hz, 1H), 6.90 (dd, J = 9.7, 5.0 Hz, 1H), 6.83-6.77 (m, 4H), 5.48 (d, J = 5.7 Hz, 1H), 5.36 (p, J = 6.3 Hz, 1H), 4.67 (p, J = 7.2 Hz, 1H), 3.90 (s, 3H), 2.39 (s, 3H), 1.39 (d, J = 6.4 Hz, 3H), 1.30 (d, J = 7.2 Hz, 3H). $^{13}$C NMR (151 MHz, CDCl$_3$) δ 171.83, 168.89, 162.35, 159.47, 157.08, 146.63, 141.44, 137.51, 129.87-129.60 (m), 129.52, 121.60, 121.01-120.03 (m), 115.60, 111.99 (d, J = 21.3 Hz), 109.78, 104.59-102.56 (m), 73.99, 72.93, 56.28, 47.88, 20.74, 18.36, 15.97. $^{19}$F NMR (376 MHz, CDCl$_3$) δ-109.62 (d, J = 7.6 Hz), −113.92 (d, J = 7.5 Hz). |
| 252 | | HRMS-ESI (m/z) ([M + H]$^+$) calcd for C$_{29}$H$_{33}$N$_2$O$_8$, 537.2231; found, 537.2235. | $^1$H NMR (400 MHz, CDCl$_3$) δ 8.28 (d, J = 7.8 Hz, 1H), 8.24 (d, J = 5.4 Hz, 1H), 7.28 (d, J = 8.0 Hz, 2H), 7.19-7.10 (m, 4H), 6.93 (d, J = 5.4 Hz, 1H), 6.87 (t, J = 7.4 Hz, 1H), 6.84-6.80 (m, 2H), 5.75-5.70 (m, 2H), 5.26 (dt, J = 11.4, 5.7 Hz, 1H), 5.18 (d, J = 5.0 Hz, 1H), 4.67 (p, J = 7.2 Hz, 1H), 3.90 (s, 3H), 2.31 (s, 3H), 2.06 (s, 3H), 1.38 (d, J = 6.4 Hz, 3H), 1.28 (d, J = 7.2 Hz, 3H). $^{13}$C NMR (101 MHz, CDCl$_3$) δ 172.25, 170.27, 162.95, 160.27, 157.96, 145.68, 144.01, 142.49, 137.82, 134.51, 129.31, 129.19, 126.89, 121.06, 115.98, 109.53, 89.58, 81.10, 74.38, 56.17, 48.16, 21.14, 20.87, 18.23, 15.00. |
| 253 | | HRMS-ESI (m/z) ([M + H]$^+$) calcd for C$_{29}$H$_{32}$FN$_2$O$_8$, 555.2142; found, 555.2138 | $^1$H NMR (400 MHz, CDCl$_3$) δ 8.30-8.21 (m, 2H), 7.25 (d, J = 7.7 Hz, 2H), 7.12 (d, J = 7.8 Hz, 2H), 6.93 (d, J = 5.4 Hz, 1H), 6.86-6.80 (m, 2H), 6.80-6.66 (m, 2H), 5.77-5.68 (m, 2H), 5.32-5.18 (m, 1H), 5.09 (d, J = 4.8 Hz, 1H), 4.76-4.59 (m, 1H), 3.90 (s, 3H), 2.31 (s, 3H), 2.06 (s, 3H), 1.36 (d, J = 6.4 Hz, 3H), 1.29 (d, J = 7.2 Hz, 3H). $^{13}$C NMR (101 MHz, CDCl$_3$) δ 172.17, 170.21, 162.97, 160.29, 157.37 (d, J = 238.8 Hz), 154.09 (d, J = 2.1 Hz), 145.64, 144.02, 142.48, 137.97, 134.24, 129.23, 126.87, 117.13 (d, J = 7.9 Hz), 115.66 (d, J = 23.1 Hz), 109.55, 89.56, 82.06, 74.25, 56.15, 48.20, 21.11, 20.83, 18.16, 14.83. $^{19}$F NMR (376 MHz, CDCl$_3$) δ-123.35. |

TABLE 2-continued

Analytical Data

| *Cmpd. No. | IR (cm$^{-1}$) | MASS | NMR ($^1$H, $^{13}$C or $^{19}$F) |
|---|---|---|---|
| 254 | | HRMS-ESI (m/z) ([M + H]$^+$) calcd for C$_{28}$H$_{29}$F$_2$N$_2$O$_8$, 559.1892; found, 559.1891 | $^1$H NMR (400 MHz, CDCl$_3$) δ 8.30-8.16 (m, 2H), 7.41-7.30 (m, 2H), 7.01 (t, J = 8.6 Hz, 2H), 6.94 (d, J = 5.4 Hz, 1H), 6.89-6.79 (m, 2H), 6.81-6.69 (m, 2H), 5.81-5.64 (m, 2H), 5.32-5.18 (m, 1H), 5.10 (d, J = 5.1 Hz, 1H), 4.66 (p, J = 7.3 Hz, 1H), 3.90 (s, 3H), 2.06 (s, 3H), 1.37 (d, J = 6.4 Hz, 3H), 1.30 (d, J = 7.2 Hz, 3H). $^{19}$F NMR (376 MHz, CDCl$_3$) δ-113.53, −122.83. |
| 255 | | HRMS-ESI (m/z) ([M + H]$^+$) calcd for C$_{29}$H$_{33}$N$_2$O$_9$, 553.2181; found, 553.2183. | $^1$H NMR (400 MHz, CDCl$_3$) δ 8.30 (d, J = 7.8 Hz, 1H), 8.22 (d, J = 5.4 Hz, 1H), 7.39 (d, J = 7.6 Hz, 1H), 7.26-7.21 (m, 1H), 7.15 (t, J = 8.0 Hz, 2H), 6.93-6.80 (m, 6H), 5.75-5.70 (m, 2H), 5.69 (d, J = 4.6 Hz, 1H), 5.43-5.36 (m, 1H), 4.68 (p, J = 7.2 Hz, 1H), 3.90 (d, J = 6.0 Hz, 6H), 2.06 (s, 3H), 1.34 (d, J = 6.5 Hz, 3H), 1.30 (d, J = 7.1 Hz, 3H). $^{13}$C NMR (101 MHz, CDCl$_3$) δ 172.11, 170.21, 162.92, 160.25, 157.93, 156.67, 145.64, 143.96, 142.63, 129.26, 129.09, 127.86, 125.54, 120.84, 115.66, 110.20, 109.49, 89.59, 74.92, 73.12, 56.14, 55.47, 48.21, 20.84, 18.27, 15.04. |
| 256 | | HRMS-ESI (m/z) ([M + H]$^+$) calcd for C$_{29}$H$_{32}$N$_2$O$_9$, 571.2086; found, 571.2095. | $^1$H NMR (400 MHz, CDCl$_3$) δ 8.29 (d, J = 7.7 Hz, 1H), 8.22 (d, J = 5.4 Hz, 1H), 7.37-7.31 (m, 1H), 7.16 (t, J = 7.9 Hz, 2H), 6.92 (d, J = 5.4 Hz, 1H), 6.86 (t, J = 7.3 Hz, 1H), 6.80 (d, J = 8.1 Hz, 2H), 6.59 (ddd, J = 10.5, 9.5, 2.2 Hz, 2H), 5.75-5.71 (m, 2H), 5.61 (d, J = 4.7 Hz, 1H), 5.40-5.32 (m, 1H), 4.69 (p, J = 7.3 Hz, 1H), 3.90 (s, 6H), 2.06 (s, 3H), 1.35-1.28 (m, 6H). $^{13}$C NMR (101 MHz, CDCl$_3$) δ 172.06, 170.21, 163.39 (d, J = 246.1 Hz), 162.93, 160.27, 157.85 (d, J = 9.7 Hz), 157.69, 145.64, 143.99, 142.57, 129.31, 129.04 (d, J = 10.1 Hz), 121.30 (d, J = 3.2 Hz), 121.02, 115.62, 109.52, 107.37 (d, J = 21.2 Hz), 98.67 (d, J = 25.8 Hz), 89.58, 74.54, 72.98, 56.15, 55.78, 48.18, 20.83, 18.26, 15.11. $^{19}$F NMR (376 MHz, CDCl$_3$) δ-111.31 (s, 1F). |
| 257 | | HRMS-ESI (m/z) ([M + H]$^+$) calcd for C$_{30}$H$_{35}$N$_2$O$_8$, 551.2388; found, 551.2394 | $^1$H NMR (400 MHz, CDCl$_3$) δ 8.27 (d, J = 7.7 Hz, 1H), 8.24 (d, J = 5.4 Hz, 1H), 7.27 (d, J = 7.6 Hz, 2H), 7.10 (d, J = 7.7 Hz, 2H), 6.97-6.91 (m, 3H), 6.80-6.68 (m, 2H), 5.72 (d, J = 2.5 Hz, 2H), 5.30-5.21 (m, 1H), 5.13 (d, J = 5.1 Hz, 1H), 4.66 (p, J = 7.3 Hz, 1H), 3.89 (s, 3H), 2.30 (s, 3H), 2.20 (s, 3H), 1.37 (d, J = 6.4 Hz, 3H), 1.28 (d, J = 7.3 Hz, 3H). $^{13}$C NMR (101 MHz, CDCl$_3$) δ 172.19, 170.16, 162.94, 160.26, 155.85, 145.64, 143.96, 142.55, 137.69, 134.70, 130.26, 129.72, 129.11, 126.90, 115.86, 109.53, 89.52, 81.30, 74.34, 56.13, 48.16, 21.08, 20.80, 20.38, 18.19, 15.01. |

TABLE 2-continued

Analytical Data

| *Cmpd. No. | IR (cm$^{-1}$) | MASS | NMR ($^1$H, $^{13}$C or $^{19}$F) |
|---|---|---|---|
| 258 | | HRMS-ESI (m/z) ([M + H]$^+$) calcd for C$_{29}$H$_{33}$N$_2$O$_9$, 553.2181; found, 553.2187. | $^1$H NMR (400 MHz, CDCl$_3$) δ 8.28 (d, J = 7.9 Hz, 1H), 8.24 (d, J = 5.4 Hz, 1H), 7.23 (t, J = 7.9 Hz, 1H), 7.20-7.14 (m, 2H), 6.99 (d, J = 7.7 Hz, 1H), 6.95-6.91 (m, 2H), 6.90-6.78 (m, 4H), 5.75-5.70 (m, 2H), 5.26 (dt, J = 11.4, 5.7 Hz, 1H), 5.19 (d, J = 5.0 Hz, 1H), 4.67 (p, J = 7.2 Hz, 1H), 3.90 (s, 3H), 3.76 (d, J = 6.6 Hz, 3H), 2.06 (s, 3H), 1.39 (d, J = 6.4 Hz, 3H), 1.28 (d, J = 7.2 Hz, 3H). $^{13}$C NMR (101 MHz, CDCl$_3$) δ 172.24, 170.22, 162.97, 160.27, 159.78, 157.98, 145.67, 144.00, 142.50, 139.30, 129.54, 129.33, 121.19, 119.35, 115.99, 113.51, 112.48, 109.54, 89.56, 81.17, 74.33, 56.15, 55.20, 48.16, 20.84, 18.17, 14.96. |
| 259 | | HRMS-ESI (m/z) ([M + H]$^+$) calcd for C$_{29}$H$_{32}$FN$_2$O$_8$, 555.2137; found, 555.2146. | $^1$H NMR (300 MHz, CDCl$_3$) δ 8.25 (t, J = 7.0 Hz, 2H), 7.38 (dd, J = 8.5, 5.9 Hz, 1H), 7.21-7.13 (m, 2H), 6.93 (d, J = 5.4 Hz, 1H), 6.92-6.79 (m, 3H), 6.77-6.71 (m, 2H), 5.76-5.68 (m, 2H), 5.39 (d, J = 5.0 Hz, 1H), 5.26-5.15 (m, 1H), 4.66 (p, J = 7.2 Hz, 1H), 3.90 (s, 3H), 2.51 (s, 3H), 2.06 (s, 3H), 1.43 (d, J = 6.4 Hz, 3H), 1.23 (d, J = 7.2 Hz, 3H). $^{13}$C NMR (101 MHz, CDCl$_3$) δ 172.31, 170.23, 162.98, 162.17 (d, J = 246.4 Hz), 160.29, 157.73, 145.65, 144.04, 142.39, 137.90 (d, J = 7.9 Hz), 131.54 (d, J = 3.0 Hz), 129.41, 128.68 (d, J = 8.5 Hz), 121.29, 117.15 (d, J = 21.2 Hz), 115.75, 113.22 (d, J = 21.2 Hz), 109.57, 89.56, 77.76, 73.35, 56.16, 48.11, 20.84, 19.29 (d, J = 1.1 Hz), 18.03, 14.86. $^{19}$F NMR (376 MHz, CDCl$_3$) δ-114.90. |
| 260 | | HRMS-ESI (m/z) ([M + H]$^+$) calcd for C$_{28}$H$_{29}$ClFN$_2$O$_8$, 575.1591; found, 575.1596. | $^1$H NMR (300 MHz, CDCl$_3$) δ 8.28 (d, J = 7.9 Hz, 1H), 8.24 (d, J = 5.4 Hz, 1H), 7.49 (dd, J = 8.8, 6.1 Hz, 1H), 7.24-7.15 (m, 2H), 7.14-7.09 (m, 1H), 6.97-6.87 (m, 3H), 6.82-6.76 (m, 2H), 5.76-5.70 (m, 2H), 5.63 (d, J = 5.4 Hz, 1H), 5.41-5.31 (m, 1H), 4.70 (p, J = 7.2 Hz, 1H), 3.90 (s, 3H), 2.06 (s, 3H), 1.41 (d, J = 6.4 Hz, 3H), 1.31 (d, J = 7.2 Hz, 3H). $^{13}$C NMR (101 MHz, CDCl$_3$) δ 171.96, 170.22, 162.94, 162.06 (d, J = 251.0 Hz), 160.29, 157.12, 145.64, 144.03, 142.45, 133.97 (d, J = 10.2 Hz), 131.24 (d, J = 3.5 Hz), 130.03 (d, J = 8.9 Hz), 129.52, 121.51, 116.69 (d, J = 24.7 Hz), 115.56, 114.80 (d, J = 21.2 Hz), 109.57, 89.55, 76.67, 72.95, 56.16, 48.13, 20.84, 18.16, 15.62. $^{19}$F NMR (376 MHz, CDCl$_3$) δ-111.30. |
| 261 | | HRMS-ESI (m/z) ([M + H]$^+$) calcd for C$_{29}$H$_{32}$FN$_2$O$_8$, 555.2137; found, 555.2145. | $^1$H NMR (400 MHz, CDCl$_3$) δ 8.29 (d, J = 7.8 Hz, 1H), 8.25 (d, J = 5.4 Hz, 1H), 7.31 (t, J = 7.7 Hz, 1H), 7.22-7.15 (m, 2H), 6.93 (d, J = 5.4 Hz, 1H), 6.87 (ddd, J = 17.3, 7.4, 4.4 Hz, 5H), 5.76-5.70 (m, 2H), 5.50 (d, J = 5.6 Hz, 1H), 5.38 (p, J = 6.2 Hz, 1H), 4.68 (p, J = 7.2 Hz, 1H), 3.90 (s, 3H), 2.30 (s, 3H), 2.06 |

TABLE 2-continued

Analytical Data

| *Cmpd. No. | IR (cm⁻¹) | MASS | NMR ($^1$H, $^{13}$C or $^{19}$F) |
|---|---|---|---|
| | | | (s, 3H), 1.40 (d, J = 6.4 Hz, 3H), 1.30 (d, J = 7.2 Hz, 3H). $^{13}$C NMR (101 MHz, CDCl$_3$) δ 172.01, 170.23, 162.91, 160.27, 160.25 (d, J = 245.8 Hz), 157.41, 145.65, 143.99, 142.56, 140.44 (d, J = 8.0 Hz), 129.41, 128.26 (d, J = 4.2 Hz), 125.32 (d, J = 3.0 Hz), 121.39 (d, J = 13.3 Hz), 121.29, 115.67 (d, J = 21.6 Hz), 115.61, 109.52, 89.57, 74.35, 73.10, 56.15, 48.14, 21.05 (d, J = 1.3 Hz), 20.84, 18.20, 15.84. $^{19}$F NMR (376 MHz, CDCl$_3$) δ-119.14. |
| 262 | | HRMS-ESI (m/z) ([M + H]⁺) calcd for C$_{32}$H$_{33}$N$_2$O$_8$, 573.2231; found, 573.2238. | $^1$H NMR (400 MHz, CDCl$_3$) δ 8.43 (d, J = 8.5 Hz, 1H), 8.27 (d, J = 7.9 Hz, 1H), 8.25 (d, J = 5.4 Hz, 1H), 7.89 (d, J = 8.0 Hz, 1H), 7.79 (d, J = 8.2 Hz, 1H), 7.63 (dd, J = 11.1, 4.1 Hz, 2H), 7.53 (t, J = 7.1 Hz, 1H), 7.45-7.38 (m, 1H), 7.15-7.08 (m, 2H), 6.93 (d, J = 5.4 Hz, 1H), 6.84 (t, J = 7.4 Hz, 1H), 6.82-6.77 (m, 2H), 6.12 (d, J = 4.1 Hz, 1H), 5.75-5.69 (m, 2H), 5.49-5.41 (m, 1H), 4.67 (p, J = 7.2 Hz, 1H), 3.90 (s, 3H), 2.06 (s, 3H), 1.42 (d, J = 6.5 Hz, 3H), 1.14 (d, J = 7.2 Hz, 3H). $^{13}$C NMR (101 MHz, CDCl$_3$) δ 172.73, 170.24, 163.00, 160.30, 158.04, 145.66, 144.05, 142.46, 133.73, 133.05, 130.59, 129.36, 128.98, 128.64, 126.82, 125.84, 125.46, 124.71, 122.94, 121.09, 115.69, 109.56, 89.59, 77.50, 73.92, 56.16, 48.11, 20.85, 17.93, 14.33. |
| 263 | | HRMS-ESI (m/z) ([M + H]⁺) calcd for C$_{32}$H$_{33}$N$_2$O$_8$, 573.2231; found, 573.2236. | $^1$H NMR (400 MHz, CDCl$_3$) δ 8.26 (d, J = 7.8 Hz, 1H), 8.23 (d, J = 5.4 Hz, 1H), 7.86 (s, 1H), 7.80 (dd, J = 8.5, 6.2 Hz, 3H), 7.54 (dd, J = 8.5, 1.6 Hz, 1H), 7.49-7.44 (m, 2H), 7.18-7.12 (m, 2H), 6.92 (d, J = 5.4 Hz, 1H), 6.86 (dd, J = 10.9, 4.3 Hz, 3H), 5.74-5.69 (m, 2H), 5.42-5.34 (m, 2H), 4.67 (p, J = 7.2 Hz, 1H), 3.90 (s, 3H), 2.05 (s, 3H), 1.43 (d, J = 6.2 Hz, 3H), 1.23 (d, J = 7.2 Hz, 3H). $^{13}$C NMR (101 MHz, CDCl$_3$) δ 172.27, 170.22, 162.96, 160.27, 157.99, 145.66, 144.01, 142.48, 135.18, 133.17, 133.10, 129.36, 128.44, 127.94, 127.72, 126.29, 126.17, 124.38, 121.24, 116.08, 109.54, 89.57, 81.46, 74.38, 56.16, 48.15, 20.85, 18.16, 14.98. |
| 264 | | HRMS-ESI (m/z) ([M + H]⁺) calcd for C$_{30}$H$_{32}$FN$_2$O$_8$, 567.2137; found, 567.2148. | $^1$H NMR (400 MHz, CDCl$_3$) δ 8.50 (d, J = 5.5 Hz, 1H), 8.27 (d, J = 5.4 Hz, 1H), 7.35 (t, J = 7.6 Hz, 1H), 7.19-7.13 (m, 2H), 6.98 (d, J = 5.5 Hz, 1H), 6.87 (t, J = 7.3 Hz, 1H), 6.84-6.78 (m, 2H), 6.63-6.55 (m, 2H), 6.09 (ddt, J = 17.2, 10.4, 5.1 Hz, 1H), 5.65 (d, J = 4.6 Hz, 1H), 5.47 (ddd, J = 17.3, 3.0, 1.5 Hz, 1H), 5.42-5.32 (m, 2H), 4.72-4.63 (m, 1H), 4.61 (d, J = 5.0 Hz, 2H), 3.90 (s, 3H), 2.39 (s, 3H), 1.35-1.29 (m, 6H). $^{13}$C NMR (101 MHz, CDCl$_3$) δ 171.94, 168.86, 163.21 (d, J = 246.3 Hz), 162.34, 159.44, 157.65, 156.74 (d, J = 10.0 Hz), 146.62, 141.58, 137.49, 132.40, 129.31, 129.21 (d, J = 10.2 Hz), 121.48 (d, J = 3.2 Hz), |

TABLE 2-continued

Analytical Data

| *Cmpd. No. | IR (cm⁻¹) | MASS | NMR ($^1$H, $^{13}$C or $^{19}$F) |
|---|---|---|---|
| | | | 121.03, 117.97, 115.64, 109.71, 107.60 (d, J = 21.4 Hz), 99.80 (d, J = 25.8 Hz), 74.56, 73.01, 69.22, 56.26, 47.97, 20.73, 18.50, 15.24. $^{19}$F NMR (376 MHz, CDCl$_3$) δ -111.31. |
| 265 | | HRMS-ESI (m/z) ([M + H]$^+$) calcd for C$_{29}$H$_{32}$FN$_2$O$_8$, 555.2137; found, 555.2143. | $^1$H NMR (400 MHz, CDCl$_3$) δ 8.50 (d, J = 5.8 Hz, 1H), 8.28 (d, J = 5.1 Hz, 1H), 7.33 (dd, J = 8.3, 6.9 Hz, 1H), 7.17 (dd, J = 8.5, 7.5 Hz, 2H), 6.98 (d, J = 5.4 Hz, 1H), 6.87 (t, J = 7.3 Hz, 1H), 6.81 (d, J = 7.9 Hz, 2H), 6.62-6.53 (m, 2H), 5.61 (d, J = 4.5 Hz, 1H), 5.43-5.35 (m, 1H), 4.68 (p, J = 7.2 Hz, 1H), 4.09 (tt, J = 8.1, 4.1 Hz, 2H), 3.90 (s, 3H), 2.39 (s, 3H), 1.49 (t, J = 7.0 Hz, 3H), 1.32 (d, J = 6.8 Hz, 6H). $^{19}$F NMR (376 MHz, CDCl$_3$) δ -111.56. |
| 266 | | HRMS-ESI (m/z) ([M + H]$^+$) calcd for C$_{29}$H$_{31}$ClFN$_2$O$_8$, 589.1747; found, 589.1749. | $^1$H NMR (400 MHz, CDCl$_3$) δ 8.50 (d, J = 6.6 Hz, 1H), 8.28 (d, J = 5.4 Hz, 1H), 7.38 (dd, J = 9.2, 6.7 Hz, 1H), 7.12 (d, J = 1.7 Hz, 1H), 6.98 (d, J = 5.5 Hz, 1H), 6.81-6.76 (m, 1H), 6.61 (ddd, J = 10.8, 5.5, 2.3 Hz, 2H), 6.55 (d, J = 8.4 Hz, 1H), 5.63 (d, J = 4.4 Hz, 1H), 5.42-5.35 (m, 1H), 4.72-4.64 (m, 1H), 3.90 (s, 3H), 3.88 (s, 3H), 2.39 (s, 3H), 2.19 (s, 3H), 1.35 (d, J = 6.5 Hz, 3H), 1.33 (d, J = 7.2 Hz, 3H). $^{13}$C NMR (101 MHz, CDCl$_3$) δ 171.95, 168.85, 163.47 (d, J = 246.5 Hz), 159.42, 162.34, 157.82 (d, J = 9.7 Hz), 150.89, 146.60, 141.58, 137.48, 131.22, 130.67, 129.17 (d, J = 10.1 Hz), 127.84, 122.93, 120.74 (d, J = 3.4 Hz), 114.38, 109.67, 107.46 (d, J = 21.3 Hz), 98.64 (d, J = 25.9 Hz), 75.32, 73.02, 56.25, 55.78, 47.97, 20.71, 20.20, 18.44, 14.99. $^{19}$F NMR (376 MHz, CDCl$_3$) δ -110.97 (d, J = 2.0 Hz). |
| 267 | | HRMS-ESI (m/z) ([M + H]$^+$) calcd for C$_{29}$H$_{30}$FN$_2$O$_9$, 569.1930; found, 569.1951. | $^1$H NMR (400 MHz, CDCl$_3$) δ 8.41 (d, J = 6.8 Hz, 1H), 8.29 (d, J = 5.4 Hz, 1H), 7.41 (dd, J = 9.4, 6.2 Hz, 1H), 7.17 (dd, J = 8.5, 7.5 Hz, 2H), 6.98 (d, J = 5.5 Hz, 1H), 6.90 (tt, J = 7.5, 3.9 Hz, 3H), 6.78 (d, J = 8.0 Hz, 2H), 5.43 (d, J = 3.9 Hz, 1H), 5.23 (qd, J = 6.5, 4.0 Hz, 1H), 4.65 (p, J = 7.2 Hz, 1H), 3.90 (s, 3H), 2.44 (s, 3H), 2.38 (s, 3H), 1.32 (d, J = 6.6 Hz, 3H), 1.28 (d, J = 7.2 Hz, 3H). $^{13}$C NMR (101 MHz, CDCl$_3$) δ 172.13, 169.16, 168.84, 162.39, 162.31 (d, J = 248.8 Hz), 159.45, 157.63, 148.71 (d, J = 10.9 Hz), 146.58, 141.52, 137.52, 129.46, 129.05 (d, J = 9.4 Hz), 125.46 (d, J = 3.6 Hz), 121.41, 115.63, 113.49 (d, J = 21.2 Hz), 110.65 (d, J = 24.6 Hz), 109.74, 75.35, 72.75, 56.26, 47.94, 21.01, 20.72, 18.26, 13.95. $^{19}$F NMR (376 MHz, CDCl$_3$) δ -111.42. |
| 268 | | HRMS-ESI (m/z) ([M + H]$^+$) calcd for C$_{30}$H$_{34}$FN$_2$O$_8$, 569.2294; found, 569.2289. | $^1$H NMR (400 MHz, CDCl$_3$) δ 8.50 (d, J = 6.4 Hz, 1H), 8.28 (d, J = 5.4 Hz, 1H), 7.33 (dd, J = 8.3, 6.8 Hz, 1H), 7.20-7.13 (m, 2H), 6.98 (d, J = 5.5 Hz, 1H), 6.87 (t, J = 7.3 Hz, 1H), 6.83-6.79 (m, 2H), 6.62-6.53 (m, 2H), 5.62 (d, J = 4.6 Hz, 1H), 5.41-5.33 (m, 1H), 4.67 (p, J = 7.2 Hz, 1H), 3.98 (t, J = 6.4 Hz, 2H), |

TABLE 2-continued

Analytical Data

| *Cmpd. No. | IR (cm⁻¹) | MASS | NMR ($^1$H, $^{13}$C or $^{19}$F) |
|---|---|---|---|
| | | | 3.90 (s, 3H), 2.39 (s, 3H), 1.95-1.85 (m, 2H), 1.32 (t, J = 7.0 Hz, 6H), 1.10 (t, J = 7.4 Hz, 3H). $^{13}$C NMR (101 MHz, CDCl$_3$) δ 171.95, 168.86, 163.31 (d, J = 246.0 Hz), 162.33, 159.43, 157.73, 157.24 (d, J = 9.8 Hz), 146.62, 141.59, 137.48, 129.30, 129.00 (d, J = 10.2 Hz), 121.22 (d, J = 3.2 Hz), 120.97, 115.59, 109.69, 107.15 (d, J = 21.3 Hz), 99.21 (d, J = 25.7 Hz), 74.62, 73.06, 69.99, 56.25, 47.96, 22.49, 20.72, 18.51, 15.18, 10.68. $^{19}$F NMR (376 MHz, CDCl$_3$) δ-111.49. |
| 269 | | HRMS-ESI (m/z) ([M + H]⁺) calcd for C$_{29}$H$_{33}$N$_2$O$_8$, 537.2231; found, 537.2220. | $^1$H NMR (400 MHz, CDCl$_3$) δ 8.52 (d, J = 5.5 Hz, 1H), 8.26 (d, J = 5.4 Hz, 1H), 7.24 (s, 1H), 7.18-7.12 (m, 2H), 6.97 (d, J = 5.5 Hz, 1H), 6.84 (dd, J = 14.9, 7.6 Hz, 3H), 6.70 (d, J = 6.4 Hz, 2H), 5.63 (d, J = 4.5 Hz, 1H), 5.40-5.33 (m, 1H), 4.67 (p, J = 7.2 Hz, 1H), 3.89 (s, 3H), 3.89 (s, 3H), 2.39 (s, 3H), 2.31 (s, 3H), 1.32 (d, J = 6.5 Hz, 3H), 1.30 (d, J = 7.2 Hz, 3H). $^{13}$C NMR (101 MHz, CDCl$_3$) δ 172.02, 168.85, 162.32, 159.41, 157.97, 156.57, 146.60, 141.65, 139.16, 137.46, 129.23, 127.70, 122.40, 121.51, 120.73, 115.65, 111.09, 109.64, 74.86, 73.22, 56.24, 55.40, 48.01, 21.56, 20.73, 18.47, 14.97. |
| 270 | | HRMS-ESI (m/z) ([M + H]⁺) calcd for C$_{28}$H$_{30}$FN$_2$O$_8$, 541.1981; found, 541.1987. | $^1$H NMR (400 MHz, CDCl$_3$) δ 8.50 (d, J = 5.6 Hz, 1H), 8.26 (d, J = 5.4 Hz, 1H), 7.34 (dd, J = 8.4, 6.8 Hz, 1H), 7.20-7.13 (m, 2H), 6.97 (d, J = 5.5 Hz, 1H), 6.87 (t, J = 7.3 Hz, 1H), 6.83-6.78 (m, 2H), 6.63-6.55 (m, 2H), 5.61 (d, J = 4.7 Hz, 1H), 5.39-5.31 (m, 1H), 4.68 (p, J = 7.2 Hz, 1H), 3.89 (s, 6H), 2.39 (s, 3H), 1.34-1.28 (m, 6H). $^{13}$C NMR (101 MHz, CDCl$_3$) δ 171.95, 168.85, 163.38 (d, J = 246.3 Hz), 162.34, 159.44, 157.84 (d, J = 9.8 Hz), 157.69, 146.61, 141.57, 137.49, 129.31, 129.05 (d, J = 10.1 Hz), 121.27 (d, J = 3.3 Hz), 121.02, 115.63, 109.70, 107.36 (d, J = 21.4 Hz), 98.66 (d, J = 25.8 Hz), 74.52, 73.01, 56.25, 55.77, 47.97, 20.72, 18.45, 15.10. $^{19}$F NMR (376 MHz, CDCl$_3$) δ-111.28. |
| 271 | | HRMS-ESI (m/z) ([M + H]⁺) calcd for C$_{29}$H$_{32}$FN$_2$O$_8$, 555.2137; found, 555.2136. | $^1$H NMR (400 MHz, CDCl$_3$) δ 8.50 (d, J = 5.4 Hz, 1H), 8.27 (d, J = 5.4 Hz, 1H), 7.36-7.31 (m, 1H), 7.00-6.93 (m, 3H), 6.70 (t, J = 5.7 Hz, 2H), 6.62-6.55 (m, 2H), 5.56 (d, J = 4.7 Hz, 1H), 5.37-5.30 (m, 1H), 4.67 (p, J = 7.2 Hz, 1H), 3.90 (s, 3H), 3.88 (s, 3H), 2.39 (s, 3H), 2.21 (s, 3H), 1.33-1.28 (m, 6H). $^{13}$C NMR (101 MHz, CDCl$_3$) δ 171.97, 168.85, 163.34 (d, J = 246.0 Hz), 162.33, 159.44, 157.85 (d, J = 9.7 Hz), 155.58, 146.61, 141.59, 137.49, 130.22, 129.76, 129.07 (d, J = 10.1 Hz), 121.46 (d, J = 3.0 Hz), 115.48, 109.68, 107.33 (d, J = 21.4 Hz), 98.63 (d, J = 25.9 Hz), 74.66, 73.04, 56.25, 55.75, 47.96, 20.72, 20.42, 18.46, 15.11. $^{19}$F NMR (376 MHz, CDCl$_3$) δ-111.44. |

TABLE 2-continued

Analytical Data

| *Cmpd. No. | IR (cm⁻¹) | MASS | NMR ($^1$H, $^{13}$C or $^{19}$F) |
|---|---|---|---|
| 272 | | HRMS-ESI (m/z) ([M + H]$^+$) calcd for C$_{31}$H$_{34}$FN$_2$O$_8$, 581.2294; found, 581.2296. | $^1$H NMR (400 MHz, CDCl$_3$) δ 8.50 (d, J = 5.6 Hz, 1H), 8.28 (d, J = 5.4 Hz, 1H), 7.34 (dd, J = 9.2, 6.7 Hz, 1H), 7.17 (dd, J = 8.5, 7.5 Hz, 2H), 6.98 (d, J = 5.5 Hz, 1H), 6.90-6.81 (m, 3H), 6.59-6.53 (m, 2H), 5.66 (d, J = 4.6 Hz, 1H), 5.44-5.37 (m, 1H), 4.68 (p, J = 7.1 Hz, 1H), 3.90 (s, 3H), 3.88 (d, J = 7.0 Hz, 2H), 2.39 (s, 3H), 1.36-1.26 (m, 7H), 0.71-0.64 (m, 2H), 0.40 (q, J = 4.7 Hz, 2H). $^{13}$C NMR (101 MHz, CDCl$_3$) δ 171.93, 168.85, 163.27 (d, J = 246.3 Hz), 162.33, 159.44, 157.71, 157.13 (d, J = 9.9 Hz), 146.62, 141.60, 137.49, 129.29, 129.13 (d, J = 10.2 Hz), 121.35 (d, J = 3.1 Hz), 120.95, 115.61, 109.69, 107.23 (d, J = 21.3 Hz), 99.37 (d, J = 25.8 Hz), 74.52, 73.11, 72.95, 56.25, 47.98, 20.72, 18.55, 15.31, 10.08, 3.26, 3.12. $^{19}$F NMR (376 MHz, CDCl$_3$) δ-111.49. |
| 273 | | HRMS-ESI (m/z) ([M + H]$^+$) calcd for C$_{29}$H$_{30}$F$_3$N$_2$O$_8$, 591.1949; found, 591.1943. | $^1$H NMR (400 MHz, CDCl$_3$) δ 8.46 (d, J = 7.3 Hz, 1H), 8.29 (d, J = 5.4 Hz, 1H), 7.38 (dd, J = 8.6, 6.6 Hz, 1H), 7.21-7.14 (m, 2H), 6.99 (d, J = 5.5 Hz, 1H), 6.88 (t, J = 7.4 Hz, 1H), 6.82-6.77 (m, 2H), 6.67 (td, J = 8.3, 2.3 Hz, 1H), 6.59 (dd, J = 10.2, 2.3 Hz, 1H), 6.23 (tt, J = 54.8, 4.0 Hz, 1H), 5.60 (d, J = 4.3 Hz, 1H), 5.40-5.32 (m, 1H), 4.66 (p, J = 7.2 Hz, 1H), 4.31-4.17 (m, 2H), 3.90 (s, 3H), 2.39 (s, 3H), 1.33 (d, J = 3.8 Hz, 3H), 1.31 (d, J = 4.4 Hz, 3H). $^{13}$C NMR (101 MHz, CDCl$_3$) δ 171.96, 168.87, 163.12 (d, J = 247.7 Hz), 162.36, 159.46, 157.56, 155.60 (d, J = 9.7 Hz), 146.63, 141.54, 137.51, 129.58 (d, J = 9.9 Hz), 129.39, 121.84 (d, J = 3.5 Hz), 121.23, 115.62, 109.74, 108.83 (d, J = 21.1 Hz), 99.64 (d, J = 26.1 Hz), 74.60, 72.81, 68.12-66.92 (m), 56.27, 47.93, 20.71, 18.42, 14.85. $^{19}$F NMR (376 MHz, CDCl$_3$) δ-110.59, −124.95 (d, J = 296.7 Hz), −125.92 (d, J = 296.7 Hz). |
| 274 | | HRMS-ESI (m/z) ([M + H]$^+$) calcd for C$_{30}$H$_{35}$N$_2$O$_8$, 551.2388; found, 551.2384. | $^1$H NMR (400 MHz, CDCl$_3$) δ 8.52 (d, J = 4.2 Hz, 1H), 8.27 (d, J = 5.4 Hz, 1H), 7.24 (d, J = 7.7 Hz, 1H), 6.96 (dd, J = 10.9, 7.0 Hz, 3H), 6.75-6.66 (m, 4H), 5.58 (d, J = 4.5 Hz, 1H), 5.41-5.31 (m, 1H), 4.67 (p, J = 7.2 Hz, 1H), 3.90 (s, 3H), 3.87 (s, 3H), 2.39 (s, 3H), 2.30 (s, 3H), 2.20 (s, 3H), 1.34-1.27 (m, 6H). $^{13}$C NMR (101 MHz, CDCl$_3$) δ 172.04, 168.87, 162.32, 159.42, 156.59, 155.86, 146.60, 141.66, 139.07, 137.47, 129.89, 129.69, 127.72, 122.60, 121.50, 115.50, 111.07, 109.64, 74.99, 73.26, 56.24, 55.38, 48.02, 21.56, 20.72, 20.41, 18.48, 14.97. |
| 275 | | HRMS-ESI (m/z) ([M + H]$^+$) calcd for C$_{31}$H$_{34}$FN$_2$O$_8$, 603.2137; found, 603.2133. | $^1$H NMR (400 MHz, CDCl$_3$) δ 8.49 (d, J = 6.7 Hz, 1H), 8.27 (d, J = 5.4 Hz, 1H), 7.48 (dd, J = 8.7, 6.5 Hz, 1H), 7.44-7.38 (m, 2H), 7.24-7.15 (m, 3H), 7.12-7.06 (m, 2H), 6.98 (d, J = 5.5 Hz, 1H), 6.93-6.84 (m, 3H), 6.71 (td, J = 8.3, 2.5 Hz, 1H), 6.48 (dd, J = 10.1, 2.5 Hz, 1H), 5.72 |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | (d, J = 5.0 Hz, 1H), 5.52-5.44 (m, 1H), 4.71 (p, J = 7.2 Hz, 1H), 3.89 (s, 3H), 2.39 (s, 3H), 1.40 (d, J = 6.4 Hz, 3H), 1.34 (d, J = 7.2 Hz, 3H). $^{19}$F NMR (376 MHz, CDCl$_3$) δ-110.73. |
| 276 | | ESIMS m/z 336 ([M + H]$^+$) | |
| 277 | | ESIMS m/z 254 ([M − OCH$_2$cPr]$^+$) | |
| 278 | | ESIMS m/z 356 ([M + H]$^+$) | |
| 279 | | ESIMS m/z 340 ([M + H]$^+$) | |
| 280 | | ESIMS m/z 312 ([M + H]$^+$) | |
| 281 | | ESIMS m/z 312 ([M + H]$^+$) | |
| 282 | | ESIMS m/z 458 ([M + Na]$^+$) | $^1$H NMR (400 MHz, CDCl$_3$) δ 7.31 (dd, J = 8.5, 6.7 Hz, 1H), 6.69 (td, J = 8.3, 2.4 Hz, 1H), 6.60 (dd, J = 10.8, 2.4 Hz, 1H), 5.85 (tt, J = 55.4, 4.1 Hz, 1H), 5.22-5.12 (m, 1H), 5.01 (d, J = 8.2 Hz, 1H), 4.84 (d, J = 5.0 Hz, 1H), 4.25 (t, J = 7.5 Hz, 1H), 3.82 (s, 3H), 3.64-3.50 (m, 2H), 1.44 (s, 9H), 1.24-1.17 (m, 6H). $^{19}$F NMR (471 MHz, CDCl$_3$) δ-111.01(dd, J = 16.7, 7.9 Hz), −124.47-125.21 (m), −125.21-125.96 (m). |
| 283 | | ESIMS m/z 448 ([M + Na]$^+$) | $^1$H NMR (400 MHz, CDCl$_3$) δ 7.34 (dd, J = 8.3, 7.0 Hz, 1H), 6.66 (td, J = 8.3, 2.3 Hz, 1H), 6.57 (dd, J = 10.9, 2.3 Hz, 1H), 5.14 (p, J = 6.3 Hz, 1H), 5.04 (d, J = 6.4 Hz, 1H), 4.78 (d, J = 5.5 Hz, 1H), 4.29-4.17 (m, 1H), 3.81 (s, 3H), 3.18 (qd, J = 10.3, 6.8 Hz, 2H), 1.43 (s, 9H), 1.24 (d, J = 6.4 Hz, 3H), 1.18 (d, J = 7.2 Hz, 3H), 1.06-0.95 (m, 1H), 0.54-0.41 (m, 2H), 0.12 (dqd, J = 14.0, 9.3, 4.7 Hz, 2H). $^{19}$F NMR (376 MHz, CDCl$_3$) δ-112.12 (s). |
| 284 | | ESIMS m/z 478 ([M + Na]$^+$) | $^1$H NMR (400 MHz, CDCl$_3$) δ 7.26-7.21 (m, 1H), 6.65 (td, J = 8.3, 2.4 Hz, 1H), 6.60 (dd, J = 10.8, 2.4 Hz, 1H), 6.23 (d, J = 4.2 Hz, 1H), 5.36-5.28 (m, 1H), 5.05 (d, J = 7.4 Hz, 1H), 4.33-4.20 (m, 1H), 3.84 (s, 3H), 1.44 (s, 9H), 1.29 (d, J = 7.2 Hz, 3H), 1.24 (s, 9H), 1.19 (d, J = 6.5 Hz, 3H). $^{19}$F NMR (376 MHz, CDCl$_3$) δ-111.22 (s). |
| 285 | | ESIMS m/z 462 ([M + Na]$^+$) | $^1$H NMR (300 MHz, CDCl$_3$) δ 7.31-7.27 (m, 1H), 6.66 (td, J = 8.3, 2.4 Hz, 1H), 6.59 (dd, J = 10.8, 2.4 Hz, 1H), 6.26 (d, J = 4.2 Hz, 1H), 5.37-5.27 (m, 1H), 5.04 (d, J = 7.7 Hz, 1H), 4.35-4.21 (m, 1H), 3.83 (s, 3H), 1.68 (ddd, J = 15.2, 7.9, 4.6 Hz, 1H), 1.44 (s, 9H), 1.28 (d, J = 7.2 Hz, 3H), 1.18 (d, J = 6.5 Hz, 3H), 1.08-0.84 (m, 4H). |
| 286 | | ESIMS m/z 434 ([M + Na]$^+$) | $^1$H NMR (400 MHz, CDCl$_3$) δ 7.41-7.35 (m, 1H), 6.67 (td, J = 8.3, 2.4 Hz, 1H), 6.60 (dd, J = 10.9, 2.4 Hz, 1H), 5.20-5.12 (m, 1H), 5.02 (d, J = 6.6 Hz, 1H), 4.79 (d, J = 5.7 Hz, 1H), 4.31-4.19 (m, 1H), 3.83 (s, 3H), 3.19 (ddd, J = 8.8, 6.1, 3.0 Hz, 1H), 1.43 (s, 9H), 1.27-1.19 (m, 3H), 1.14 (dd, J = 12.7, 6.1 Hz, 3H), 0.69-0.62 (m, 1H), 0.56-0.42 (m, 2H), 0.36 (dt, J = 13.0, 5.6 Hz, 1H). $^{19}$F NMR (376 MHz, CDCl$_3$) δ-111.92 (s). |

TABLE 2-continued

Analytical Data

| *Cmpd. No. | IR (cm$^{-1}$) | MASS | NMR ($^1$H, $^{13}$C or $^{19}$F) |
|---|---|---|---|
| 287 | | ESIMS m/z 434 ([M + Na]$^+$) | $^1$H NMR (400 MHz, CDCl$_3$) δ 7.36 (dd, J = 8.3, 7.0 Hz, 1H), 6.67 (td, J = 8.4, 2.3 Hz, 1H), 6.59 (dd, J = 10.9, 2.3 Hz, 1H), 5.13 (dt, J = 12.8, 6.4 Hz, 1H), 5.03 (d, J = 5.6 Hz, 1H), 4.84 (d, J = 5.0 Hz, 1H), 4.30-4.19 (m, 1H), 3.83 (s, 3H), 3.24 (ddd, J = 8.9, 6.0, 2.8 Hz, 1H), 1.44 (s, 9H), 1.21 (d, J = 7.2 Hz, 3H), 1.16 (d, J = 6.4 Hz, 3H), 0.67-0.60 (m, 1H), 0.57-0.50 (m, 1H), 0.47-0.34 (m, 2H). $^{19}$F NMR (376 MHz, CDCl$_3$) δ-112.09 (s). |
| 288 | | HRMS-ESI (m/z) ([M + H]$^+$) calcd for C$_{22}$H$_{26}$F$_3$N$_2$O$_7$, 487.1687; found, 487.1690. | $^1$H NMR (500 MHz, CDCl$_3$) δ 12.12 (s, 1H), 8.43 (d, J = 7.9 Hz, 1H), 7.99 (d, J = 5.2 Hz, 1H), 7.31 (dd, J = 8.5, 6.8 Hz, 1H), 6.87 (d, J = 5.2 Hz, 1H), 6.66 (td, J = 8.3, 2.4 Hz, 1H), 6.59 (dd, J = 10.8, 2.4 Hz, 1H), 5.83 (tt, J = 55.5, 4.1 Hz, 1H), 5.26-5.20 (m, 1H), 4.86 (d, J = 4.8 Hz, 1H), 4.67 (p, J = 7.2 Hz, 1H), 3.94 (s, 3H), 3.81 (s, 3H), 3.62-3.50 (m, 2H), 1.40 (d, J = 7.2 Hz, 3H), 1.24 (d, J = 6.5 Hz, 3H). $^{13}$C NMR (126 MHz, CDCl$_3$) δ 171.24, 168.67, 163.50 (d, J = 246.6 Hz), 158.42 (d, J = 9.7 Hz), 155.40, 148.76, 140.49, 130.41, 128.90 (d, J = 10.1 Hz), 120.72 (d, J = 3.2 Hz), 114.27 (t, J = 241.2 Hz), 109.48, 107.23 (d, J = 21.3 Hz), 98.76 (d, J = 25.8 Hz), 77.76, 73.01, 68.71 (t, J = 28.1 Hz), 56.09, 55.68, 48.00, 18.04, 14.82. $^{19}$F NMR (471 MHz, CDCl$_3$) δ-110.96 (dt, J = 10.7, 7.5 Hz), −124.47-125.22 (m), −125.22-125.96 (m). |
| 289 | | HRMS-ESI (m/z) ([M + H]$^+$) calcd for C$_{24}$H$_{30}$FN$_2$O$_7$, 477.2032; found, 477.2028. | $^1$H NMR (500 MHz, CDCl$_3$) δ 12.15 (s, 1H), 8.45 (d, J = 7.8 Hz, 1H), 7.98 (d, J = 5.2 Hz, 1H), 7.34 (dd, J = 8.4, 6.9 Hz, 1H), 6.87 (d, J = 5.2 Hz, 1H), 6.64 (td, J = 8.3, 2.4 Hz, 1H), 6.56 (dd, J = 10.9, 2.4 Hz, 1H), 5.24-5.18 (m, 1H), 4.80 (d, J = 5.3 Hz, 1H), 4.65 (p, J = 7.2 Hz, 1H), 3.94 (s, 3H), 3.80 (s, 3H), 3.21 (dd, J = 10.3, 6.7 Hz, 1H), 3.15 (dd, J = 10.2, 6.9 Hz, 1H), 1.36 (d, J = 7.2 Hz, 3H), 1.26 (d, J = 6.4 Hz, 3H), 1.03-0.95 (m, 1H), 0.51-0.40 (m, 2H), 0.16-0.05 (m, 2H). $^{13}$C NMR (126 MHz, CDCl$_3$) δ 171.35, 168.62, 163.17 (d, J = 245.6 Hz), 158.46 (d, J = 9.7 Hz), 155.36, 148.73, 140.44, 130.50, 129.05 (d, J = 10.0 Hz), 122.41 (d, J = 3.2 Hz), 109.41, 106.95 (d, J = 21.1 Hz), 98.51 (d, J = 25.7 Hz), 75.99, 73.94, 73.55, 56.07, 55.61, 47.98, 18.09, 15.34, 10.63, 3.12, 2.72. $^{19}$F NMR (471 MHz, CDCl$_3$) δ-112.03 (dt, J = 10.8, 7.6 Hz). |
| 290 | | HRMS-ESI (m/z) ([M + H]$^+$) calcd for C$_{25}$H$_{32}$FN$_2$O$_8$, 507.2137; found, 507.2130. | $^1$H NMR (500 MHz, CDCl$_3$) δ 12.13 (s, 1H), 8.44 (d, J = 7.9 Hz, 1H), 7.99 (d, J = 5.2 Hz, 1H), 7.24 (dd, J = 8.7, 6.6 Hz, 1H), 6.88 (d, J = 5.2 Hz, 1H), 6.62-6.55 (m, 2H), 6.25 (d, J = 4.1 Hz, 1H), 5.37 (qd, J = 6.5, 4.2 Hz, 1H), 4.68 (p, J = 7.2 Hz, 1H), 3.95 (s, 3H), 3.84 (s, 3H), 1.46 (d, J = 7.2 Hz, 3H), 1.23 (s, 9H), 1.21 (d, J = 6.6 Hz, 3H). $^{13}$C NMR (126 MHz, CDCl$_3$) δ |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 176.88, 171.22, 168.67, 163.44 (d, J = 246.4 Hz), 157.80 (d, J = 9.9 Hz), 155.39, 148.77, 140.48, 130.43, 128.41 (d, J = 10.1 Hz), 120.70 (d, J = 3.3 Hz), 109.48, 106.95 (d, J = 21.4 Hz), 98.89 (d, J = 25.8 Hz), 72.17, 70.06, 56.09, 55.79, 47.93, 38.91, 27.11, 18.17, 14.83. |
| 291 | | HRMS-ESI (m/z) ([M + H]$^+$) calcd for C$_{24}$H$_{28}$FN$_2$O$_8$, 491.1824; found, 491.1820 | $^1$H NMR (400 MHz, CDCl$_3$) δ 12.13 (s, 1H), 8.44 (d, J = 7.8 Hz, 1H), 8.00 (d, J = 5.2 Hz, 1H), 7.30-7.24 (m, 1H), 6.88 (d, J = 5.2 Hz, 1H), 6.59 (t, J = 8.0 Hz, 2H), 6.28 (d, J = 4.2 Hz, 1H), 5.42-5.34 (m, 1H), 4.69 (p, J = 7.3 Hz, 1H), 3.95 (s, 3H), 3.83 (s, 3H), 1.68 (ddd, J = 12.7, 8.2, 4.7 Hz, 1H), 1.46 (d, J = 7.2 Hz, 3H), 1.20 (d, J = 6.5 Hz, 3H), 1.06-0.95 (m, 2H), 0.95-0.83 (m, 2H). $^{13}$C NMR (101 MHz, CDCl$_3$) δ 173.42, 171.27, 168.70, 163.47 (d, J = 246.5 Hz), 157.82 (d, J = 9.9 Hz), 155.41, 148.80, 140.46, 130.49, 128.77 (d, J = 10.1 Hz), 120.61 (d, J = 3.3 Hz), 109.49, 106.96 (d, J = 21.4 Hz), 98.88 (d, J = 25.8 Hz), 72.02, 70.17, 56.07, 55.79, 47.97, 18.11, 14.91, 12.97, 8.58. $^{19}$F NMR (376 MHz, CDCl$_3$) δ-111.11 (s). |
| 292 | | HRMS-ESI (m/z) ([M + H]$^+$) calcd for C$_{23}$H$_{28}$FN$_2$O$_7$, 463.1875; found, 463.1873 | $^1$H NMR (400 MHz, CDCl$_3$) δ 12.15 (s, 1H), 8.43 (d, J = 7.7 Hz, 1H), 7.98 (d, J = 5.2 Hz, 1H), 7.39 (dd, J = 8.3, 7.0 Hz, 1H), 6.86 (d, J = 5.2 Hz, 1H), 6.66-6.57 (m, 2H), 5.24-5.15 (m, 1H), 4.82 (d, J = 5.6 Hz, 1H), 4.70-4.61 (m, 1H), 3.94 (s, 3H), 3.83 (s, 3H), 3.20 (ddd, J = 9.1, 6.1, 3.0 Hz, 1H), 1.39 (d, J = 7.2 Hz, 3H), 1.18 (d, J = 6.5 Hz, 3H), 0.70-0.63 (m, 1H), 0.56-0.42 (m, 2H), 0.39-0.32 (m, 1H). $^{13}$C NMR (101 MHz, CDCl$_3$) δ 171.59, 168.55, 163.26 (d, J = 245.8 Hz), 158.24 (d, J = 9.6 Hz), 155.35, 148.75, 140.38, 130.58, 129.23 (d, J = 10.0 Hz), 122.42 (d, J = 3.2 Hz), 109.40, 106.86 (d, J = 21.1 Hz), 98.86 (d, J = 25.7 Hz), 77.62, 73.37, 56.04, 55.67, 52.37, 47.96, 18.40, 16.14, 6.27, 5.48. $^{19}$F NMR (376 MHz, CDCl$_3$) δ-111.84 (s). |
| 293 | | ESIMS m/z 485 ([M + Na]$^+$) | $^1$H NMR (400 MHz, CDCl$_3$) δ 12.15 (s, 1H), 8.45 (d, J = 7.9 Hz, 1H), 7.99 (d, J = 5.1 Hz, 1H), 7.36 (dd, J = 8.3, 7.0 Hz, 1H), 6.87 (d, J = 5.2 Hz, 1H), 6.65 (td, J = 8.4, 2.4 Hz, 1H), 6.59 (dd, J = 10.9, 2.3 Hz, 1H), 5.23-5.15 (m, 1H), 4.86 (d, J = 4.8 Hz, 1H), 4.67 (p, J = 7.3 Hz, 1H), 3.94 (s, 3H), 3.83 (s, 3H), 3.24 (dq, J = 9.0, 3.0 Hz, 1H), 1.40 (d, J = 7.2 Hz, 3H), 1.18 (d, J = 6.4 Hz, 3H), 0.66-0.58 (m, 1H), 0.56-0.49 (m, 1H), 0.46-0.31 (m, 2H). $^{13}$C NMR (101 MHz, CDCl$_3$) δ 171.26, 168.61, 163.26 (d, J = 245.7 Hz), 158.24 (d, J = 9.7 Hz), 155.39, 148.78, 140.40, 130.54, 129.24 (d, J = 10.1 Hz), 122.32 (d, J = 3.3 Hz), 109.44, 106.91 (d, J = 21.2 Hz), 98.67 (d, J = 25.7 Hz), 73.08, 56.06, 55.66, 52.43, 48.00, 18.19, 14.83, 6.10, 5.70. $^{19}$F NMR (376 MHz, CDCl$_3$) δ-112.01 (s). |

TABLE 2-continued

Analytical Data

| *Cmpd. No. | IR (cm⁻¹) | MASS | NMR ($^1$H, $^{13}$C or $^{19}$F) |
|---|---|---|---|
| 294 | | HRMS-ESI (m/z) ([M + H]⁺) calcd for C$_{24}$H$_{28}$F$_3$N$_2$O$_8$, 529.1792; found, 529.1788. | $^1$H NMR (400 MHz, CDCl$_3$) δ 8.48 (d, J = 6.8 Hz, 1H), 8.32 (d, J = 5.4 Hz, 1H), 7.32 (dd, J = 8.5, 6.8 Hz, 1H), 7.00 (d, J = 5.5 Hz, 1H), 6.66 (td, J = 8.3, 2.4 Hz, 1H), 6.59 (dd, J = 10.8, 2.4 Hz, 1H), 5.83 (tt, J = 55.5, 4.2 Hz, 1H), 5.24-5.16 (m, 1H), 4.85 (d, J = 4.7 Hz, 1H), 4.67 (p, J = 7.2 Hz, 1H), 3.91 (s, 3H), 3.81 (s, 3H), 3.57 (td, J = 13.8, 4.2 Hz, 2H), 2.39 (s, 3H), 1.34 (d, J = 7.2 Hz, 3H), 1.21 (d, J = 6.5 Hz, 3H). $^{13}$C NMR (101 MHz, CDCl$_3$) δ 171.74, 168.86, 163.48 (d, J = 246.5 Hz), 162.35, 159.49, 158.38 (d, J = 9.8 Hz), 146.63, 141.53, 137.54, 128.91 (d, J = 10.0 Hz), 120.94 (d, J = 3.0 Hz), 114.30 (t, J = 241.1 Hz), 109.77, 107.18 (d, J = 21.3 Hz), 98.73 (d, J = 25.8 Hz), 77.81, 72.84, 68.83 (t, J = 28.1 Hz), 56.28, 55.65, 47.99, 20.71, 18.34, 14.74. $^{19}$F NMR (376 MHz, CDCl$_3$) δ -111.16 (s), -124.83 (d, J = 293.2 Hz), -125.66 (d, J = 293.2 Hz). |
| 295 | | HRMS-ESI (m/z) ([M + H]⁺) calcd for C$_{26}$H$_{32}$FN$_2$O$_8$, 519.2137; found, 519.2131. | $^1$H NMR (400 MHz, CDCl$_3$) δ 8.50 (d, J = 6.2 Hz, 1H), 8.32 (d, J = 5.4 Hz, 1H), 7.35 (dd, J = 8.3, 7.1 Hz, 1H), 6.99 (d, J = 5.5 Hz, 1H), 6.64 (td, J = 8.3, 2.3 Hz, 1H), 6.57 (dd, J = 10.9, 2.3 Hz, 1H), 5.18 (p, J = 6.3 Hz, 1H), 4.79 (d, J = 5.4 Hz, 1H), 4.65 (p, J = 7.2 Hz, 1H), 3.90 (s, 3H), 3.80 (s, 3H), 3.22 (dd, J = 10.2, 6.7 Hz, 1H), 3.15 (dd, J = 10.2, 6.9 Hz, 1H), 2.39 (s, 3H), 1.28 (d, J = 7.2 Hz, 3H), 1.25 (d, J = 6.4 Hz, 3H), 1.04-0.95 (m, 1H), 0.52-0.40 (m, 2H), 0.11 (dtt, J = 14.2, 9.5, 4.8 Hz, 2H). $^{13}$C NMR (101 MHz, CDCl$_3$) δ 171.89, 168.88, 163.16 (d, J = 245.6 Hz), 162.30, 159.45, 158.48 (d, J = 9.7 Hz), 146.62, 141.64, 137.49, 129.07 (d, J = 10.0 Hz), 122.60 (d, J = 3.5 Hz), 109.70, 106.93 (d, J = 21.1 Hz), 98.49 (d, J = 25.7 Hz), 76.03, 73.93, 73.37, 56.26, 55.59, 47.97, 20.72, 18.42, 15.38, 10.64, 3.09, 2.70. |
| 296 | | HRMS-ESI (m/z) ([M + H]⁺) calcd for C$_{27}$H$_{34}$FN$_2$O$_9$, 549.2243; found, 549.2239 | $^1$H NMR (400 MHz, CDCl$_3$) δ 8.51 (d, J = 6.7 Hz, 1H), 8.33 (d, J = 5.4 Hz, 1H), 7.26-7.22 (m, 1H), 7.01 (d, J = 5.5 Hz, 1H), 6.62-6.56 (m, 2H), 6.24 (d, J = 4.1 Hz, 1H), 5.39-5.31 (m, 1H), 4.68 (p, J = 7.2 Hz, 1H), 3.91 (s, 3H), 3.83 (s, 3H), 2.39 (s, 3H), 1.41 (d, J = 7.2 Hz, 3H), 1.23 (s, 9H), 1.19 (d, J = 6.5 Hz, 3H). $^{13}$C NMR (101 MHz, CDCl$_3$) δ 176.86, 171.78, 168.86, 163.44 (d, J = 246.4 Hz), 162.35, 159.48, 157.82 (d, J = 10.1 Hz), 146.64, 141.55, 137.54, 128.46 (d, J = 10.2 Hz), 120.81 (d, J = 2.9 Hz), 109.76, 106.94 (d, J = 21.4 Hz), 98.87 (d, J = 25.8 Hz), 71.93, 70.12, 56.28, 55.77, 47.92, 38.90, 27.12, 20.72, 18.53, 14.86. |

TABLE 2-continued

Analytical Data

| *Cmpd. No. | IR (cm$^{-1}$) | MASS | NMR ($^1$H, $^{13}$C or $^{19}$F) |
|---|---|---|---|
| 297 | | HRMS-ESI (m/z) ([M + H]$^+$) calcd for C$_{26}$H$_{30}$FN$_2$O$_9$, 533.1930; found, 533.1923. | $^1$H NMR (400 MHz, CDCl$_3$) δ 8.50 (d, J = 6.4 Hz, 1H), 8.33 (d, J = 5.2 Hz, 1H), 7.29 (d, J = 7.4 Hz, 1H), 7.01 (d, J = 5.4 Hz, 1H), 6.60 (t, J = 9.5 Hz, 2H), 6.27 (d, J = 4.2 Hz, 1H), 5.39-5.31 (m, 1H), 4.70 (p, J = 7.3 Hz, 1H), 3.91 (s, 3H), 3.82 (s, 3H), 2.39 (s, 3H), 1.67 (ddd, J = 12.7, 8.1, 4.5 Hz, 1H), 1.40 (d, J = 7.2 Hz, 3H), 1.18 (d, J = 6.5 Hz, 3H), 1.04-0.95 (m, 2H), 0.89 (d, J = 2.7 Hz, 2H). $^{13}$C NMR (101 MHz, CDCl$_3$) δ 173.42, 171.83, 168.85, 163.45 (d, J = 246.3 Hz), 162.36, 159.48, 157.82 (d, J = 9.8 Hz), 146.64, 141.55, 137.53, 128.82 (d, J = 10.1 Hz), 120.67 (d, J = 3.2 Hz), 109.77, 106.95 (d, J = 21.4 Hz), 98.84 (d, J = 25.9 Hz), 71.79, 70.18, 56.28, 55.78, 47.95, 20.72, 18.50, 14.95, 12.99, 8.57, 8.55. |
| 298 | | HRMS-ESI (m/z) ([M + H]$^+$) calcd for C$_{25}$H$_{30}$FN$_2$O$_8$, 505.1981; found, 505.1972 | $^1$H NMR (400 MHz, CDCl$_3$) δ 8.48 (s, 1H), 8.32 (d, J = 5.5 Hz, 1H), 7.39 (dd, J = 8.3, 7.0 Hz, 1H), 6.99 (d, J = 5.5 Hz, 1H), 6.65 (td, J = 8.3, 2.3 Hz, 1H), 6.59 (dd, J = 10.9, 2.4 Hz, 1H), 5.17 (p, J = 6.4 Hz, 1H), 4.82 (d, J = 5.9 Hz, 1H), 4.71-4.62 (m, 1H), 3.90 (s, 3H), 3.83 (s, 3H), 3.18 (dq, J = 9.1, 3.0 Hz, 1H), 2.39 (s, 3H), 1.35 (d, J = 7.1 Hz, 3H), 1.14 (d, J = 6.5 Hz, 3H), 0.69-0.62 (m, 1H), 0.56-0.47 (m, 1H), 0.47-0.40 (m, 1H), 0.35 (dt, J = 11.1, 5.8 Hz, 1H). $^{13}$C NMR (101 MHz, CDCl$_3$) δ 172.14, 168.87, 164.47, 164.18 (d, J = 228.4 Hz), 162.25, 162.03, 159.43, 158.30 (d, J = 9.8 Hz), 146.62, 141.70, 137.48, 129.32 (d, J = 9.8 Hz), 122.50 (d, J = 3.5 Hz), 109.68, 106.88 (d, J = 21.3 Hz), 98.83 (d, J = 25.8 Hz), 77.57, 73.17, 56.25, 55.66, 52.30, 47.98, 20.72, 18.72, 16.09, 6.26, 5.47. $^{19}$F NMR (376 MHz, CDCl$_3$) δ-111.93 (s). |
| 299 | | HRMS-ESI (m/z) ([M + H]$^+$) calcd for C$_{25}$H$_{30}$FN$_2$O$_8$, 505.1981; found, 505.1982 | $^1$H NMR (400 MHz, CDCl$_3$) δ 8.51 (d, J = 6.2 Hz, 1H), 8.33 (d, J = 5.4 Hz, 1H), 7.36 (dd, J = 8.3, 7.0 Hz, 1H), 7.00 (d, J = 5.4 Hz, 1H), 6.65 (td, J = 8.3, 2.4 Hz, 1H), 6.59 (dd, J = 10.9, 2.3 Hz, 1H), 5.20-5.12 (m, 1H), 4.86 (d, J = 4.8 Hz, 1H), 4.72-4.63 (m, 1H), 3.91 (s, 3H), 3.82 (s, 3H), 3.25 (ddd, J = 9.0, 6.0, 2.9 Hz, 1H), 2.40 (s, 3H), 1.33 (d, J = 7.1 Hz, 3H), 1.16 (d, J = 6.4 Hz, 3H), 0.66-0.59 (m, 1H), 0.54 (ddd, J = 14.0, 6.6, 4.2 Hz, 1H), 0.39 (dtd, J = 14.4, 10.1, 4.3 Hz, 2H). $^{13}$C NMR (101 MHz, CDCl$_3$) δ 171.83, 168.88, 163.24 (d, J = 245.4 Hz), 162.29, 159.47, 158.23 (d, J = 9.5 Hz), 146.61, 141.61, 137.51, 129.22 (d, J = 10.0 Hz), 122.44 (d, J = 3.5 Hz), 109.72, 106.88 (d, J = 21.2 Hz), 98.64 (d, J = 25.8 Hz), 72.88, 56.27, 55.65, 52.44, 47.98, 20.73, 18.55, 14.83, 6.11, 5.74. $^{19}$F NMR (376 MHz, CDCl$_3$) δ-112.15 (s). |

*Cmpd. No.—Compound Number

TABLE 3

Biological Testing Rating Scale
Rating Table for Fungal Pathogens

| % Control | Rating |
|---|---|
| >80 | A |
| ≤80 | B |
| Not Tested | C |
| ≤0 | D |

TABLE 4

Biological Activity - High Volume Cereal Activity at 100 ppm

| *Cmpd. No. | PUCCRT* 1 DP* | PUCCRT* 3 DC* | SEPTTR* 1 DP* | SEPTTR* 3 DC* |
|---|---|---|---|---|
| 113 | A | B | A | A |
| 114 | A | A | A | A |
| 115 | D | A | D | B |
| 116 | D | D | D | B |
| 117 | A | A | A | A |
| 118 | A | A | A | A |
| 119 | A | A | B | A |
| 120 | A | B | A | B |
| 121 | A | B | B | A |
| 122 | A | A | A | A |
| 123 | A | B | B | B |
| 124 | A | A | A | A |
| 125 | B | D | B | B |
| 126 | B | D | D | B |
| 127 | A | A | A | A |
| 128 | A | B | D | B |
| 129 | B | B | A | B |
| 130 | C | C | C | C |
| 131 | B | B | D | B |
| 132 | A | B | B | D |
| 133 | B | D | D | D |
| 134 | A | A | A | B |
| 135 | A | D | A | A |
| 136 | D | B | B | D |
| 137 | A | A | A | A |
| 138 | A | A | B | B |
| 139 | C | C | C | C |
| 140 | B | A | D | B |
| 141 | C | C | C | C |
| 142 | A | A | B | B |
| 143 | C | C | C | C |
| 144 | A | B | A | B |
| 145 | A | B | A | A |
| 146 | A | A | A | A |
| 147 | A | B | A | A |
| 148 | A | B | B | A |
| 149 | A | A | A | A |
| 150 | A | A | A | B |
| 151 | A | A | A | B |
| 152 | A | A | A | A |
| 153 | C | C | C | C |
| 154 | A | A | A | A |
| 162 | A | A | A | A |
| 163 | A | A | A | A |
| 164 | A | A | A | A |
| 165 | A | A | A | A |
| 166 | A | A | A | A |
| 167 | A | A | A | A |
| 168 | A | A | A | A |
| 169 | A | B | A | A |
| 172 | A | A | A | A |
| 173 | A | A | A | A |
| 175 | A | A | A | B |
| 176 | A | A | A | A |
| 177 | B | D | A | A |
| 178 | A | B | A | A |
| 288 | A | A | B | A |
| 289 | A | A | A | A |
| 290 | A | A | A | A |
| 291 | B | B | D | A |

*Cmpd. No.—Compound Number
*PUCCRT -Wheat Brown Rust (*Puccinia triticina*)
*SEPTTR-Wheat Leaf Blotch (*Zymoseptoria tritici*)
*1 DP—1 Day Protectant
*3 DC—3 Day Curative
*ppm—Parts Per Million

TABLE 5

Biological Activity - Low Volume Cereal Activity at 121.5 g/Ha

| *Cmpd. No. | PUCCRT* 1 DP* | PUCCRT* 3 DC* | SEPTTR* 1 DP* | SEPTTR* 3 DC* |
|---|---|---|---|---|
| 182 | A | A | A | A |
| 183 | A | A | A | A |
| 184 | A | A | A | A |
| 185 | A | A | A | A |
| 186 | D | D | B | B |
| 187 | A | A | A | A |
| 188 | A | A | A | A |
| 189 | A | B | B | D |
| 190 | A | B | B | D |
| 191 | A | A | D | B |
| 192 | A | A | A | B |
| 193 | A | A | B | D |
| 194 | A | B | B | D |
| 195 | A | B | A | A |
| 196 | A | B | A | A |
| 197 | A | B | A | D |
| 198 | A | B | A | D |
| 199 | A | B | A | A |
| 200 | A | B | A | A |
| 201 | A | A | A | A |
| 202 | A | B | A | A |
| 203 | A | B | A | A |
| 204 | A | A | B | A |
| 205 | A | A | A | A |
| 206 | A | B | A | A |
| 207 | A | B | A | A |
| 208 | A | B | A | A |
| 209 | A | B | A | A |
| 210 | B | B | B | B |
| 211 | D | B | D | B |
| 212 | B | A | D | B |
| 213 | A | A | D | B |
| 214 | A | B | A | A |
| 215 | B | B | B | B |
| 216 | A | B | A | A |
| 217 | A | B | A | A |
| 218 | D | D | A | B |
| 219 | A | A | A | A |
| 220 | A | A | B | A |
| 221 | A | B | A | B |
| 222 | A | A | A | A |
| 223 | A | B | A | A |
| 224 | A | A | B | B |
| 225 | A | A | B | A |
| 226 | A | A | B | B |
| 227 | A | A | B | A |
| 228 | A | A | B | A |
| 229 | D | A | D | B |
| 230 | A | A | D | A |
| 231 | D | A | D | A |
| 232 | A | A | D | A |
| 233 | A | A | A | A |
| 234 | A | B | A | A |
| 235 | A | A | A | A |

TABLE 5-continued

Biological Activity - Low Volume Cereal Activity at 121.5 g/Ha

| *Cmpd. No. | PUCCRT* 1 DP* | PUCCRT* 3 DC* | SEPTTR* 1 DP* | SEPTTR* 3 DC* |
|---|---|---|---|---|
| 236 | A | A | A | A |
| 237 | A | A | A | A |
| 238 | A | A | A | A |
| 239 | A | B | A | A |
| 240 | A | B | A | A |
| 241 | A | A | A | A |
| 242 | A | A | A | A |
| 243 | A | B | A | A |
| 244 | A | B | A | A |
| 245 | A | B | A | A |
| 246 | A | A | A | A |
| 247 | A | A | A | A |
| 248 | A | A | A | A |
| 249 | A | A | A | A |
| 250 | A | A | A | A |
| 251 | A | A | A | A |
| 252 | A | A | A | A |
| 253 | A | A | A | A |
| 254 | A | A | A | A |
| 255 | A | A | A | A |
| 256 | A | A | A | A |
| 257 | A | A | A | A |
| 258 | A | A | A | A |
| 259 | A | A | A | A |
| 260 | A | A | A | A |
| 261 | A | A | A | A |
| 262 | A | A | A | A |
| 263 | A | A | A | A |
| 264 | A | D | A | A |
| 265 | A | A | A | A |
| 266 | A | B | A | A |
| 267 | B | D | A | B |
| 268 | A | A | A | A |
| 269 | A | A | A | A |
| 270 | A | A | A | A |
| 271 | A | D | A | A |
| 272 | A | A | A | A |
| 273 | A | A | A | A |
| 274 | A | B | A | A |
| 275 | A | A | A | B |
| 294 | B | B | A | A |
| 295 | A | B | A | A |
| 296 | A | D | A | A |
| 297 | D | D | D | B |
| 298 | B | A | B | D |
| 299 | A | B | A | A |

*Cmpd. No.—Compound Number
*PUCCRT-Wheat Brown Rust (*Puccinia triticina*)
*SEPTTR-Wheat Leaf Blotch (*Zymoseptoria tritici*)
*1 DP—1 Day Protectant
*3 DC—3 Day Curative
*g/H—Grams Per Hectare

TABLE 6

Biological Activity - High Volume Disease Control at 25 ppm

| *Cmpd. No. | PHAKPA* 1 DP* | PHAKPA* 3 DC* |
|---|---|---|
| 182 | A | B |
| 183 | B | B |
| 184 | B | B |
| 185 | B | D |
| 186 | D | D |
| 187 | A | B |
| 188 | A | B |
| 202 | A | B |
| 203 | C | C |
| 204 | A | B |
| 205 | B | B |
| 206 | C | C |
| 207 | B | B |
| 220 | A | B |
| 225 | A | B |
| 228 | A | D |
| 230 | B | B |
| 233 | A | B |
| 235 | B | B |
| 236 | A | D |
| 237 | B | B |
| 238 | B | B |
| 241 | A | D |
| 242 | A | B |
| 250 | A | B |
| 255 | A | D |
| 256 | A | D |
| 259 | A | D |
| 260 | A | B |
| 261 | A | D |
| 262 | A | D |
| 264 | B | B |
| 265 | B | D |
| 266 | B | D |
| 267 | B | B |
| 268 | B | B |
| 269 | A | B |
| 270 | B | D |
| 271 | B | B |
| 272 | B | D |
| 273 | B | D |
| 274 | B | D |
| 275 | B | D |
| 294 | B | B |
| 295 | A | B |
| 296 | B | B |
| 297 | B | B |
| 298 | A | B |
| 299 | A | B |

*Cmpd. No.—Compound Number
*PHAKPA-Asian Soybean Rust (*Phakopsora pachyrhizi*)
*1 DP—1 Day Protectant
*3 DC—3 Day Curative

TABLE 7

Biological Activity - 1DP High Volume Disease Control at 100 ppm

| *Cmpd. No. | ALTESO* | CERCBE* | COLLLA* | LEPTNO* | PYRIOR* | RHYNSE* | VENTIN* |
|---|---|---|---|---|---|---|---|
| 183 | B | A | A | A | A | A | B |
| 185 | B | B | C | C | C | C | B |
| 186 | B | B | C | C | C | C | B |
| 187 | B | A | A | A | A | A | C |
| 202 | D | B | B | B | B | D | C |
| 205 | B | A | A | A | A | B | C |
| 207 | D | A | A | A | A | A | A |
| 235 | B | A | A | A | A | A | B |
| 236 | B | A | B | A | A | A | A |
| 237 | B | A | B | A | A | A | B |
| 238 | A | A | B | A | A | A | A |
| 250 | D | B | A | D | B | B | C |
| 252 | D | A | A | A | A | A | B |
| 255 | D | A | A | A | A | B | B |
| 256 | B | A | A | A | A | A | C |
| 259 | D | A | A | A | A | A | B |
| 260 | D | A | A | A | A | A | B |
| 263 | D | A | A | A | A | A | B |

*Cmpd. No.—Compound Number
*ALTESO-Tomato Early Blight (*Alternaria solani*)
*CERCBE-Leaf Spot of Sugar Beets (*Cercospora beticola*)
*COLLLA-Cucumber Anthracnose (*Colletotricum lagenarium*)
*LEPTNO-Wheat Glume Blotch (*Leptosphaeria nodorum*)
*PYRIOR-Rice Blast (*Pyricularia oryzae*)
*RHYNSE-Barley Scald (*Rhyncosporium secalis*)
*VENTIN-Apple Scab (*Venturia inaequalis*)
*1DP—1 Day Protectant

What is claimed is:

1. A compound of Formula I

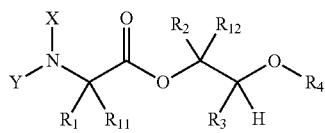

I

X is hydrogen or $C(O)R_5$;
Y is hydrogen, $C(O)R_5$, or Q;
Q is

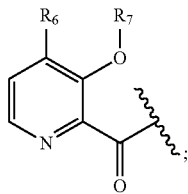

$R_1$ and $R_{11}$ are independently chosen from hydrogen or alkyl, optionally substituted with 0, 1 or multiple $R_8$; alternatively, $R_1$ and $R_{11}$ may be taken together to form a 3-6 membered saturated or partially saturated carbocycle or heterocycle, optionally substituted with 0, 1 or multiple $R_8$;
$R_2$ and $R_{12}$ are independently chosen from hydrogen or methyl;
$R_3$ is chosen from aryl or heteroaryl, each optionally substituted with 0, 1 or multiple $R_8$;
$R_4$ is chosen from alkyl, aryl, or acyl, each optionally substituted with 0, 1, or multiple $R_8$;
$R_5$ is chosen from alkoxy or benzyloxy, each optionally substituted with 0, 1, or multiple $R_8$;
$R_6$ is chosen from hydrogen, alkoxy, or halo, each optionally substituted with 0, 1, or multiple $R_8$;
$R_7$ is chosen from hydrogen, $C(O)R_9$, or —$CH_2OC(O)R_9$;
$R_8$ is chosen from hydrogen, alkyl, aryl, acyl, halo, alkenyl, alkoxy, or heterocyclyl, each optionally substituted with 0, 1, or multiple $R_{10}$;
$R_9$ is chosen from alkyl, alkoxy, or aryl, each optionally substituted with 0, 1, or multiple $R_8$; and
$R_{10}$ is chosen from hydrogen, alkyl, aryl, acyl, halo, alkenyl, alkoxy, or heterocyclyl.

2. A compound according to claim 1, wherein X and Y are hydrogen.

3. A compound according to claim 2, wherein $R_1$ and $R_{11}$ are independently chosen from hydrogen or alkyl.

4. A compound according to claim 2, wherein $R_3$ is aryl, optionally substituted with 0, 1 or multiple $R_8$.

5. A compound according to claim 2, wherein $R_4$ is chosen from alkyl or aryl, each optionally substituted with 0, 1 or multiple $R_8$.

6. A compound according to claim 2, wherein $R_1$ and $R_{11}$ are independently chosen from hydrogen or alkyl, $R_3$ is aryl, optionally substituted with 0, 1 or multiple $R_8$, and $R_4$ is chosen from alkyl or aryl, each optionally substituted with 0, 1 or multiple $R_8$.

7. A compound according to claim 1, wherein X is $C(O)R_5$ and Y is hydrogen.

8. A compound according to claim 7, wherein $R_1$ and $R_{11}$ are independently chosen from hydrogen or alkyl.

9. A compound according to claim 7, wherein $R_3$ is aryl, optionally substituted with 0, 1 or multiple $R_8$.

10. A compound according to claim 7, wherein $R_4$ is chosen from alkyl or aryl, each optionally substituted with 0, 1 or multiple $R_8$.

11. A compound according to claim 7, wherein $R_1$ and $R_{11}$ are independently chosen from hydrogen or alkyl, $R_3$ is aryl, optionally substituted with 0, 1 or multiple $R_8$, and $R_4$ is chosen from alkyl or aryl, each optionally substituted with 0, 1 or multiple $R_8$.

12. A compound according to claim 1, wherein X is hydrogen and Y is Q.

13. A compound according to claim 12, wherein $R_7$ is hydrogen.

14. A compound according to claim 13, wherein $R_6$ is alkoxy.

15. A compound according to claim 14, wherein $R_1$ and $R_{11}$ are independently chosen from hydrogen or alkyl.

16. A compound according to claim 14, wherein $R_3$ is aryl, optionally substituted with 0, 1 or multiple $R_8$.

17. A compound according to claim 14, wherein $R_4$ is chosen from alkyl or aryl, each optionally substituted with 0, 1 or multiple $R_8$.

18. A compound according to claim 14, wherein $R_1$ and $R_{11}$ are independently chosen from hydrogen or alkyl, $R_3$ is aryl, optionally substituted with 0, 1 or multiple $R_8$; and $R_4$ is chosen from alkyl or aryl, each optionally substituted with 0, 1 or multiple $R_8$.

19. A compound according to claim 12, wherein $R_7$ is chosen from —C(O)$R_9$, or —CH$_2$OC(O)$R_9$.

20. A compound according to claim 19, wherein $R_9$ is alkyl, optionally substituted with 0, 1 or multiple $R_8$.

21. A compound according to claim 20, wherein $R_1$ and $R_{11}$ are independently chosen from hydrogen or alkyl.

22. A compound according to claim 20, wherein $R_3$ is aryl, optionally substituted with 0, 1 or multiple $R_8$.

23. A compound according to claim 20, wherein $R_4$ is chosen from alkyl or aryl, each optionally substituted with 0, 1 or multiple $R_8$.

24. A compound according to claim 20, wherein $R_1$ and $R_{11}$ are independently chosen from hydrogen or alkyl, $R_3$ is aryl, optionally substituted with 0, 1 or multiple $R_8$; and $R_4$ is chosen from alkyl or aryl, each optionally substituted with 0, 1 or multiple $R_8$.

25. A compound according to claim 24, wherein $R_9$ is chosen from —CH$_3$, —CH$_2$OCH$_2$CH$_3$, —CH$_2$CH$_2$OCH$_3$, —CH(CH$_3$)$_2$, —CH$_2$CH$_2$CH$_2$CH$_3$, or -cyclopropyl.

* * * * *